(12) United States Patent
Lee et al.

(10) Patent No.: US 12,167,688 B2
(45) Date of Patent: Dec. 10, 2024

(54) LIGHT EMITTING DEVICE

(71) Applicant: Samsung Display Co., Ltd., Yongin-si (KR)

(72) Inventors: Youngki Lee, Hwaseong-si (KR); Jungsub Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 633 days.

(21) Appl. No.: 17/445,981

(22) Filed: Aug. 26, 2021

(65) Prior Publication Data

US 2022/0216425 A1 Jul. 7, 2022

(30) Foreign Application Priority Data

Jan. 5, 2021 (KR) .......................... 10-2021-0000693

(51) Int. Cl.
*H01L 51/00* (2006.01)
*C07D 471/04* (2006.01)
(Continued)

(52) U.S. Cl.
CPC ....... *H10K 85/6572* (2023.02); *C07D 471/04* (2013.01); *H10K 85/6574* (2023.02);
(Continued)

(58) Field of Classification Search
None
See application file for complete search history.

(56) References Cited

U.S. PATENT DOCUMENTS 9,502,669 B2 11/2016 Huh et al.

FOREIGN PATENT DOCUMENTS

KR 10-2012-0079411 * 7/2012
KR 10-1298349 B1 8/2013
(Continued)

OTHER PUBLICATIONS

Machine English translation of Lee et al. (KR-10-2012-0079411). Apr. 2, 2024.*

*Primary Examiner* — Jay Yang
(74) *Attorney, Agent, or Firm* — Lewis Roca Rothgerber Christie LLP

(57) ABSTRACT

A light emitting device of an embodiment includes a first electrode oppositely disposed to a second electrode, and multiple organic layers disposed between the first electrode and the second electrode, wherein at least one among the organic layers includes a fused polycyclic compound represented by Formula 1, thereby showing improved emission efficiency:

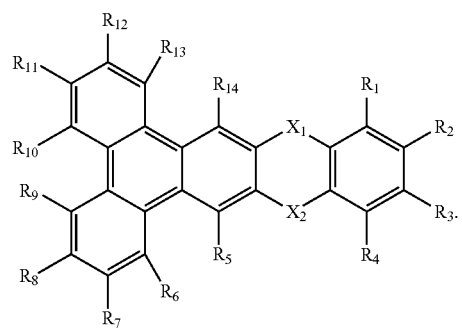

Formula 1

20 Claims, 6 Drawing Sheets

(51) Int. Cl.
  *H10K 85/60*   (2023.01)
  *H10K 50/11*   (2023.01)
  *H10K 59/122*  (2023.01)

(52) U.S. Cl.
  CPC ......... *H10K 85/6576* (2023.02); *H10K 50/11* (2023.02); *H10K 59/122* (2023.02)

(56)     References Cited

FOREIGN PATENT DOCUMENTS

KR       10-1375360 B1    3/2014
KR       10-1772746 B1    8/2017
WO    WO-2012/093862 A2 *  7/2012

* cited by examiner

LIGHT EMITTING DEVICE

CROSS-REFERENCE TO RELATED APPLICATION

This application claims priority to and the benefit of Korean Patent Application No. 10-2021-0000693, filed on Jan. 5, 2021, the entire content of which is hereby incorporated by reference.

BACKGROUND

One or more aspects of embodiments of the present disclosure relate to a light emitting device, and for example, to an organic electroluminescence device including a novel fused polycyclic compound as a light emitting material.

Organic electroluminescence displays are recently being developed as image displays. An organic electroluminescence display is different from a liquid crystal display, and is so-called a self-luminescent display, in which holes and electrons respectively injected from a first electrode and a second electrode recombine in an emission layer so that a light emitting material in the emission layer emits light to achieve display.

In the application of an organic electroluminescence device to a display, a decrease in driving voltage, and an increase in emission efficiency and life (e.g., life span) of the organic electroluminescence device are desired, and development of materials for an organic electroluminescence device capable of stably achieving such requirements is continuously desired.

For example, recently, in order to accomplish an organic electroluminescence device with high efficiency, materials capable of phosphorescence emission utilizing triplet state energy, delayed fluorescence emission utilizing triplet-triplet annihilation (TTA) (in which singlet excitons are generated via collision between triplet excitons), and/or thermally activated delayed fluorescence (TADF) emission are continually being developed.

SUMMARY

One or more aspects of embodiments of the present disclosure are directed toward a light emitting device showing improved emission efficiency and/or device life span.

One or more aspects of embodiments of the present disclosure are directed toward a fused polycyclic compound capable of improving the emission efficiency and device life span of a light emitting device.

One or more embodiments of the present disclosure provide a light emitting device including a first electrode, a second electrode oppositely disposed to the first electrode, and multiple organic layers disposed between the first electrode and the second electrode, wherein at least one organic layer among the organic layers includes a fused polycyclic compound, and the fused polycyclic compound is represented by Formula 1:

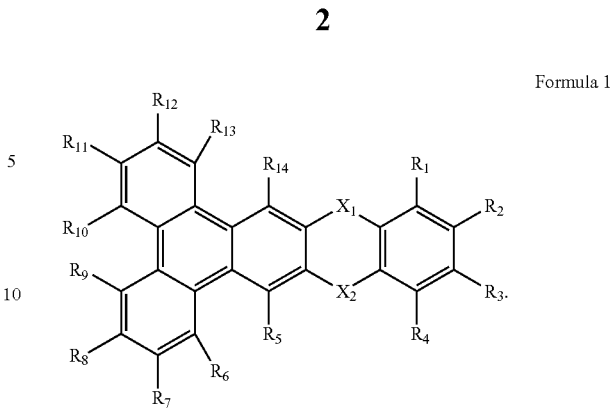

Formula 1

In Formula 1, $X_1$ and $X_2$ may each independently be $NR_{15}$, O or S, at least one among (i.e., at least one selected from) $X_1$ and $X_2$ may be $NR_{15}$, $R_1$ to $R_{15}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and/or combined with an adjacent group to form a ring, and at least one among $R_1$ to $R_{15}$ may be a substituent represented by Formula 2:

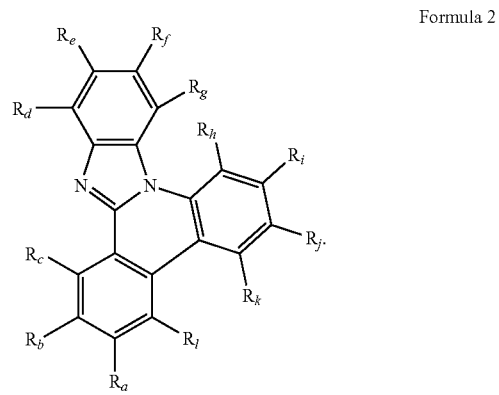

Formula 2

In Formula 2, $R_a$ to $R_l$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and/or combined with an adjacent group (e.g., an adjacent one of $R_a$ to $R_l$) to form a ring, and any one among $R_a$ to $R_l$ may be a position connected with Formula 1.

In an embodiment, the organic layers may include a hole transport region disposed on the first electrode, an emission layer disposed on the hole transport region, and an electron transport region disposed on the emission layer, and the emission layer may include the fused polycyclic compound represented by Formula 1.

In an embodiment, the emission layer may be to emit delayed fluorescence.

In an embodiment, the emission layer may be a delayed fluorescence emission layer including a host and a dopant, and the host may include the fused polycyclic compound represented by Formula 1.

In an embodiment, the emission layer may be to emit light with a central wavelength of about 430 nm to about 490 nm.

In an embodiment, the fused polycyclic compound represented by Formula 1 may be represented by Formula 1-1 or Formula 1-2:

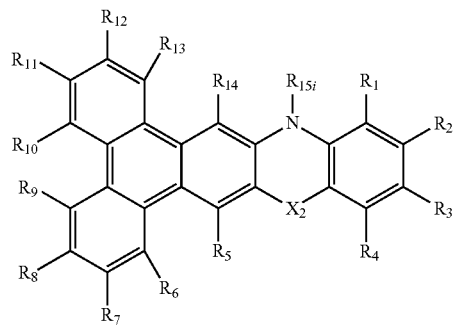

Formula 1-1

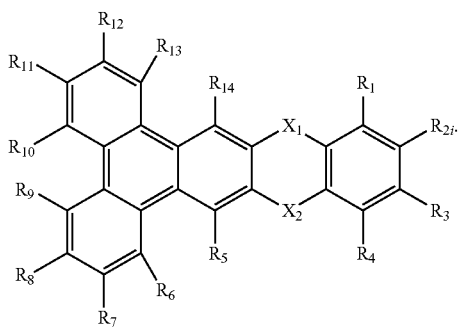

Formula 1-2

In Formula 1-1 and Formula 1-2, $R_{2i}$ and $R_{15i}$ may each independently be the substituent represented by Formula 2.

In Formula 1-1 and Formula 1-2, $X_1$, $X_2$, and $R_1$ to $R_{15}$ may each independently be the same as defined in Formula 1.

In an embodiment, the substituent represented by Formula 2 may be represented by any one among Formula 2-1 to Formula 2-4:

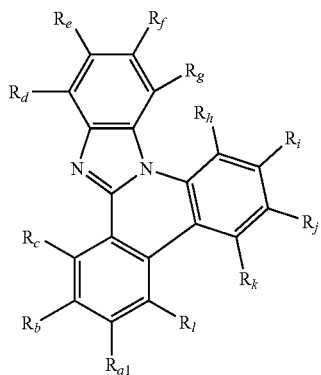

Formula 2-1

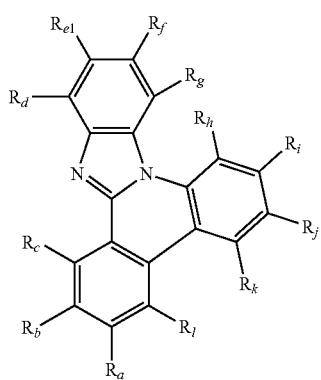

Formula 2-2

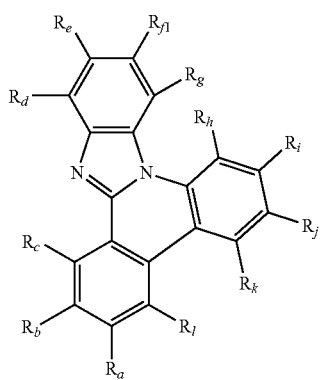

Formula 2-3

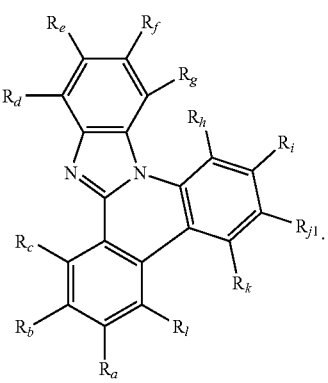

Formula 2-4

In Formula 2-1 to Formula 2-4, $R_{a1}$, $R_{e1}$, $R_{f1}$, and $R_{j1}$ may each independently be a position connected with Formula 1.

In Formula 2-1 to Formula 2-4, $R_a$ to $R_l$ may each independently be the same as defined in Formula 2.

In an embodiment, the fused polycyclic compound represented by Formula 1 may be represented by any one among Formula 3-1 to Formula 3-9:

Formula 3-1
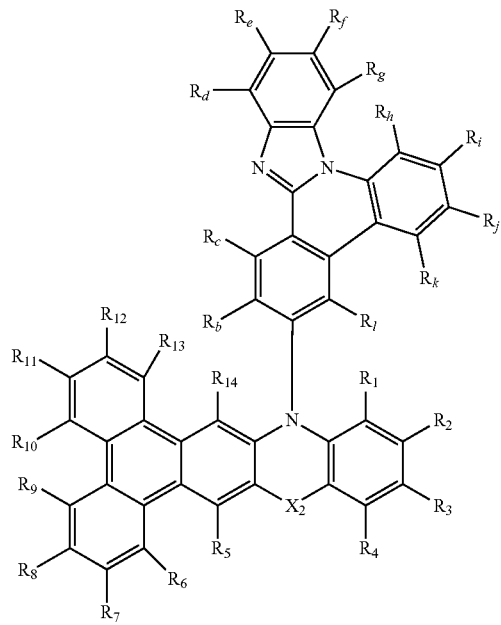
Formula 3-2
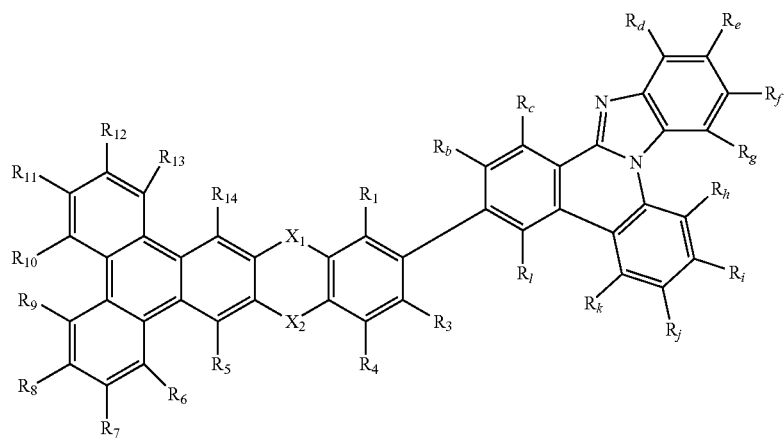
Formula 3-3
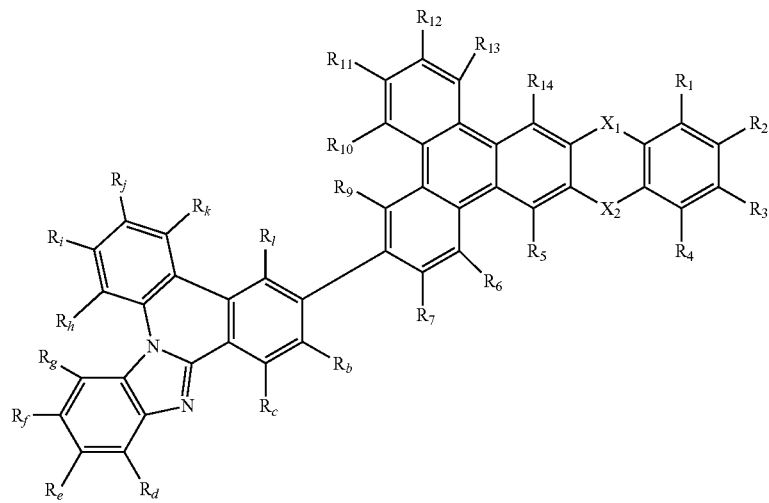

Formula 3-4
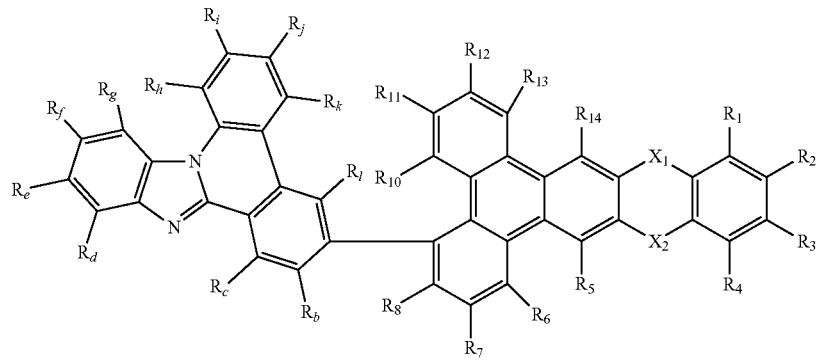
Formula 3-5
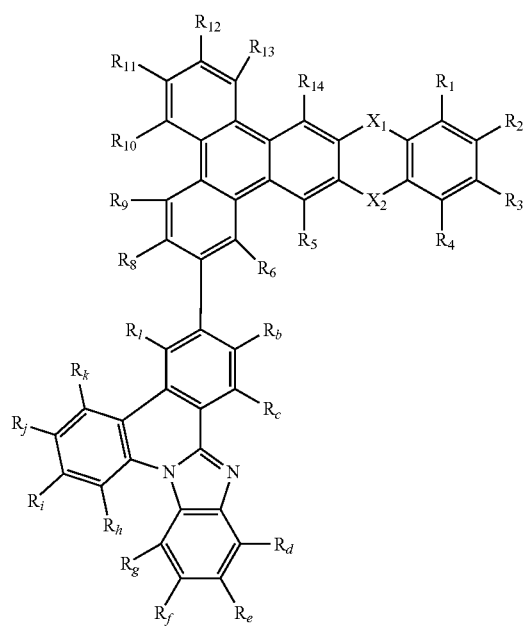
Formula 3-6
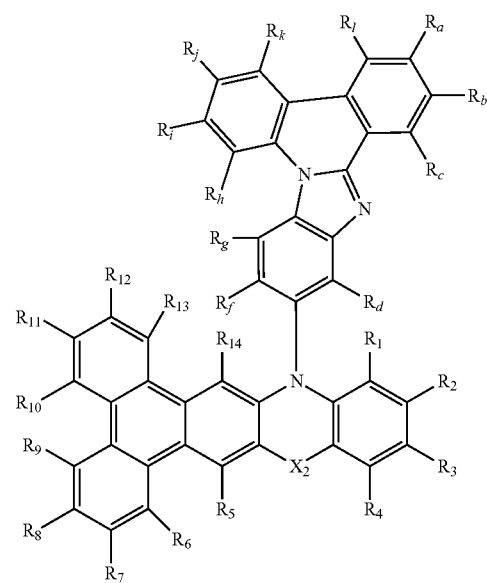
Formula 3-7
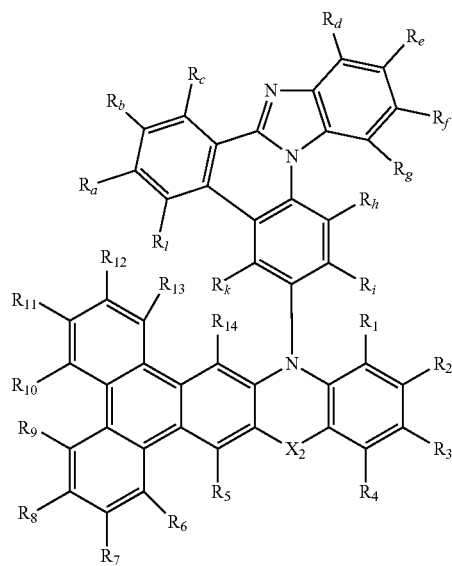

Formula 3-8
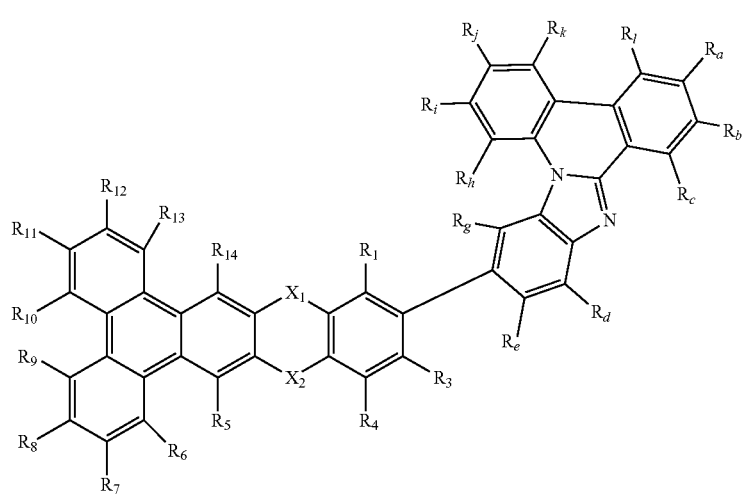
Formula 3-9
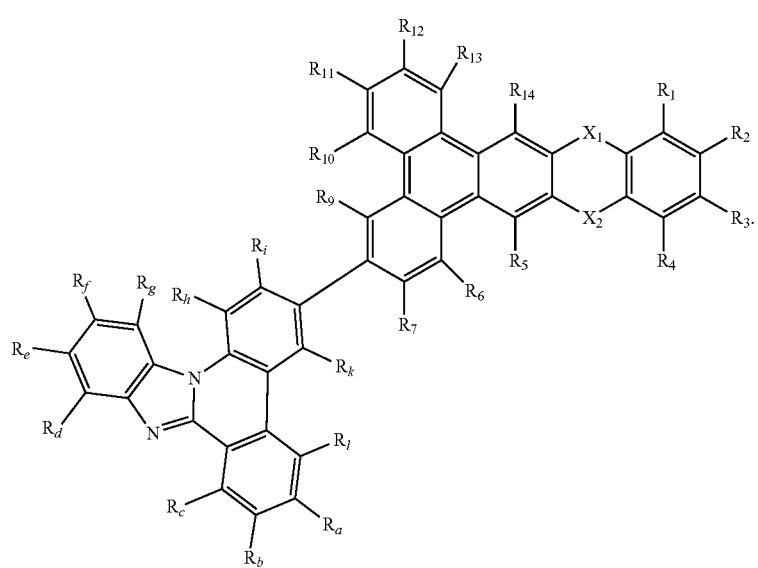
In Formula 3-1 to Formula 3-9, $X_1$, $X_2$, $R_1$ to $R_{15}$, and $R_a$ to $R_l$ may each independently be the same as defined in Formula 1 and Formula 2.
In an embodiment, the fused polycyclic compound represented by Formula 1 may be represented by any one among Formula 4-1 to Formula 4-3.
Formula 4-1
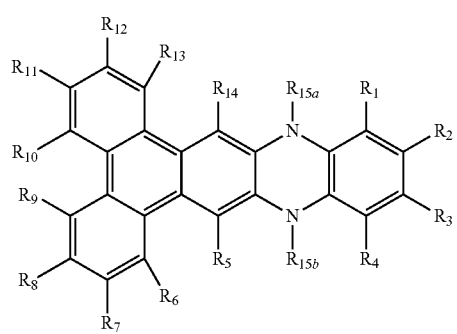
-continued
Formula 4-2
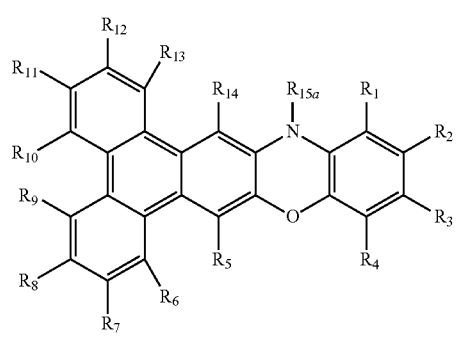

-continued

Formula 4-3

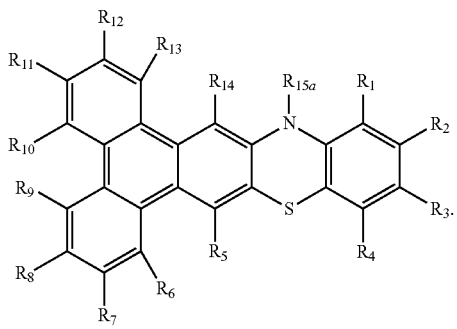

In Formula 4-1 to Formula 4-3, $R_{15a}$ and $R_{15b}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, a substituted or unsubstituted heteroaryl group of 2 to 60 ring-forming carbon atoms, or the substituent represented by Formula 2.

In Formula 4-1 to Formula 4-3, $R_1$ to $R_{14}$ may each independently be the same as defined in Formula 1.

In an embodiment, in Formula 1, $R_1$ to $R_{15}$ may each independently be a hydrogen atom, a deuterium atom, a halogen atom, a substituted or unsubstituted silyl group, a substituted or unsubstituted phenyl group, a substituted or unsubstituted carbazole group, a substituted or unsubstituted dibenzofuran group, or a substituted or unsubstituted dibenzothiophene group, or represented by Formula 2.

In an embodiment, in Formula 2, $R_a$ to $R_l$ may each independently be a hydrogen atom or a deuterium atom, or a position connected with Formula 1.

In an embodiment, a capping layer disposed on the second electrode may be further included, and the capping layer may have a refractive index of about 1.6 or more.

In an embodiment, the dopant may include a compound represented by Formula D:

Formula D

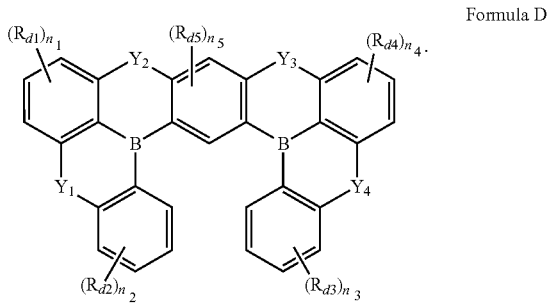

In Formula D, $Y_1$ to $Y_4$ may each independently be $NR_{d6}$, O or S, $R_{d1}$ to $R_{d6}$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, and/or combined with an adjacent group from each other to form a ring, "$n_1$" and "$n_4$" may each independently be an integer of 0 to 3, "$n_2$" and "$n_3$" may each independently be an integer of 0 to 4, and "$n_5$" may be an integer of 0 to 2.

BRIEF DESCRIPTION OF THE FIGURES

The accompanying drawings are included to provide a further understanding of the present disclosure, and are incorporated in and constitute a part of this specification. The drawings illustrate embodiments of the present disclosure and, together with the description, serve to explain principles of the present disclosure. In the drawings.

DETAILED DESCRIPTION

Figure 1:
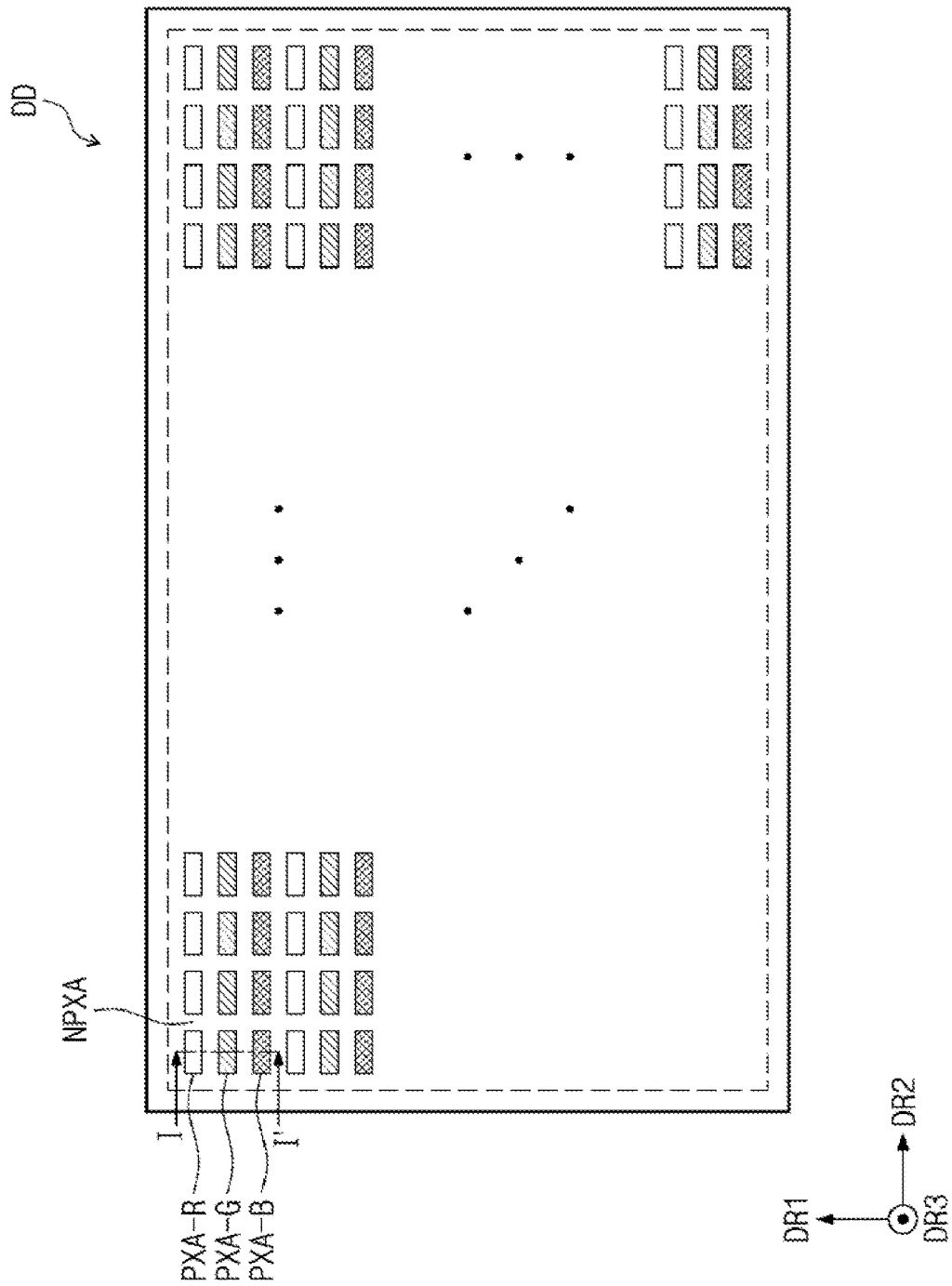
FIG. 1 is a plan view of a display apparatus according to an embodiment of the present disclosure.

The present disclosure may have various modifications and may be embodied in different forms, and embodiments will be explained in more detail with reference to the accompany drawings. The present disclosure may, however, be embodied in different forms and should not be construed as limited to the embodiments set forth herein. Rather, all modifications, equivalents, and substituents which are included in the spirit and technical scope of the present disclosure should be included in the present disclosure.

Like reference numerals refer to like elements throughout, and duplicative descriptions thereof may not be provided. In the drawings, the dimensions of structures may be exaggerated for clarity of illustration. It will be understood that, although the terms first, second, etc. may be utilized herein to describe one or more suitable elements, these elements should not be limited by these terms. These terms are only utilized to distinguish one element from another element. Thus, a first element could be termed a second element without departing from the teachings of the present disclosure. Similarly, a second element could be termed a first element. As used herein, singular forms such as "a," "an," and "the" are intended to include the plural forms as well, unless the context clearly indicates otherwise.

In the description, it will be further understood that the terms "includes," "including," "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

In the description, when a layer, a film, a region, a plate, etc. is referred to as being "on" or "above" another part, it can be "directly on" the other part, or intervening layers may also be present. In contrast, when a layer, a film, a region, a plate, etc. is referred to as being "under" or "below" another part, it can be "directly under" the other part, or intervening layers may also be present. When an element is referred to as being "directly on," or "directly under," another element, there are no intervening elements present. Also, when an element is referred to as being disposed "on" another element, it can be disposed under the other element.

As used herein, the terms "use," "using," and "used" may be considered synonymous with the terms "utilize," "utilizing," and "utilized," respectively. Expressions such as "at least one of," "one of," and "selected from," when preceding a list of elements, modify the entire list of elements and do not modify the individual elements of the list. The term "and/or" includes any and all combinations of one or more of the associated listed items. Further, the use of "may" when describing embodiments of the present disclosure refers to "one or more embodiments of the present disclosure".

In the description, the term "substituted or unsubstituted" corresponds to a state of being unsubstituted, or substituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine group, a phosphine oxide group, a phosphine sulfide group, an alkyl group, an alkenyl group, an alkynyl group, an alkoxy group, a hydrocarbon ring group, an aryl group, and a heterocyclic group. In some embodiments, each of the listed substituents may be further substituted or unsubstituted. For example, a biphenyl group may be interpreted as a named aryl group, or as a phenyl group substituted with a phenyl group.

In the description, the terms "forming a ring via the combination with an adjacent group" and "combined with an adjacent group to form a ring" may refer to forming a substituted or unsubstituted hydrocarbon ring, or a substituted or unsubstituted heterocycle via combination with an adjacent group. The hydrocarbon ring may be an aliphatic hydrocarbon ring or an aromatic hydrocarbon ring. The heterocycle may be an aliphatic heterocycle or an aromatic heterocycle. The hydrocarbon ring and the heterocycle may each independently be monocycles or polycycles. In some embodiments, the ring formed via combination with an adjacent group may be combined with (e.g., linked to) another ring to form a spiro structure.

In the description, the term "adjacent group" may refer to a substituent on the same atom or point, a substituent on an atom that is directly connected to the base atom or point, or a substituent sterically positioned (e.g., within intramolecular bonding distance) to the corresponding substituent. For example, in 1,2-dimethylbenzene, two methyl groups may be interpreted as "adjacent groups" to each other, and in 1,1-diethylcyclopentane, two ethyl groups may be interpreted as "adjacent groups" to each other. In some embodiments, in 4,5-dimethylphenanthrene, two methyl groups may be interpreted as "adjacent groups" to each other. In some embodiments, in 1,13-dimethylquinolino[3,2,1-de]acridine-5,9-dione, the two methyl groups at carbon positions 1 and 13 may be interpreted as "adjacent groups" to each other.

In the description, the halogen atom may be a fluorine atom, a chlorine atom, a bromine atom or an iodine atom.

In the description, the alkyl group may be a linear, branched or cyclic group. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the term "hydrocarbon ring group" refers to an optional functional group or substituent derived from an aliphatic hydrocarbon ring. The hydrocarbon ring group may be a saturated hydrocarbon ring group of 5 to 30 or 5 to 20 ring-forming carbon atoms.

In the description, the term "aryl group" refers to an optional functional group or substituent derived from an aromatic hydrocarbon ring. The aryl group may be a monocyclic aryl group or a polycyclic aryl group. The carbon number for forming rings in the aryl group may be 6 to 60, 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the description, the fluorenyl group may be substituted, and two substituents may be combined with each other to form a spiro structure. Examples of a substituted fluorenyl group are as follows, but embodiments of the present disclosure are not limited thereto.

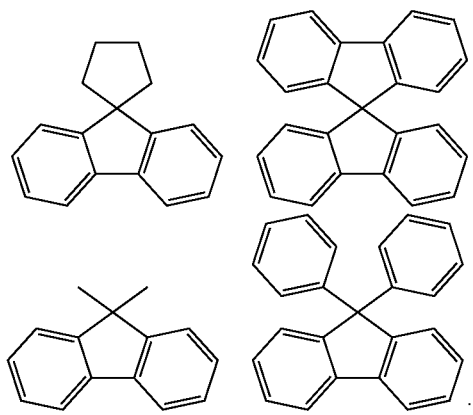

In the description, the term "heterocyclic group" refers to an optional functional group or substituent derived from a ring including one or more among boron (B), oxygen (O), nitrogen (N), phosphorus (P), silicon (Si), sulfur (S) and selenium (Se) as heteroatoms. The heterocyclic group may be an aliphatic heterocyclic group or an aromatic heterocyclic group. The aromatic heterocyclic group may be a heteroaryl group. The aliphatic heterocyclic group and the aromatic heterocyclic group may each independently be a monocycle or a polycycle.

In the description, the heterocyclic group may include one or more among B, O, N, P, Si and S as heteroatoms. When the heterocyclic group includes two or more heteroatoms, the two or more heteroatoms may be the same or different. The heterocyclic group may be a monocyclic heterocyclic group or a polycyclic heterocyclic group, and has the concept including a heteroaryl group. The carbon number for forming rings of the heteroaryl group may be 2 to 60, 2 to 30, 2 to 20, and 2 to 10.

In the description, the aliphatic heterocyclic group may include one or more among B, O, N, P, Si and S as heteroatoms. The number of ring-forming carbon atoms of the aliphatic heterocyclic group may be 2 to 60, 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include one or more among B, O, N, P, Si and S as heteroatoms. When the heteroaryl group includes two or more heteroatoms, two or more heteroatoms may be the same or different. The heteroaryl group may be a monocyclic heterocyclic group or a polycyclic heterocyclic group. The carbon number for forming rings of the heteroaryl group may be 2 to 60, 2 to 30, 2 to 20, or 2 to 10. Examples of the heteroaryl group may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc., without limitation.

In the description, the explanation of the aryl group may be applied to the arylene group, except that the arylene group is a divalent group. The explanation of the heteroaryl group may be applied to the heteroarylene group, except that the heteroarylene group is a divalent group.

In the description, the alkenyl group may be a linear chain or a branched chain alkenyl. The carbon number is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the description, the carbon number of the alkynyl group is not specifically limited, but may be 2 to 30, 2 to 20 or 2 to 10. Examples of the alkynyl group may include a vinyl group, a 2-butynyl group, a 2-pentynyl group, and/or a 1,3-pentadiynyl aryl group, without limitation.

In the description, the explanations of the alkyl group, alkenyl group, alkynyl group, aryl group, and heteroaryl group may be applied to the alkyl connecting group, alkenyl connecting group, aryl connecting group, and heteroaryl connecting group, respectively, except that these are divalent, trivalent or tetravalent groups.

In the description, the term "silyl group" includes an alkyl silyl group and an aryl silyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

In the description, the carbon number of a carbonyl group is not specifically limited, but the carbon number may be 1 to 40, 1 to 30, or 1 to 20. For example, the carbonyl group may have the structures below, but is not limited thereto.

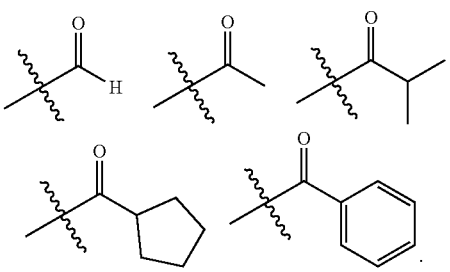

In the description, the carbon number of the sulfinyl group and sulfonyl group is not specifically limited, but may be 1 to 30. The term "sulfinyl group" may include an alkyl sulfinyl group and an aryl sulfinyl group. The term "sulfonyl group" may include an alkyl sulfonyl group and an aryl sulfonyl group.

In the description, the term "thiol group" may include an alkyl thio group and an aryl thio group. The term "thiol group" may refer to the above-defined alkyl group or aryl group combined with a sulfur atom. Examples of the thiol group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

In the description, the term "oxy group" may refer to the above-defined alkyl group or aryl group combined with an oxygen atom. The term "oxy group" may include an alkoxy group and an aryl oxy group. The alkoxy group may be a linear, branched or cyclic chain. The carbon number of the alkoxy group is not specifically limited but may be, for example, 1 to 20 or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc. However, embodiments of the present disclosure are not limited thereto.

In the description, the term "boron group" may refer to the above-defined alkyl group or aryl group combined with a boron atom. The term "boron group" includes an alkyl boron group and an aryl boron group. Examples of the boron group may include a trimethylboron group, a triethylboron group, a t-butyldimethylboron group, a triphenylboron group, a diphenylboron group, a phenylboron group, etc., without limitation.

In the description, the carbon number of the amine group is not specifically limited, but may be 1 to 30. The term "amine group" may include an alkyl amine group and an aryl amine group. Examples of the amine group may include a methylamine group, a dimethylamine group, a phenylamine group, a diphenylamine group, a naphthylamine group, a 9-methyl-anthracenylamine group, a triphenylamine group, etc., without limitation.

In the description, an alkyl group in the alkylthio group, alkylsulfoxy group, alkylaryl group, alkylamino group, alkylboron group, alkyl silyl group, and alkyl amine group may each independently be the same as the examples of the above-described alkyl group.

In the description, the aryl group in the aryloxy group, arylthio group, arylsulfoxy group, aryl amino group, arylboron group, and aryl silyl group may each be the same as the examples of the above-described aryl group.

In the description, the term "direct linkage" may refer to a single bond.

In the description, "⸺" and "⸺＊" refer to positions to be connected.

Hereinafter, embodiments of the present disclosure will be explained by referring to the drawings.

Figure 2:
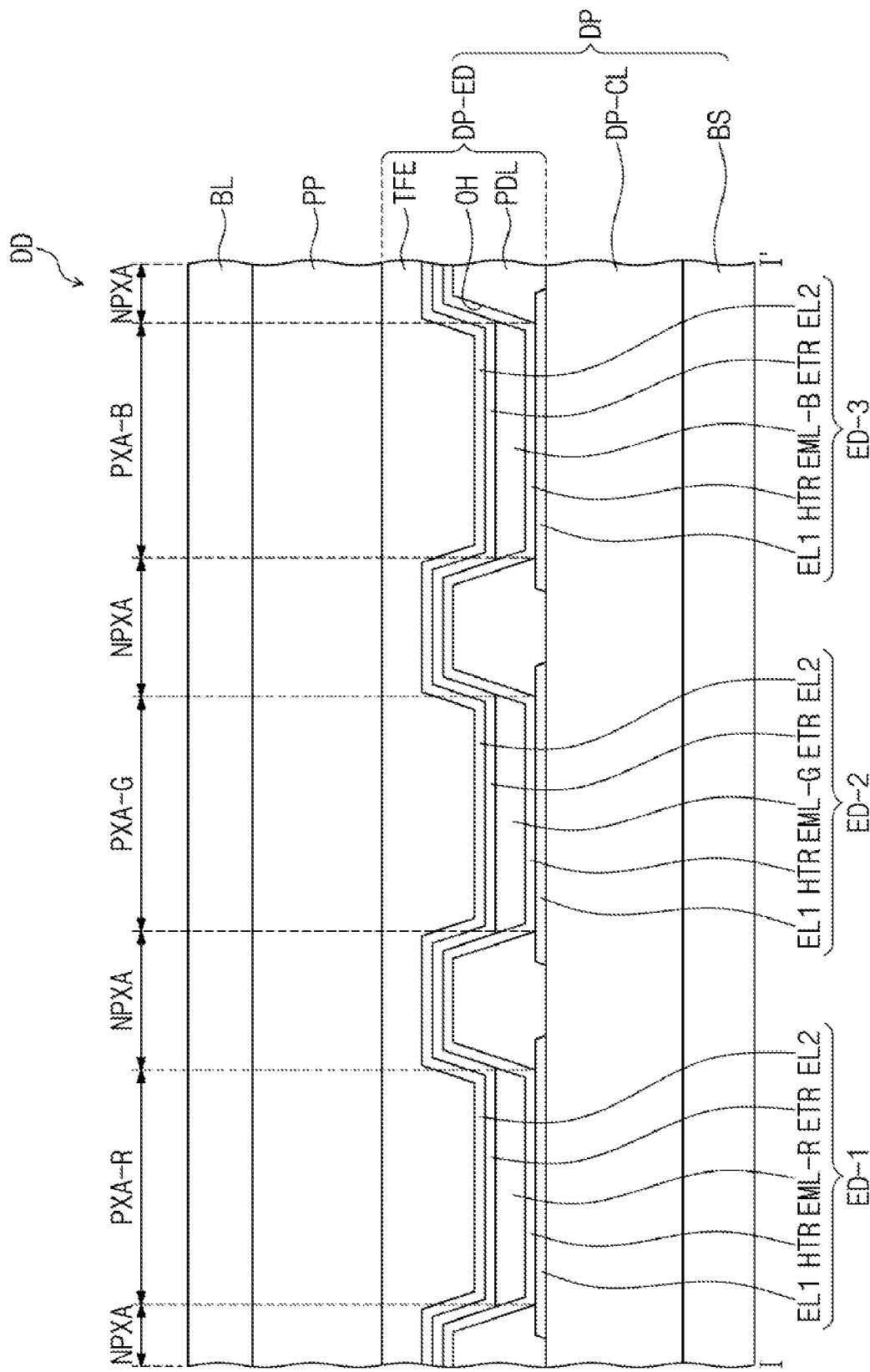
FIG. 2 is a cross-sectional view of a display apparatus according to an embodiment of the present disclosure.

FIG. 1 is a plan view showing an embodiment of a display apparatus DD. FIG. 2 is a cross-sectional view of a display apparatus DD of an embodiment. FIG. 2 is a cross-sectional view showing a part corresponding to line I-I'.

The display apparatus DD may include a display panel DP and an optical layer PP disposed on the display panel DP. The display panel DP includes light emitting devices ED-1, ED-2 and ED-3. The display apparatus DD may include multiple light emitting devices ED-1, ED-2 and ED-3. The optical layer PP may be disposed on the display panel DP and control reflected light by external light at the display panel DP. The optical layer PP may include, for example, a polarization layer or a color filter layer. In some embodiments, the optical layer PP may not be provided in the display apparatus DD of an embodiment.

On the optical layer PP, an upper base layer BL may be disposed. The upper base layer BL may be a member providing a base surface where the optical layer PP is disposed. The upper base layer BL may be a glass substrate, a metal substrate, a plastic substrate, etc. However, embodiments of the present disclosure are not limited thereto, and the upper base layer BL may be an inorganic layer, an organic layer or a composite material layer. In some embodiments, the upper base layer BL may not be provided in an embodiment.

The display apparatus DD according to an embodiment may further include a plugging layer. The plugging layer may be disposed between a display device layer DP-ED and an upper base layer BL. The plugging layer may be an organic layer. The plugging layer may include at least one among (i.e., at least one selected from) an acrylic resin, a silicon-based resin and an epoxy-based resin.

The display panel DP may include a base layer BS, a circuit layer DP-CL provided on the base layer BS and a display device layer DP-ED. The display device layer DP-ED may include a pixel definition layer PDL, light emitting devices ED-1, ED-2 and ED-3 disposed in the pixel definition layer PDL, and an encapsulating layer TFE disposed on the light emitting devices ED-1, ED-2 and ED-3.

The base layer BS may be a member providing a base surface where the display device layer DP-ED is disposed. The base layer BS may be a glass substrate, a metal substrate, a plastic substrate, etc. However, embodiments of the present disclosure are not limited thereto, and the base layer BS may be an inorganic layer, an organic layer or a composite material layer.

In an embodiment, the circuit layer DP-CL is disposed on the base layer BS, and the circuit layer DP-CL may include multiple transistors. Each of the transistors may include a control (e.g., gate) electrode, an input electrode, and an output electrode. For example, the circuit layer DP-CL may include switching transistors and driving transistors for driving the light emitting devices ED-1, ED-2 and ED-3 of the display device layer DP-ED.

Each of the light emitting devices ED-1, ED-2 and ED-3 may have the structures of light emitting devices ED of embodiments according to FIG. 3 to FIG. 6, which will be explained later. Each of the light emitting devices ED-1, ED-2 and ED-3 may include a first electrode EL1, a hole transport region HTR, emission layers EML-R, EML-G and EML-B, an electron transport region ETR, and a second electrode EL2.

In FIG. 2, shown is an embodiment where the emission layers EML-R, EML-G and EML-B of light emitting devices ED-1, ED-2 and ED-3 are disposed in opening portions OH defined in a pixel definition layer PDL, and a hole transport region HTR, an electron transport region ETR and a second electrode EL2 are provided as common layers in all light emitting devices ED-1, ED-2 and ED-3. However, embodiments of the present disclosure are not limited thereto. Different from FIG. 2, in an embodiment, the hole transport region HTR and the electron transport region ETR may be patterned and provided in the opening portions OH defined in the pixel definition layer PDL. For example, in an embodiment, the hole transport region HTR, the emission layers EML-R, EML-G and EML-B, and the electron transport region ETR of the light emitting devices ED-1, ED-2 and ED-3 may be patterned and provided by an ink jet printing method.

An encapsulating layer TFE may cover the light emitting devices ED-1, ED-2 and ED-3. The encapsulating layer TFE may encapsulate the display device layer DP-ED. The encapsulating layer TFE may be a thin film encapsulating layer. The encapsulating layer TFE may be one layer or a stacked layer of multiple layers. The encapsulating layer TFE includes at least one insulating layer. The encapsulating layer TFE according to an embodiment may include at least one inorganic layer (hereinafter, encapsulating inorganic layer). In some embodiments, the encapsulating layer TFE according to an embodiment may include at least one organic layer (hereinafter, encapsulating organic layer) and at least one encapsulating inorganic layer.

The encapsulating inorganic layer protects the display device layer DP-ED from moisture/oxygen, and the encapsulating organic layer protects the display device layer DP-ED from foreign materials (such as dust particles). The encapsulating inorganic layer may include silicon nitride, silicon oxy nitride, silicon oxide, titanium oxide, or aluminum oxide, without specific limitation. The encapsulating organic layer may include an acrylic compound, an epoxy-based compound, etc. The encapsulating organic layer may include a photopolymerizable organic material, without specific limitation.

The encapsulating layer TFE may be disposed on the second electrode EL2 and may be disposed while filling the opening portion OH.

Referring to FIG. 1 and FIG. 2, the display apparatus DD may include a non-luminous area NPXA and luminous areas PXA-R, PXA-G and PXA-B. The luminous areas PXA-R, PXA-G and PXA-B may be areas emitting light produced from the light emitting devices ED-1, ED-2 and ED-3, respectively. The luminous areas PXA-R, PXA-G and PXA-B may be separated from each other on a plane.

The luminous areas PXA-R, PXA-G and PXA-B may be areas separated by the pixel definition layer PDL. The non-luminous areas NPXA may be areas between neighboring luminous areas PXA-R, PXA-G and PXA-B and may be areas corresponding to the pixel definition layer PDL. Each of the luminous areas PXA-R, PXA-G and PXA-B may correspond to each pixel. The pixel definition layer PDL may divide the light emitting devices ED-1, ED-2 and ED-3. The emission layers EML-R, EML-G and EML-B of the light emitting devices ED-1, ED-2 and ED-3 may be disposed and divided in the opening portions OH defined in the pixel definition layer PDL.

The luminous areas PXA-R, PXA-G and PXA-B may be divided into multiple groups according to the color of light produced from the light emitting devices ED-1, ED-2 and ED-3. In the display apparatus DD of an embodiment, shown in FIG. 1 and FIG. 2, three luminous areas PXA-R, PXA-G and PXA-B emitting red light, green light and blue light are illustrated as an embodiment. For example, the display apparatus DD of an embodiment may include a red luminous area PXA-R, a green luminous area PXA-G and a blue luminous area PXA-B, which are separated from each other.

In the display apparatus DD according to an embodiment, multiple light emitting devices ED-1, ED-2 and ED-3 may be to emit light having different wavelength regions. For example, in an embodiment, the display apparatus DD may include a first light emitting device ED-1 to emit red light, a second light emitting device ED-2 to emit green light, and a third light emitting device ED-3 to emit blue light. For example, the red luminous area PXA-R, the green luminous area PXA-G, and the blue luminous area PXA-B of the display apparatus DD may each respectively correspond to the first light emitting device ED-1, the second light emitting device ED-2, and the third light emitting device ED-3.

However, embodiments of the present disclosure are not limited thereto, and the first to third light emitting devices ED-1, ED-2 and ED-3 may be to emit light in the same wavelength region, or at least one thereof may be to emit light in a different wavelength region. For example, all of the first to third light emitting devices ED-1, ED-2 and ED-3 may be to emit blue light.

The luminous areas PXA-R, PXA-G and PXA-B in the display apparatus DD according to an embodiment may be arranged in a stripe shape. Referring to FIG. 1, multiple red luminous areas PXA-R may be arranged with each other along a second directional axis DR2, multiple green luminous areas PXA-G may be arranged with each other along the second directional axis DR2, and multiple blue luminous areas PXA-B may be arranged with each other along the second directional axis DR2. In some embodiments, a red luminous area PXA-R, a green luminous area PXA-G and a blue luminous area PXA-B may be arranged with each other (e.g., by turns) along a first directional axis DR1 perpendicular to the second directional axis DR2.

In FIG. 1 and FIG. 2, the areas (e.g., sizes) of the luminous areas PXA-R, PXA-G and PXA-B are shown as being similar, but embodiments of the present disclosure are not limited thereto. The areas of the luminous areas PXA-R, PXA-G and PXA-B may be different from each other according to the wavelength region of light emitted. The areas of the luminous areas PXA-R, PXA-G and PXA-B may refer to areas on a plane defined by the first directional axis DR1 and the second directional axis DR2 (e.g., planar areas).

In some embodiments, the arrangement type or pattern of the luminous areas PXA-R, PXA-G and PXA-B is not limited to the configuration shown in FIG. 1, and the arrangement order of the red luminous areas PXA-R, the green luminous areas PXA-G and the blue luminous areas PXA-B may be provided in various suitable combinations according to the properties of display quality required for the display apparatus DD. For example, the arrangement pattern of the luminous areas PXA-R, PXA-G and PXA-B may be a PENTILE® arrangement pattern, or a diamond arrangement pattern.

In some embodiments, the areas of the luminous areas PXA-R, PXA-G and PXA-B may be different from each other. For example, in an embodiment, the area of the green luminous area PXA-G may be smaller than the area of the blue luminous area PXA-B, but embodiments of the present disclosure are not limited thereto.

Hereinafter, FIG. 3 to FIG. 6 are cross-sectional views schematically showing light emitting devices according to embodiments. The light emitting device ED according to an embodiment may include a first electrode EL1, a hole transport region HTR, an emission layer EML, an electron transport region ETR, and a second electrode EL2 stacked in order.

Figure 3:
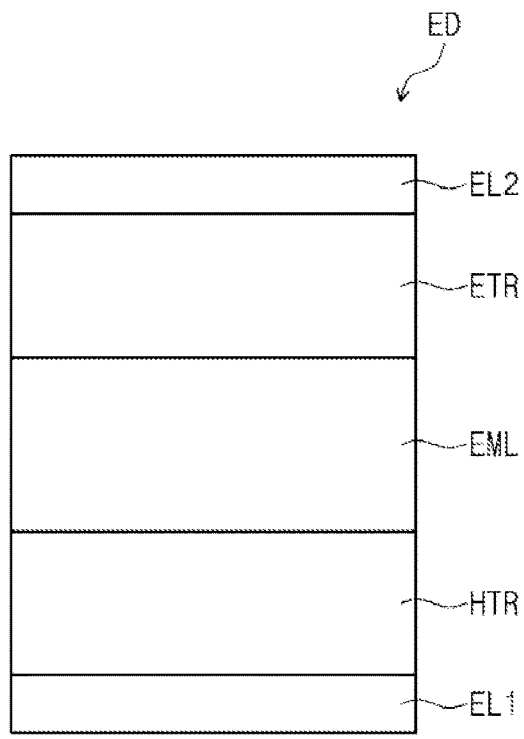
FIG. 3 is a cross-sectional view schematically showing a light emitting device according to an embodiment of the present disclosure.
Figure 4:
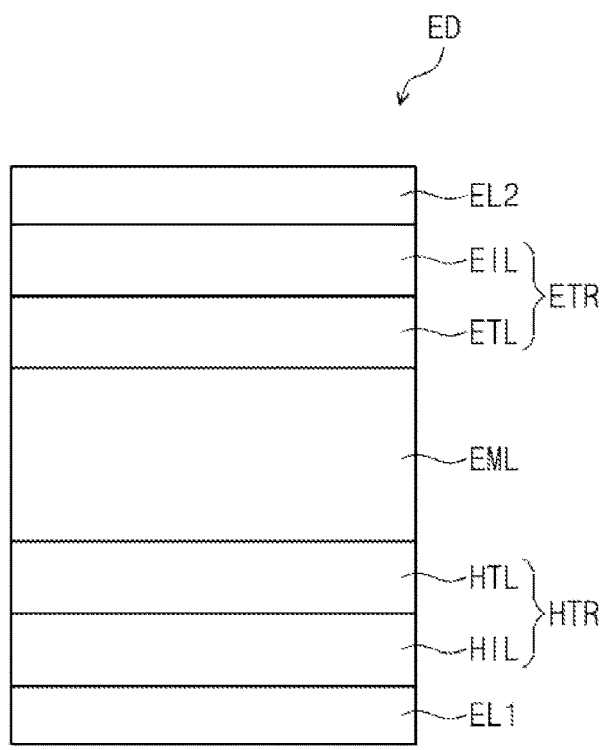
FIG. 4 is a cross-sectional view schematically showing a light emitting device according to an embodiment of the present disclosure.
Figure 5:
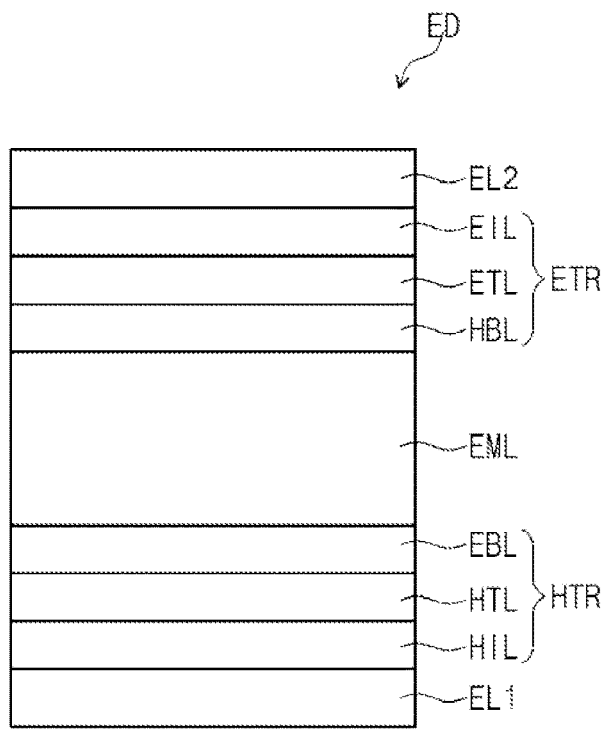
FIG. 5 is a cross-sectional view schematically showing a light emitting device according to an embodiment of the present disclosure.
Figure 6:
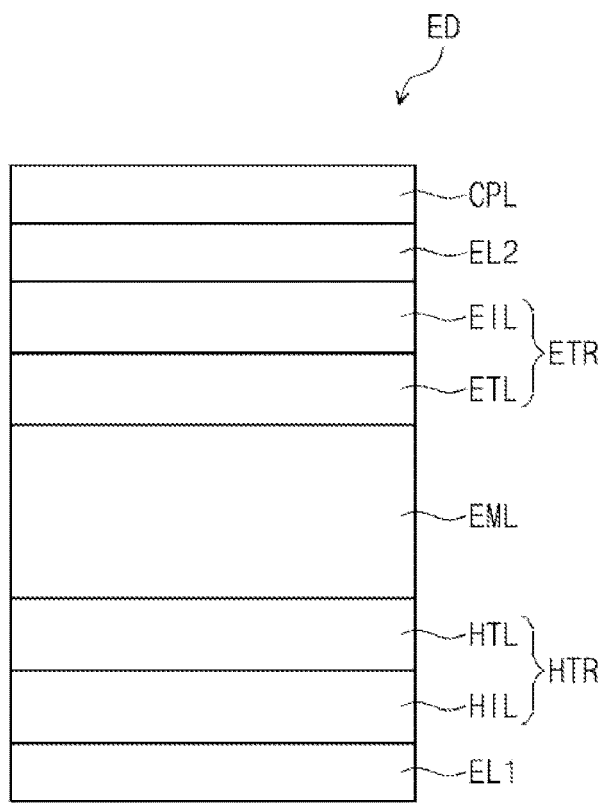
FIG. 6 is a cross-sectional view schematically showing a light emitting device according to an embodiment of the present disclosure.

Compared with FIG. 3, FIG. 4 shows the cross-sectional view of a light emitting device ED of an embodiment, wherein a hole transport region HTR includes a hole injection layer HIL and a hole transport layer HTL, and an electron transport region ETR includes an electron injection layer EIL and an electron transport layer ETL. Compared with FIG. 3, FIG. 5 shows the cross-sectional view of a light emitting device ED of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared with FIG. 4, FIG. 6 shows the cross-sectional view of a light emitting device ED of an embodiment, including a capping layer CPL disposed on the second electrode EL2.

The first electrode EL1 has conductivity. The first electrode EL1 may be formed of a metal material, a metal alloy and/or a conductive compound. The first electrode EL1 may be an anode or a cathode. However, embodiments of the present disclosure are not limited thereto. In some embodiments, the first electrode EL1 may be a pixel electrode. The first electrode EL1 may be a transmissive electrode, a transflective electrode, or a reflective electrode. When the first electrode EL1 is a transmissive electrode, the first electrode EL1 may include a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), tungsten (W), indium (In), zinc (Zn), tin (Sn), one or more compounds thereof, or one or more mixtures thereof (for example, a mixture of Ag and Mg). In some embodiments, the first electrode EL1 may have a structure including multiple layers, including a reflective layer or a transflective layer formed utilizing the above materials, and a transmissive conductive layer formed utilizing ITO, IZO, ZnO, or ITZO. For example, the first electrode EL1 may include a three-layer structure of ITO/Ag/ITO. However, embodiments of the present disclosure are not limited thereto. The first electrode EL1 may include the above-described metal materials, combinations of two or more metal materials selected from the above-described metal materials, or oxides of the above-described metal materials. The thickness of the first electrode EL1 may be about 700 Å to about 10,000 Å. For example, the thickness of the first electrode EL1 may be about 1,000 Å to about 3,000 Å.

The hole transport region HTR is provided on the first electrode EL1. The hole transport region HTR may include at least one of a hole injection layer HIL, a hole transport layer HTL, a buffer layer, an emission auxiliary layer or an electron blocking layer EBL. The thickness of the hole transport region HTR may be about 50 Å to about 15,000 Å.

The hole transport region HTR may have a single layer formed utilizing a single material, a single layer formed utilizing multiple different materials, or a multilayer structure including multiple layers formed utilizing multiple different materials.

For example, the hole transport region HTR may have the structure of a single layer of a hole injection layer HIL or a hole transport layer HTL, or may have a structure of a single layer formed utilizing a hole injection material and a hole transport material. In some embodiments, the hole transport region HTR may have a structure of a single layer formed utilizing multiple different materials, or a structure stacked from the first electrode EL1 of hole injection layer HIL/hole transport layer HTL, hole injection layer HIL/hole transport layer HTL/buffer layer, hole injection layer HIL/buffer layer, hole transport layer HTL/buffer layer, or hole injection layer HIL/hole transport layer HTL/electron blocking layer EBL, without limitation.

The hole transport region HTR may be formed utilizing one or more suitable methods (such as a vacuum deposition method, a spin coating method, a cast method, a Langmuir-Blodgett (LB) method, an inkjet printing method, a laser printing method, and/or a laser induced thermal imaging (LITI) method).

The hole transport region HTR may include a compound represented by Formula H-1:

Formula H-1

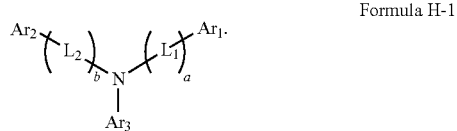

In Formula H-1, $L_1$ and $L_2$ may each independently be a direct linkage, a substituted or unsubstituted arylene group of 6 to 30 ring-forming carbon atoms, or a substituted or unsubstituted heteroarylene group of 2 to 30 ring-forming carbon atoms. "a" and "b" may each independently be an integer of 0 to 10. In some embodiments, when "a" or "b" is an integer of 2 or more, multiple $L_1$ and $L_2$ may each independently be a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. In some embodiments, in Formula H-1, $Ar_3$ may be a substituted or unsubstituted aryl group of 6 to 30 ring-forming carbon atoms.

The compound represented by Formula H-1 may be a monoamine compound. In some embodiments, the compound represented by Formula H-1 may be a diamine compound in which at least one among $Ar_1$ to $Ar_3$ includes an amine group as a substituent. In some embodiments, the compound represented by Formula H-1 may be a carbazole-based compound in which at least one among $Ar_1$ to $Ar_3$ includes a substituted or unsubstituted carbazole group, or a fluorene-based compound in which at least one among $Ar_1$ to $Ar_3$ includes a substituted or unsubstituted fluorene group.

The compound represented by Formula H-1 may be represented by any one among the compounds in Compound Group H. However, the compounds shown in Compound Group H are only illustrations, and the compound represented by Formula H-1 is not limited to the compounds represented in Compound Group H:

Compound Group H

H-1-1

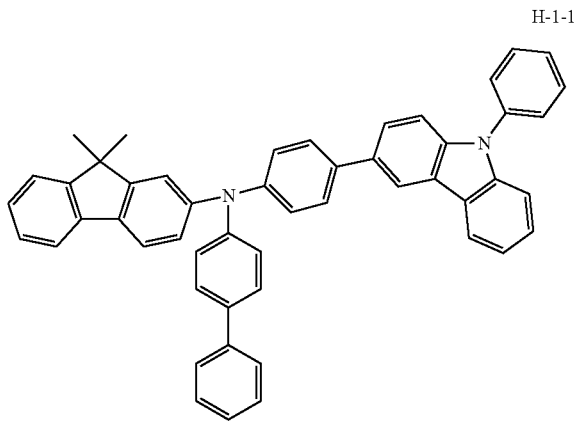

H-1-2

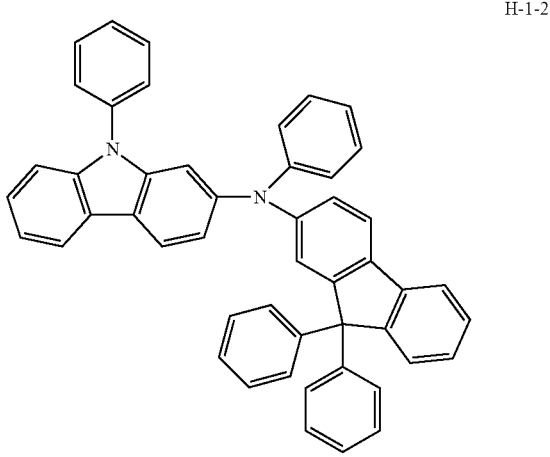

H-1-3
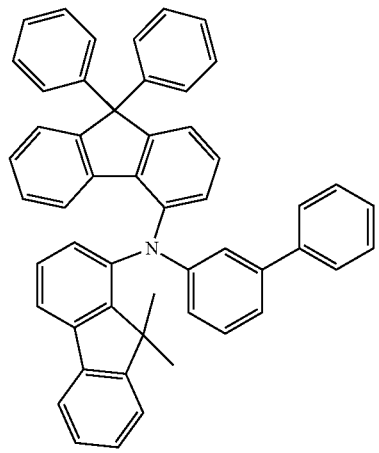
H-1-4
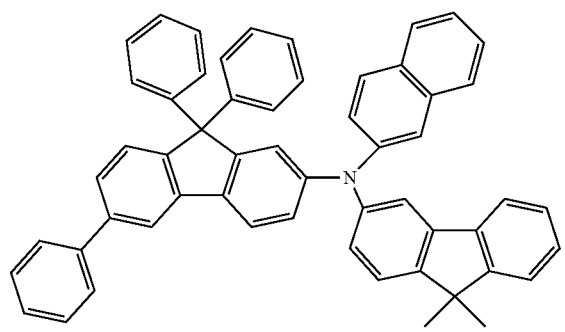
H-1-5
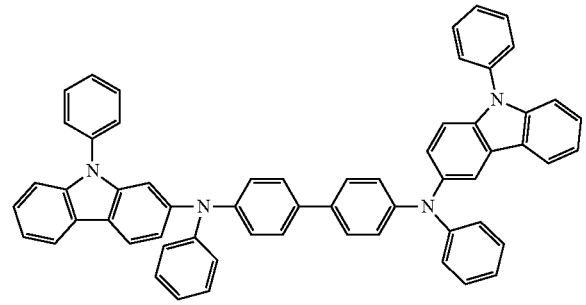
H-1-6
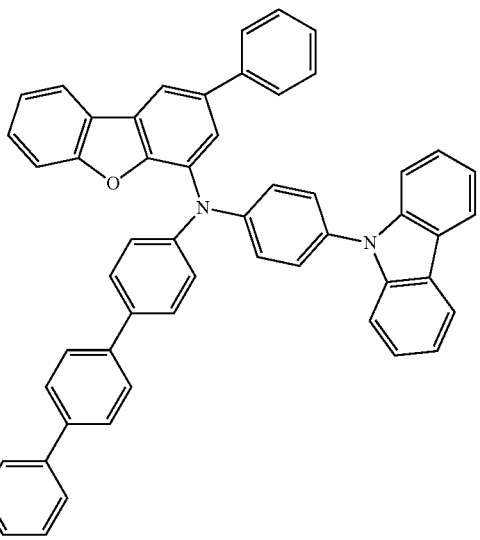
H-1-7
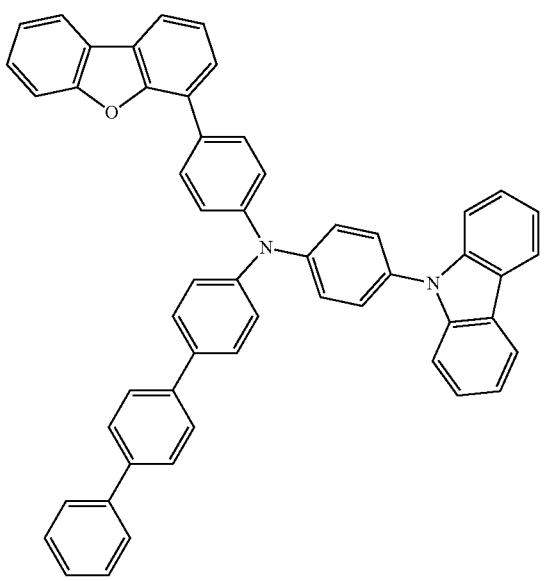
H-1-8
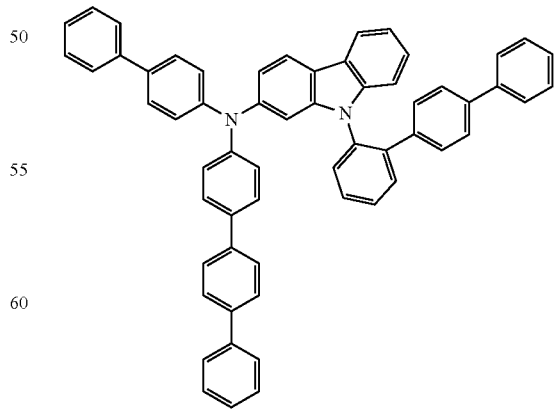

H-1-9
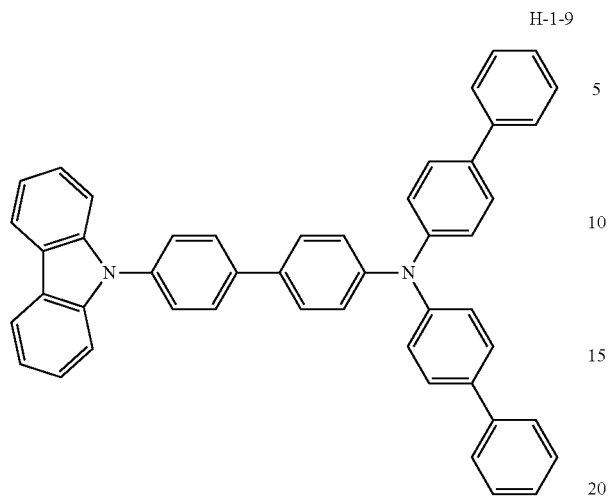
H-1-12
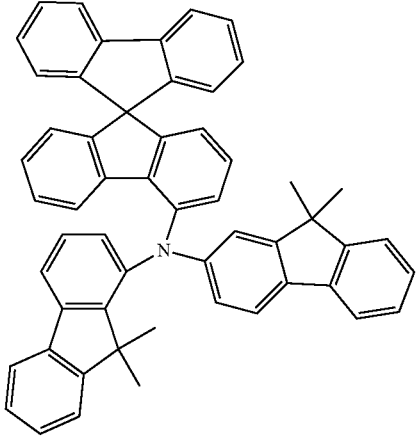
H-1-13
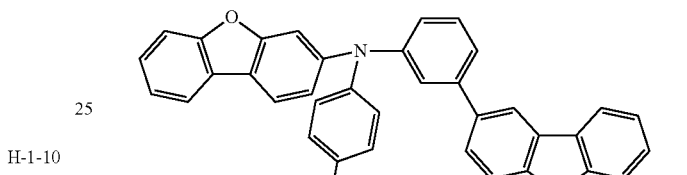
H-1-10
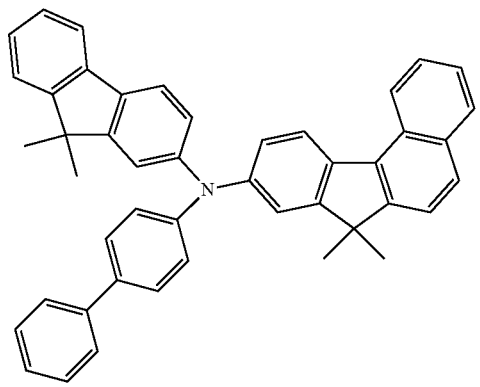
H-1-14
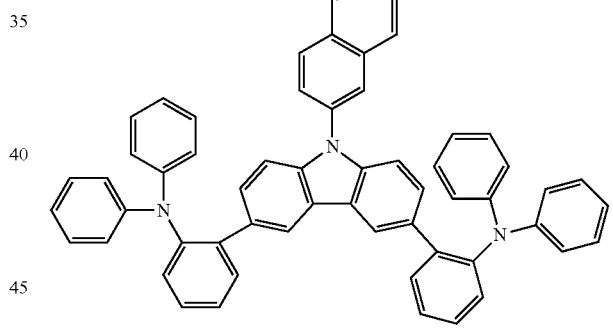
H-1-11
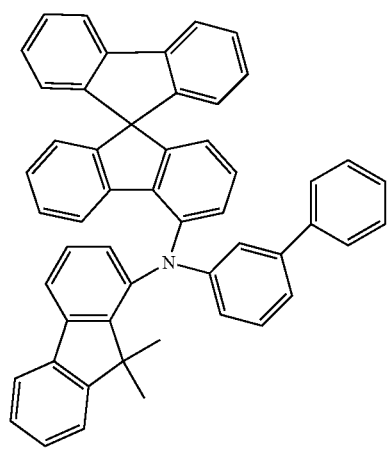
H-1-15
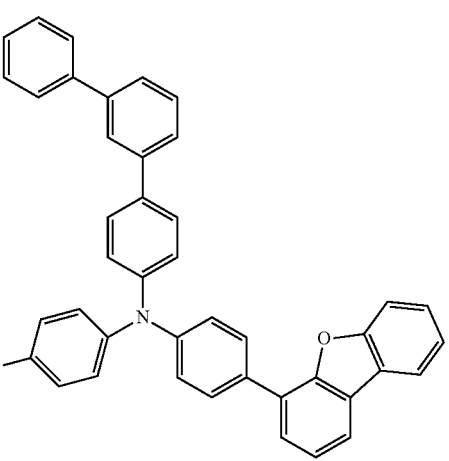

H-1-16

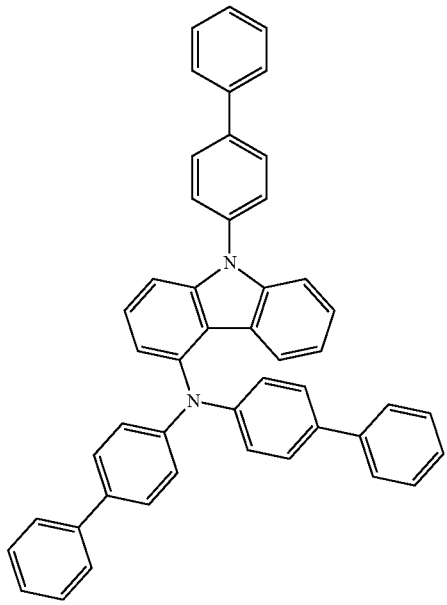

H-1-17

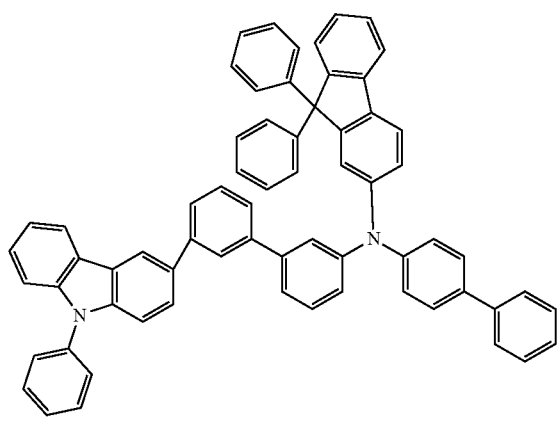

H-1-18

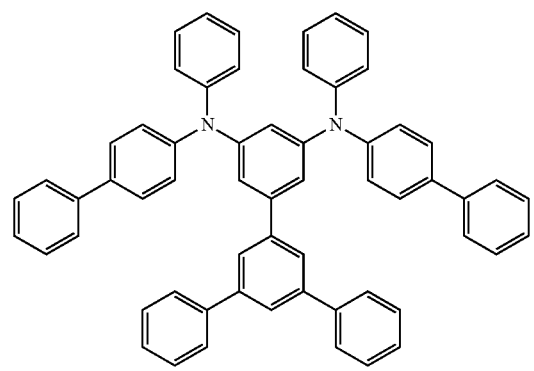

H-1-19

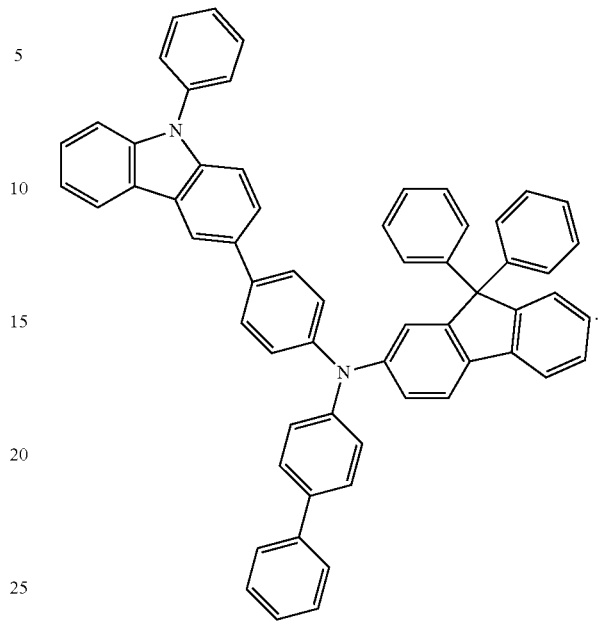

The hole transport region HTR may include a phthalocyanine compound (such as copper phthalocyanine), $N^1,N^{1'}$-([1,1'-biphenyl]-4,4'-diyl)bis($N^1$-phenyl-$N^4,N^4$-di-m-tolyl-benzene-1,4-diamine) (DNTPD), 4,4',4"-[tris(3-methylphenyl)phenylamino]triphenylamine (m-MTDATA), 4,4',4"-tris(N,N-diphenylamino)triphenylamine (TDATA), 4,4',4"-tris[N(2-naphthyl)-N-phenylamino]-triphenylamine (2-TNATA), poly(3,4-ethylene dioxythiophene)/poly(4-styrene sulfonate) (PEDOT/PSS), polyaniline/dodecylbenzene sulfonic acid (PANI/DBSA), polyaniline/camphor sulfonic acid (PANI/CSA), polyaniline/poly(4-styrene sulfonate) (PANI/PSS), N,N'-di(1-naphthalene-1-yl)-N,N'-diphenyl-benzidine (NPB), triphenylamine-containing polyether ketone (TPAPEK), 4-isopropyl-4'-methyldiphenyliodonium [tetrakis(pentafluorophenyl)borate], and dipyrazino[2,3-f:2',3'-h] quinoxaline-2,3,6,7,10,11-hexacarbonitrile (HAT-CN).

The hole transport region HTR may include carbazole derivatives (such as N-phenyl carbazole and/or polyvinyl carbazole), fluorene-based derivatives, N,N'-bis(3-methylphenyl)-N,N'-diphenyl-[1,1'-biphenyl]-4,4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), etc.

In some embodiments, the hole transport region HTR may include 9-(4-tert-butylphenyl)-3,6-bis(triphenylsilyl)-9H-carbazole (CzSi), 9-phenyl-9H-3,9'-bicarbazole (CCP), or 1,3-(bis(1,8-dimethyl-9H-carbazol-9-yl)benzene (mDCP).

The hole transport region HTR may include the compounds of the hole transport region in at least one among the hole injection layer HIL, hole transport layer HTL, and electron blocking layer EBL.

The thickness of the hole transport region HTR may be about 100 Å to about 10,000 Å, for example, about 100 Å to about 5,000 Å. When the hole transport region HTR includes a hole injection layer HIL, the thickness of the hole injection region HIL may be, for example, about 30 Å to about 1,000 Å. In case where the hole transport region HTR includes a hole transport layer HTL, the thickness of the hole transport layer HTL may be about 30 Å to about 1,000 Å. For example, in case where the hole transport region HTR includes an electron blocking layer, the thickness of the electron blocking layer EBL may be from about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material to increase conductivity in addition to the above-described materials. The charge generating material may be dispersed substantially uniformly or non-uniformly in the hole transport region HTR. The charge generating material may be, for example, a p-dopant. The p-dopant may include at least one of metal halide compounds, quinone derivatives, metal oxides, or cyano group-containing compounds, without limitation. For example, the p-dopant may include metal halide compounds (such as CuI and/or RbI), quinone derivatives (such as tetracyanoquinodimethane (TCNQ) and/or 2,3,5,6-tetrafluoro-7,7',8,8-tetracyanoquinodimethane (F4-TCNQ)), metal oxides (such as tungsten oxide and/or molybdenum oxide), cyano group-containing compounds (such as dipyrazino[2,3-f: 2',3'-h]quinoxaline-2,3,6,7,10,11-hexacarbonitrile (HATCN) and/or 4-[[2,3-bis[cyano-(4-cyano-2,3,5,6-tetrafluorophenyl)methylidene]cyclopropylidene]-cyanomethyl]-2,3,5,6-tetrafluorobenzonitrile), etc., without limitation.

As described above, the hole transport region HTR may further include at least one among a buffer layer and an electron blocking layer EBL in addition to the hole injection layer HIL and the hole transport layer HTL. The buffer layer may compensate for a resonance distance of the wavelength of light emitted from an emission layer EML and may thereby increase the light emitting efficiency of the device. Materials that may be included in the hole transport region HTR may be utilized in the buffer layer. The electron blocking layer EBL may block or reduce injection of electrons from an electron transport region ETR to a hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed utilizing a single material, a single layer formed utilizing multiple different materials, or a multilayer structure having multiple layers formed utilizing multiple different materials.

In the light emitting device ED according to an embodiment, the emission layer EML may include a fused polycyclic compound of an embodiment.

The fused polycyclic compound of an embodiment is a compound in which a fused polycyclic substituent including an imidazole moiety is substituted on a skeleton structure of triphenylene fused via a heteroatom (e.g., via two heteroatoms) to an additional ring. The fused polycyclic compound of an embodiment may be a compound in which a substituent including an imidazole moiety is directly bonded to the triphenylene fused skeleton.

The fused polycyclic compound of an embodiment is represented by Formula 1.

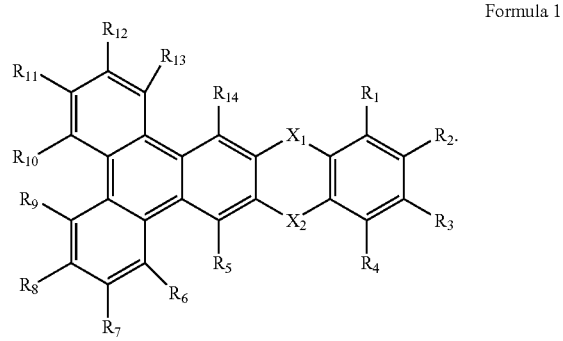

Formula 1

In Formula 1, $X_1$ and $X_2$ may each independently be $NR_{15}$, O or S. The fused polycyclic compound represented by Formula 1 may be a compound having an additional fused structure through $X_1$ and $X_2$, e.g., an additional connecting group (such as an amine group, an oxy group, a thio group and/or a carbonyl group).

At least one among $X_1$ and $X_2$ may be $NR_{15}$. $X_1$ and $X_2$ may be the same or different. In an embodiment, both (e.g., simultaneously) $X_1$ and $X_2$ may be $NR_{15}$. In some embodiments, any one among $X_1$ and $X_2$ may be $NR_{15}$, and the remainder may be O or S.

In Formula 1, $R_1$ to $R_{15}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms. For example, $R_1$ to $R_{15}$ may each independently be a hydrogen atom, a deuterium atom, a halogen atom, a substituted or unsubstituted silyl group, a substituted or unsubstituted phenyl group, a substituted or unsubstituted carbazole group, a substituted or unsubstituted dibenzofuran group, or a substituted or unsubstituted dibenzothiophene group. In Formula 1, one or more of $R_1$ to $R_{15}$ may be combined with an adjacent group to form a ring.

At least one among $R_1$ to $R_{15}$ is a substituent represented by Formula 2. In the fused polycyclic compound of an embodiment, represented by Formula 1, any one among $R_1$ to $R_{15}$ may be the substituent represented by Formula 2. For example, the fused polycyclic compound represented by Formula 1 may include one substituent represented by Formula 2:

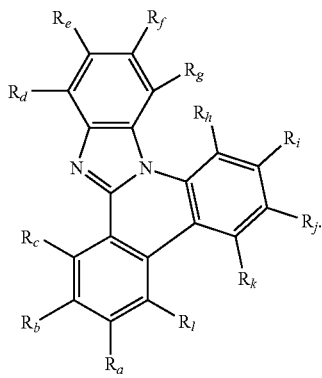

Formula 2

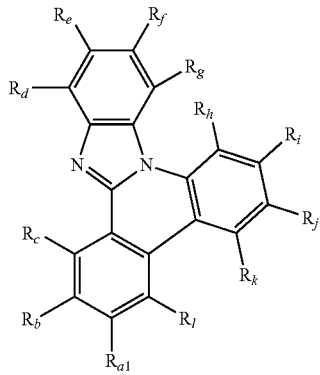

Formula 2-1

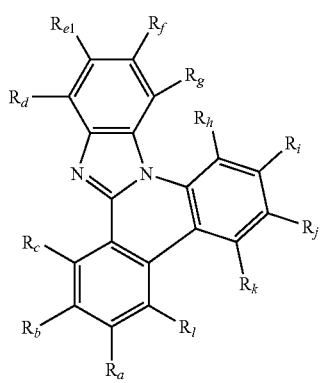

Formula 2-2

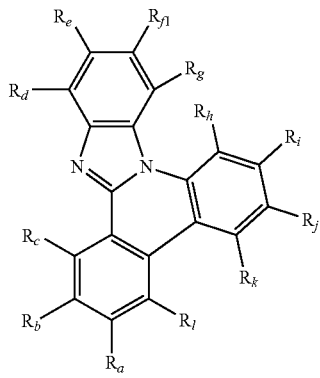

Formula 2-3

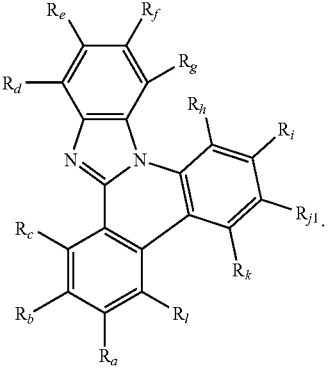

Formula 2-4

In Formula 2, $R_a$ to $R_l$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms. For example, $R_a$ to $R_l$ may each independently be a hydrogen atom or a deuterium atom. In Formula 2, one or more of $R_a$ to $R_l$ may be combined with an adjacent group to form a ring.

Any one among $R_a$ to $R_l$ may be a position connected with Formula 1. For example, Formula 2 may be connected, through any one position among $R_a$ to $R_l$, with a corresponding position among $R_1$ to $R_{15}$ of Formula 1. For example, any one among $R_a$ to $R_l$ may have a fused polycyclic skeleton structure represented by Formula 1.

The fused polycyclic compound of an embodiment includes a structure represented by Formula 1. The fused polycyclic compound of an embodiment has a skeleton structure in which a triphenylene moiety is fused to an additional structure (e.g., additional ring) via an additional connecting group (such as an amine group (NR), an oxy group (O), a thio group (S) and/or a carbonyl group (CO)), and further includes a fused polycyclic substituent including an imidazole moiety. The fused polycyclic compound of an embodiment includes an imidazole moiety substituent substituted on the fused triphenylene skeleton, and if included in an emission layer, the electron concentration in the emission layer may be suitably controlled. Accordingly, the formation of excitons in the emission layer may be improved, and when applied to a light emitting device, the efficiency and/or life span of the light emitting device may be improved.

In Formula 1, the substituent represented by Formula 2 may be represented by any one among Formula 2-1 to Formula 2-4:

Each of Formula 2-1 to Formula 2-4 represents an embodiment of Formula 2 in which the position connected with Formula 1 is specified.

In Formula 2-1, $R_{a1}$ is a position connected with Formula 1. In Formula 2-2, $R_{e1}$ is a position connected with Formula 1. In Formula 2-3, $R_{f1}$ is a position connected with Formula 1. In Formula 2-4, $R_{j1}$ is a position connected with Formula 1. In the fused polycyclic compound of an embodiment, through the positions of $R_{a1}$, $R_{e1}$, $R_{f1}$, or $R_{j1}$, Formula 2 may be connected with corresponding positions among positions represented by $R_1$ to $R_{15}$ of Formula 1 (e.g., as shown in Formulae 2-1 to 2-4, respectively). In Formula 2-1 to Formula 2-4, $R_{a1}$, $R_{e1}$, $R_{f1}$, and $R_{j1}$ may each independently be the fused polycyclic skeleton structure represented by Formula 1.

In some embodiments, in Formula 2-1 to Formula 2-4, $R_a$ to $R_l$ may each independently be the same as defined in Formula 2.

In some embodiments, the fused polycyclic compound represented by Formula 1 may be represented by Formula 1-1 or Formula 1-2.

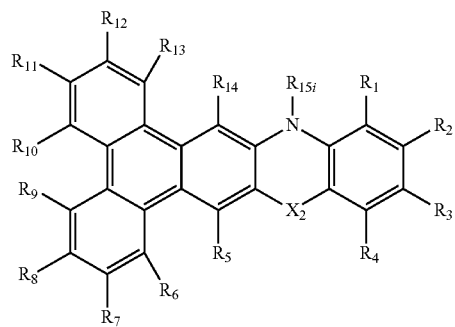

Formula 1-1

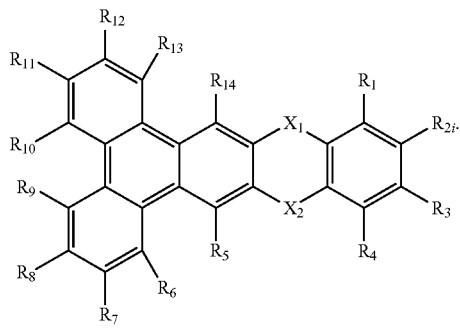

Formula 1-2

Each of Formula 1-1 and Formula 1-2 represents an embodiment of Formula 1 in which the connection position of the substituent represented by Formula 2 is specified. Formula 1-1 represents an embodiment of Formula 1 where $X_1$ is $NR_{15}$, and $R_{15}$ is the substituent represented by Formula 2. Formula 1-2 represents an embodiment of Formula 1 where $R_2$ of Formula 1 is the substituent represented by Formula 2.

In Formula 1-1 and Formula 1-2, $R_{2i}$ and $R_{15i}$ are respectively and each independently the substituent represented by Formula 2. In Formula 1-1, the substituent represented by Formula 2 may be connected at a position represented by $R_{2i}$. In Formula 1-2, the substituent represented by Formula 2 may be connected at a position represented by $R_{15i}$.

In Formula 1-1 and Formula 1-2, $X_1$, $X_2$, and $R_1$ to $R_{15}$ may each independently be the same as defined in Formula 1.

The fused polycyclic compound represented by Formula 1 may be represented by any one among Formula 3-1 to Formula 3-9:

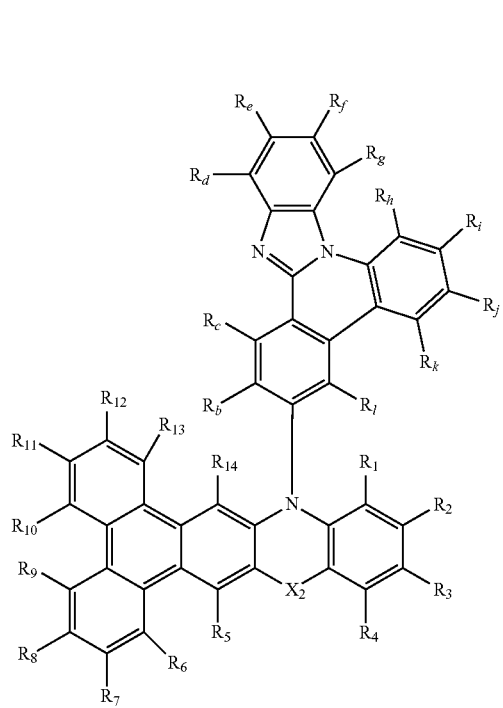

Formula 3-1

Formula 3-2
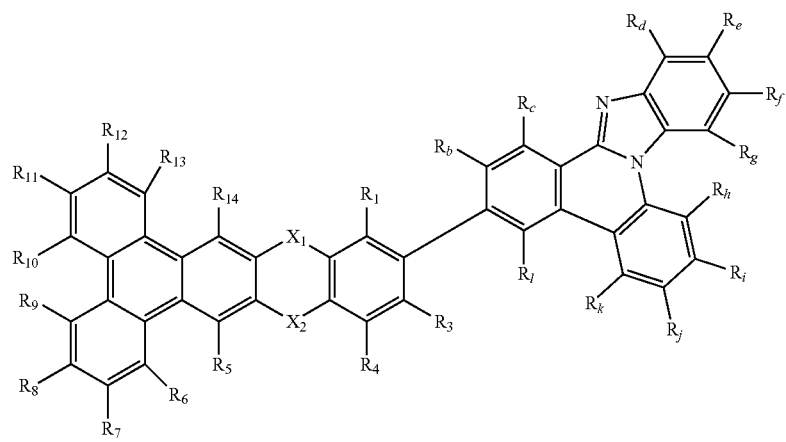
Formula 3-3
Formula 3-4
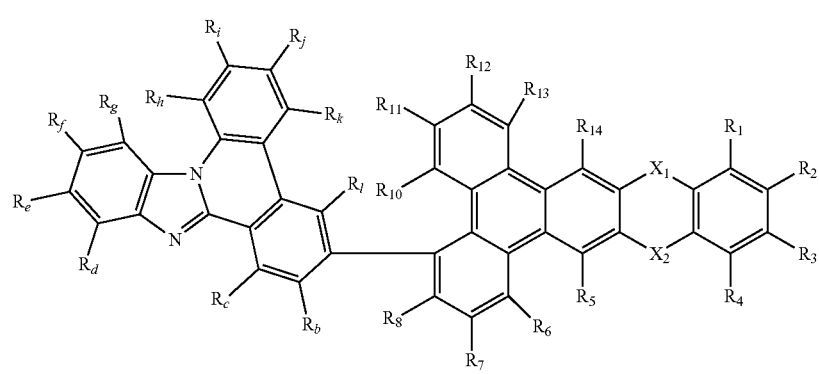

Formula 3-5
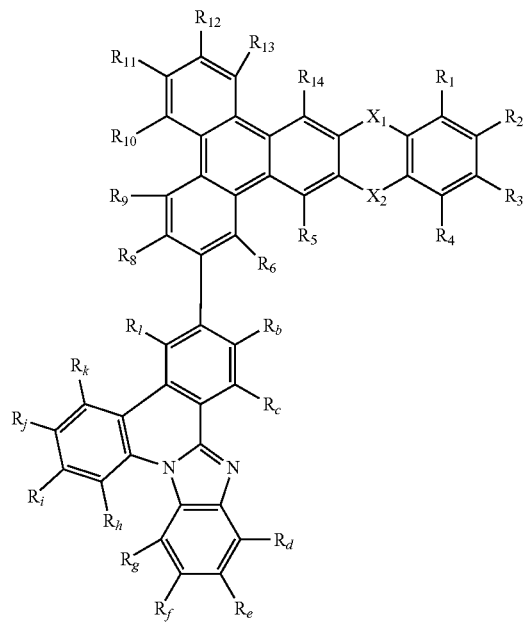
Formula 3-6
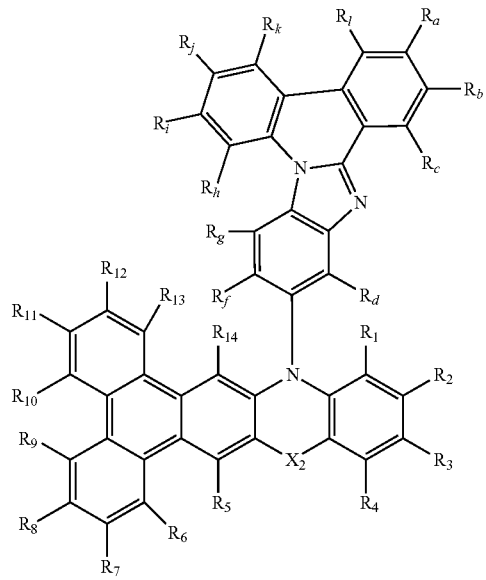
Formula 3-7
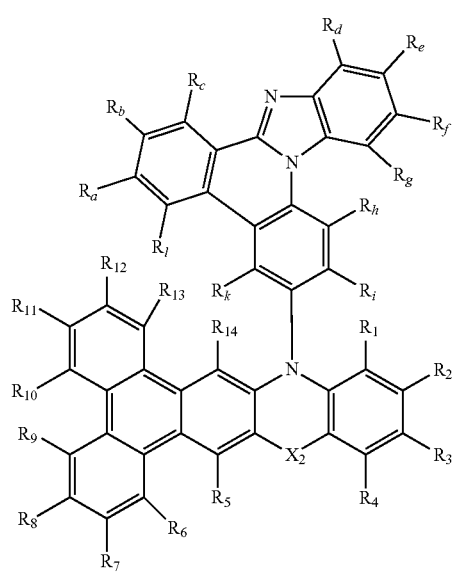

-continued

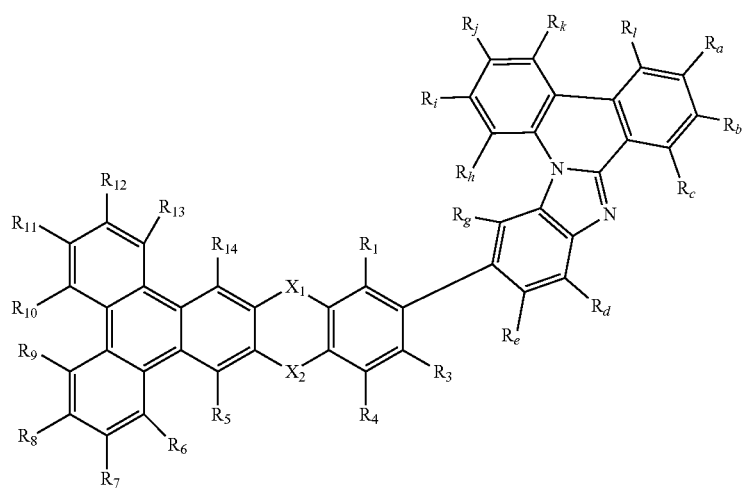

Formula 3-8

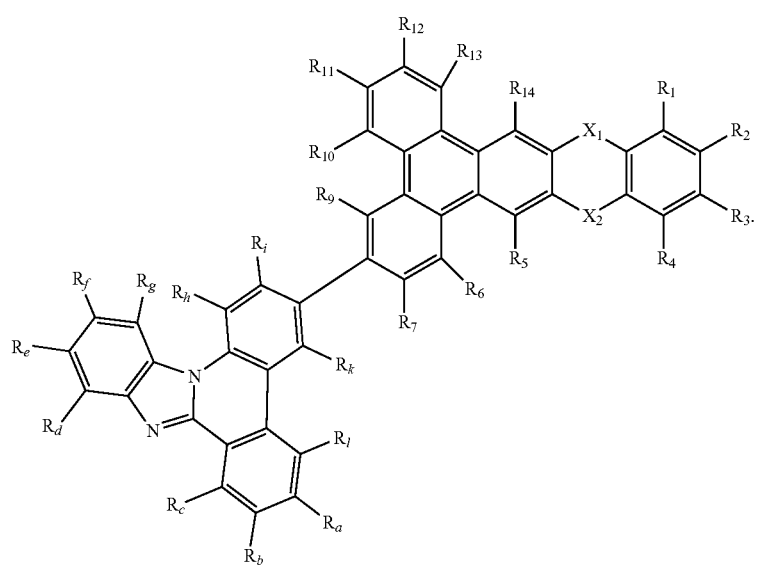

Formula 3-9

Each of Formula 3-1 to Formula 3-9 represents an embodiment of Formula 1 in which the position connected of the substituent represented by Formula 2 and the position of the carbon bonded of the substituent represented by Formula 2 are specified (e.g., an embodiment of Formula 1 in which the connection positions between Formula 1 and Formula 2 are specified on both moieties).

Formula 3-1 represents a case where $X_1$ of Formula 1 is $NR_{15}$, $R_{15}$ is the substituent represented by Formula 2, and Formula 2 is connected with the structure of Formula 1 through the carbon position corresponding to $R_a$. Formula 3-2 represents a case where $R_2$ of Formula 1 is the substituent represented by Formula 2, and Formula 2 is connected with the structure of Formula 1 through the carbon position corresponding to $R_a$. Formula 3-3 represents a case where $R_8$ of Formula 1 is the substituent represented by Formula 2, and Formula 2 is connected with the structure of Formula 1 through the carbon position corresponding to $R_a$. Formula 3-4 represents a case where $R_9$ of Formula 1 is the substituent represented by Formula 2, and Formula 2 is connected with the structure of Formula 1 through the carbon position corresponding to $R_a$. Formula 3-5 represents a case where $R_7$ of Formula 1 is the substituent represented by Formula 2, and Formula 2 is connected with the structure of Formula 1 through the carbon position corresponding to $R_a$. Formula 3-6 represents a case where $X_1$ of Formula 1 is $NR_{15}$, $R_{15}$ is the substituent represented by Formula 2, and Formula 2 is connected with the structure of Formula 1 through the carbon position corresponding to $R_e$. Formula 3-7 represents a case where $X_1$ of Formula 1 is $NR_{15}$, $R_{15}$ is the substituent represented by Formula 2, and Formula 2 is connected with the structure of Formula 1 through the carbon position corresponding to $R_j$. Formula 3-8 represents a case where $R_2$ of Formula 1 is the substituent represented by Formula 2, and Formula 2 is connected with the structure of Formula 1 through the carbon position corresponding to $R_j$. Formula 3-9 represents a case where $R_8$ of Formula 1 is the substituent represented by Formula 2, and Formula 2 is connected with the structure of Formula 1 through the carbon position corresponding to $R_j$.

In Formula 3-1 to Formula 3-9, $X_1$, $X_2$, $R_1$ to $R_{15}$, and $R_a$ to $R_l$ may each independently be the same as defined in Formula 1 and Formula 2.

The fused polycyclic compound represented by Formula 1 may be represented by any one among Formula 4-1 to Formula 4-3:

Formula 4-1

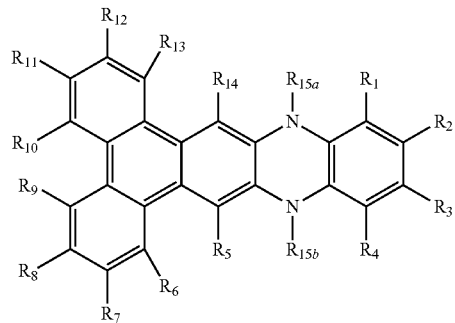

Formula 4-2

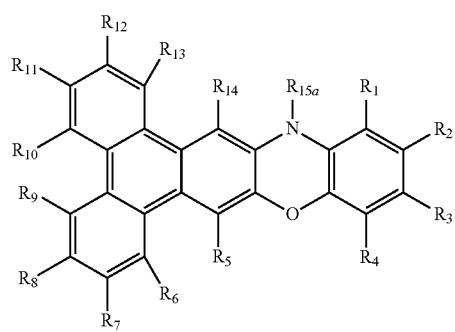

-continued

Formula 4-3

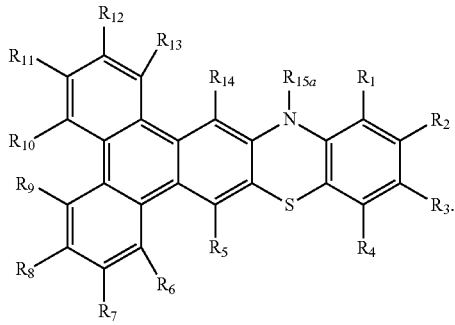

Each of Formula 4-1 to Formula 4-3 correspond to an embodiment of Formula 1 where $X_1$ and $X_2$ are specified. Formula 4-1 represents a case where both (e.g., simultaneously) $X_1$ and $X_2$ are $NR_{15}$. Formula 4-2 represents a case where $X_1$ is $NR_{15}$, and $X_2$ is O. Formula 4-3 represents a case where $X_1$ is $NR_{15}$, and $X_2$ is S.

In Formula 4-1 to Formula 4-3, $R_{15a}$ and $R_{15b}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms. For example, $R_{15a}$ and $R_{15b}$ may each independently be a hydrogen atom, a deuterium atom, a halogen atom, a substituted or unsubstituted silyl group, a substituted or unsubstituted phenyl group, a substituted or unsubstituted carbazole group, a substituted or unsubstituted dibenzofuran group, or a substituted or unsubstituted dibenzothiophene group. In Formula 4-1 to Formula 4-3, one or more of $R_{15a}$ and $R_{15b}$ may be combined with an adjacent group to form a ring.

In some embodiments, in Formula 4-1 to Formula 4-3, $R_1$ to $R_{14}$ may each independently be the same as defined in Formula 1.

The fused polycyclic compound of an embodiment may be any one among the compounds represented in Compound Group 1. A light emitting device ED of an embodiment may include at least one fused polycyclic compound among the compounds represented in Compound Group 1 in an emission layer EML.

Compound Group 1
1
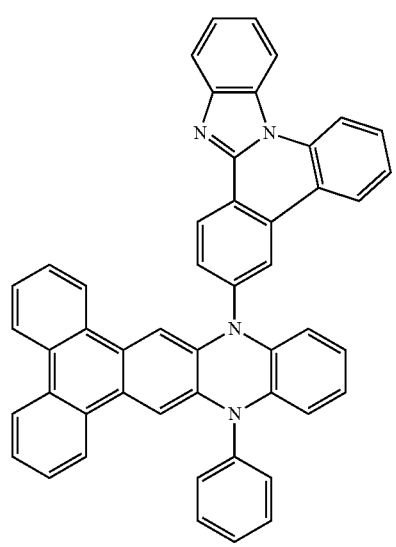
2
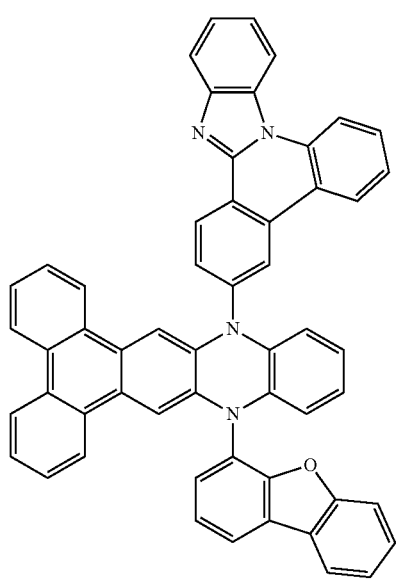
3
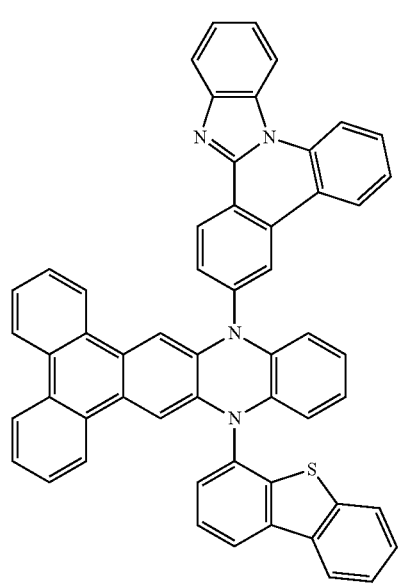
4
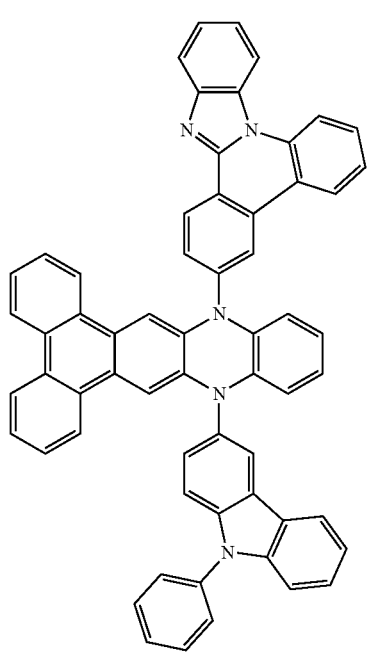

-continued
5
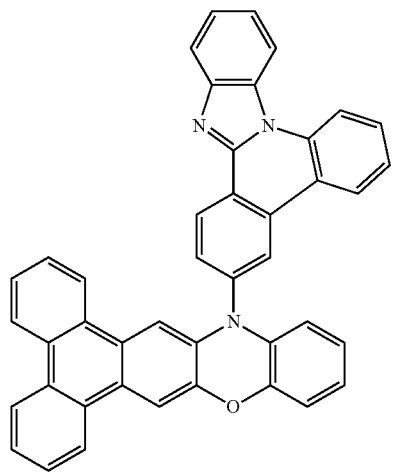
6
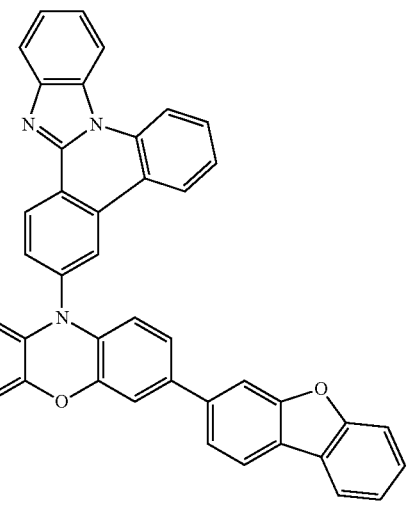
7
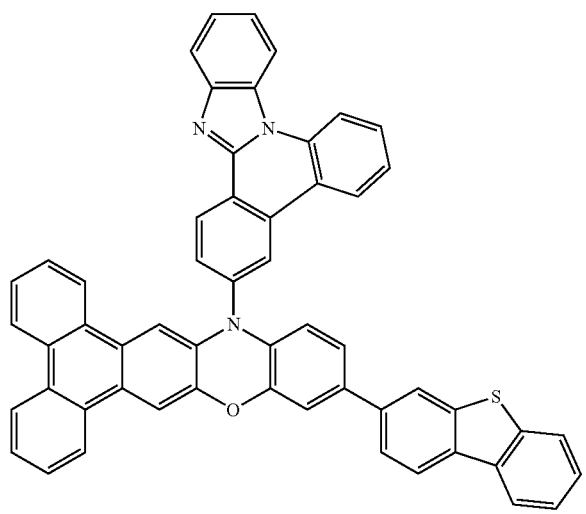
8
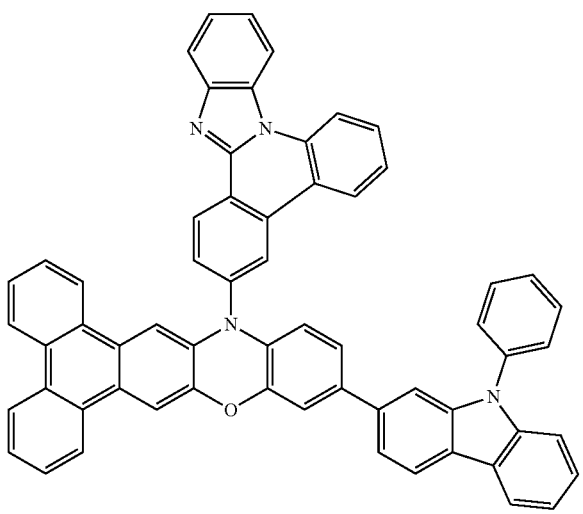
9
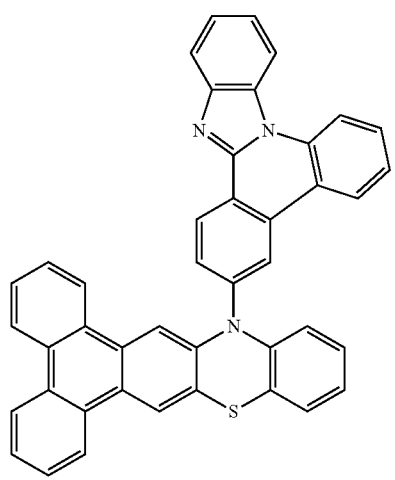
10
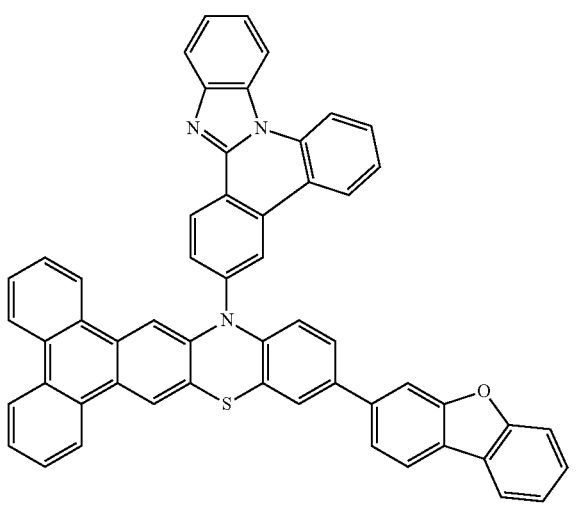

-continued
11
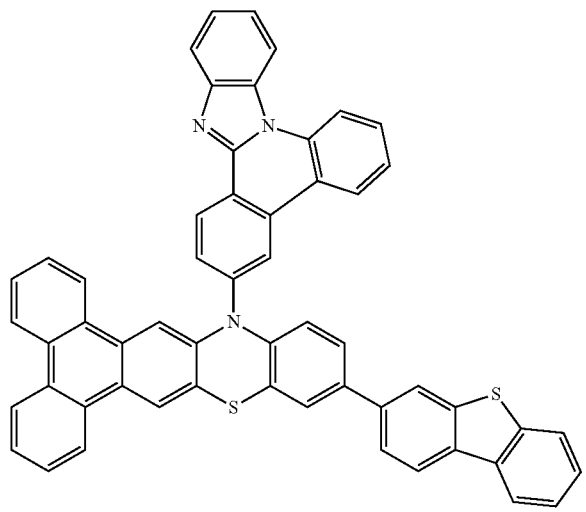
12
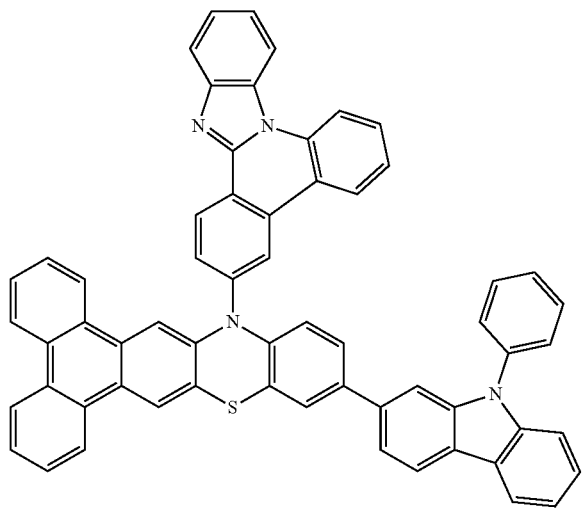
13
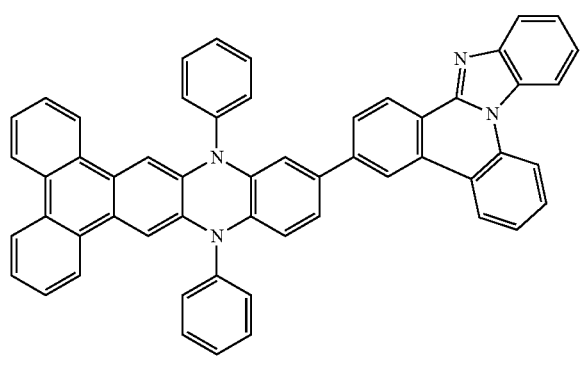
14
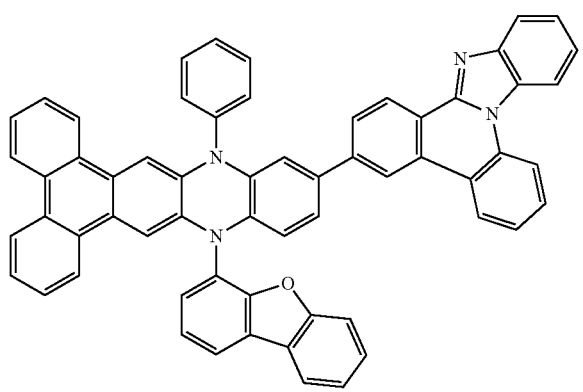
15
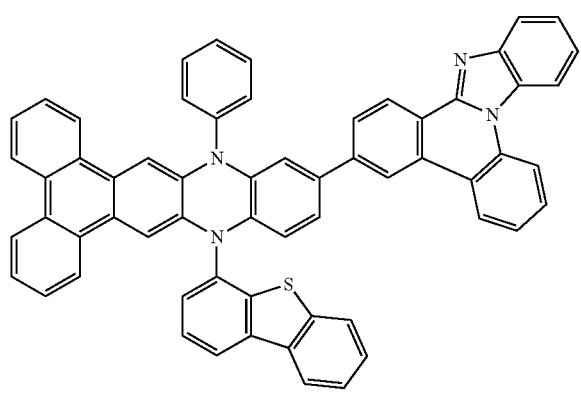
16
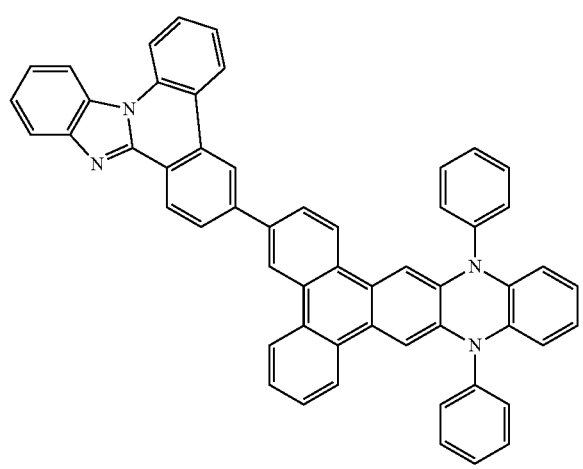

-continued
17
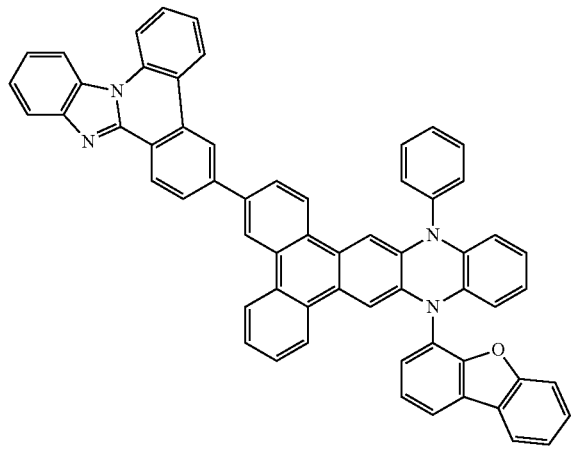
18
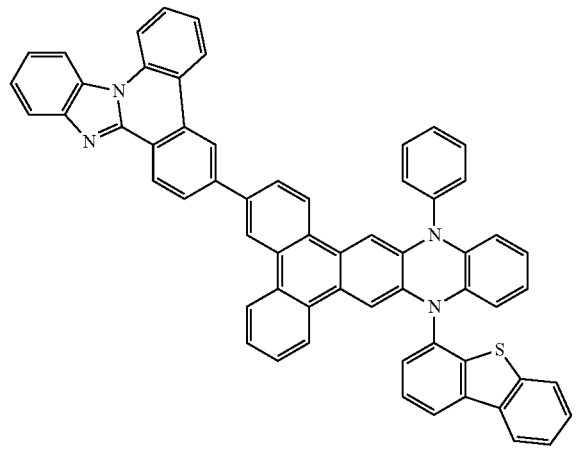
19
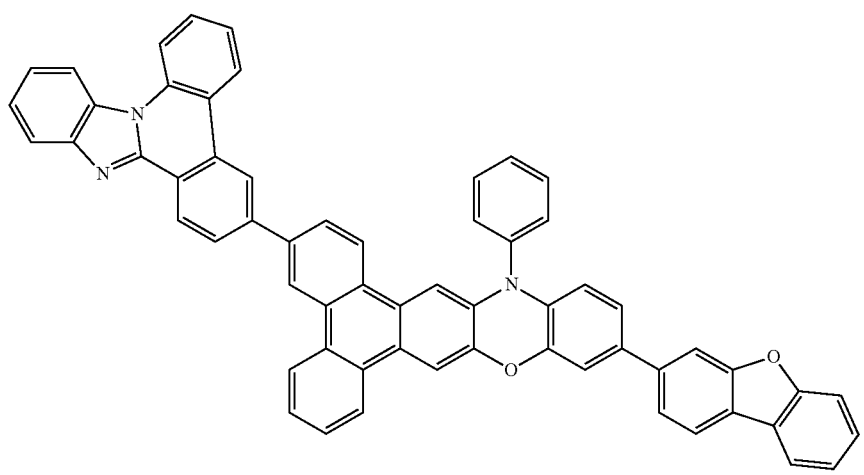
20
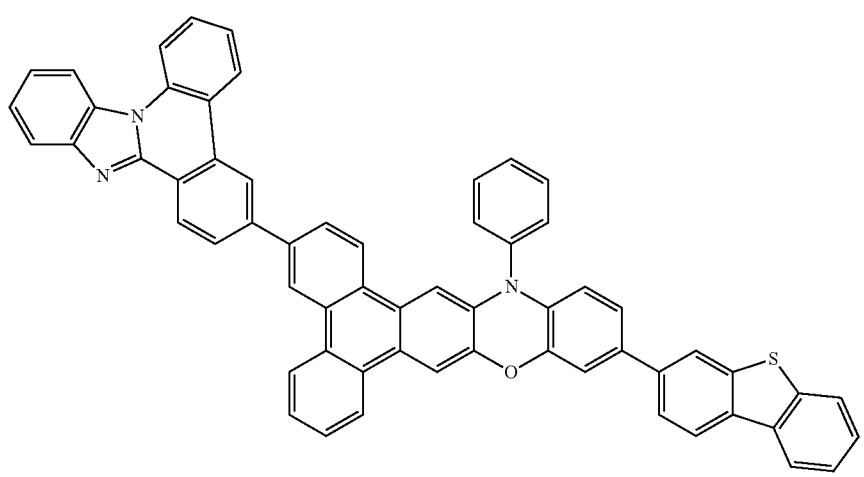

21
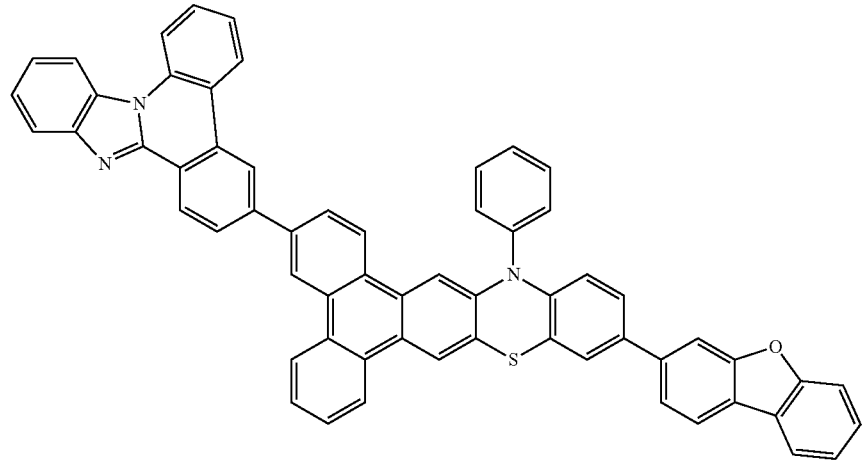
22
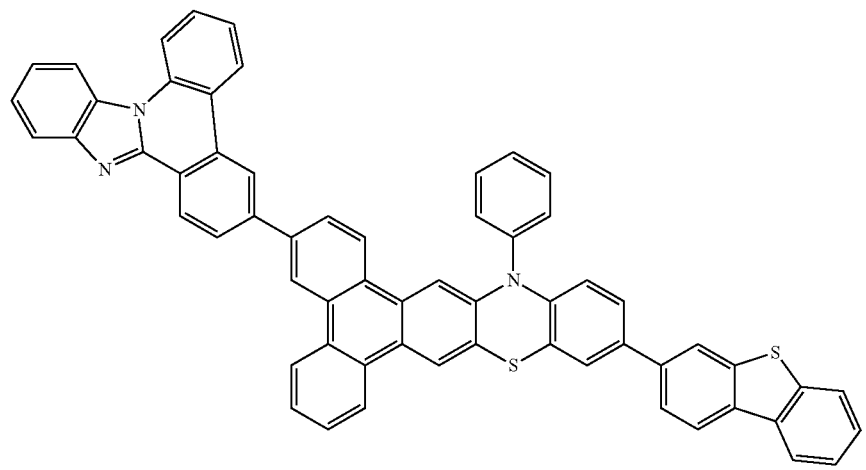
23 24
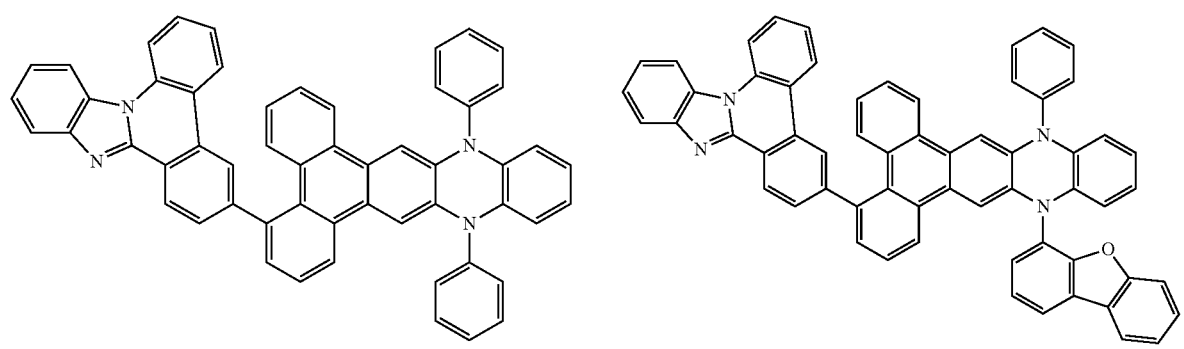

-continued
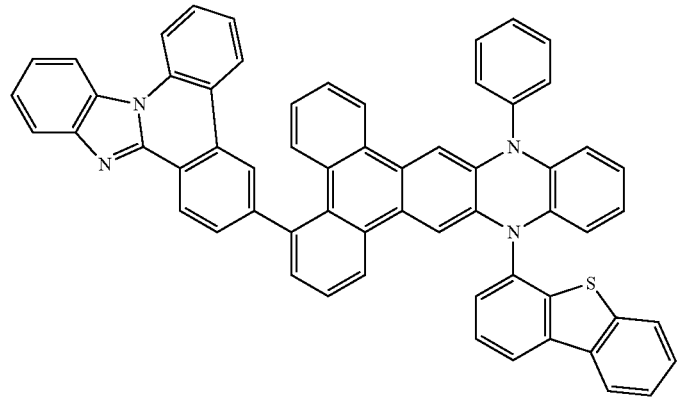
25
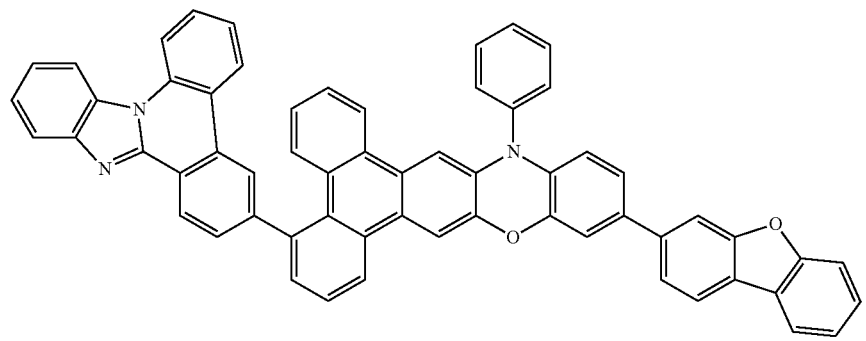
26
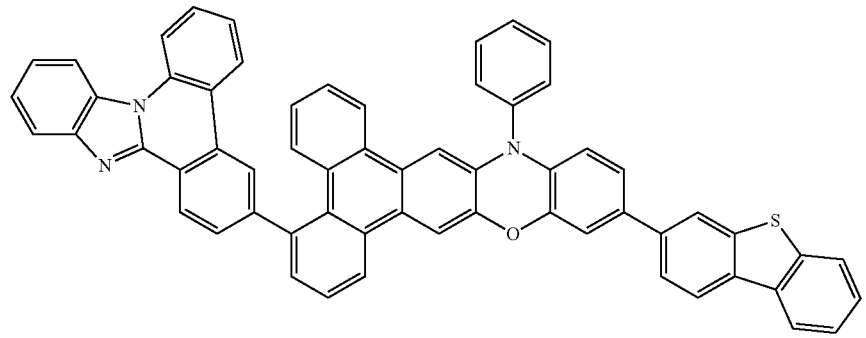
27
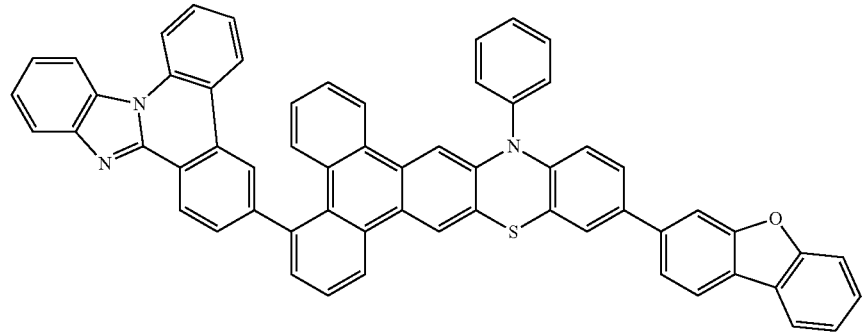
28

-continued
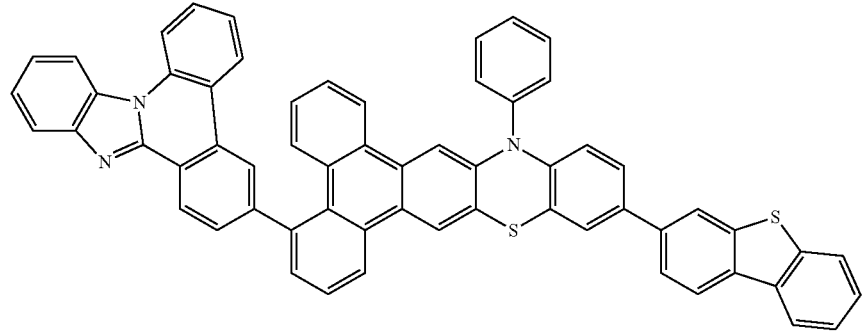
29
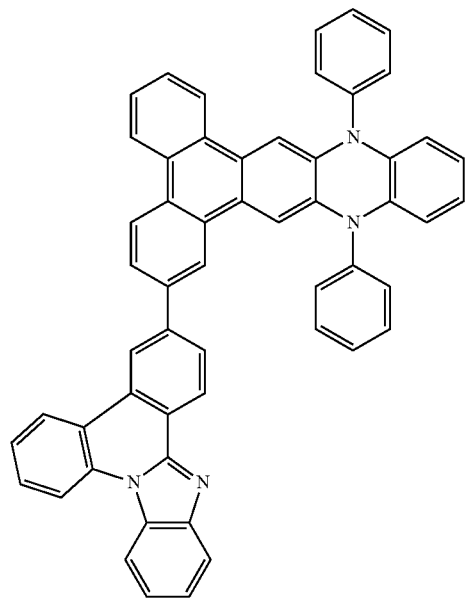
30
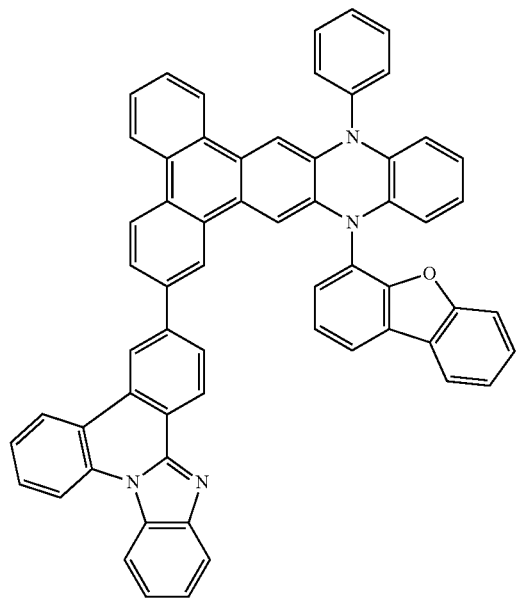
31
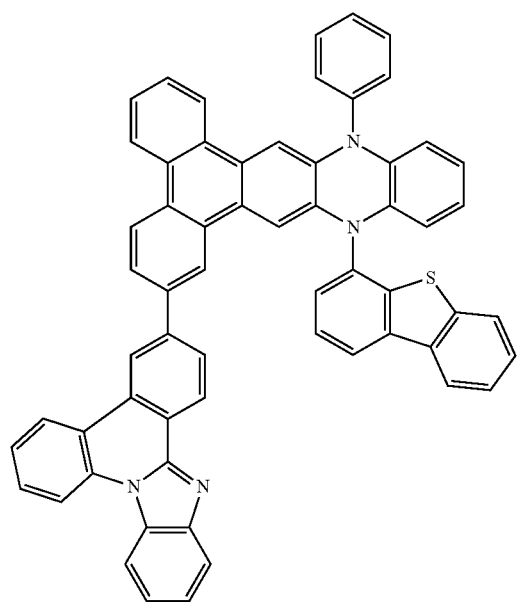
32
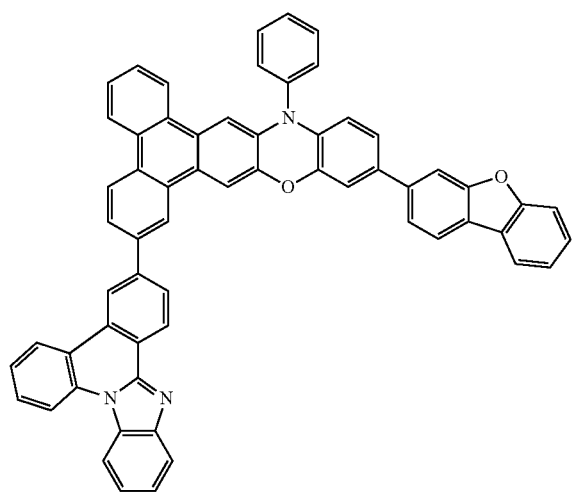
33

-continued
34
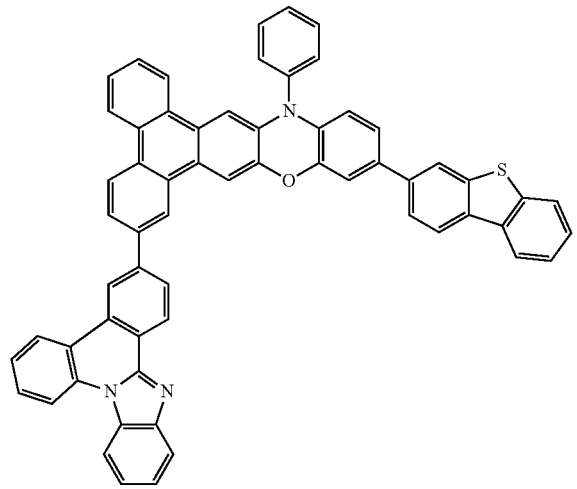
35
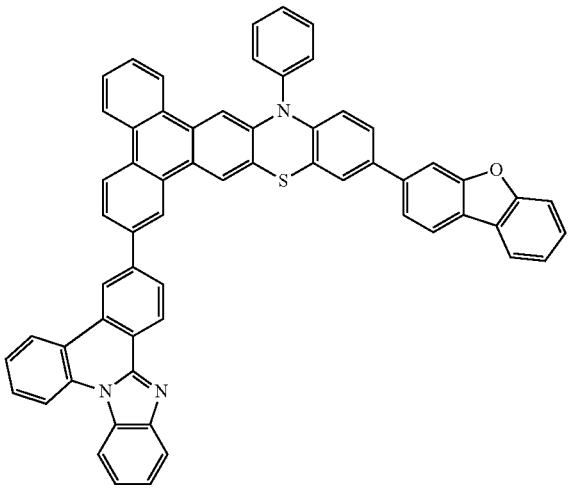
36
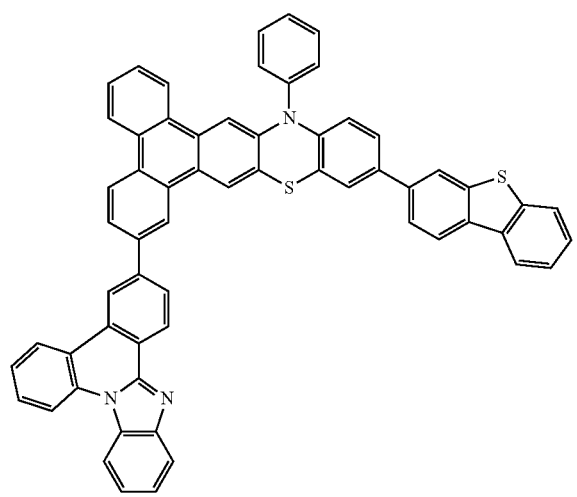
37
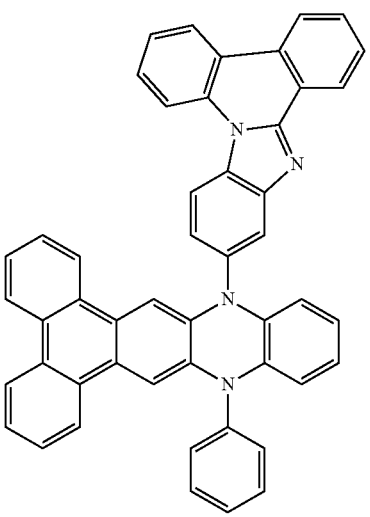
38
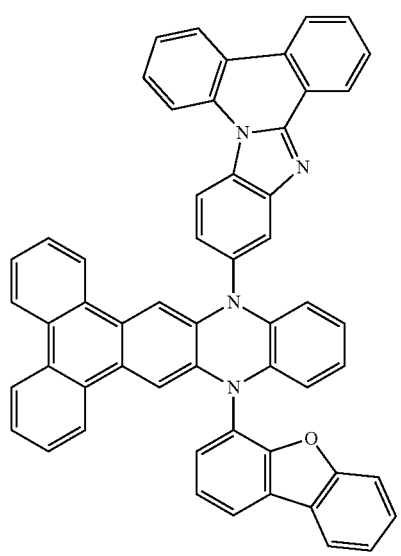
39
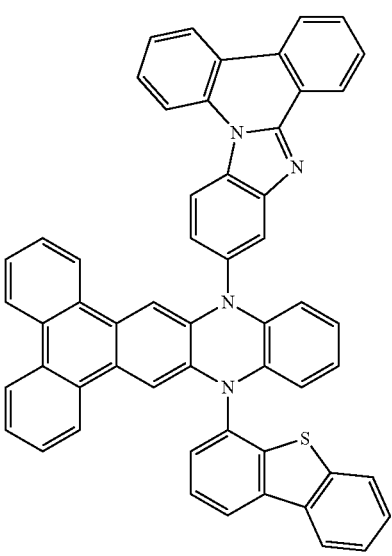

-continued
40
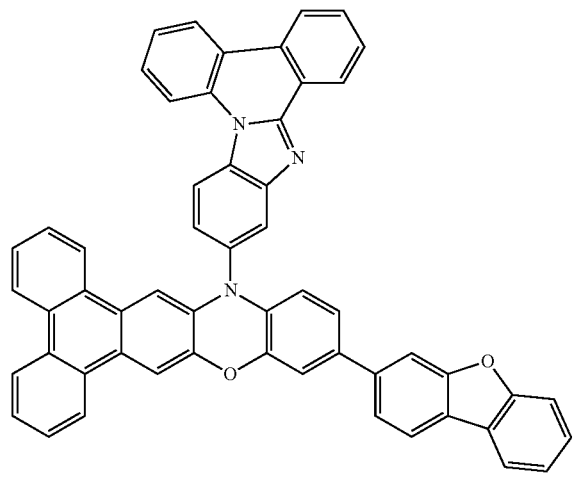
41
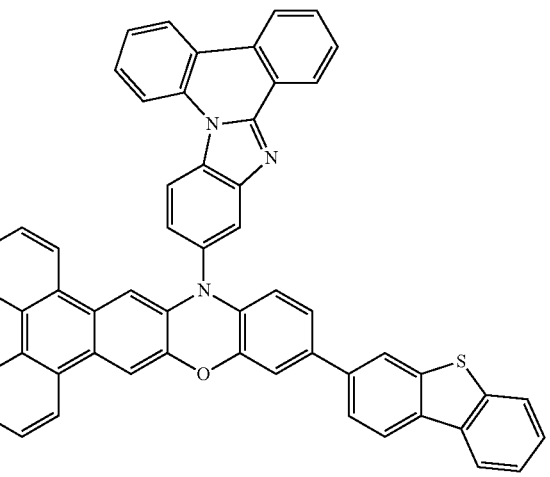
42
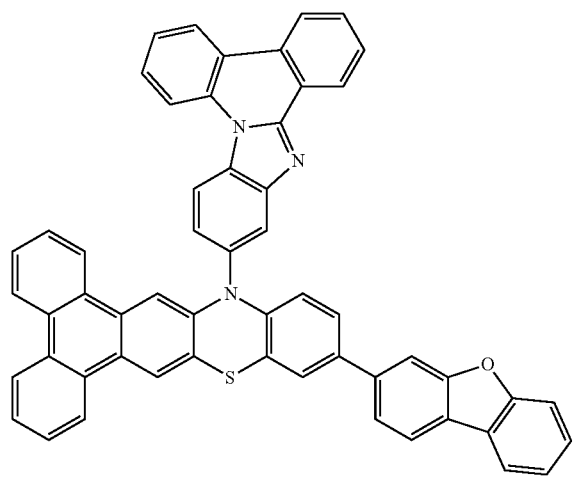
43
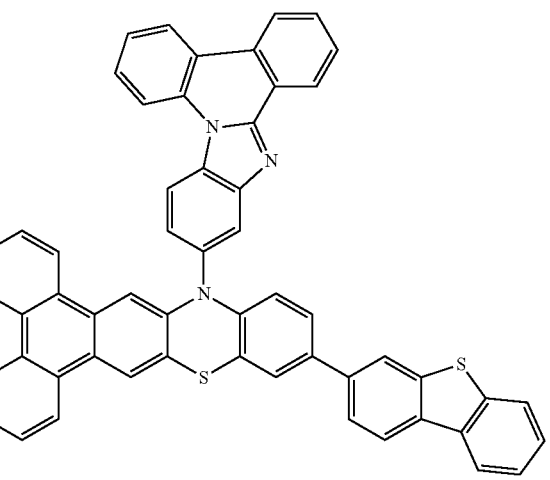
44
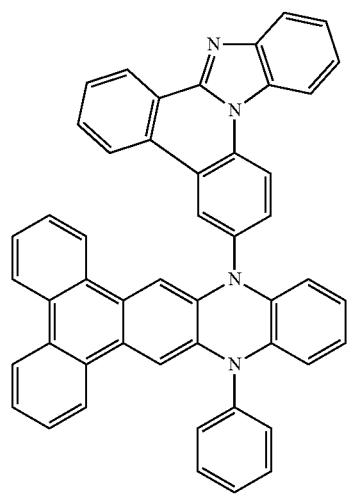
45
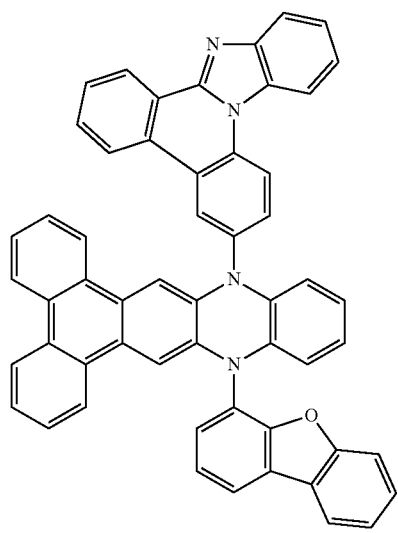

-continued
46
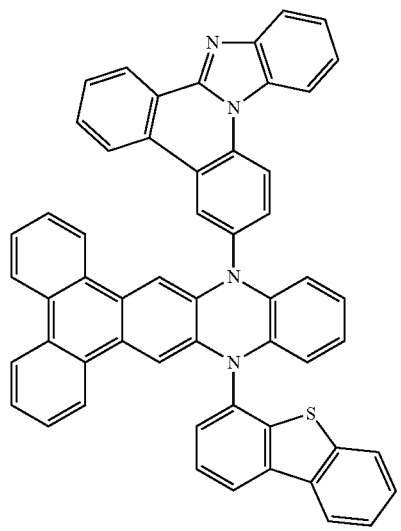
47
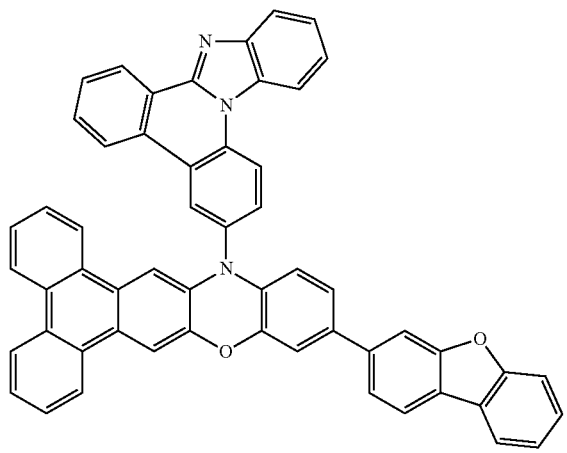
48
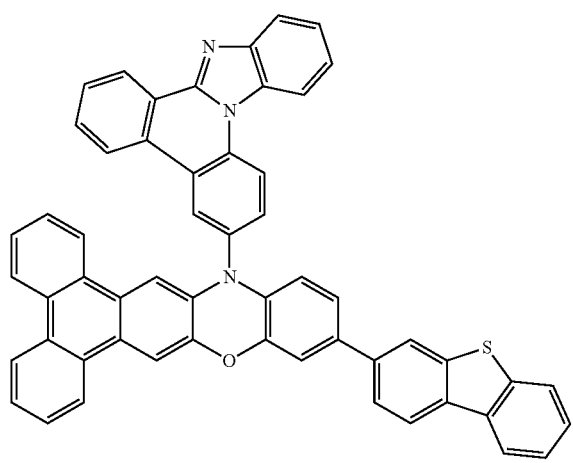
49
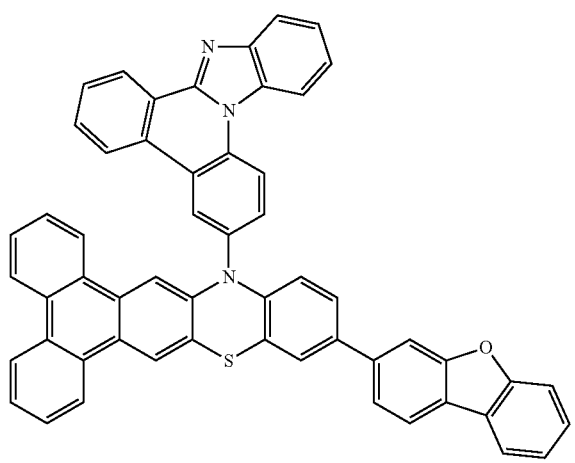
50
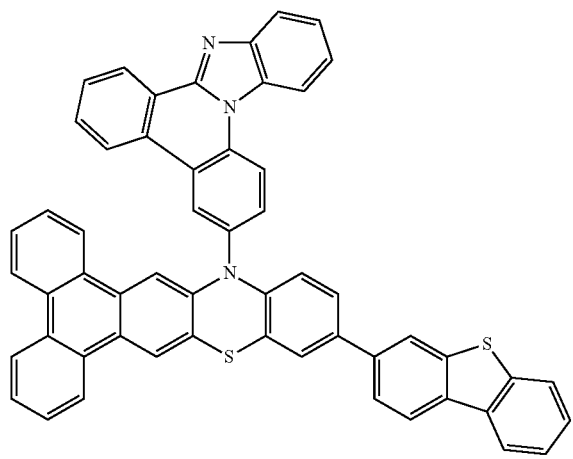
51
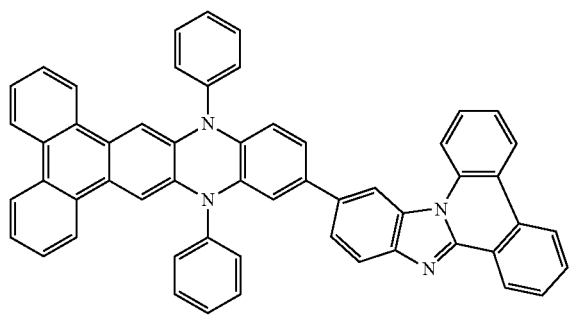

-continued
52
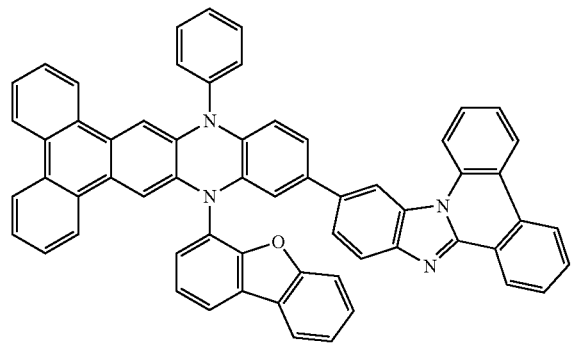
53
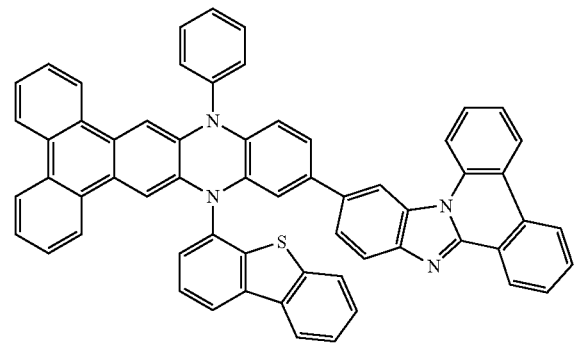
54
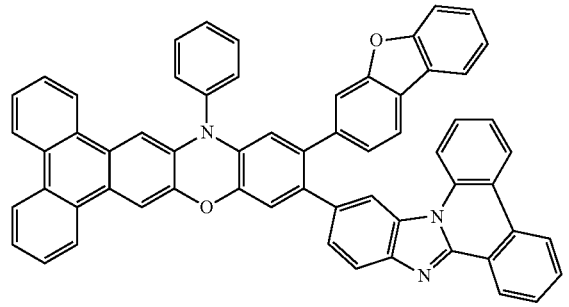
55
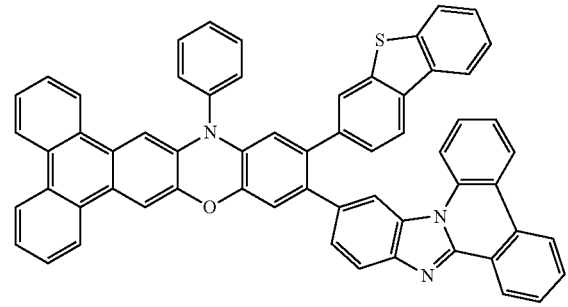
56
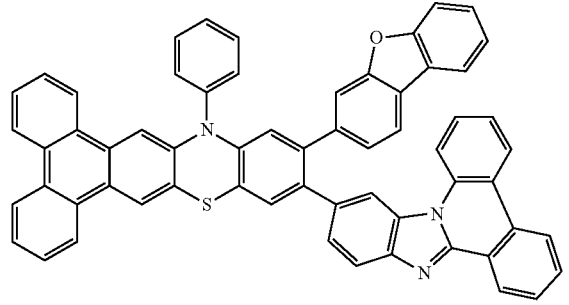
57
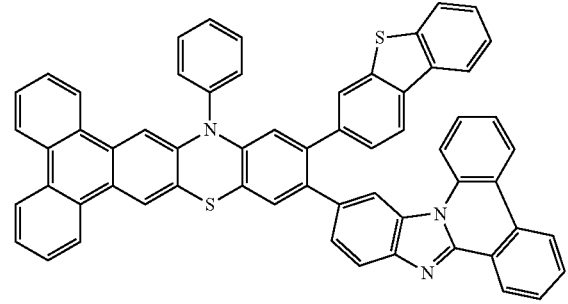
58
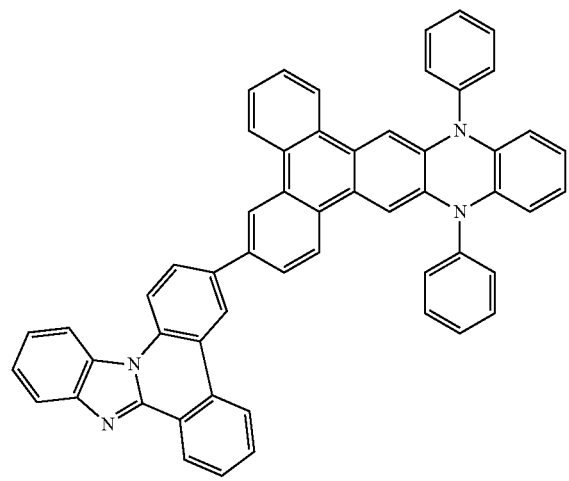
59
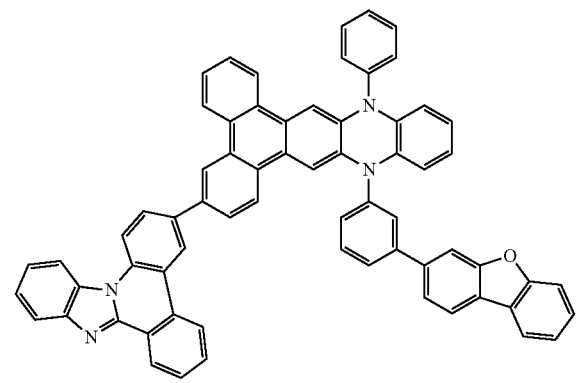

-continued
60
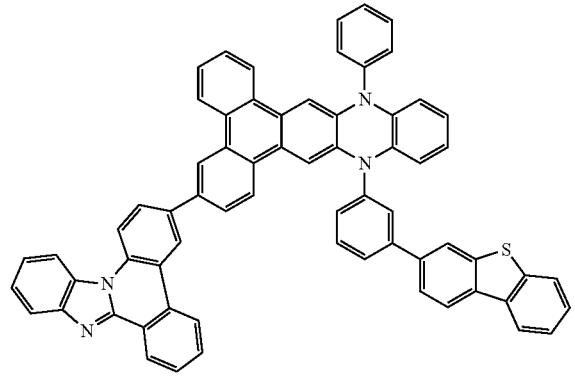
61
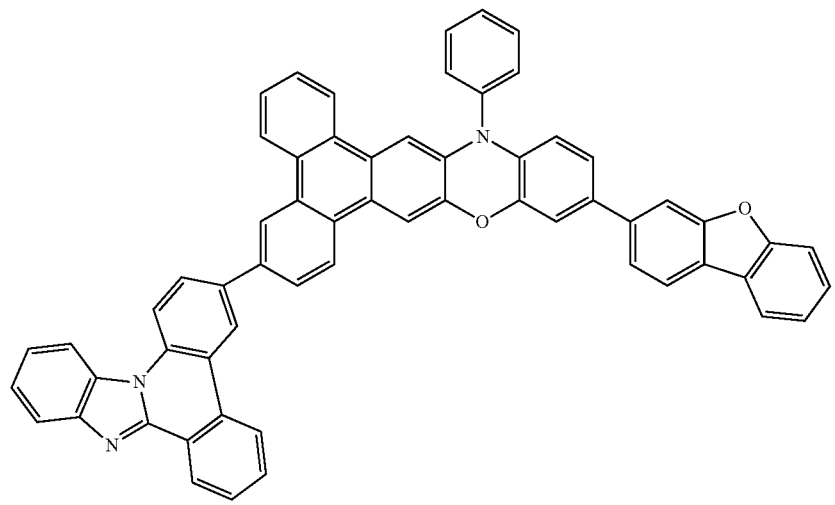
62
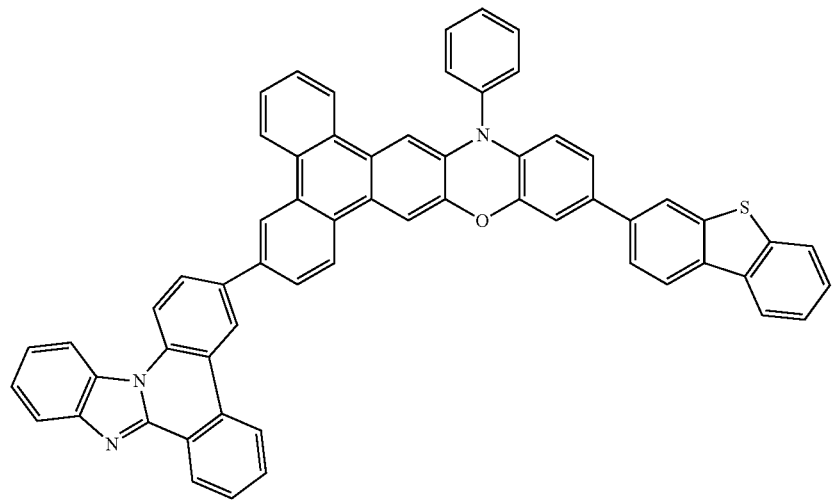

63
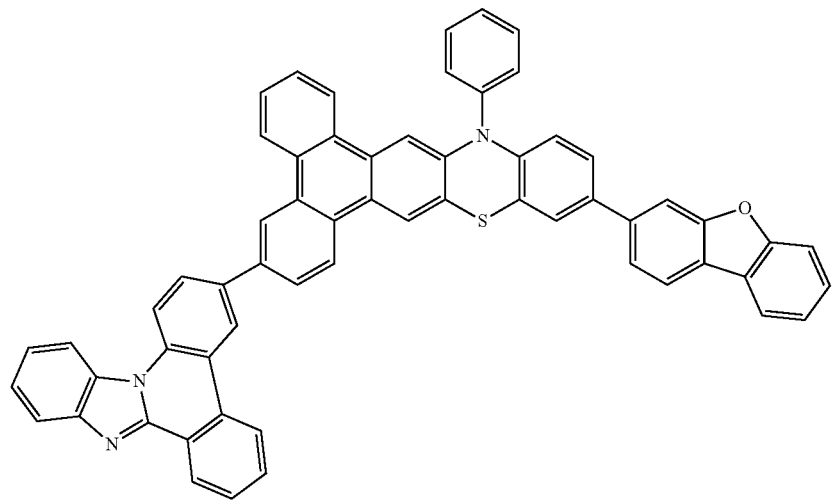
64
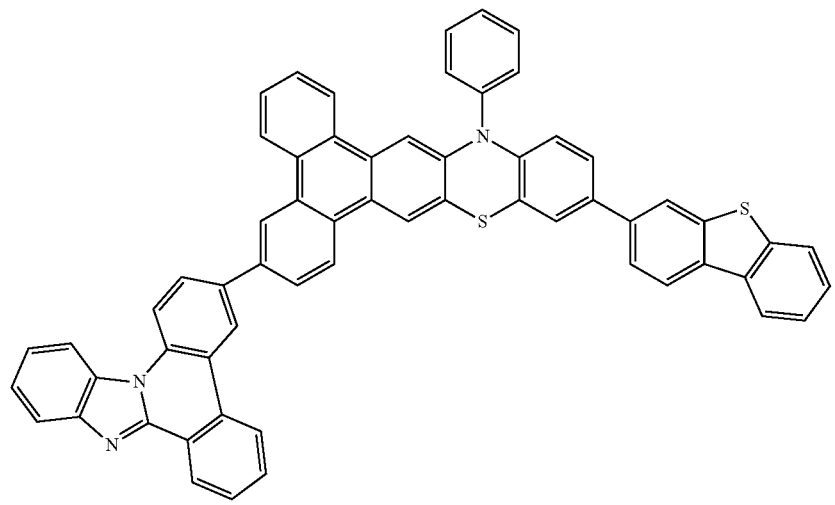
65
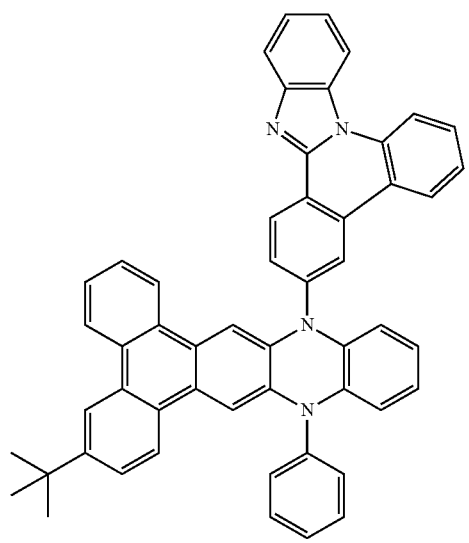
66
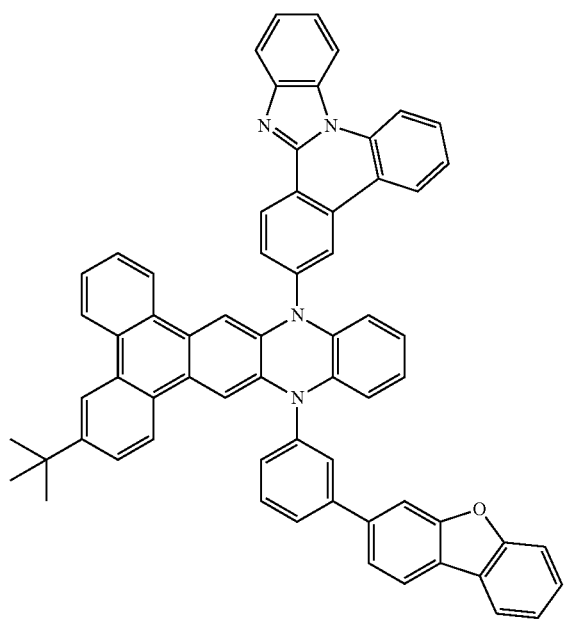

67
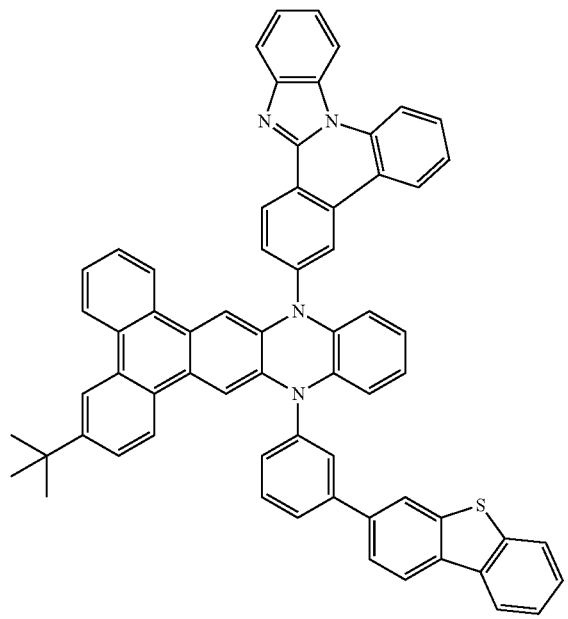
68
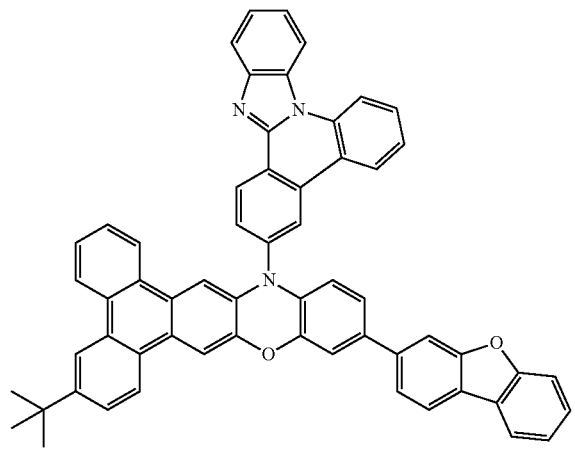
69
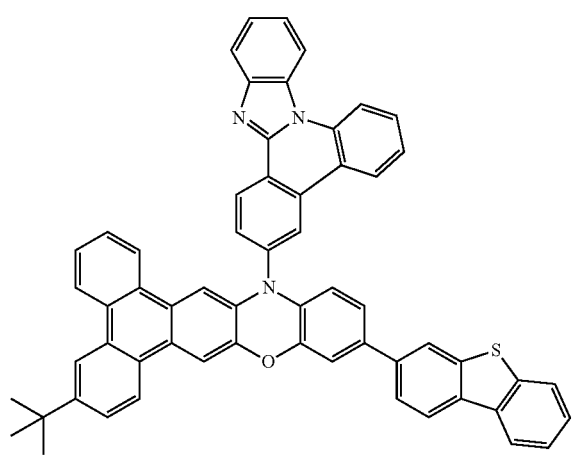
70
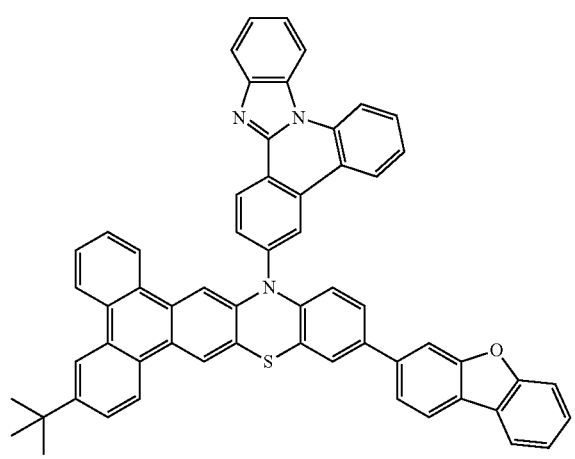

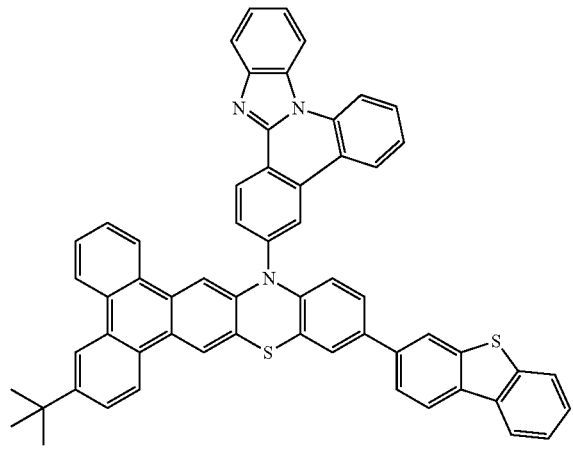
71

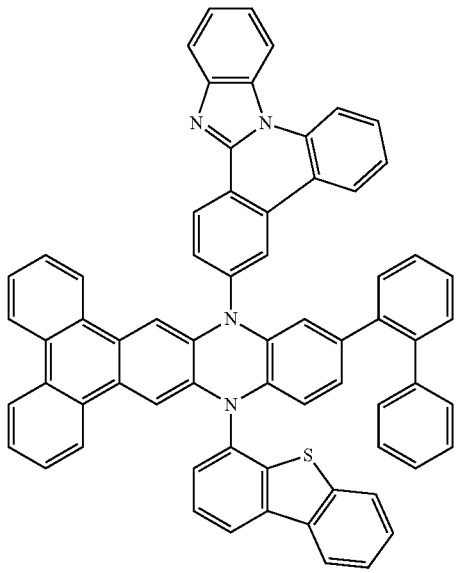
72

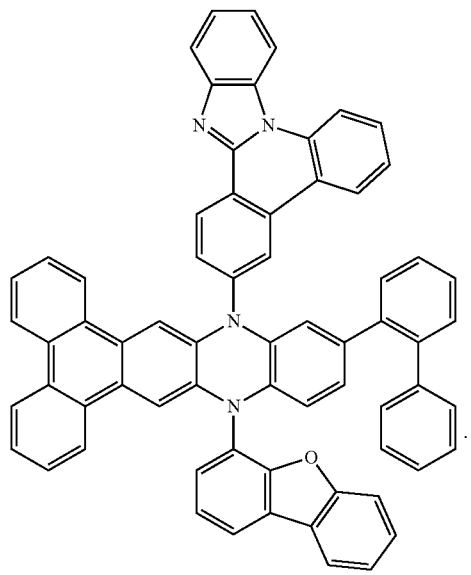
73

The fused polycyclic compound of an embodiment, represented by Formula 1 may be a light emitting material having a central wavelength in a wavelength region of about 430 nm to about 490 nm. The emission layer of a light emitting device ED may include the fused polycyclic compound of an embodiment, represented by Formula 1 and may be to emit blue light. For example, the emission layer EML of the light emitting device ED of an embodiment may be to emit blue light in a region of about 490 nm or less. However, an embodiment of the present disclosure is not limited thereto, and the emission layer EML may be to emit green light or red light.

In some embodiments, the emission layer EML may include a host and a dopant and may include the fused polycyclic compound as the host. The fused polycyclic compound of an embodiment, represented by Formula 1 may be a host material of an emission layer.

For example, in the light emitting device ED of an embodiment, the emission layer EML may include a host for emitting phosphorescence and a dopant for emitting phosphorescence, and may include the fused polycyclic compound of an embodiment as the host for emitting phosphorescence. In some embodiments, in the light emitting device ED of an embodiment, the emission layer EML may include a host for emitting fluorescence and a dopant for emitting fluorescence, and may include the fused polycyclic compound of an embodiment as the host for emitting fluorescence.

In the light emitting device ED of an embodiment, the emission layer EML may include a host for emitting delayed fluorescence and a dopant for emitting delayed fluorescence, and may include the fused polycyclic compound of an embodiment as the host for emitting delayed fluorescence. In the light emitting device ED of an embodiment, the emission layer EML may include a host for emitting blue thermally activated delayed fluorescence (TADF) and a dopant for emitting blue thermally activated delayed fluorescence, and may include the fused polycyclic compound of an embodiment as the host for emitting blue thermally activated delayed fluorescence. The emission layer EML may include at least one among the fused polycyclic compounds represented in Compound Group 1 as the host material of the emission layer.

In some embodiments, in the light emitting device ED of an embodiment, the emission layer EML may further include a suitable material. The emission layer EML may include anthracene derivatives, pyrene derivatives, fluoranthene derivatives, chrysene derivatives, dihydrobenzanthracene derivatives, or triphenylene derivatives. For example, the emission layer EML may include anthracene derivatives or pyrene derivatives.

In the light emitting devices ED of embodiments, shown in FIG. 3 to FIG. 6, the emission layer EML may include a host and a dopant, and the emission layer EML may include a compound represented by Formula E-1. The compound represented by Formula E-1 may be utilized as a fluorescence host material or a delayed fluorescence host material.

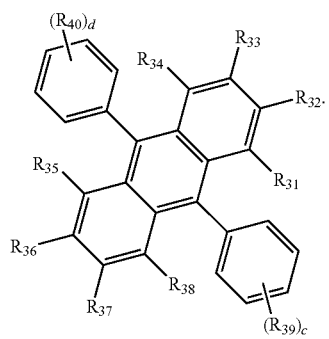

[Formula E-1]

In Formula E-1, $R_{31}$ to $R_{40}$ may each independently be a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 ring-forming carbon atoms, or a substituted or unsubstituted heteroaryl group of 2 to 30 ring-forming carbon atoms, and/or combined with an adjacent group to form a ring. In some embodiments, one or more of $R_{31}$ to $R_{40}$ may be combined with an adjacent group to form a saturated hydrocarbon ring or an unsaturated hydrocarbon ring.

In Formula E-1, "c" and "d" may each independently be an integer of 0 to 5.

Formula E-1 may be represented by any one among the compounds represented in Compound Group E-1.

Compound Group E-1

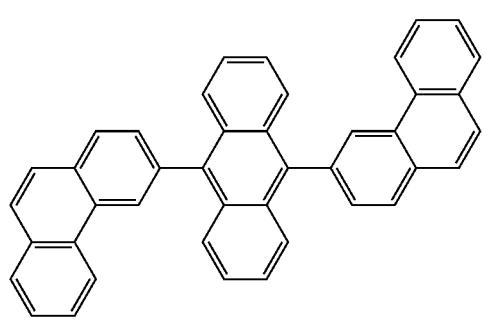

E1

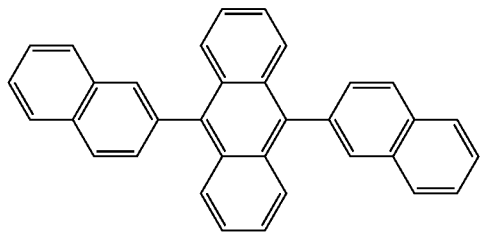

E2

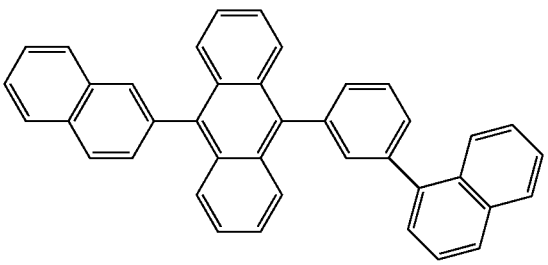

E3

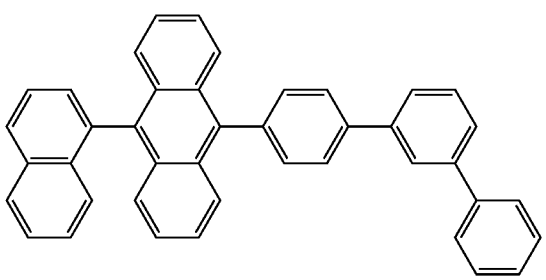

E4

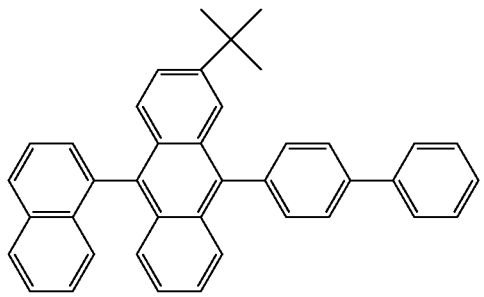

E5

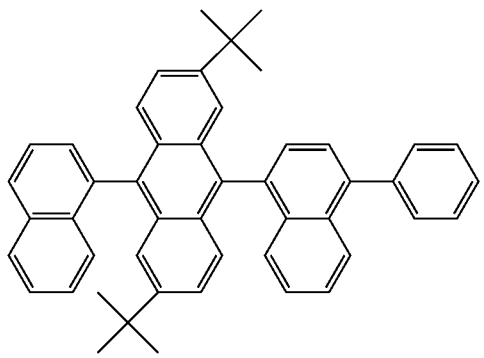

E6

E7
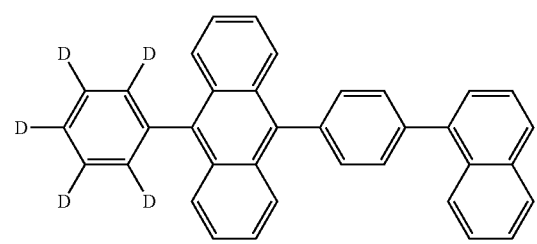
E8
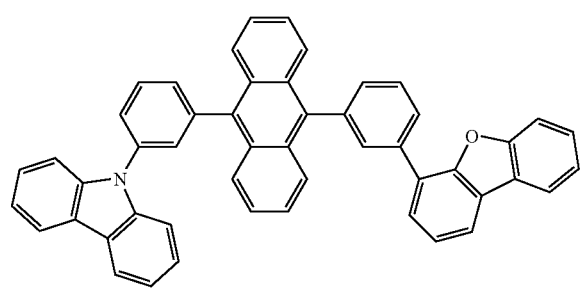
E9
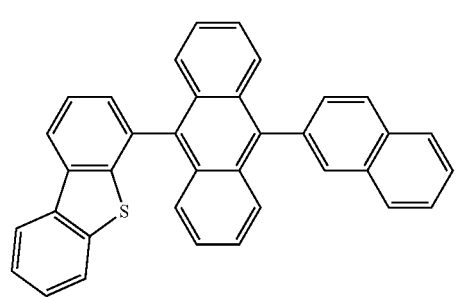
E10
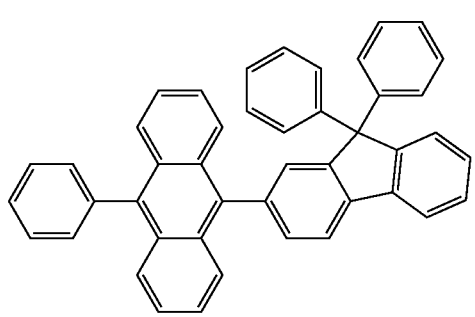
E11
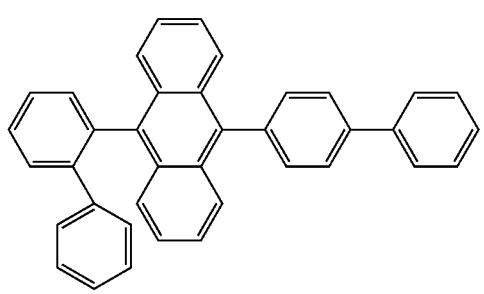
E12
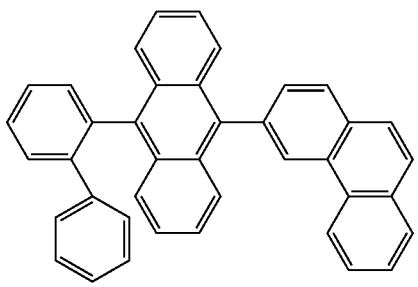
E13
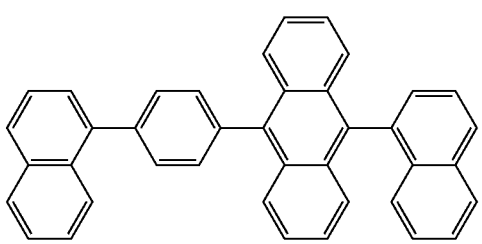
E14
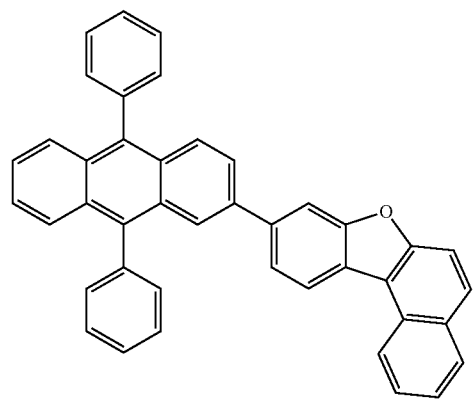
E15
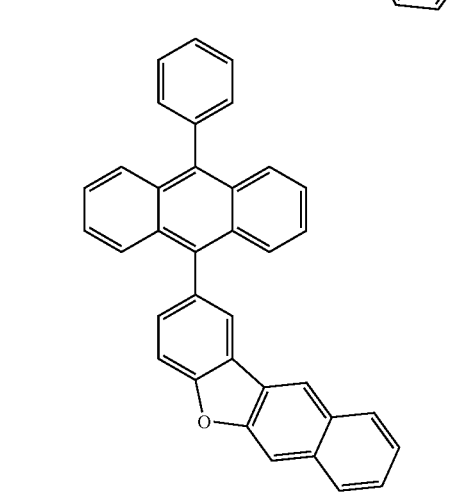
E16
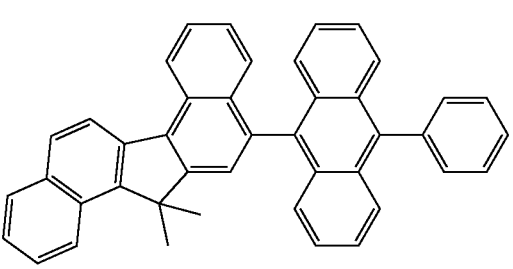

-continued

E17
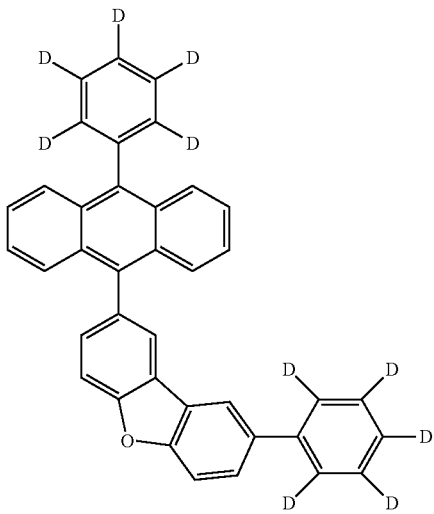

E18
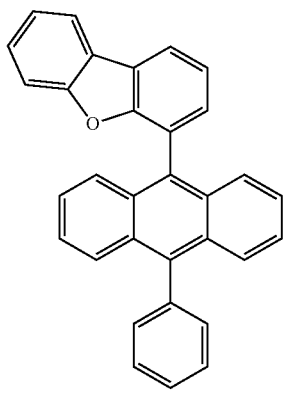

E19
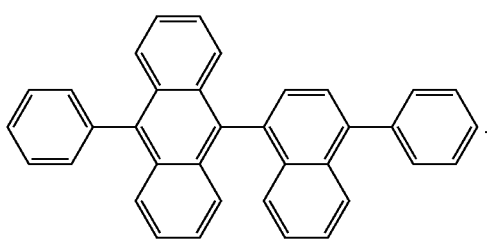

In an embodiment, the emission layer EML may include a compound represented by Formula E-2a or Formula E-2b. The compound represented by Formula E-2a or Formula E-2b may be utilized as a phosphorescence host material or a delayed fluorescence host material.

Formula E-2a
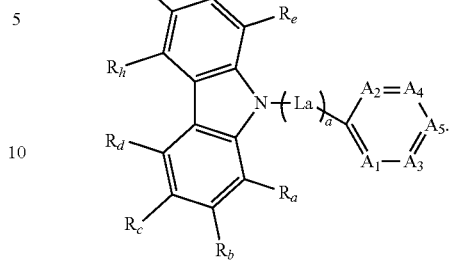

In Formula E-2b, "a" may be an integer of 0 to 10, $L_a$ may be a direct linkage, a substituted or unsubstituted arylene group of 6 to 30 ring-forming carbon atoms, or a substituted or unsubstituted heteroarylene group of 2 to 30 ring-forming carbon atoms. In some embodiments, if "a" is an integer of 2 or more, multiple $L_a$ may each independently be a substituted or unsubstituted arylene group of 6 to 30 ring-forming carbon atoms, or a substituted or unsubstituted heteroarylene group of 2 to 30 ring-forming carbon atoms.

In some embodiments, in Formula E-2a, $A_1$ to $A_5$ may each independently be N or CRi. $R_a$ to $R_j$ may each independently be a hydrogen atom, a deuterium atom, a substituted or unsubstituted amine group, a substituted or unsubstituted thio group, a substituted or unsubstituted oxy group, a substituted or unsubstituted phosphine oxide group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, and/or may be combined with an adjacent group to form a ring. One or more of $R_a$ to $R_j$ may be combined with an adjacent group to form a hydrocarbon ring or a heterocycle including N, O, S, etc. as a ring-forming atom.

In some embodiments, in Formula E-2a, two or three selected from $A_1$ to $A_5$ may be N, and the remainder may be $CR_i$.

Formula E-2b $(Cbz1)\!-\!(L_b)_b\!-\!(Cbz2)$.

In Formula E-2b, Cbz1 and Cbz2 may each independently be an unsubstituted carbazole group, or a carbazole group substituted with an aryl group of 6 to 30 ring-forming carbon atoms. $L_b$ may be a direct linkage, a substituted or unsubstituted arylene group of 6 to 30 ring-forming carbon atoms, or a substituted or unsubstituted heteroarylene group of 2 to 30 ring-forming carbon atoms. "b" may be an integer of 0 to 10, and when "b" is an integer of 2 or more, multiple $L_b$ may each independently be a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be represented by any one among the compounds in Compound Group E-2. However, the compounds shown in Compound Group E-2 are only illustrations, and the compound represented by Formula E-2a or Formula E-2b is not limited to the compounds represented in Compound Group E-2.

Compound Group E-2
E-2-1
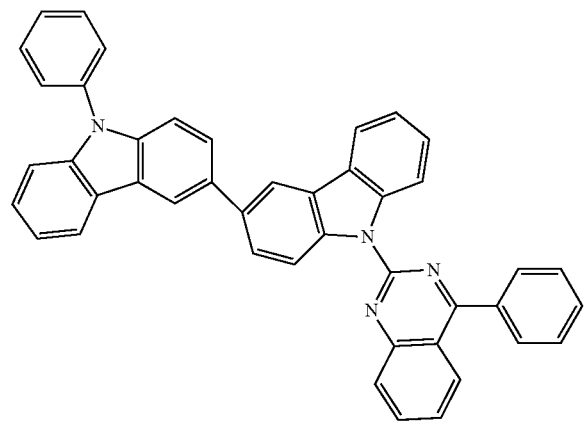
E-2-2
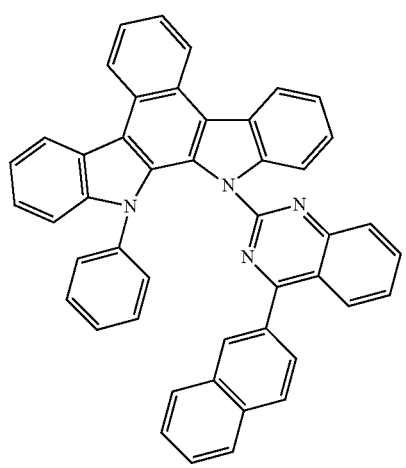
E-2-3
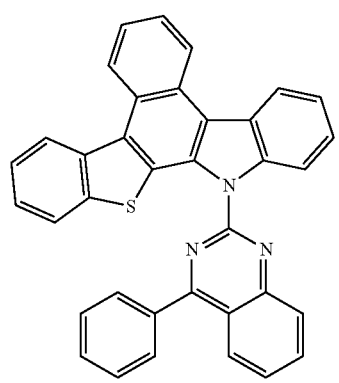
E-2-4
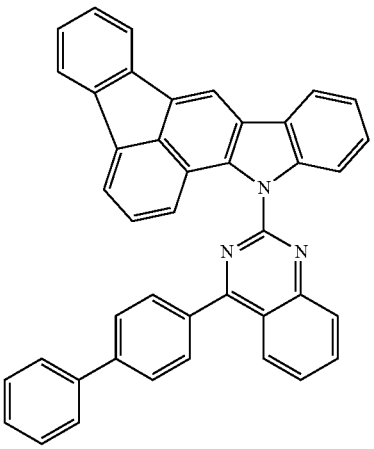
E-2-5
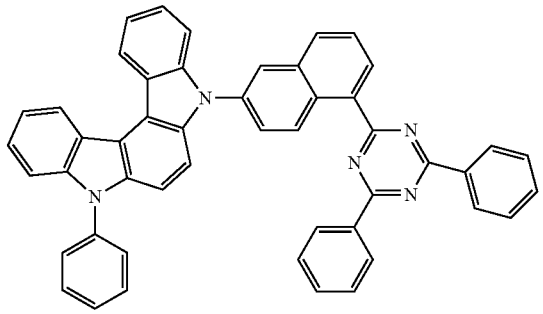
E-2-6
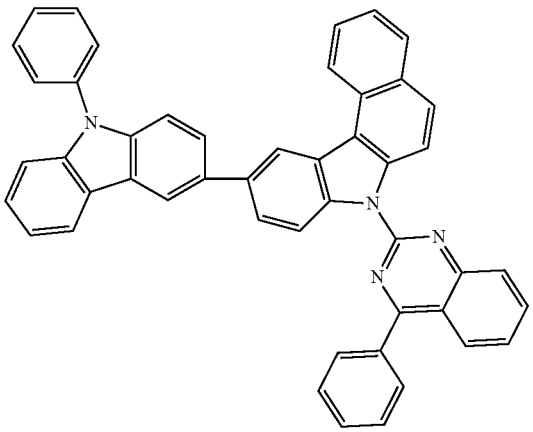

-continued
E-2-7
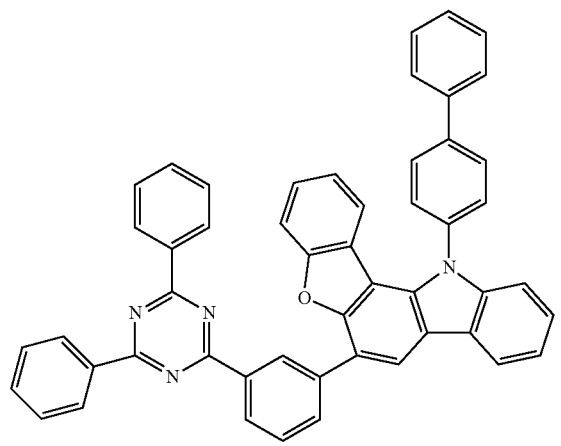
E-2-8
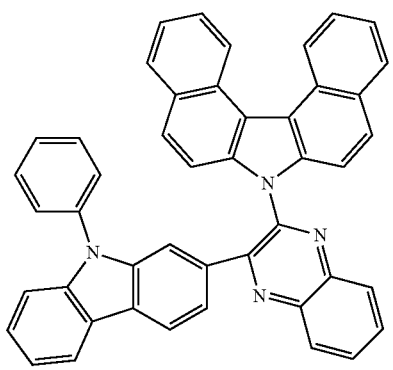
E-2-9
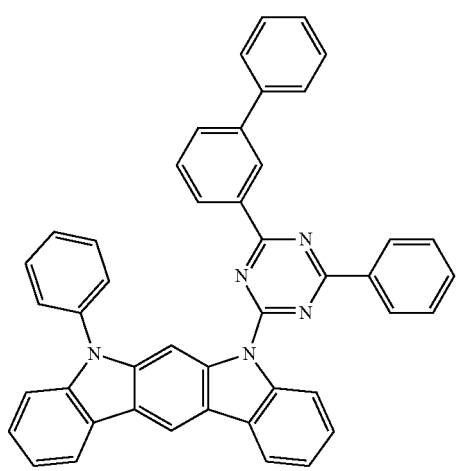
E-2-10
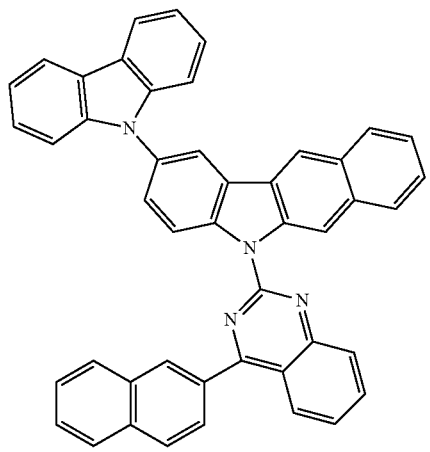
E-2-11
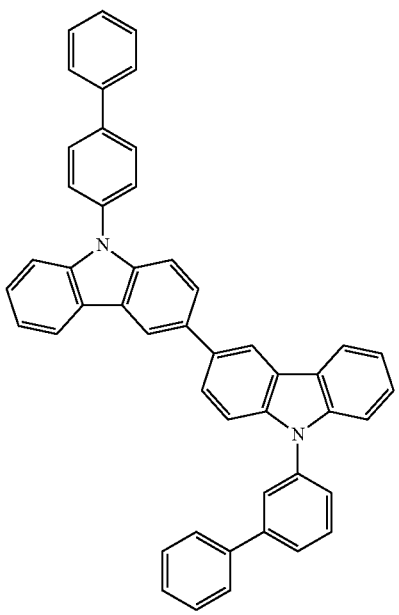
E-2-12
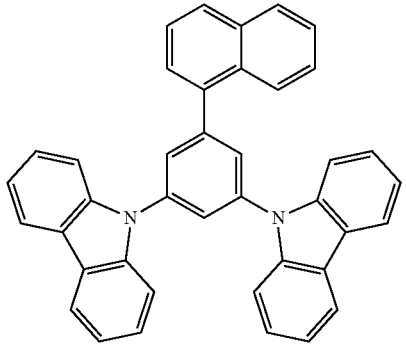

E-2-13
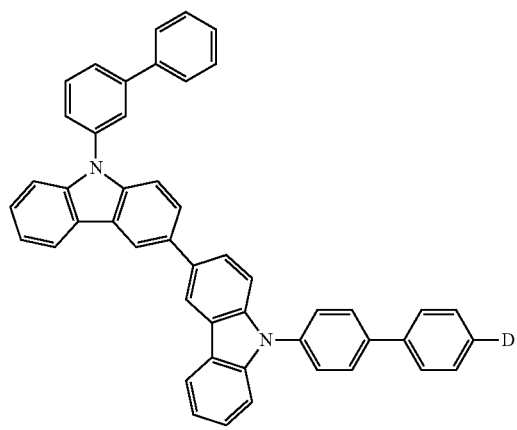
E-2-14
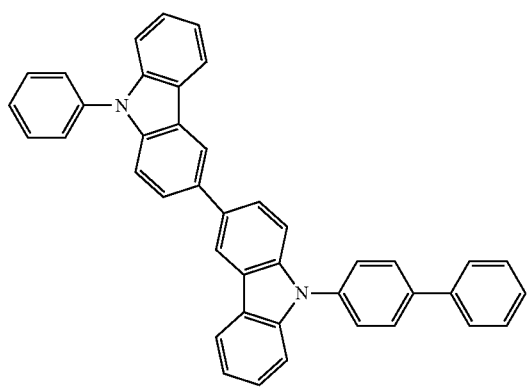
E-2-15
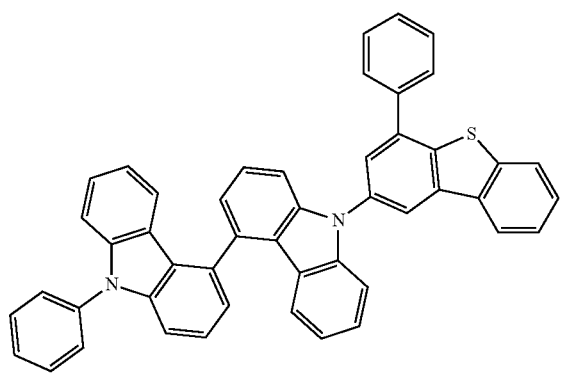
E-2-16
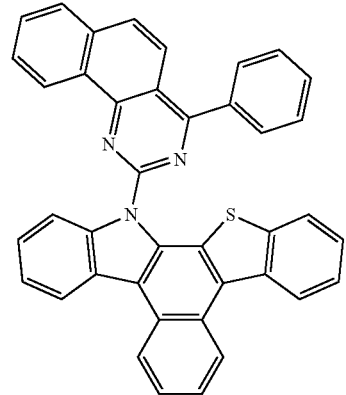
E-2-17
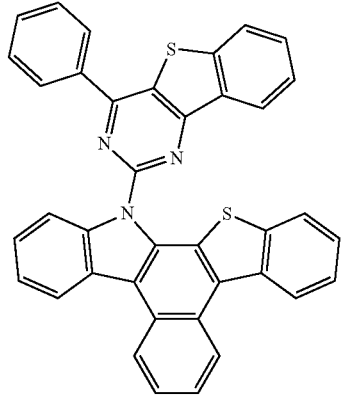
E-2-18
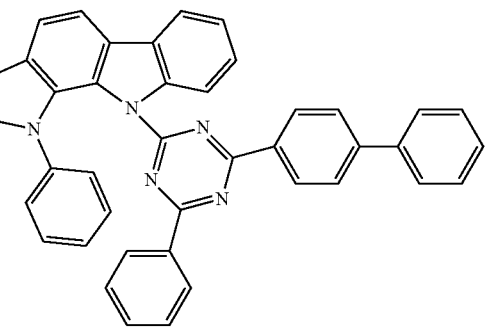
E-2-19
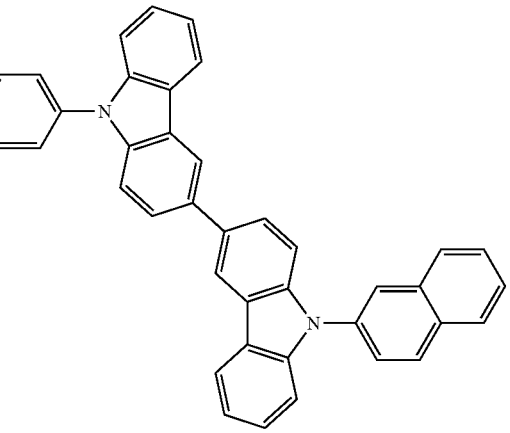
E-2-20
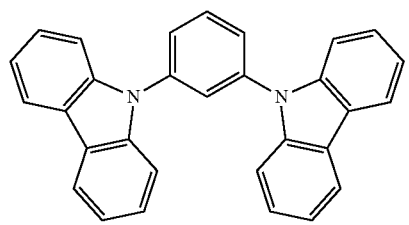

E-2-21
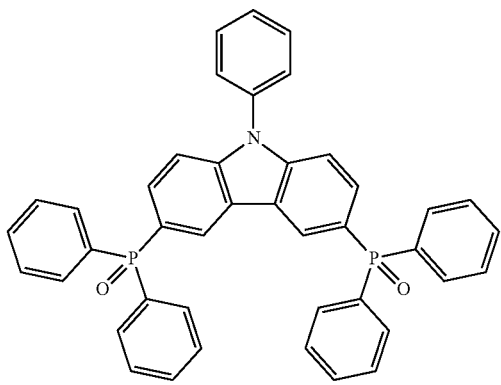

E-2-22
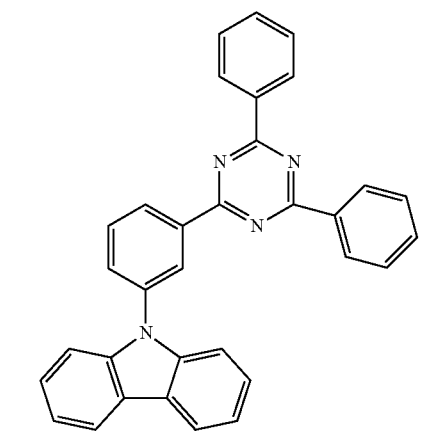

E-2-23
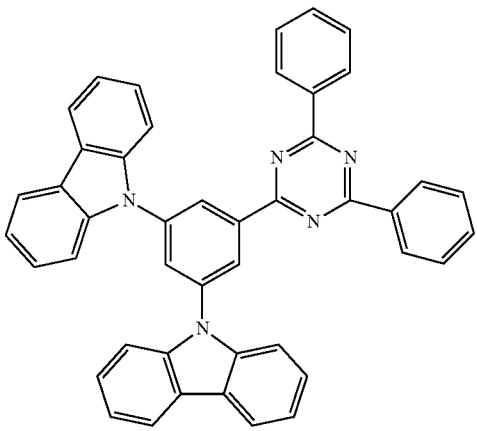

E-2-24
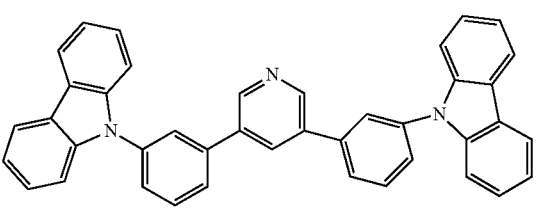

E-2-25
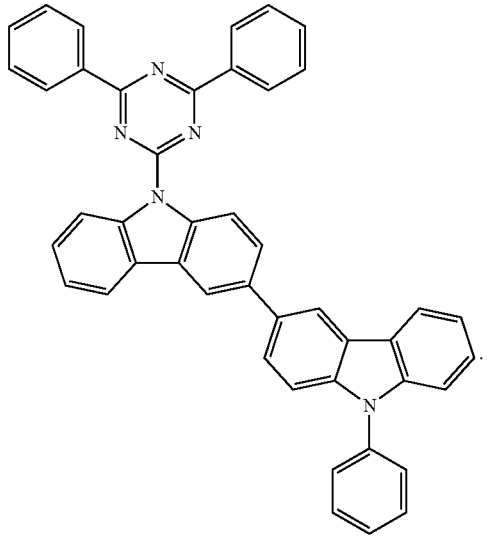

The emission layer EML may further include any suitable material in the art as a host material. For example, the emission layer EML may include, as a host material, at least one of bis[2-(diphenylphosphino)phenyl] ether oxide (DPEPO), 4,4'-bis(carbazol-9-yl)biphenyl (CBP), 1,3-bis (carbazol-9-yl)benzene (mCP), 2,8-bis(diphenylphosphoryl) dibenzo[b,d]furan (PPF), 4,4',4"-tris(carbazol-9-yl)-triphenylamine (TCTA), or 1,3,5-tris(1-phenyl-1H-benzo[d] imidazole-2-yl)benzene (TPBi). However, embodiments of the present disclosure are not limited thereto. For example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4', 4"-tris(carbazol-9-yl)-triphenylamine (TCTA), 1,3,5-tris(N-phenylbenzimidazole-2-yl)benzene (TPBi), 2-tert-butyl-9, 10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis (triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc. may be utilized as the host material.

The emission layer EML may include a compound represented by Formula M-a or Formula M-b. The compound represented by Formula M-a or Formula M-b may be utilized as a phosphorescence dopant material.

Formula M-a
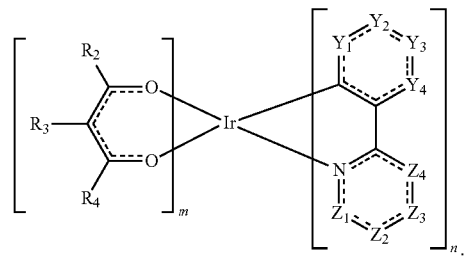

In Formula M-a, $Y_1$ to $Y_4$, and $Z_1$ to $Z_4$ may each independently be $CR_1$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, and/or may be combined with an adjacent group to form a ring. In Formula M-a, "m" may be 0 or 1, and "n" may be 2 or 3. In Formula M-a, when "m" is 0, "n" may be 3, and when "m" is 1, "n" may be 2.

The compound represented by Formula M-a may be utilized as a red phosphorescence dopant or a green phosphorescence dopant.

The compound represented by Formula M-a may be represented by any one among Compounds M-a1 to M-a19. However, Compounds M-a1 to M-a19 are examples, and the compound represented by Formula M-a is not limited to the compounds represented by Compounds M-a1 to M-a19.

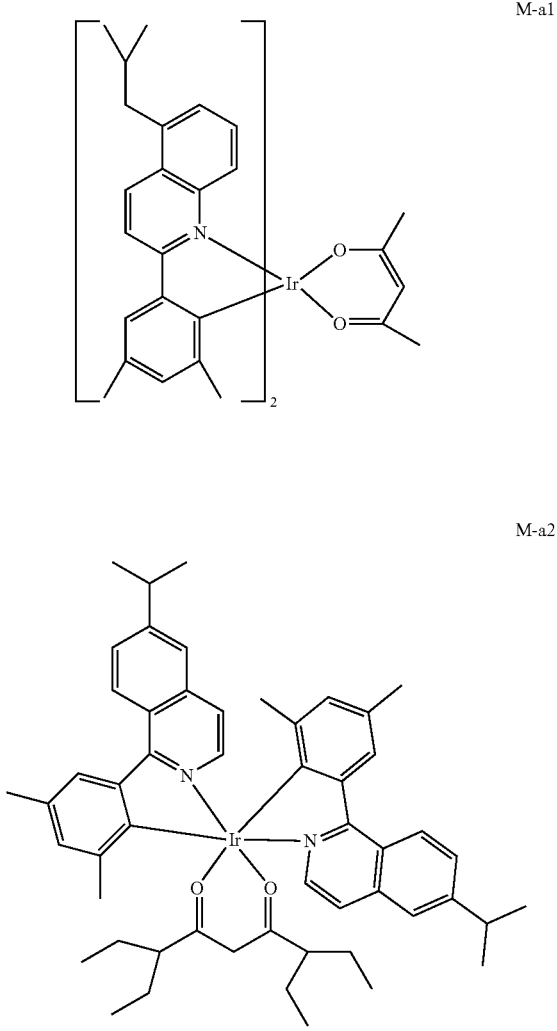

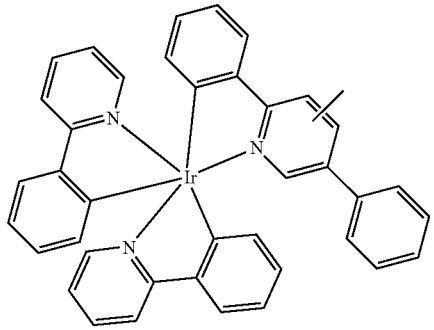

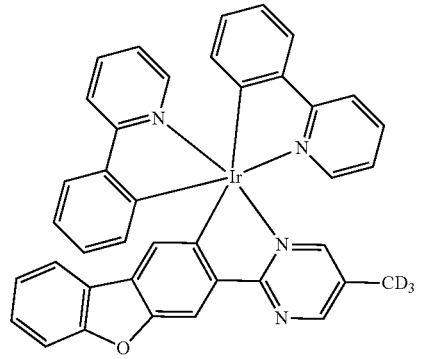

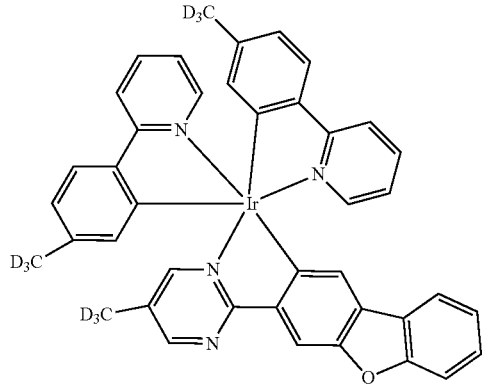

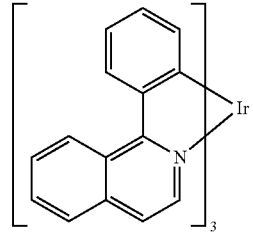

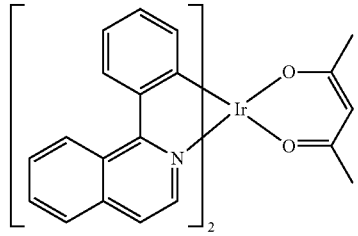

-continued
M-a8
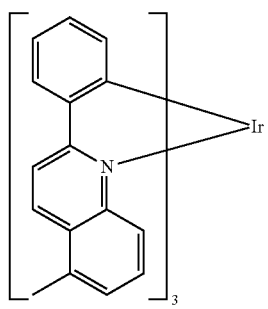
M-a9
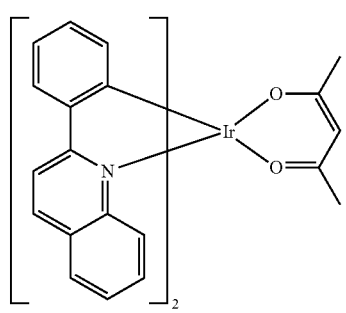
M-a10
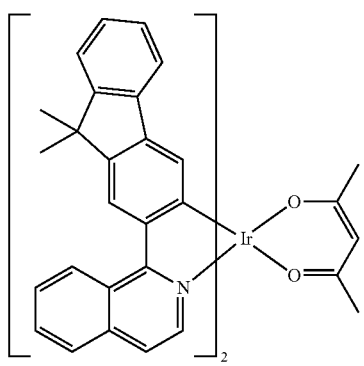
M-a11
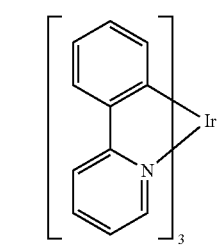
M-a12
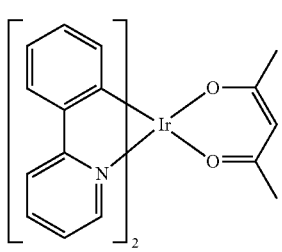
-continued
M-a13
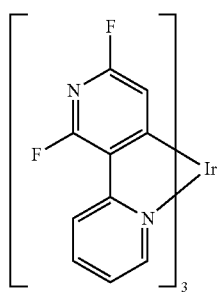
M-a14
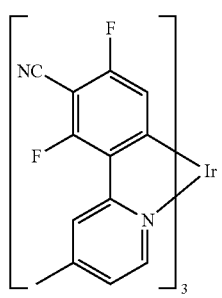
M-a15
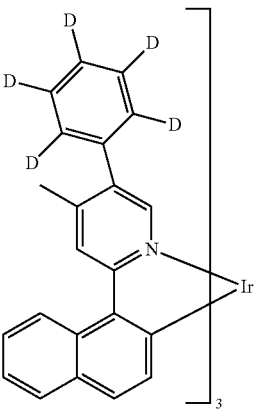
M-a16
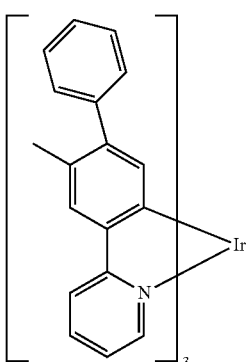

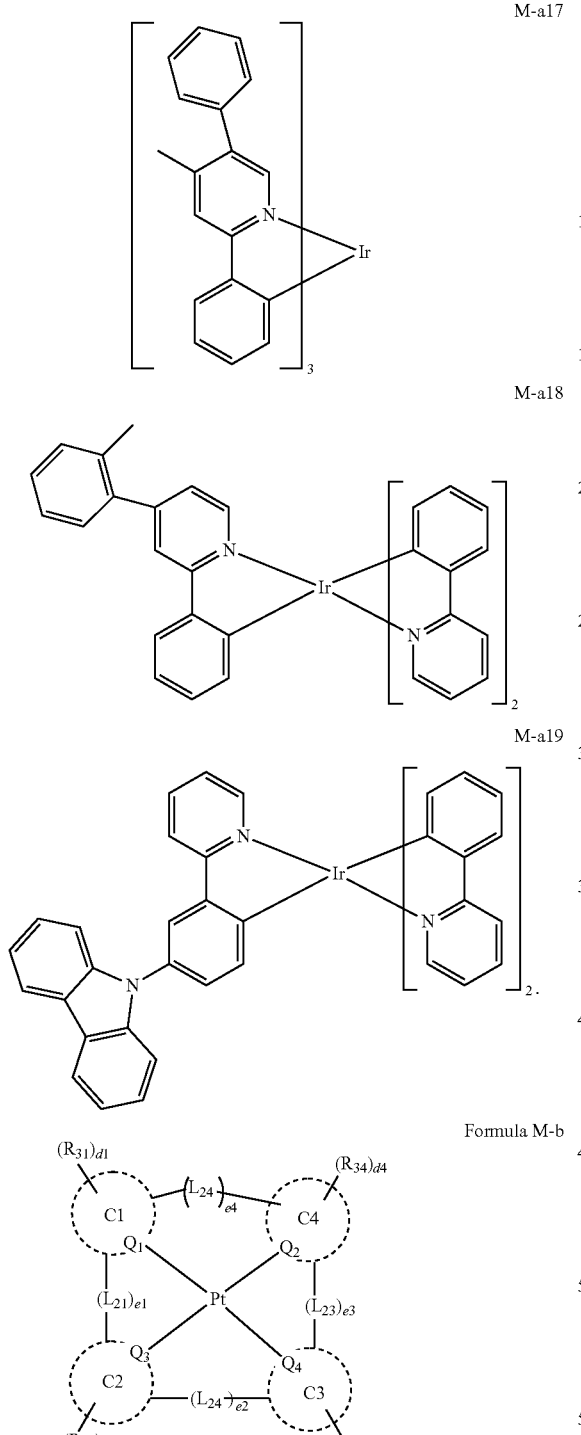

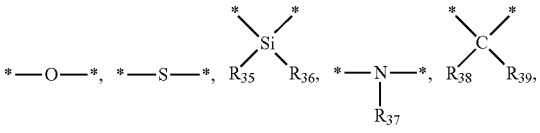

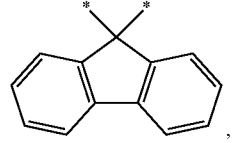

a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 may each independently be 0 or 1. $R_{31}$ to $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, and/or may be combined with an adjacent group to form a ring, and d1 to d4 may each independently be an integer of 0 to 4.

The compound represented by Formula M-b may be utilized as a blue phosphorescence dopant or a green phosphorescence dopant.

The compound represented by Formula M-b may be represented by any one among the compounds. However, the compounds are illustrations, and the compound represented by Formula M-b is not limited to the compounds represented.

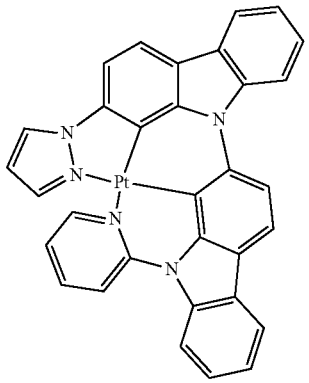

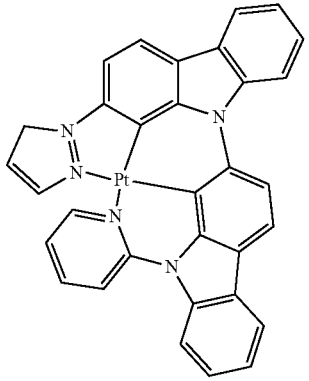

In Formula M-b, Q1 to Q4 may each independently be C or N, C1 to C4 may each independently be a substituted or unsubstituted hydrocarbon ring of 5 to 30 ring-forming carbon atoms, or a substituted or unsubstituted heterocycle of 2 to 30 ring-forming carbon atoms. $L_{21}$ to $L_{24}$ may each independently be a direct linkage, -continued
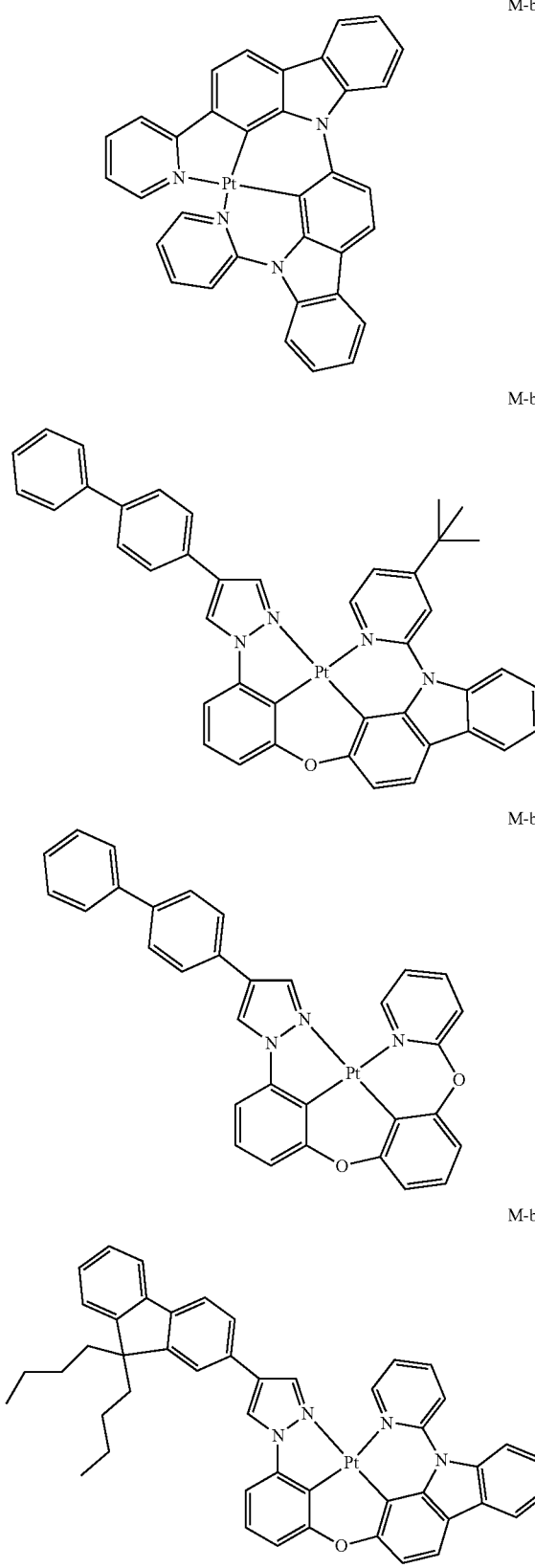
M-b-3
M-b-4
M-b-5
M-b-6
-continued
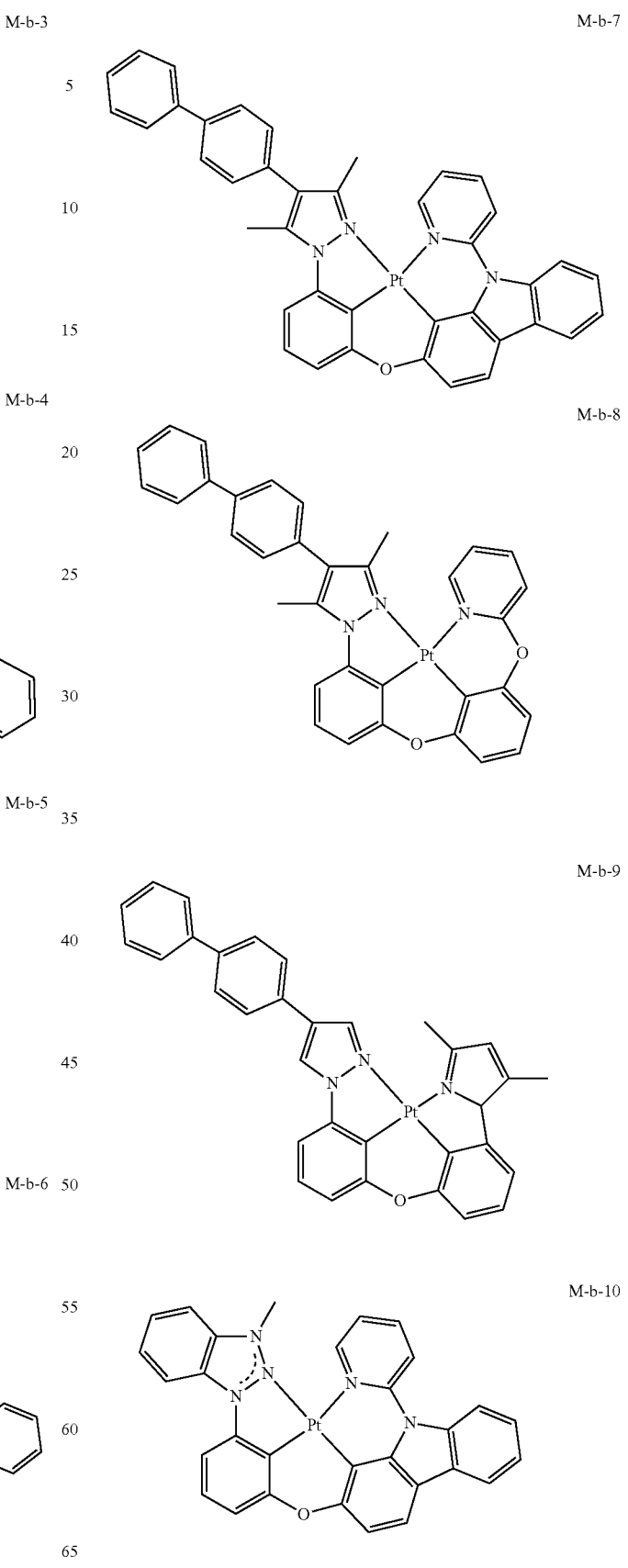
M-b-7
M-b-8
M-b-9
M-b-10

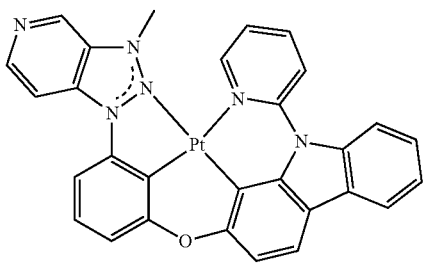

M-b-11

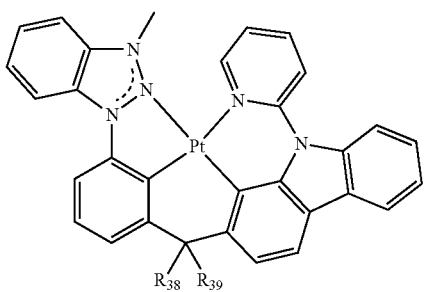

M-b-12

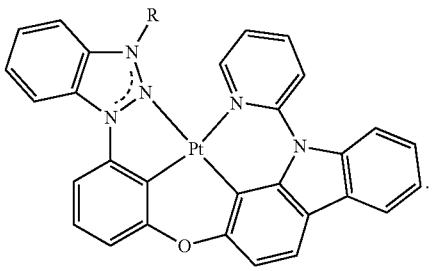

M-b-13

In the compounds above, R, $R_{38}$, and $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include any one among Formula F-a to Formula F-c. The compounds represented by Formula F-a to Formula F-c may be utilized as fluorescence dopant materials.

Formula F-a

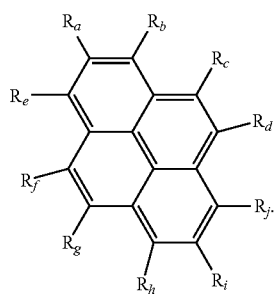

In Formula F-a, two selected from $R_a$ to $R_j$ may each independently be substituted with *—$NAr_1Ar_2$. The remainder not substituted with *—$NAr_1Ar_2$ among $R_a$ to $R_j$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In *—$NAr_1Ar_2$, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. For example, at least one among $Ar_1$ and $Ar_2$ may be a heteroaryl group including O or S as a ring-forming atom.

Formula F-b

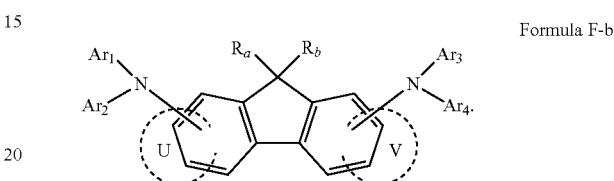

In Formula F-b, $R_a$ and $R_b$ may each independently be a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, and/or may be combined with an adjacent group to form a ring.

In Formula F-b, U and V may each independently be a substituted or unsubstituted hydrocarbon ring of 5 to 30 ring-forming carbon atoms, or a substituted or unsubstituted heterocycle of 2 to 30 ring-forming carbon atoms.

In Formula F-b, the number of rings represented by U and V may each independently be 0 or 1. For example, in Formula F-b, when the number of U or V is 1, one ring forms a fused ring at the designated part by U or V, and when the number of U or V is 0, a ring is not present at the designated part by U or V. For example, when the number of U is 0, and the number of V is 1, or when the number of U is 1, and the number of V is 0, the fused ring structure having the fluorene core of Formula F-b may be a ring compound with four rings. When the numbers of U and V are both 0 (e.g., simultaneously), the fused ring structure having the fluorene core of Formula F-b may be a ring compound with three rings. When the numbers of both U and V are both 1 (e.g., simultaneously), the fused ring structure having the fluorene core of Formula F-b may be a ring compound with five rings.

Formula F-c

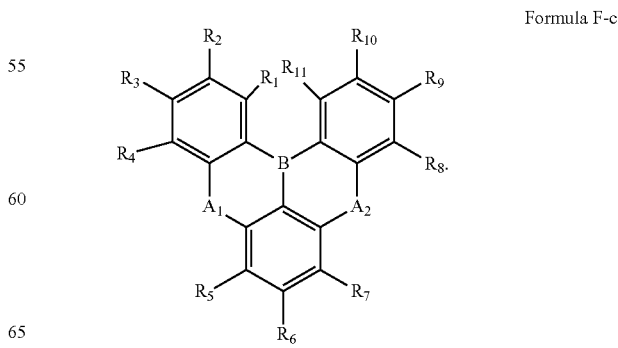

In Formula F-c, $A_1$ and $A_2$ may each independently be O, S, Se, or $NR_m$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. $R_1$ to $R_{11}$ may each independently be a hydrogen atom, a deuterium atom, a halogen atom, a cyano group, a substituted or unsubstituted amine group, a substituted or unsubstituted boron group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, and/or combined with an adjacent group to form a ring.

In Formula F-c, $A_1$ and $A_2$ may each independently be combined with the substituents of an adjacent ring to form a fused ring. For example, when $A_1$ is $NR_m$, $A_1$ may be combined with $R_4$ or $R_5$ to form a ring When $A_2$ is $NR_m$, $A_2$ may be combined with $R_7$ or $R_8$ to form a ring.

The emission layer EML may include a compound represented by Formula D. The compound represented by Formula D may be utilized as a dopant material for thermally activated delayed fluorescence.

Formula D

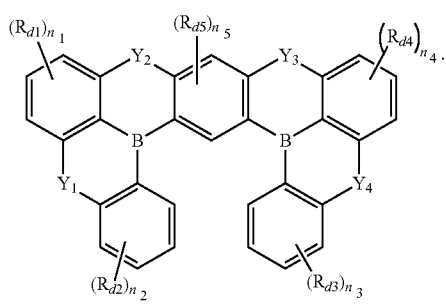

In Formula D, $Y_1$ to $Y_4$ may each independently be $NR_{d6}$, O or S. All $Y_1$ to $Y_4$ may be the same, or at least one among $Y_1$ to $Y_4$ may be different. For example, all $Y_1$ to $Y_4$ may be all $NR_{d6}$.

In Formula D, $R_{d1}$ to $R_{d6}$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms. For example, $R_{d1}$ to $R_{d6}$ may each independently be a hydrogen atom, a deuterium atom, a substituted or unsubstituted diphenylamine group, or a substituted or unsubstituted phenyl group.

In Formula D, "$n_1$" and "$n_4$" may each independently be an integer of 0 to 3. "$n_2$" and "$n_3$" may each independently be an integer of 0 to 4. "$n_5$" may be an integer of 0 to 2. When "$n_1$" to "$n_5$" are 0, the compound represented by Formula D may be unsubstituted with $R_{d1}$ to $R_{d5}$, respectively. When "$n_1$" to "$n_5$" are 2, multiple $R_{d1}$'s to $R_{d5}$'s may be the same, or at least one among multiple $R_{d1}$'s to $R_{d5}$'s may be different.

The compound represented by Formula D may be Compound D-1. However, the compound is an illustration, and the compound represented by Formula D is not limited to Compound D-1:

D-1

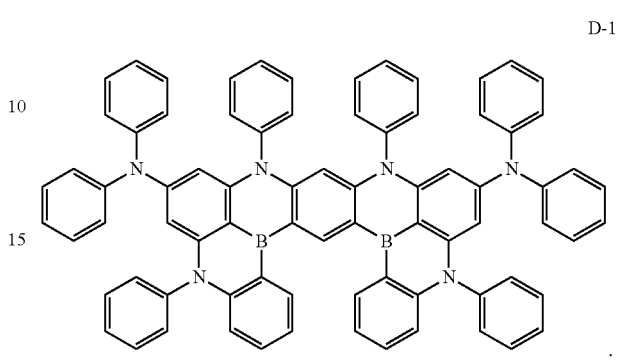

In an embodiment, the emission layer EML may include, as a suitable dopant material, styryl derivatives (for example, 1,4-bis[2-(3-N-ethylcarbazolyl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi), and 4,4'-bis[2-(4-(N,N-diphenylamino)phenyl)vinyl]biphenyl (DPAVBi)), perylene and/or derivatives thereof (for example, 2,5,8,11-tetra-t-butylperylene (TBP)), pyrene and/or derivatives thereof (for example, 1,1-dipyrene, 1,4-dipyrenylbenzene, and 1,4-bis (N,N-diphenylamino)pyrene), etc.

The emission layer EML may include any suitable phosphorescence dopant material. For example, the phosphorescence dopant may utilize a metal complex including iridium (Ir), platinum (Pt), osmium (Os), gold (Au), titanium (Ti), zirconium (Zr), hafnium (Hf), europium (Eu), terbium (Tb) and/or thulium (Tm). For example, iridium(III) bis(4,6-difluorophenylpyridinato-N,C2')picolinate (Firpic), bis(2,4-difluorophenylpyridinato)-tetrakis(1-pyrazolyl)borate iridium(III) (Fir6), and/or platinum octaethyl porphyrin (PtOEP) may be utilized as the phosphorescence dopant. However, embodiments of the present disclosure are not limited thereto.

The emission layer EML may include a quantum dot material. The core of the quantum dot may be selected from a II-VI group compound, a III-VI group compound, a I-III-VI group compound, a III-V group compound, a IV-VI group compound, a IV group element, a IV group compound, and combinations thereof.

The II-VI group compound may be selected from the group consisting of: a binary compound selected from the group consisting of CdSe, CdTe, CdS, ZnS, ZnSe, ZnTe, ZnO, HgS, HgSe, HgTe, MgSe, MgS, and mixtures thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof.

The III-VI group compound may include a binary compound (such as $In_2S_3$, and/or $In_2Se_3$), a ternary compound (such as $InGaS_3$ and/or $InGaSe_3$), or one or more optional combinations thereof.

The I-III-VI group compound may be selected from a ternary compound selected from the group consisting of AgInS, AgInS$_2$, CuInS, CuInS$_2$, AgGaS$_2$, CuGaS$_2$, CuGaO$_2$, AgGaO$_2$, AgAlO$_2$ and mixtures thereof, and a quaternary compound (such as AgInGaS$_2$ and/or CuIn-GaS$_2$).

The III-V group compound may be selected from the group consisting of a binary compound selected from the group consisting of GaN, GaP, GaAs, GaSb, AlN, AlP, AlAs, AlSb, InN, InP, InAs, InSb, and mixtures thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof. In some embodiments, the III-V group compound may further include a II group metal. For example, InZnP, etc. may be selected as a III-II-V group compound.

The IV-VI group compound may be selected from the group consisting of a binary compound selected from the group consisting of SnS, SnSe, SnTe, PbS, PbSe, PbTe, and mixtures thereof, a ternary compound selected from the group consisting of SnSeS, SnSeTe, SnSTe, PbSeS, PbSeTe, PbSTe, SnPbS, SnPbSe, SnPbTe, and mixtures thereof, and a quaternary compound selected from the group consisting of SnPbSSe, SnPbSeTe, SnPbSTe, and mixtures thereof. The IV group element may be selected from the group consisting of Si, Ge, and a mixture thereof. The IV group compound may be a binary compound selected from the group consisting of SiC, SiGe, and a mixture thereof.

In this case, the binary compound, the ternary compound and/or the quaternary compound may each independently be present at a substantially uniform concentration in a particle, or may be present at a partially different concentration distribution state in the same particle (e.g., may have non-uniform concentration within the particle). In some embodiments, a core/shell structure in which one quantum dot wraps another quantum dot may be possible. The interface of the core and the shell may have a concentration gradient in which the concentration of an element present in the shell is decreased toward the center.

In some embodiments, the quantum dot may have the above-described core-shell structure including a core including a nanocrystal and a shell wrapping the core. The shell of the quantum dot may act as a protection layer for preventing or reducing the chemical deformation of the core to maintain semiconductor properties, and/or as a charging layer for imparting the quantum dot with electrophoretic properties. The shell may have a single layer or may be a multilayer shell. Examples of the shell of the quantum dot may include a metal or non-metal oxide, a semiconductor compound, and/or one or more combinations thereof.

For example, the metal or non-metal oxide may include a binary compound (such as SiO$_2$, Al$_2$O$_3$, TiO$_2$, ZnO, MnO, Mn$_2$O$_3$, Mn$_3$O$_4$, CuO, FeO, Fe$_2$O$_3$, Fe$_3$O$_4$, CoO, Co$_3$O$_4$ and/or NiO), and/or a ternary compound (such as MgAl$_2$O$_4$, CoFe$_2$O$_4$, NiFe$_2$O$_4$ and/or CoMn$_2$O$_4$), but embodiments of the present disclosure are not limited thereto.

Also, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments of the present disclosure are not limited thereto.

The quantum dot may have a full width of half maximum (FWHM) of emission wavelength spectrum of about 45 nm or less, about 40 nm or less, or about 30 nm or less. Within this range, color purity and/or color reproducibility may be improved. As light emitted via quantum dots is emitted in all directions, the light view angle properties of a display device according to embodiments of the present disclosure may be improved.

The quantum dot may have any suitable shape in the art, without specific limitation. For example, the shape of a spherical, pyramidal, multi-arm, or cubic nanoparticle, nanotube, nanowire, nanofiber, nanoplate particle, etc. may be utilized.

The quantum dot may control the color of light emitted according to the particle size, and accordingly, the quantum dot may have one or more suitable emission colors (such as blue, red and/or green).

In the light emitting device ED of an embodiment, as shown in FIG. 3 to FIG. 6, the electron transport region ETR is provided on the emission layer EML. The electron transport region ETR may include at least one of an electron blocking layer HBL, an electron transport layer ETL or an electron injection layer EIL. However, embodiments of the present disclosure are not limited thereto.

The electron transport region ETR may have a single layer formed utilizing a single material, a single layer formed utilizing multiple different materials, or a multilayer structure having multiple layers formed utilizing multiple different materials.

For example, the electron transport region ETR may have a single layer structure of an electron injection layer EIL or an electron transport layer ETL, or a single layer structure formed utilizing an electron injection material and an electron transport material. Further, the electron transport region ETR may have a single layer structure formed utilizing multiple different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, about 1,000 Å to about 1,500 Å.

The electron transport region ETR may be formed utilizing one or more suitable methods (such as a vacuum deposition method, a spin coating method, a cast method, a Langmuir-Blodgett (LB) method, an inkjet printing method, a laser printing method, and/or a laser induced thermal imaging (LITI) method).

The electron transport region ETR may include a compound represented by Formula ET-1:

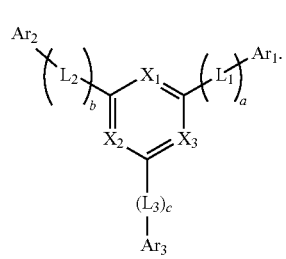

Formula ET-1

In Formula ET-1, at least one among $X_1$ to $X_3$ may be N, and the remainder may be $CR_a$. $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. $Ar_1$ to $Ar_3$ may each independently be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, "a" to "c" may each independently be an integer of 0 to 10. In Formula ET-1, $L_1$ to $L_3$ may each independently be a direct linkage, a substituted or unsubstituted arylene group of 6 to 30 ring-forming carbon atoms, or a substituted or unsubstituted heteroarylene group of 2 to 30 ring-forming carbon atoms. When "a" to "c" are integers of 2 or more, $L_1$ to $L_3$ may each independently be a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, embodiments of the present disclosure are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate (Bebq₂), 9,10-di(naphthalene-2-yl)anthracene (ADN), 1,3-bis[3,5-di(pyridin-3-yl)phenyl]benzene (BmPyPhB), and one or more mixtures thereof, without limitation.

The electron transport region ETR may include at least one among Compounds ET1 to ET36:

ET1

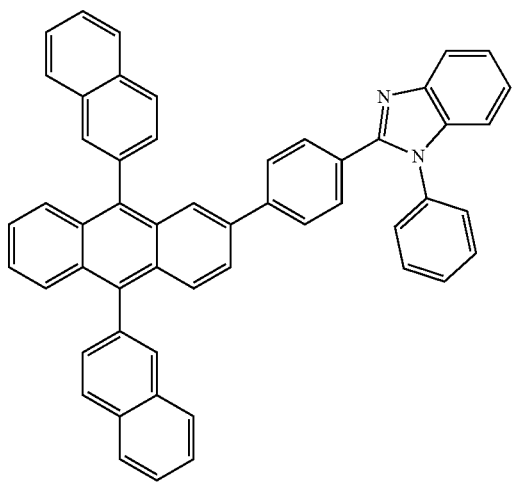

ET2

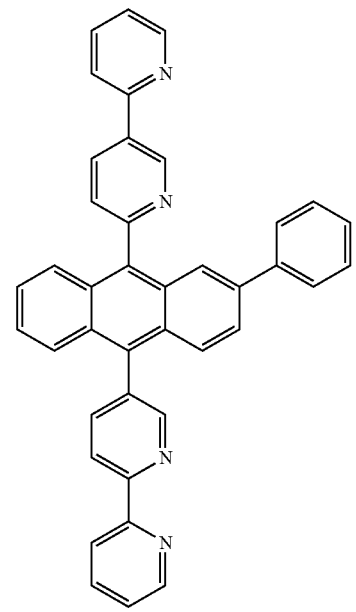

ET3

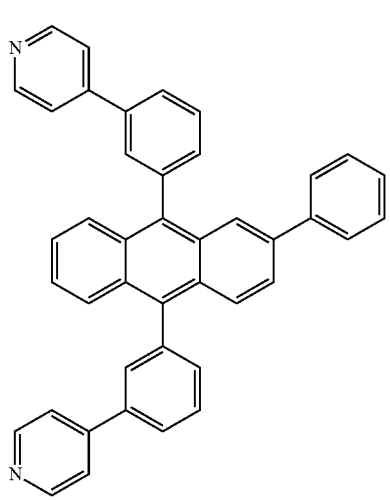

ET4

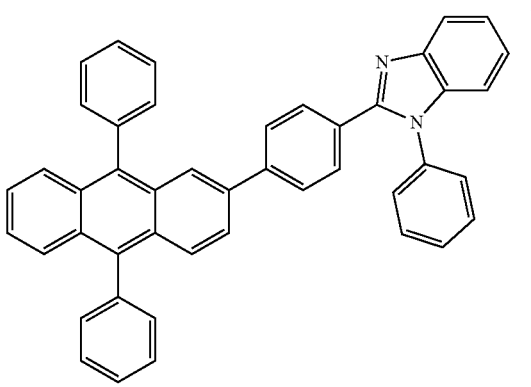

103
-continued
104
-continued
ET5
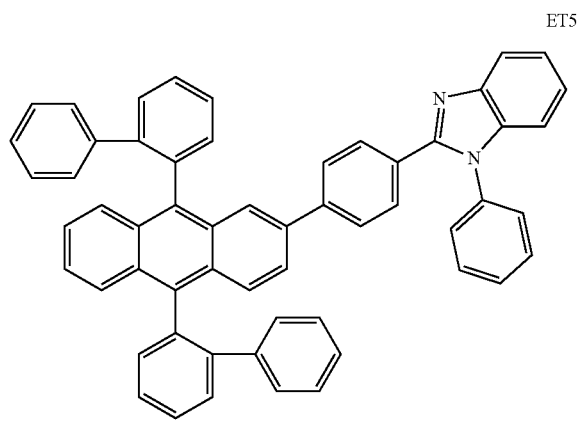
ET8
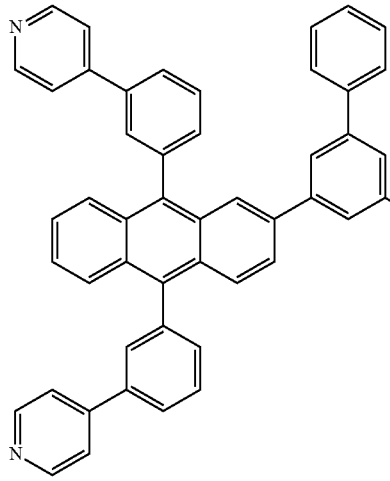
ET6
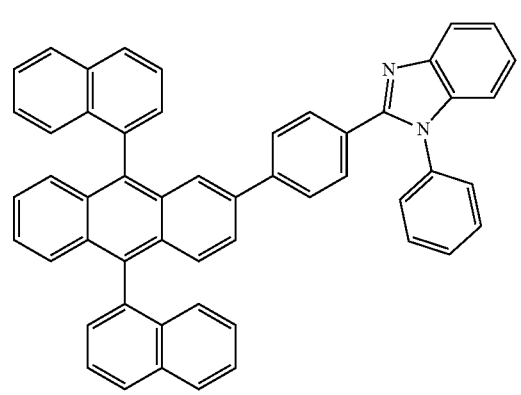
ET7
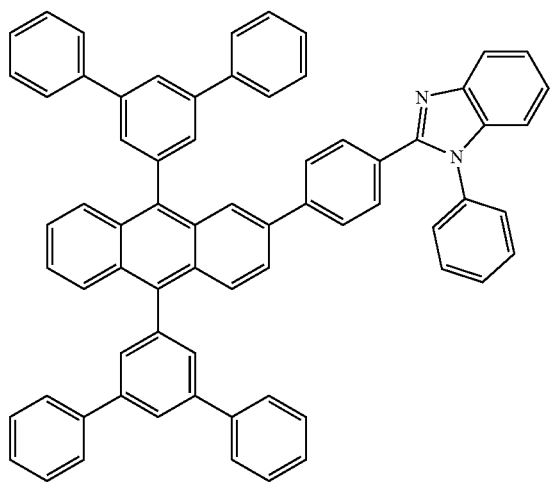
ET9
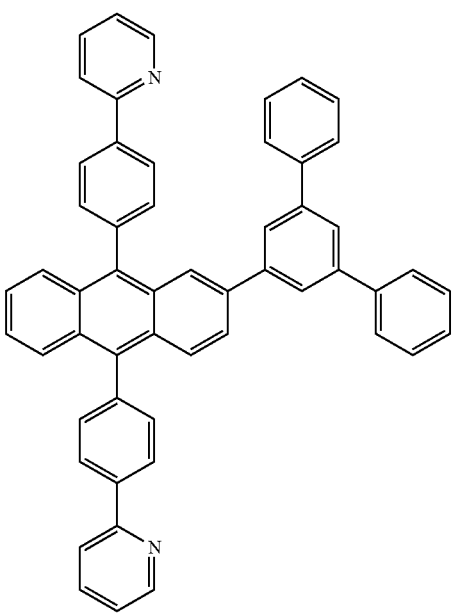

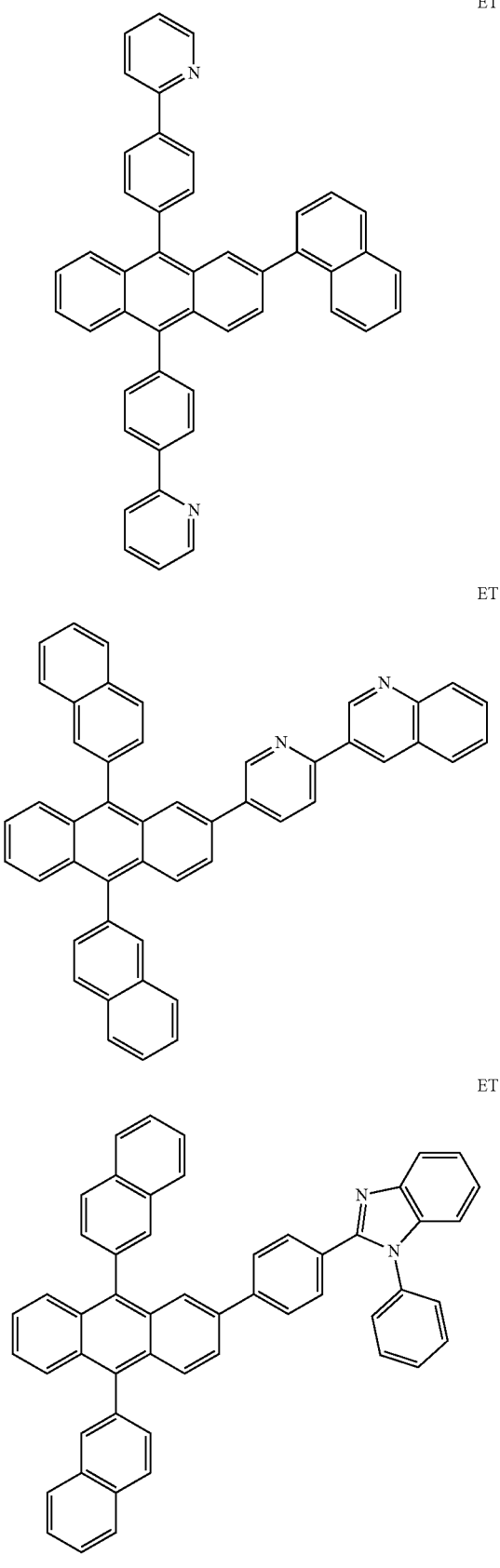
ET10
ET11
ET12
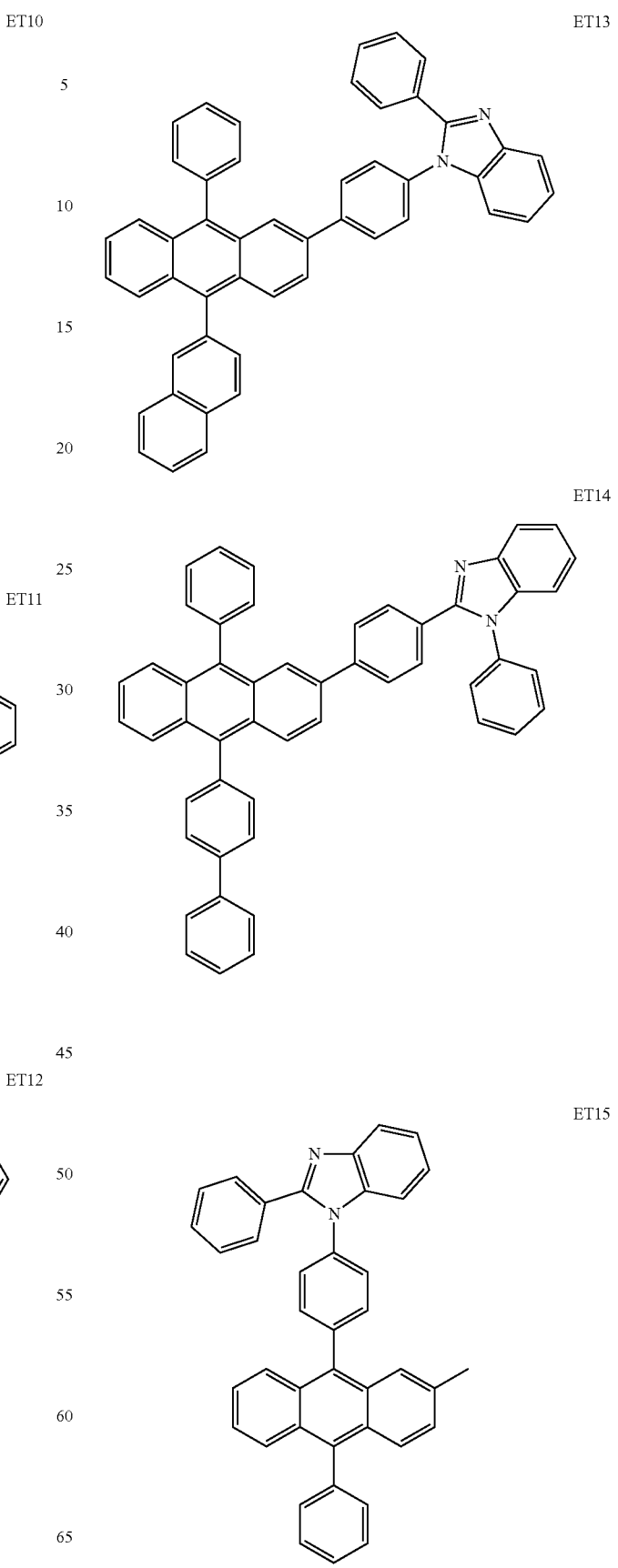
ET13
ET14
ET15

ET16
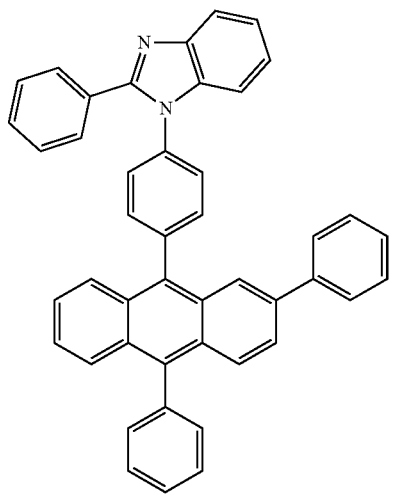
ET17
ET18
ET19
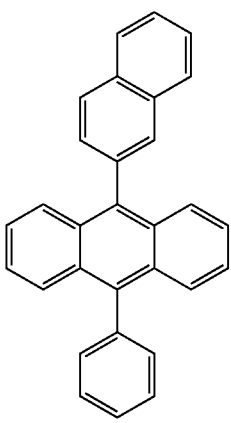
ET20
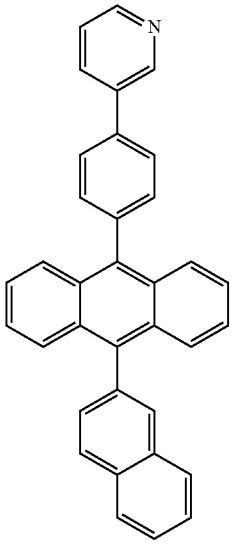
ET21
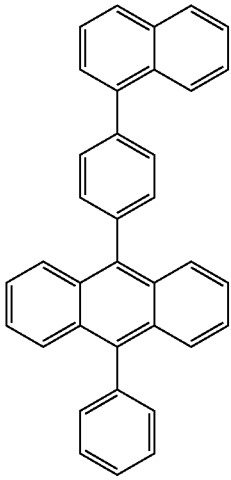

ET22
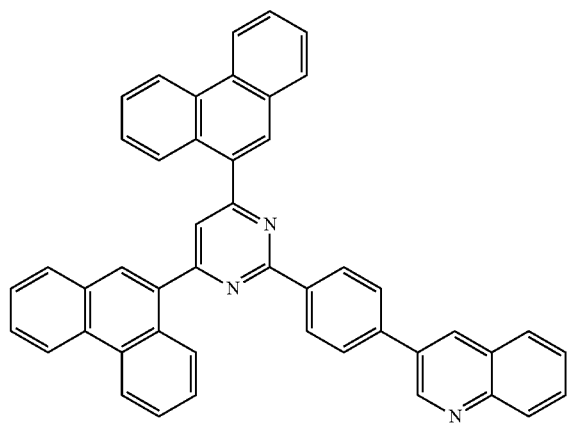
ET25
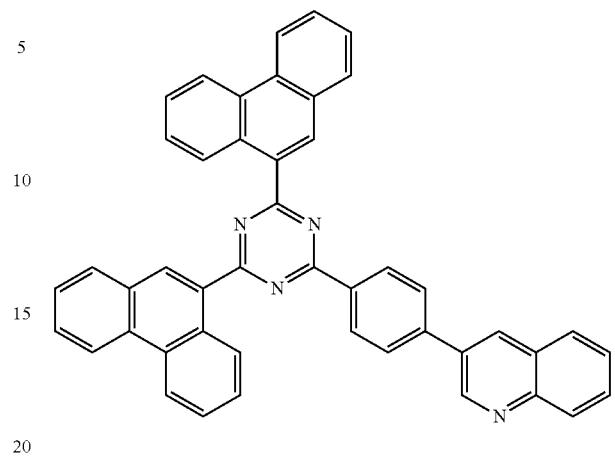
ET23
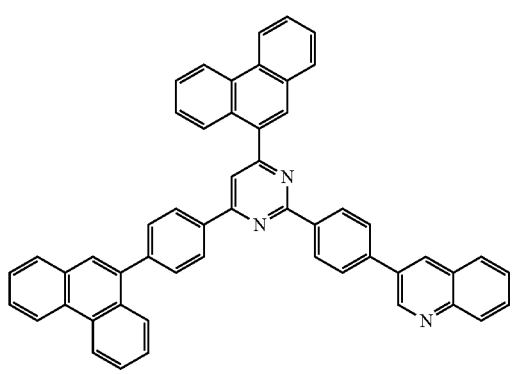
ET26
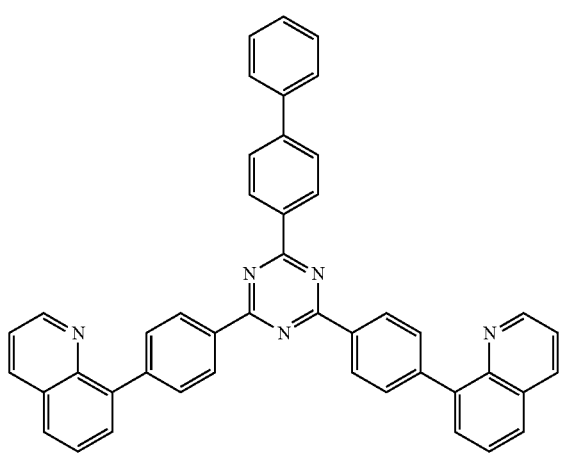
ET24
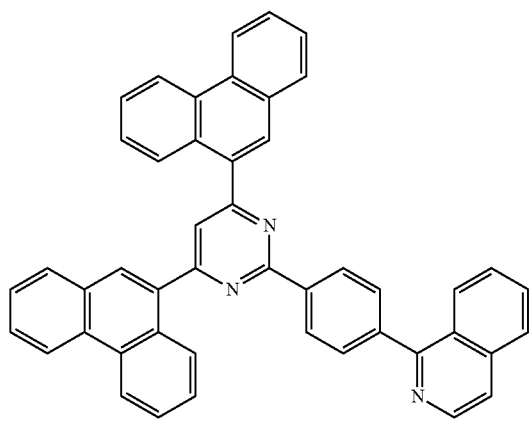
ET27
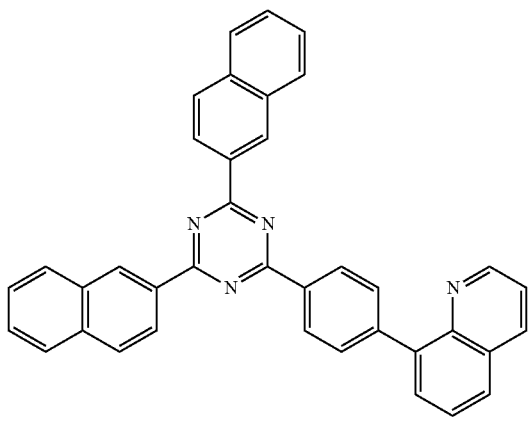

ET28
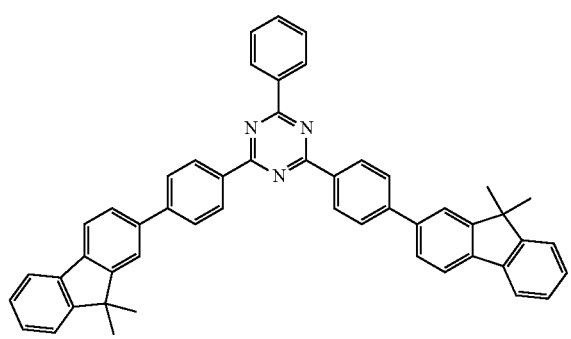
ET29
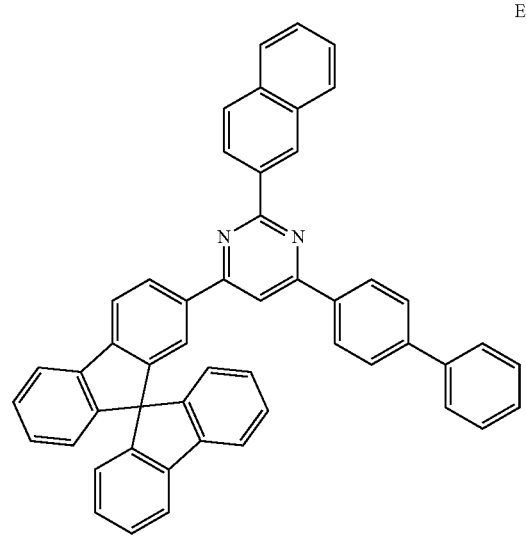
ET30
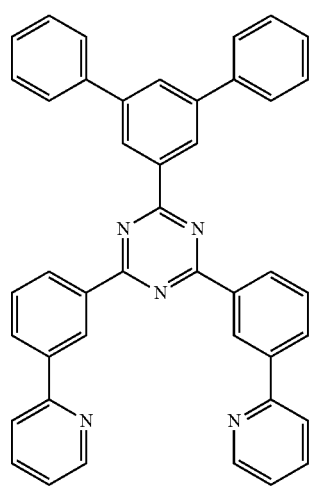
ET31
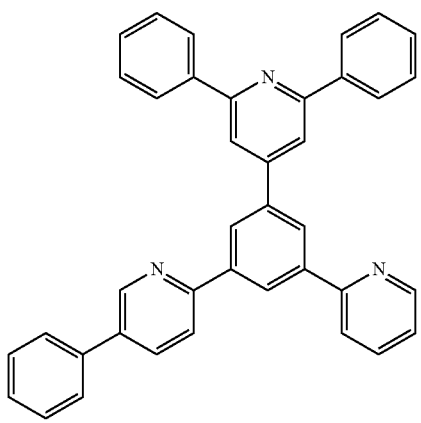
ET32
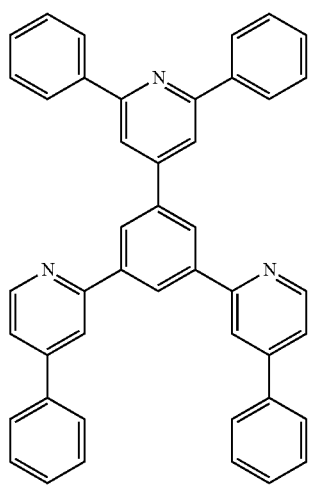
ET33
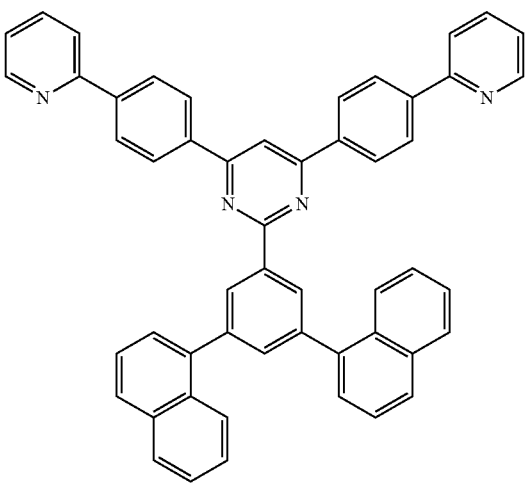

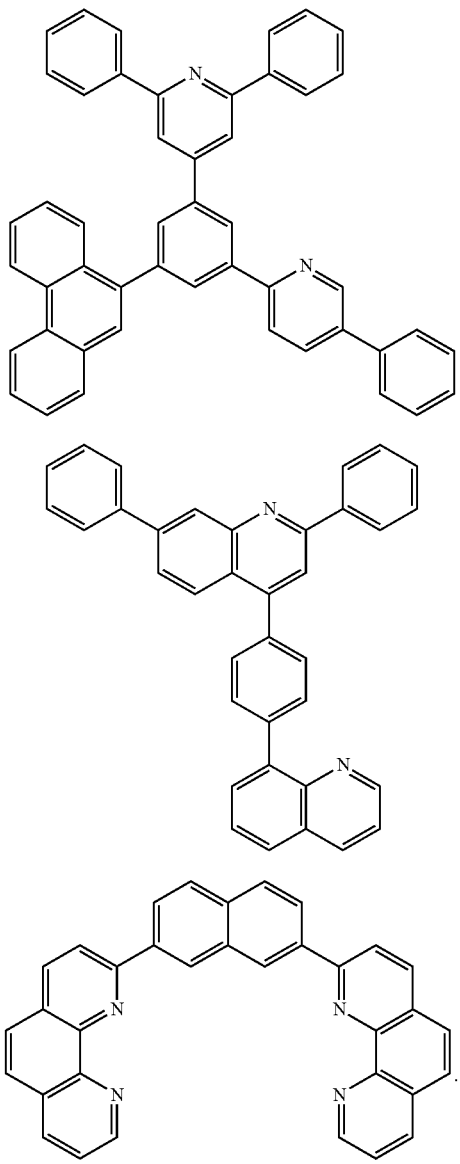

ET34

ET35

ET36

In some embodiments, the electron transport region ETR may include a metal halide (such as LiF, NaCl, CsF, RbCl, RbI, CuI and/or KI), a lanthanide metal (such as Yb), or a co-deposited mixture of the metal halide and the lanthanide metal. For example, the electron transport region ETR may include KI:Yb, RbI:Yb, etc., as the co-deposited material. In some embodiments, the electron transport region ETR may utilize a metal oxide (such as $Li_2O$ and/or BaO), or 8-hydroxy-lithium quinolate (LiQ). However, embodiments of the present disclosure are not limited thereto. The electron transport region ETR may also be formed by utilizing a mixture material of an electron transport material and an insulating organo metal salt. The organo metal salt may be a material having an energy band gap of about 4 eV or more. The organo metal salt may include, for example, metal acetates, metal benzoates, metal acetoacetates, metal acetylacetonates, and/or metal stearates.

The electron transport region ETR may include at least one of 2,9-dimethyl-4,7-diphenyl-1,10-phenanthroline (BCP), or 4,7-diphenyl-1,10-phenanthroline (Bphen) in addition to the aforementioned materials. However, embodiments of the present disclosure are not limited thereto.

The electron transport region ETR may include the compounds of the electron transport region in at least one among an electron injection layer EIL, an electron transport layer ETL, and a hole blocking layer HBL.

When the electron transport region ETR includes the electron transport layer ETL, the thickness of the electron transport layer ETL may be about 100 Å to about 1,000 Å, for example, about 150 Å to about 500 Å. When the thickness of the electron transport layer ETL satisfies the above-described range, satisfactory electron transport properties may be obtained without substantial increase of a driving voltage. When the electron transport region ETR includes the electron injection layer EIL, the thickness of the electron injection layer EIL may be about 1 Å to about 100 Å, and about 3 Å to about 90 Å. When the thickness of the electron injection layer EIL satisfies the above described range, satisfactory electron injection properties may be obtained without inducing a substantial increase in driving voltage.

The second electrode EL2 is provided on the electron transport region ETR. The second electrode EL2 may be a common electrode. The second electrode EL2 may be a cathode or an anode, but embodiments of the present disclosure are not limited thereto. For example, when the first electrode EL1 is an anode, the second cathode EL2 is a cathode, and when the first electrode EL1 is a cathode, the second electrode EL2 is an anode.

The second electrode EL2 may be a transmissive electrode, a transflective electrode or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, In, Zn, Sn, one or more compounds thereof, or one or more mixtures thereof (for example, AgMg, AgYb, or MgAg). In some embodiments, the second electrode EL2 may have a multilayered structure including a reflective layer or a transflective layer formed utilizing the above-described materials and a transparent conductive layer formed utilizing ITO, IZO, ZnO, ITZO, etc. For example, the second electrode EL2 may include the aforementioned metal material(s), combinations of two or more selected from the aforementioned metal materials, or one or more oxides of the aforementioned metal materials.

In some embodiments, the second electrode EL2 may be connected with an auxiliary electrode. When the second electrode EL2 is connected with the auxiliary electrode, the resistance of the second electrode EL2 may decrease.

In some embodiments, a capping layer CPL may be further disposed on the second electrode EL2 in the light emitting device ED of an embodiment. The capping layer CPL may include a multilayer or a single layer.

In an embodiment, the capping layer CPL may be an organic layer or an inorganic layer. For example, when the capping layer CPL includes an inorganic material, the inorganic material may include an alkali metal compound (such as LiF) and/or an alkaline earth metal compound (such as $MgF_2$, SiON, $SiN_x$, $SiO_y$, etc.)

For example, when the capping layer CPL includes an organic material, the organic material may include α-NPD, NPB, TPD, m-MTDATA, $Alq_3$, CuPc, N4,N4,N4',N4'-tetra (biphenyl-4-yl) biphenyl-4,4'-diamine (TPD15), 4,4',4''-tris (carbazol-9-yl) triphenylamine (TCTA), etc., or includes an epoxy resin, or acrylate (such as methacrylate). In some embodiments, a capping layer CPL may include at least one among Compounds P1 to P5, but embodiments of the present disclosure are not limited thereto.

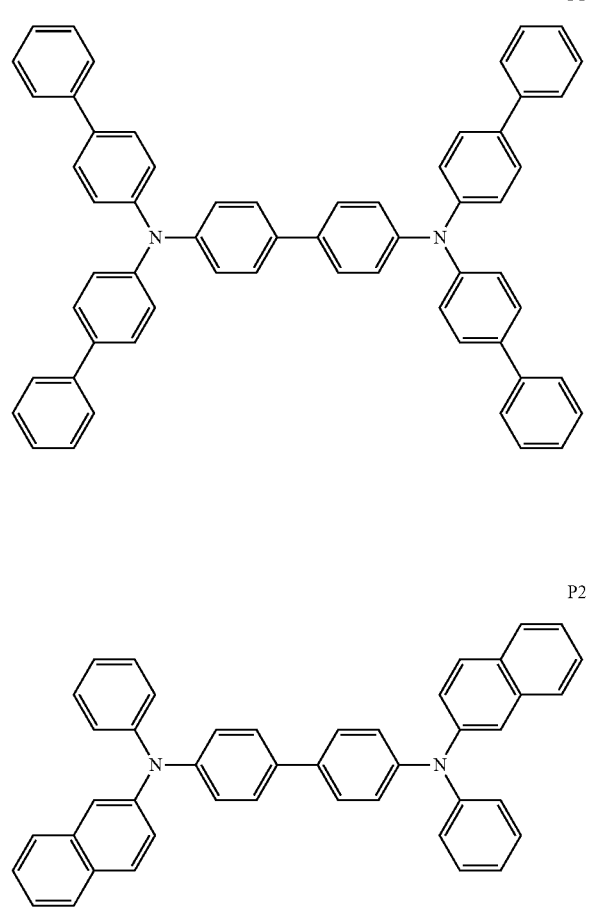

P1

P2

P3

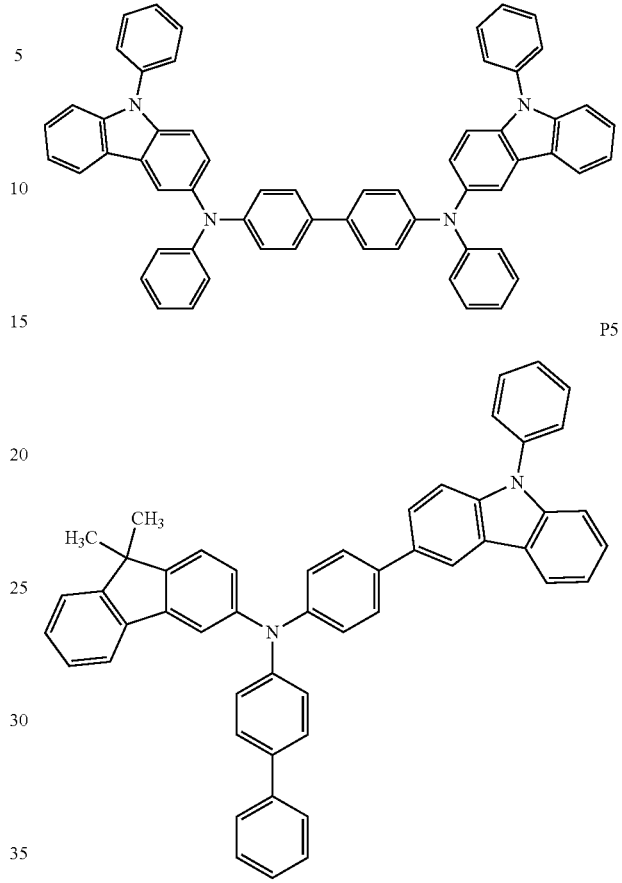

P4

P5

In some embodiments, the refractive index of the capping layer CPL may be about 1.6 or more. For example, the refractive index of the capping layer CPL with respect to light in a wavelength range of about 550 nm to about 660 nm may be about 1.6 or more.

Figure 7:
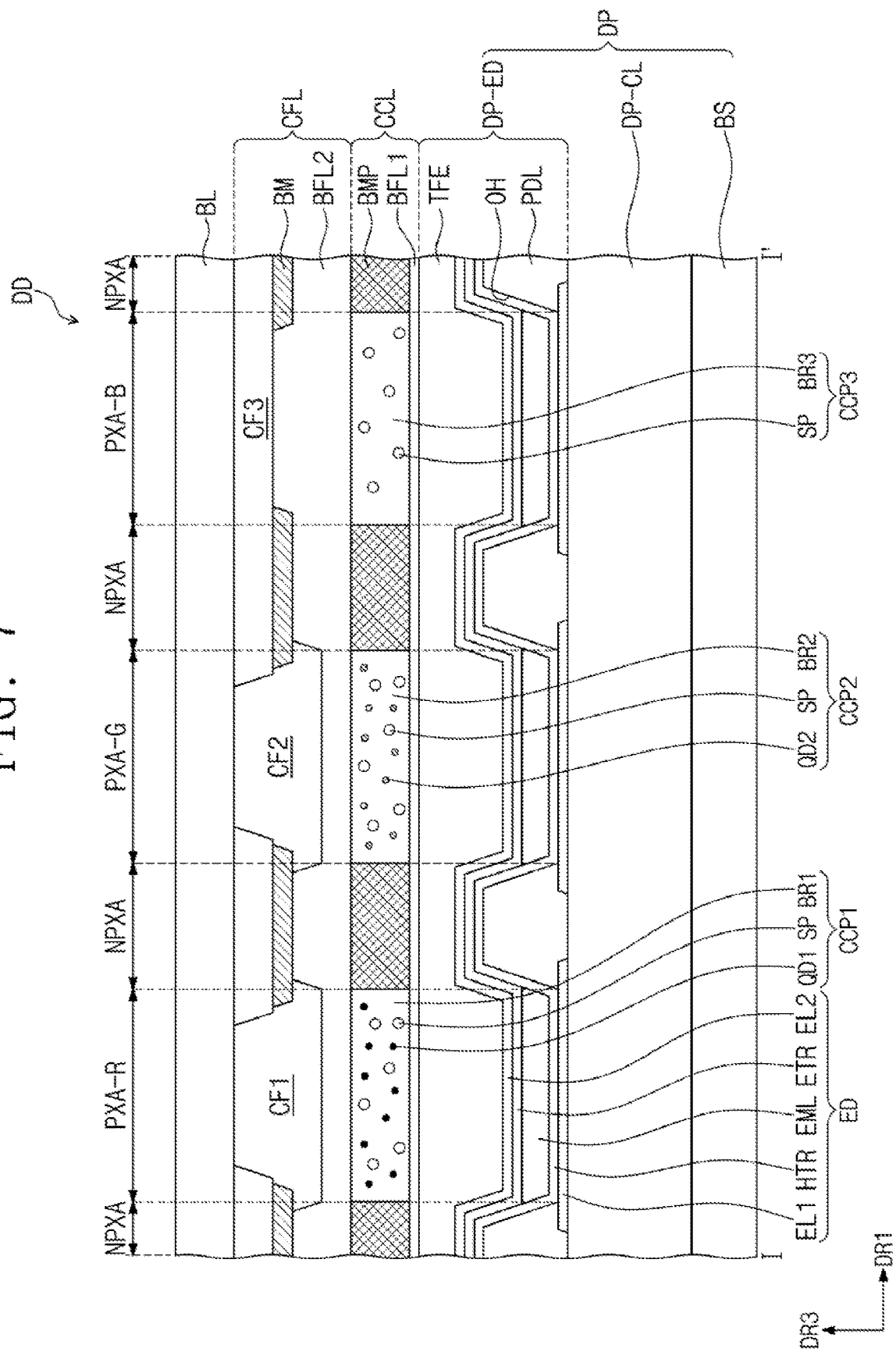
FIG. 7 and FIG. 8 are cross-sectional views on display apparatuses according to embodiments.
Figure 8:
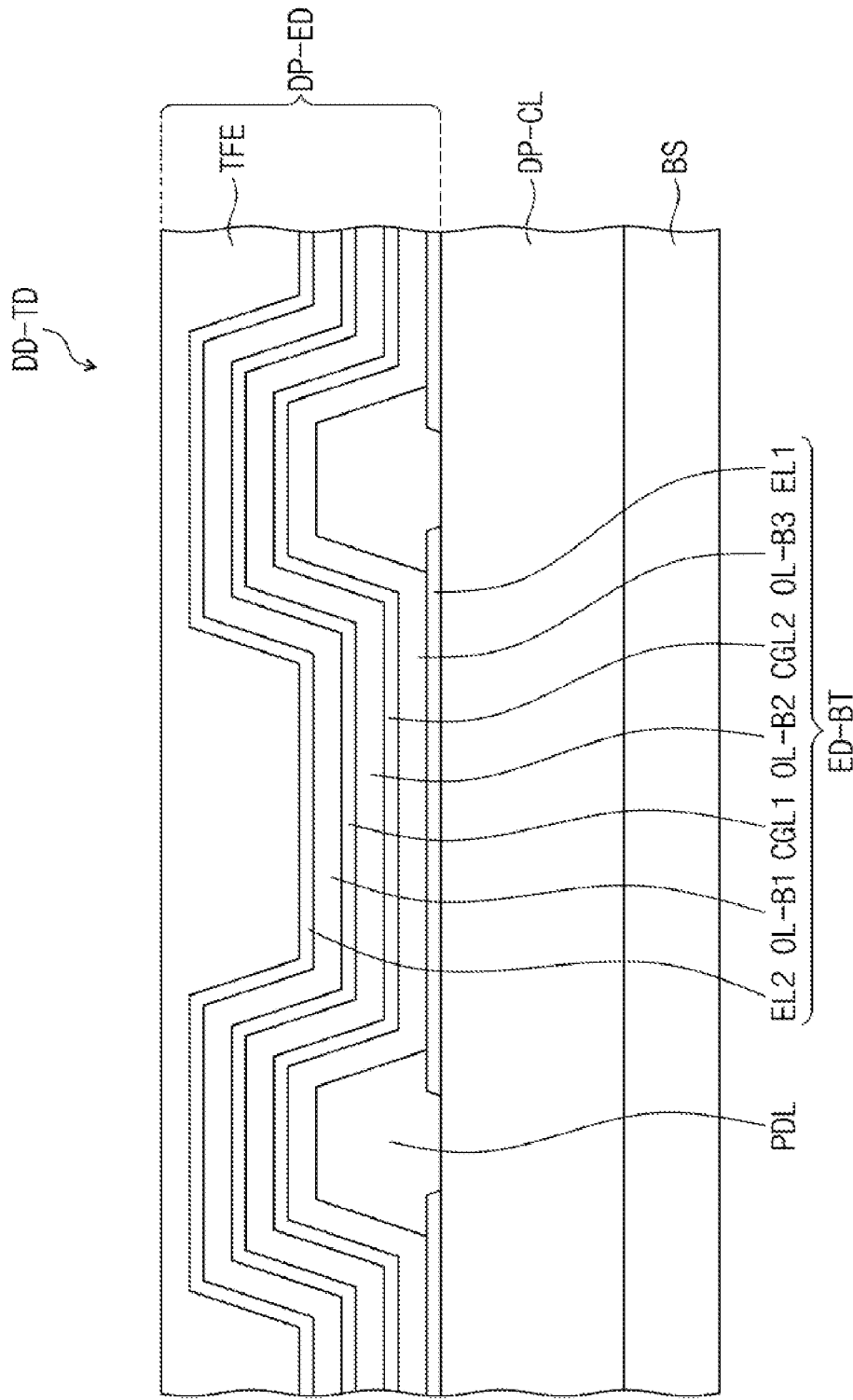

FIG. 7 and FIG. 8 are cross-sectional views on display apparatuses according to embodiments, respectively. In the explanation on the display apparatuses of embodiments, referring to FIG. 7 and FIG. 8, parts overlapping with FIG. 1 to FIG. 6 will not be explained again, and the different features will be chiefly explained.

Referring to FIG. 7, the display apparatus DD according to an embodiment may include a display panel DP including a display device layer DP-ED, a light controlling layer CCL disposed on the display panel DP and a color filter layer CFL.

In an embodiment shown in FIG. 7, the display panel DP includes a base layer BS, a circuit layer DP-CL provided on the base layer BS, and a display device layer DP-ED, and the display device layer DP-ED may include a light emitting device ED.

The light emitting device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. The same structures of the light emitting devices of FIG. 3 to FIG. 6 may be applied to the structure of the light emitting device ED shown in FIG. 7.

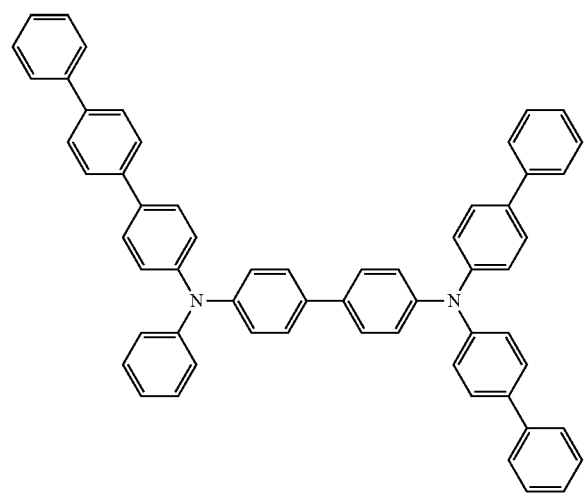

Referring to FIG. 7, the emission layer EML may be disposed in an opening part OH defined in a pixel definition layer PDL. For example, the emission layer EML divided by the pixel definition layer PDL and correspondingly provided to each of luminous areas PXA-R, PXA-G and PXA-B may be to emit light in substantially the same wavelength region in each of the luminous areas. In the display apparatus DD of an embodiment, the emission layer EML may be to emit blue light. In some embodiments, the emission layer EML may be provided as a common layer for all luminous areas PXA-R, PXA-G and PXA-B.

The light controlling layer CCL may be disposed on the display panel DP. The light controlling layer CCL may include a light converter. The light converter may be or include a quantum dot or a phosphor. The light converter may transform the wavelength of light provided (e.g., may absorb and transform incident light) and then emit light. For example, the light controlling layer CCL may be a layer including a quantum dot or a layer including a phosphor.

The light controlling layer CCL may include multiple light controlling parts CCP1, CCP2 and CCP3. The light controlling parts CCP1, CCP2 and CCP3 may be separated from one another.

Referring to FIG. 7, a partition pattern BMP may be disposed between the separated light controlling parts CCP1, CCP2 and CCP3, but embodiments of the present disclosure are not limited thereto. In FIG. 8, the partition pattern BMP is shown not to be overlapped with the light controlling parts CCP1, CCP2 and CCP3, but in some embodiments, at least a portion of the edge of the light controlling parts CCP1, CCP2 and CCP3 may be overlapped with the partition pattern BMP.

The light controlling layer CCL may include a first light controlling part CCP1 including a first quantum dot QD1 converting first color light provided from the light emitting device ED into second color light, a second light controlling part CCP2 including a second quantum dot QD2 converting first color light into third color light, and a third light controlling part CCP3 transmitting first color light (e.g., without including a quantum dot).

In an embodiment, the first light controlling part CCP1 may provide red light (which is the second color light), and the second light controlling part CCP2 may provide green light (which is the third color light). The third color controlling part CCP3 may transmit and provide blue light, which is the first color light provided from the light emitting device ED. For example, the first quantum dot QD1 may be a red quantum dot, and the second quantum dot QD2 may be a green quantum dot. Regarding the quantum dots QD1 and QD2, the same contents as those described above may be applied.

In some embodiments, the light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but include the scatterer SP.

The scatterer SP may be an inorganic particle. For example, the scatterer SP may include at least one among $TiO_2$, $ZnO$, $Al_2O_3$, $SiO_2$, and hollow silica. The scatterer SP may include at least one among $TiO_2$, $ZnO$, $Al_2O_3$, $SiO_2$, and hollow silica, or may be a mixture of two or more materials selected among $TiO_2$, $ZnO$, $Al_2O_3$, $SiO_2$, and hollow silica.

Each of the first light controlling part CCP1, the second light controlling part CCP2, and the third light controlling part CCP3 may include base resins BR1, BR2 and BR3 dispersing the quantum dots QD1 and QD2 and the scatterer SP. In an embodiment, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer particle SP dispersed in the third base resin BR3. The base resins BR1, BR2 and BR3 are mediums in which the quantum dots QD1 and QD2 and the scatterer SP are dispersed, and may be composed of one or more suitable resin compositions (which may be generally referred to as binders). For example, the base resins BR1, BR2 and BR3 may be acrylic resins, urethane-based resins, silicone-based resins, epoxy-based resins, etc. The base resins BR1, BR2 and BR3 may be transparent resins. In an embodiment, the first base resin BR1, the second base resin BR2 and the third base resin BR3 may be the same or different from each other.

The light controlling layer CCL may include a barrier layer BFL1. The barrier layer BFL1 may play the role of blocking the penetration of moisture and/or oxygen (hereinafter referred to as "humidity/oxygen"). The barrier layer BFL1 may be disposed on the light controlling parts CCP1, CCP2 and CCP3 to block or reduce exposure of the light controlling parts CCP1, CCP2 and CCP3 to humidity/oxygen. In some embodiments, the barrier layer BFL1 may cover the light controlling parts CCP1, CCP2 and CCP3. In some embodiments, the barrier layer BFL2 may be provided between a color filter layer CFL and the light controlling parts CCP1, CCP2 and CCP3.

The barrier layers BFL1 and BFL2 may include at least one inorganic layer. For example, the barrier layers BFL1 and BFL2 may be formed by including an inorganic material. For example, the barrier layers BFL1 and BFL2 may be formed by including silicon nitride, aluminum nitride, zirconium nitride, titanium nitride, hafnium nitride, tantalum nitride, silicon oxide, aluminum oxide, titanium oxide, tin oxide, cerium oxide and silicon oxynitride or a metal thin film to secure light transmittance. In some embodiments, the barrier layers BFL1 and BFL2 may further include an organic layer. The barrier layers BFL1 and BFL2 may each independently be composed of a single layer or multiple layers.

In the display apparatus DD of an embodiment, the color filter layer CFL may be disposed on the light controlling layer CCL. For example, the color filter layer CFL may be disposed directly on the light controlling layer CCL. In this case, the barrier layer BFL2 may be omitted.

The color filter layer CFL may include a light blocking part BM and filters CF-B, CF-G and CF-R. The color filter layer CFL may include a first filter CF1 to transmit second color light, a second filter CF2 to transmit third color light, and a third filter CF3 to transmit first color light. For example, the first filter CF1 may be a red filter, the second filter CF2 may be a green filter, and the third filter CF3 may be a blue filter. Each of the filters CF1, CF2 and CF3 may include a polymer photosensitive resin and/or a pigment and/or dye. The first filter CF1 may include a red pigment and/or dye, the second filter CF2 may include a green pigment and/or dye, and the third filter CF3 may include a blue pigment and/or dye. Embodiments of the present disclosure are not limited thereto, and in some embodiments the third filter CF3 may not include the pigment and/or dye. In some embodiments, the third filter CF3 may include a polymer photosensitive resin and may not include a pigment and/or dye. The third filter CF3 may be transparent. The third filter CF3 may be formed utilizing a transparent photosensitive resin.

In some embodiments, the first filter CF1 and the second filter CF2 may both be yellow filters. The first filter CF1 and the second filter CF2 may be provided as one body without distinction.

The light blocking part BM may be a black matrix. The light blocking part BM may be formed by including an organic light blocking material and/or an inorganic light blocking material including a black pigment and/or black dye. The light blocking part BM may prevent or reduce light leakage phenomenon and divide the boundaries among adjacent filters CF1, CF2 and CF3. In some embodiments, the light blocking part BM may be formed as a blue filter.

Each of the first to third filters CF1, CF2 and CF3 may be disposed to correspond to each of a red luminous area PXA-R, green luminous area PXA-G, and blue luminous area PXA-B, respectively.

An upper base layer BL may be disposed on the color filter layer CFL. The upper base layer BL may provide a base surface on which the color filter layer CFL, the light controlling layer CCL, etc. are disposed. The upper base layer BL may be a glass substrate, a metal substrate, a plastic substrate, etc. However, embodiments of the present disclosure are not limited thereto, and the upper base layer BL may be an inorganic layer, an organic layer or a composite material layer. In some embodiments, the upper base layer BL may be omitted.

FIG. 8 is a cross-sectional view showing a portion of the display apparatus according to an embodiment. In FIG. 8, the cross-sectional view of a portion corresponding to the display panel DP in FIG. 7 is shown. In a display apparatus DD-TD of an embodiment, the light emitting device ED-BT may include multiple light emitting structures OL-B1, OL-B2 and OL-B3. The light emitting device ED-BT may include oppositely disposed first electrode EL1 and second electrode EL2, and the multiple light emitting structures OL-B1, OL-B2 and OL-B3 stacked in order in a thickness direction between the first electrode EL1 and the second electrode EL2. Each of the light emitting structures OL-B1, OL-B2 and OL-B3 may include an emission layer EML (FIG. 7), and a hole transport region HTR and an electron transport region ETR disposed with the emission layer EML (FIG. 7) therebetween.

For example, the light emitting device ED-BT included in the display apparatus DD-TD of an embodiment may be a light emitting device of a tandem structure including multiple emission layers.

In an embodiment shown in FIG. 8, light to be emitted from the light emitting structures OL-B1, OL-B2 and OL-B3 may be all blue light. However, embodiments of the present disclosure are not limited thereto, and the wavelength regions of light emitted from the light emitting structures OL-B1, OL-B2 and OL-B3 may be different from each other. For example, the light emitting device ED-BT including the multiple light emitting structures OL-B1, OL-B2 and OL-B3 emitting light in different wavelength regions may be to emit white light.

Between neighboring light emitting structures OL-B1, OL-B2 and OL-B3, a charge generating layer CGL1, CGL2 may be disposed. The charge generating layer CGL1, CGL2 may include a p-type charge generating layer and/or an n-type charge generating layer.

The fused polycyclic compound of an embodiment includes a structure in which a fused structure is formed with a triphenylene skeleton via an additional connecting group (such as a direct linkage, an oxy group, a thio group, a carbonyl group and an alkyl group). Because the fused polycyclic compound according to an embodiment has a wide conjugation structure represented by Formula 1, when the fused polycyclic compound of an embodiment is utilized as a material for a light emitting device, high efficiency of the light emitting device may be achieved.

Hereinafter, the fused polycyclic compound according to an embodiment and the light emitting device of an embodiment will be particularly explained referring to embodiments and comparative embodiments. The embodiments are only illustrations to assist the understanding of the present disclosure, and the scope of the present disclosure is not limited thereto.

EXAMPLES

1. Synthesis of Fused Polycyclic Compound

First, the synthetic method of a fused polycyclic compound according to an embodiment will be explained by illustrating the synthetic methods of Compounds 1, 2, 3, 5, 6, 7, 9, 10, 11, 12, 13, 37 and 40. The synthetic methods of the fused polycyclic compounds explained hereinafter are embodiments, and the synthetic method of the fused polycyclic compound according to an embodiment of the present disclosure is not limited to the methods below.

(1) Synthesis of Compound 1

Fused Polycyclic Compound 1 according to an embodiment may be synthesized, for example, by the reaction below.

Synthesis of Intermediate Compound A

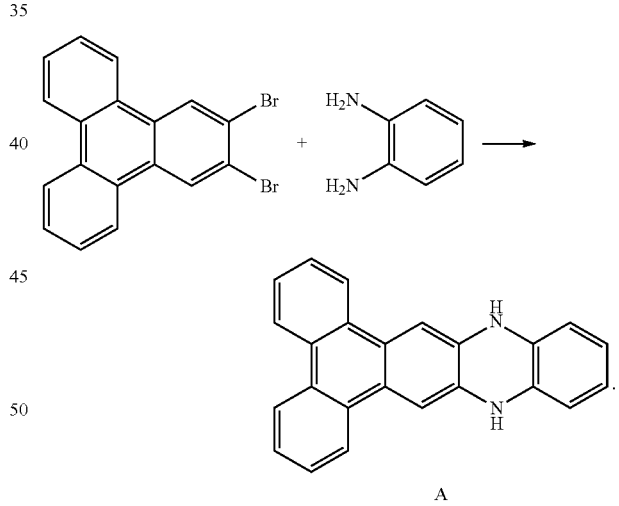

A

To a flask including 2,3-dibromotriphenylene (1 eq) and benzene-1,2-diamine (1.2 eq), Pd(dba)$_3$ (0.06 eq), (t-Bu)$_3$P (0.09 eq), t-BuONa (4.4 eq) and toluene (0.1 M, based on 1 eq reagent) were added, followed by refluxing and stirring for about 24 hours. The reaction solution was cooled to room temperature, extracted with methylene chloride (MC) and washed with distilled water. Then, the resultant solution was dried with MgSO$_4$ and distilled under a reduced pressure. The crude product thus obtained was separated utilizing a column to obtain Intermediate Compound A (yield 55.1%).

HRMS for $C_{24}H_{16}N_2$[M]+: calcd: 332.41, found: 331

Elemental Analysis for calcd: C, 86.72; H, 4.85; N, 8.43

121
Synthesis of Intermediate Compound B

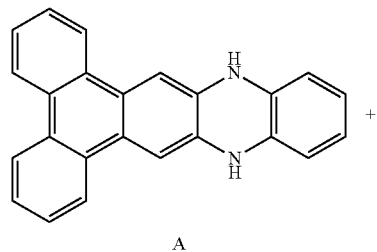

A

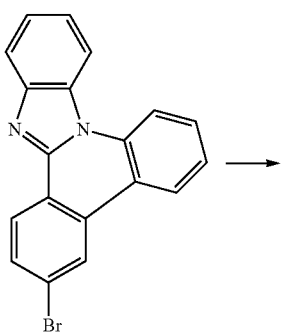

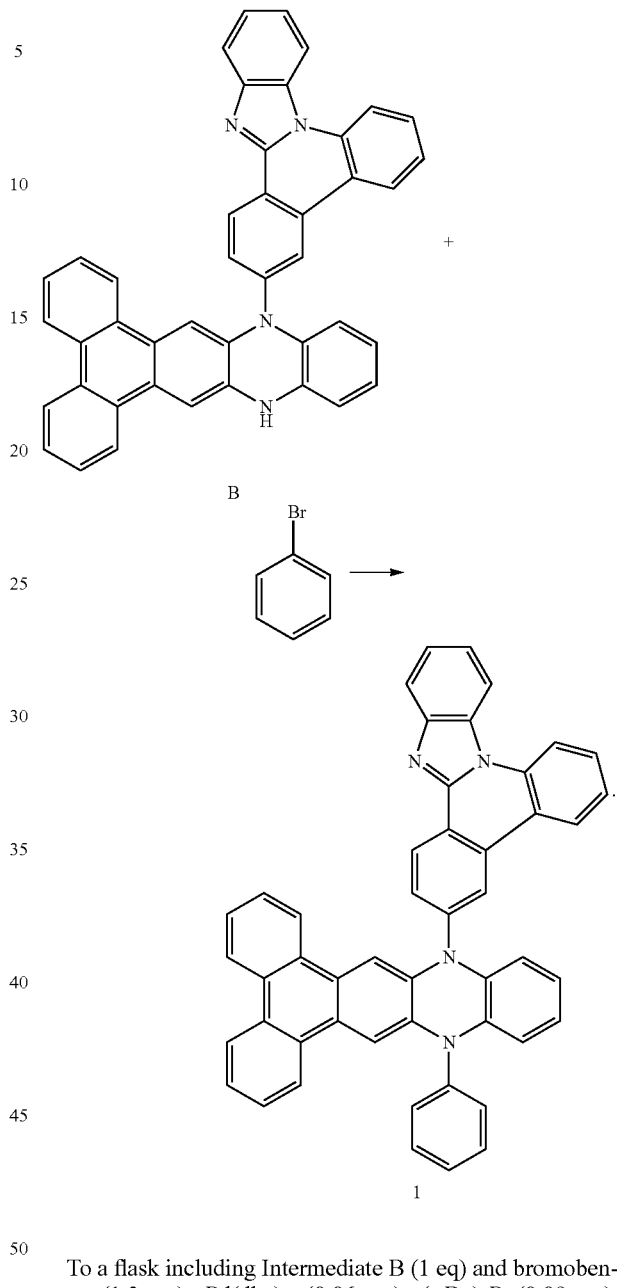

B

To a flask including Intermediate Compound A (1 eq) synthesized above and 6-bromobenzo[4,5]imidazo[1,2-f] phenanthridine (0.8 eq), Pd(dba)$_3$ (0.06 eq), (t-Bu)$_3$P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. Then, the resultant solution was dried with MgSO$_4$ and distilled under a reduced pressure. The crude product thus obtained was separated utilizing a column to obtain Intermediate Compound B (yield 84.3%).

HRMS for C$_{43}$H$_{26}$N$_4$[M]+: calcd: 598.71, found: 597

Elemental Analysis for calcd: C, 86.26; H, 4.38; N, 9.36

122
Synthesis of Compound 1

To a flask including Intermediate B (1 eq) and bromobenzene (1.2 eq), Pd(dba)$_3$ (0.06 eq), (t-Bu)$_3$P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. Then, the resultant solution was dried with MgSO$_4$ and distilled under a reduced pressure. The crude product thus obtained was separated utilizing a column to obtain Compound 1 (yield 85.7%).

HRMS for C$_{49}$H$_{30}$N$_4$[M]+: calcd: 674.81 found: 673

Elemental Analysis for calcd: C, 87.22; H, 4.48; N, 8.30

(2) Synthesis of Compound 2

Fused Polycyclic Compound 2 according to an embodiment may be synthesized, for example, by the reaction below.

Synthesis of Compound 2

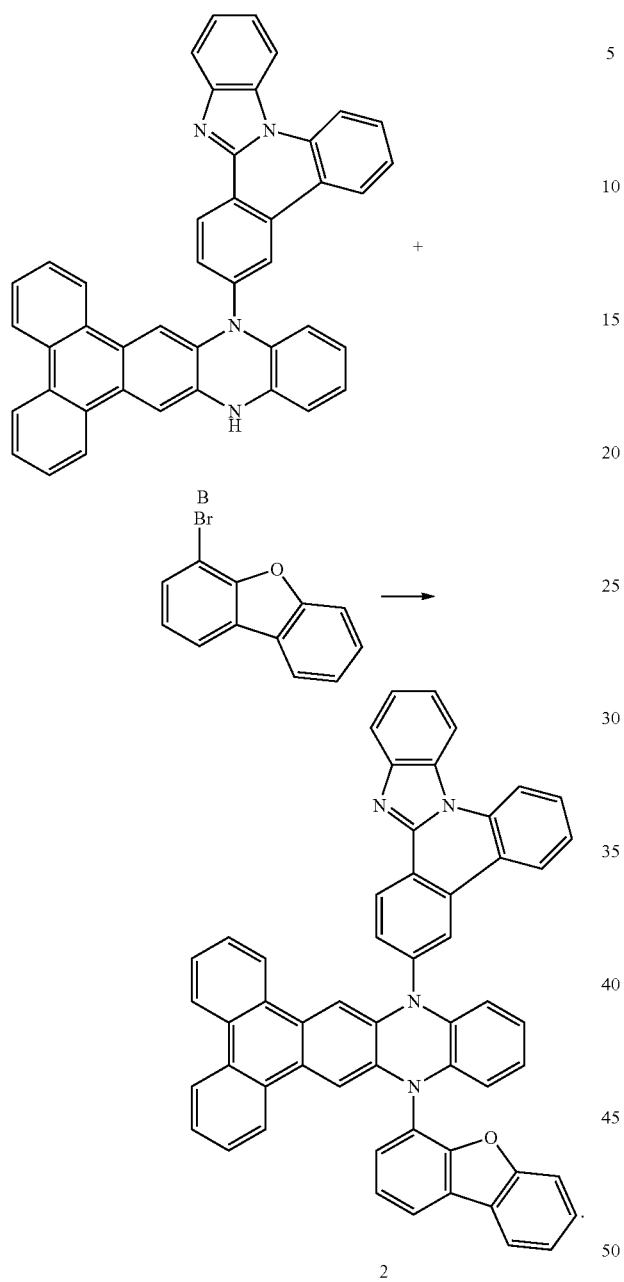

2

To a flask including the above-described Intermediate Compound B (1 eq) and 4-bromodibenzo[b,d]furan (1.2 eq), Pd(dba)₃ (0.06 eq), (t-Bu)₃P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. The resultant solution was dried with MgSO₄ and distilled under a reduced pressure, and the crude product thus obtained was separated by a column to obtain Compound 2 (yield 88.24%).

HRMS for $C_{55}H_{32}N_4O$ [M]+: calcd: 764.89 found: 763

Elemental Analysis for calcd: C, 86.37; H, 4.22; N, 7.32; O, 2.09

(3) Synthesis of Compound 3

Fused Polycyclic Compound 3 according to an embodiment may be synthesized, for example, by the reaction below.

Synthesis of Compound 3

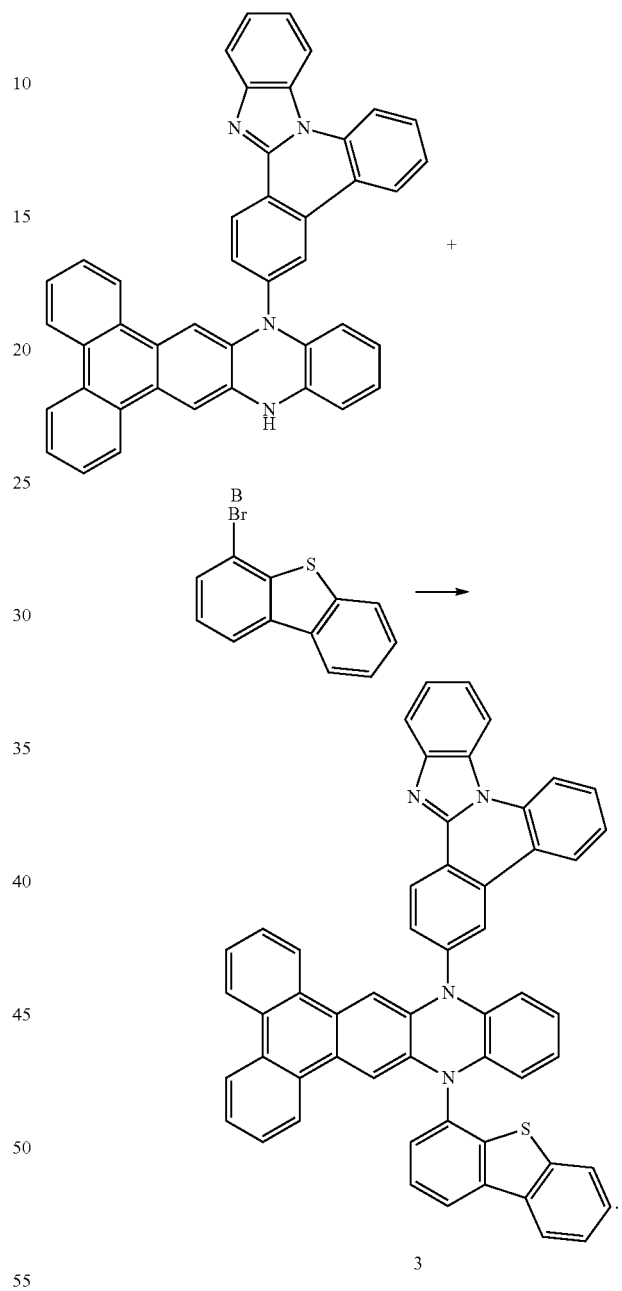

3

To a flask including Intermediate Compound B (1 eq) and 4-bromodibenzo[b,d]thiophene (1.2 eq), Pd(dba)₃ (0.06 eq), (t-Bu)₃P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. The resultant solution was dried with MgSO₄ and distilled under a reduced pressure, and the crude product thus obtained was separated by a column to obtain Compound 3 (yield 84.1%).

HRMS for $C_{55}H_{32}N_4S$ [M]+: calcd: 780.95 found: 779

Elemental Analysis for calcd: C, 84.59; H, 4.13; N, 7.17; S, 4.11

(4) Synthesis of Compound 5

Fused Polycyclic Compound 5 according to an embodiment may be synthesized, for example, by the reaction below.

Synthesis of Intermediate Compound A-2

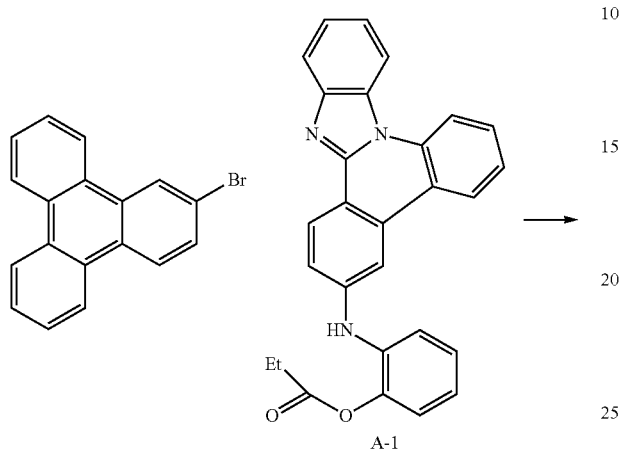

A-1

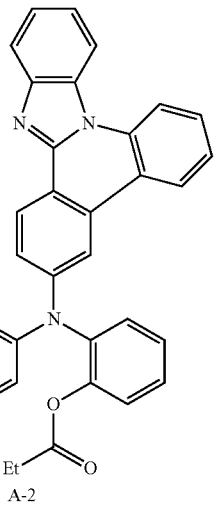

A-2

To a flask including 2-bromotriphenylene (1 eq) and Intermediate Compound A-1 (2-(benzo[4,5]imidazo[1,2-f]phenanthridin-6-yl amino)phenyl propionate) (1.2 eq), Pd(dba)$_3$ (0.06 eq), (t-Bu)$_3$P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. The resultant solution was dried with MgSO$_4$ and distilled under a reduced pressure, and the crude product thus obtained was separated by a column to obtain Intermediate Compound A-2 (yield 77.9%).

HRMS for $C_{46}H_{31}N_3O_2$[M]+: calcd: 657.77 found: 656

Elemental Analysis for calcd: C, 84.00; H, 4.75; N, 6.39; O, 4.86

Synthesis of Compound 5

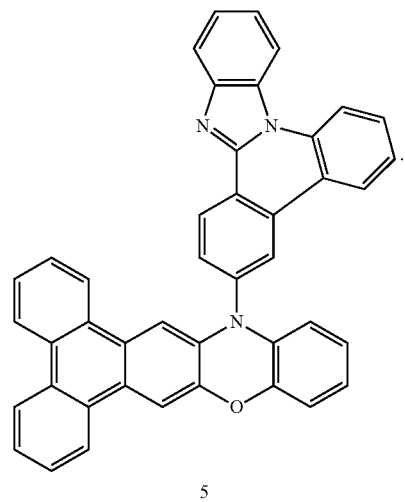

5

To a flask including Intermediate Compound A-2 (1 eq), trifluoromethanesulfonic acid (CF$_3$SO$_3$H) was added and stirred at room temperature for about 24 hours. Then, 30 mL of water and pyridine (8:1) was added thereto, followed by refluxing and stirring for about 30 minutes. The reaction solution was cooled to room temperature and extracted with MC, and the reaction product was dried with MgSO$_4$ and distilled under a reduced pressure. The crude product thus obtained was separated by a column to obtain Compound 5 (yield 41%).

HRMS for $C_{43}H_{25}N_3O$[M]+: calcd: 599.69 found: 598

Elemental Analysis for calcd: C, 86.12; H, 4.20; N, 7.01; O, 2.67

(5) Synthesis of Compound 6

Fused Polycyclic Compound 6 according to an embodiment may be synthesized, for example, by the reaction below.

Synthesis of Intermediate Compound A-3

Synthesis of Intermediate Compound A-4

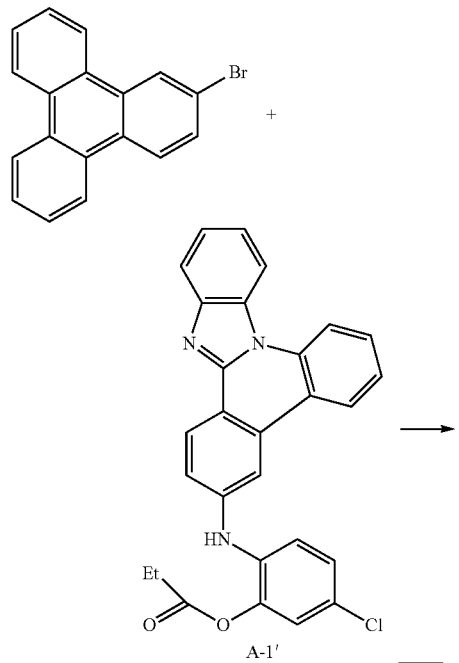

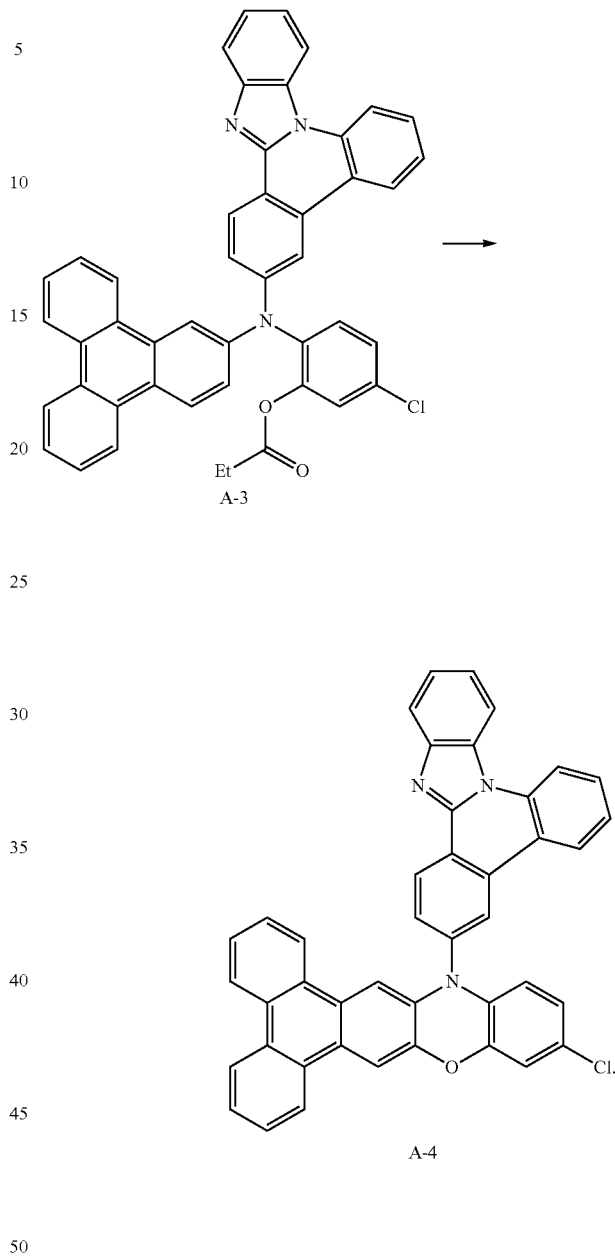

To a flask including 2-bromotriphenylene (1 eq) and Intermediate Compound A-1' (2-(benzo[4,5]imidazo[1,2-f]phenanthridin-6-ylamino)-5-chlorophenyl propionate) (1.2 eq), Pd(dba)$_3$ (0.06 eq), (t-Bu)$_3$P (0.09 eq), t-BuONa (4.4 eq) and toluene (0.1 M, based on 1 eq reagent) were added, followed by refluxing and stirring for about 12 hours. The reaction solution was cooled to room temperature, extracted with MC and washed with distilled water. The resultant solution was dried with MgSO$_4$ and distilled under a reduced pressure, and the crude product thus obtained was separated by a column to obtain Intermediate Compound A-3 (yield 75.1%).

HRMS for $C_{46}H_{31}N_3O_2$[M]+: calcd: 657.77 found: 656
Elemental Analysis for calcd: C, 84.00; H, 4.75; N, 6.39; O, 4.86

To a flask including Intermediate Compound A-3 (1 eq), trifluoromethanesulfonic acid (CF$_3$SO$_3$H) was added and stirred at room temperature for about 24 hours. Then, 30 mL of water and pyridine (8:1) was added thereto, followed by refluxing and stirring for about 30 minutes. The reaction solution was cooled to room temperature and extracted with MC, and the reaction product was dried with MgSO$_4$ and distilled under a reduced pressure. The crude product thus obtained was separated by a column to obtain Intermediate Compound A-4 (yield 39%).

HRMS for $C_{43}H_{24}ClN_3O$[M]+: calcd: 634.14 found: 633
Elemental Analysis for calcd: C, 81.45; H, 3.81; Cl, 5.59; N, 6.63; O, 2.52

Synthesis of Compound 6

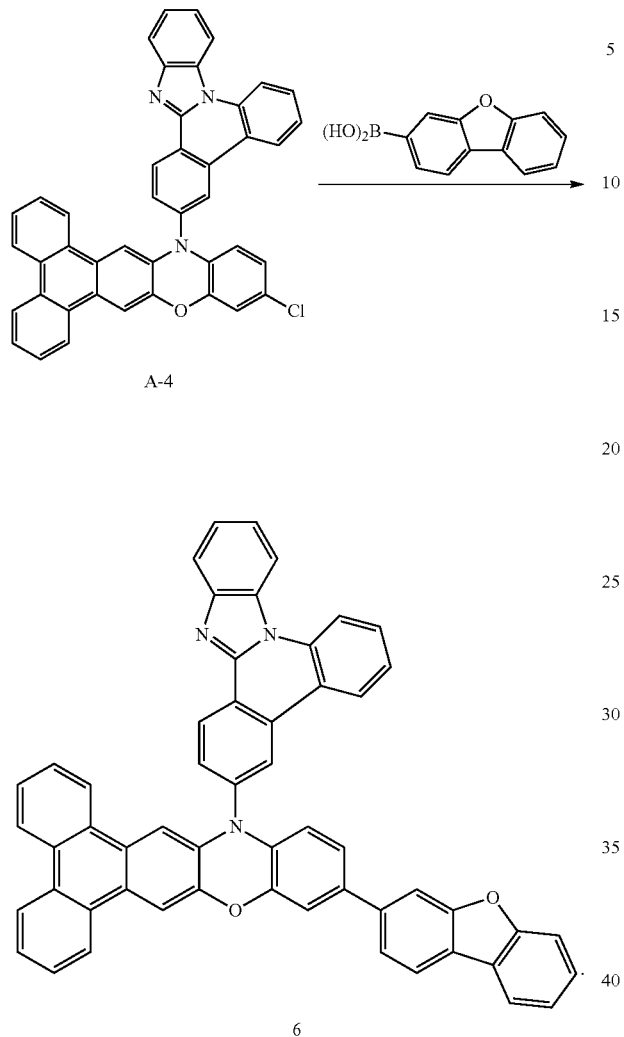

A-4

6

Synthesis of Compound 7

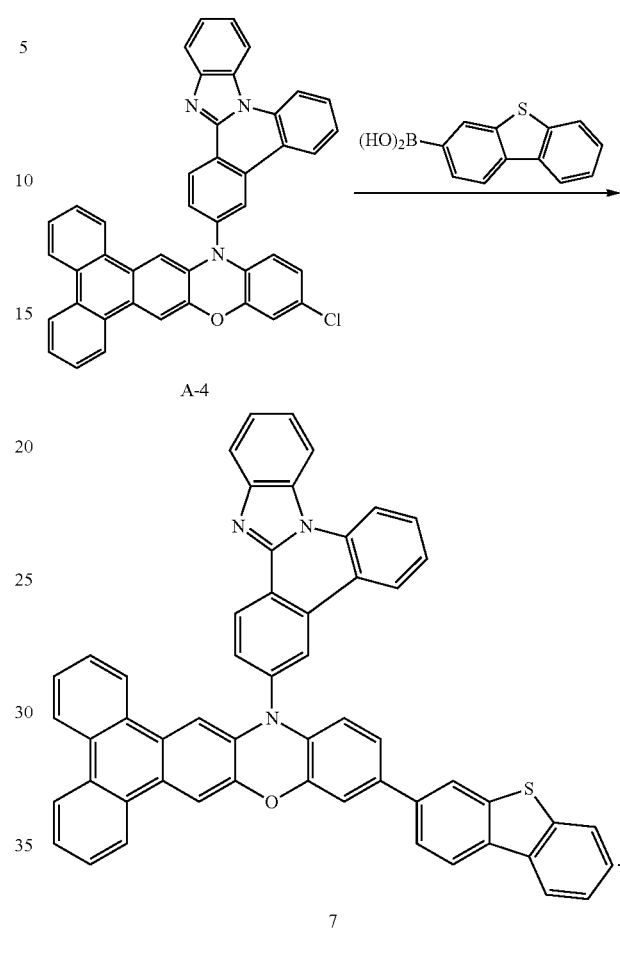

A-4

7

To a flask including Intermediate A-4 (1 eq), dibenzo[b,d]furan-3-ylboronic acid (1.2 eq) and Pd(PPh$_3$)$_4$ (0.9 g, 0.03 eq) were added and dissolved in 120 mL of toluene under nitrogen charge. 10 mL of an aqueous solution in which 10 g of sodium carbonate was dissolved was added thereto, followed by refluxing and stirring for about 12 hours. After finishing the reaction, the reaction solution was extracted with dichloromethane, and column chromatography was conducted utilizing hexane:MC=4:1 (v:v) to obtain Compound 6 (yield 84%).

HRMS for C$_{55}$H$_{31}$N$_3$O$_2$[M]+: calcd: 765.87 found: 764

Elemental Analysis for calcd: C, 86.26; H, 4.08; N, 5.49; O, 4.18

(6) Synthesis of Compound 7

Fused Polycyclic Compound 7 according to an embodiment may be synthesized, for example, by the reaction below.

By the same method as the synthetic method of Compound 6 except for utilizing dibenzo[b,d]thiophen-3-ylboronic acid instead of dibenzo[b,d]furan-3-ylboronic acid (1.2 eq), Compound 7 was obtained (yield 81%).

HRMS for C$_{55}$H$_{31}$N$_3$OS [M]+: calcd: 781.93 found: 780

Elemental Analysis for calcd: C, 84.48; H, 4.00; N, 5.37; O, 2.05; S, 4.10

(7) Synthesis of Compound 9

Fused Polycyclic Compound 9 according to an embodiment may be synthesized, for example, by the reaction below.

Synthesis of Intermediate Compound B-2

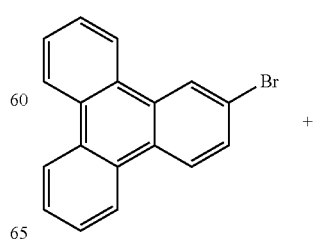

+

-continued

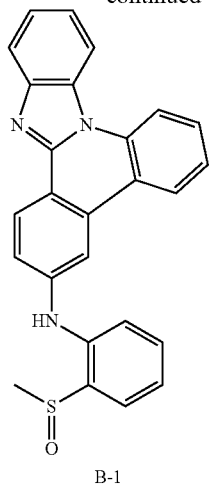

B-1

Synthesis of Compound 9

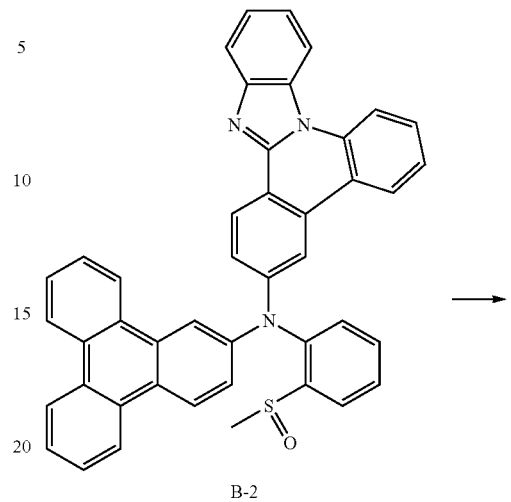

B-2

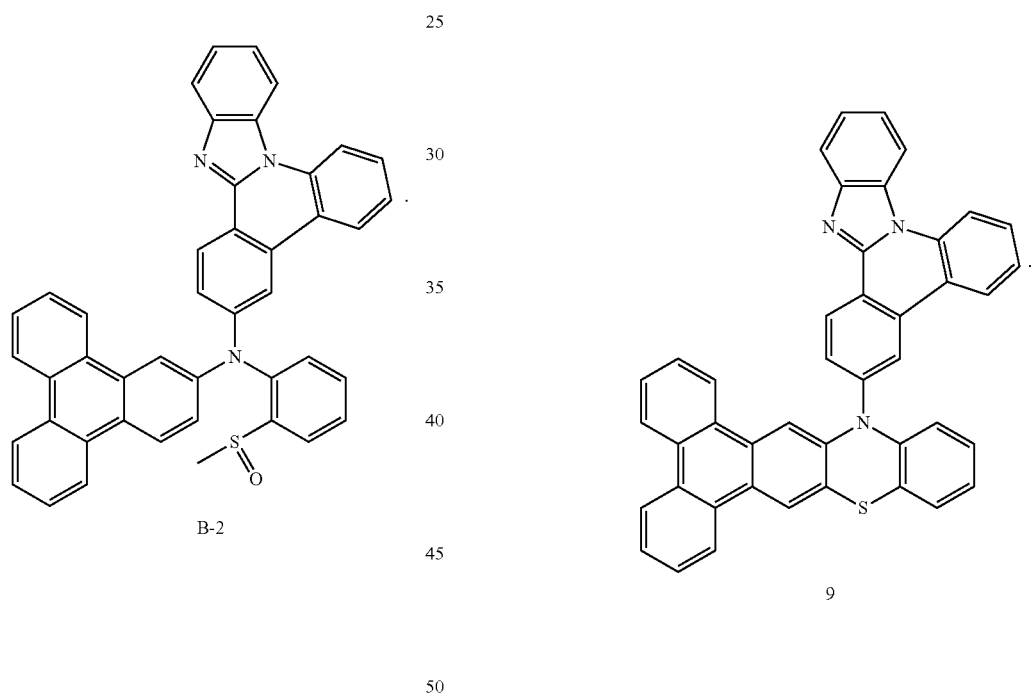

B-2

9

By the same method as the synthetic method of Intermediate Compound A-2 except for utilizing Intermediate Compound B-1 (N-(2-(methylsulfinyl)phenyl)benzo[4,5]imidazo[1,2-f]phenanthridin-6-amine) instead of Intermediate Compound A-1, Intermediate Compound B-2 was obtained (yield 71%).

HRMS for $C_{44}H_{29}N_3OS$ [M]+: calcd: 647.80 found: 646

Elemental Analysis for calcd: C, 81.58; H, 4.51; N, 6.49; O, 2.47; S, 4.95

By the same method as the synthetic method of Compound 5 except for utilizing Intermediate Compound B-2 instead of Intermediate Compound A-2, Compound 9 was obtained (yield 34%).

HRMS for $C_{43}H_{25}N_3S$ [M]+: calcd: 615.75 found: 614

Elemental Analysis for calcd: C, 83.88; H, 4.09; N, 6.82; S, 5.21

(8) Synthesis of Compound 10

Fused Polycyclic Compound 10 according to an embodiment may be synthesized, for example, by the reaction below.

Synthesis of Intermediate Compound B-3

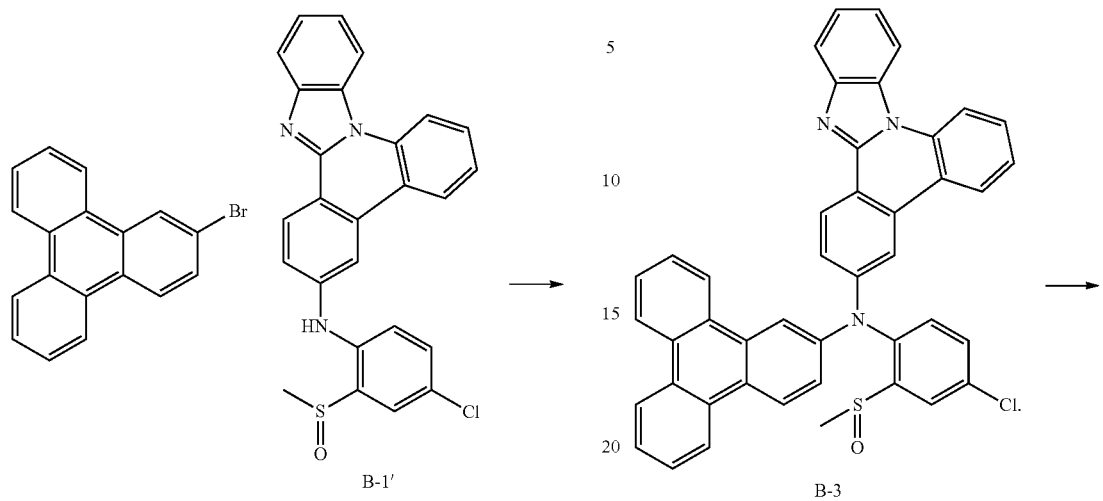

By the same method as the synthetic method of Intermediate Compound A-2 except for utilizing B-1' (N-(4-chloro-2-(methylsulfinyl)phenyl)benzo[4,5]imidazo[1,2-f]phenanthridin-6-amine) instead of Intermediate Compound A-1, Intermediate Compound B-3 was obtained (yield 73%).

HRMS for $C_{44}H_{28}ClN_3OS$ [M]+: calcd: 682.24 found: 681

Elemental Analysis for calcd: C, 77.46; H, 4.14; Cl, 5.20; N, 6.16; O, 2.35; S, 4.70

Synthesis of Intermediate Compound B-4

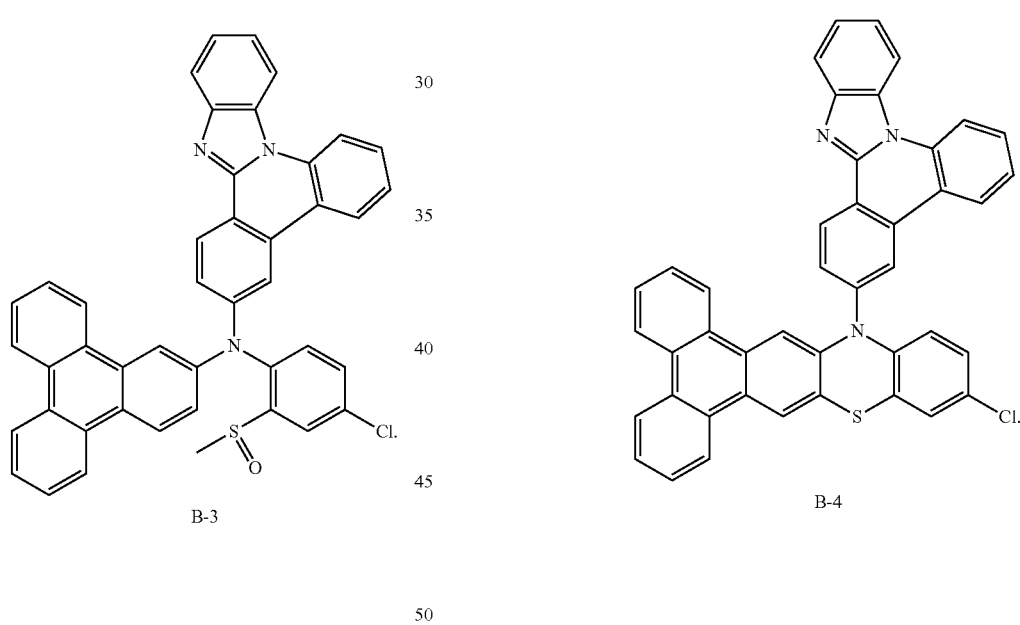

To a flask including Intermediate Compound B-3 (1 eq), trifluoromethanesulfonic acid ($CF_3SO_3H$) was added and stirred at room temperature for about 24 hours. Then, 50 mL of water and pyridine (8:1) was added thereto, followed by refluxing and stirring for about 30 minutes. The reaction solution was cooled to room temperature and extracted with MC, and the reaction product was dried with $MgSO_4$ and distilled under a reduced pressure. The crude product thus obtained was separated by a column to obtain Intermediate Compound B-4 (yield 41%).

HRMS for $C_{43}H_{24}ClN_3S$ [M]+: calcd: 650.20 found: 649

Elemental Analysis for calcd: C, 79.43; H, 3.72; Cl, 5.45; N, 6.46; S, 4.93

Synthesis of Compound 10

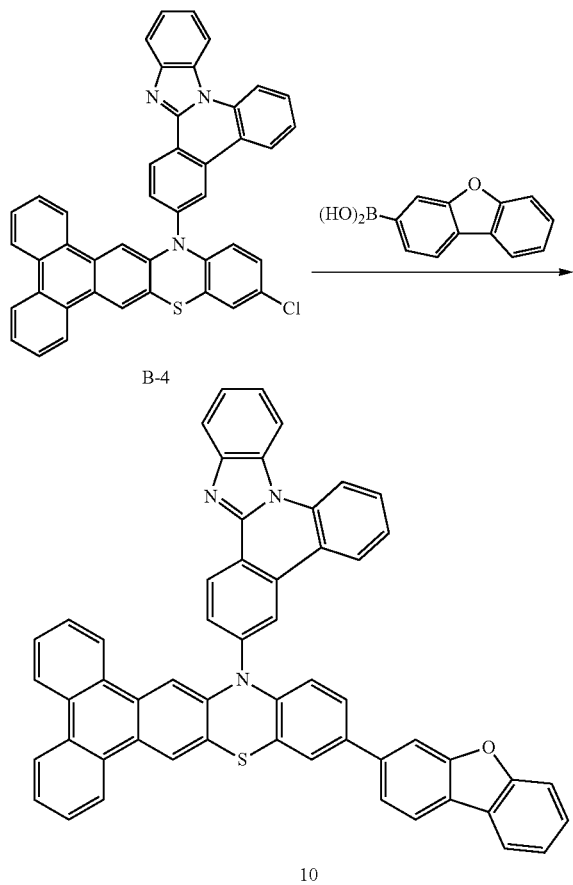

B-4

10

By the same method as the synthetic method of Compound 6 except for utilizing Intermediate Compound B-4 instead of Intermediate Compound A-4, Compound 10 was synthesized (yield 81.7%).

HRMS for $C_{55}H_{31}N_3OS$ [M]+: calcd: 781.93 found: 780

Elemental Analysis for calcd: C, 84.48; H, 4.00; N, 5.37; O, 2.05; S, 4.10

(9) Synthesis of Compound 11

Fused Polycyclic Compound 11 according to an embodiment may be synthesized, for example, by the reaction.

Synthesis of Compound 11

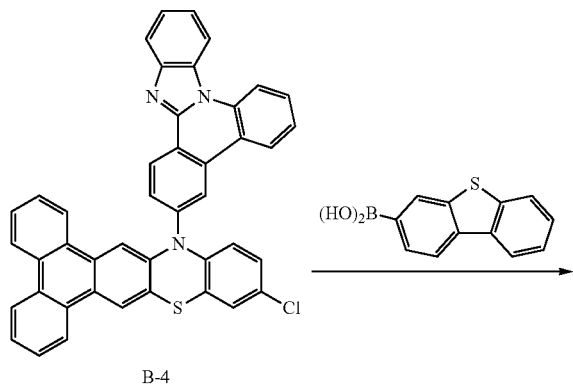

B-4

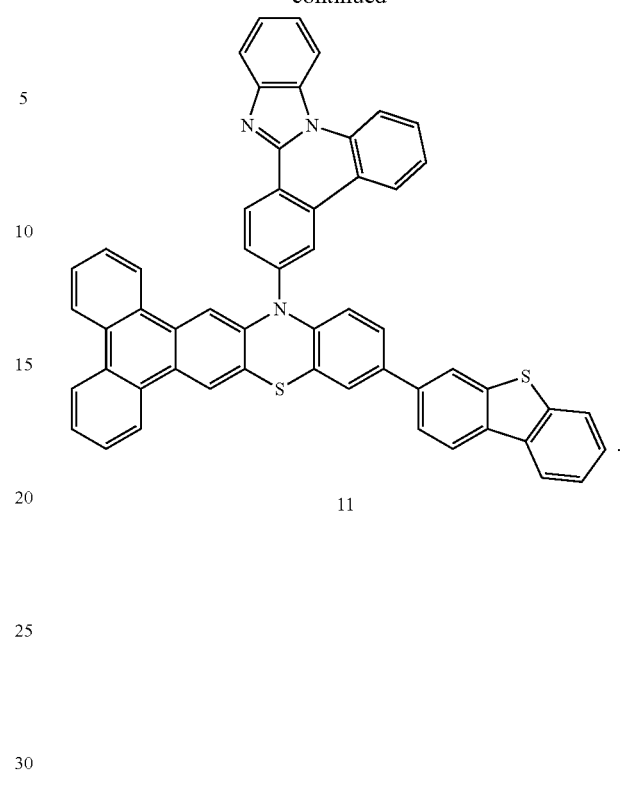

11

By the same method as the synthetic method of Compound 10 except for utilizing dibenzo[b,d]thiophen-3-ylboronic acid instead of dibenzo[b,d]furan-3-ylboronic acid (1.2 eq), Compound 11 was obtained (yield 79.7%).

HRMS for $C_{55}H_{31}N_3S_2$[M]+: calcd: 797.99 found: 796

Elemental Analysis for calcd: C, 82.78; H, 3.92; N, 5.27; S, 8.04

(10) Synthesis of Compound 12

Fused Polycyclic Compound 12 according to an embodiment may be synthesized, for example, by the reaction.

Synthesis of Compound 12

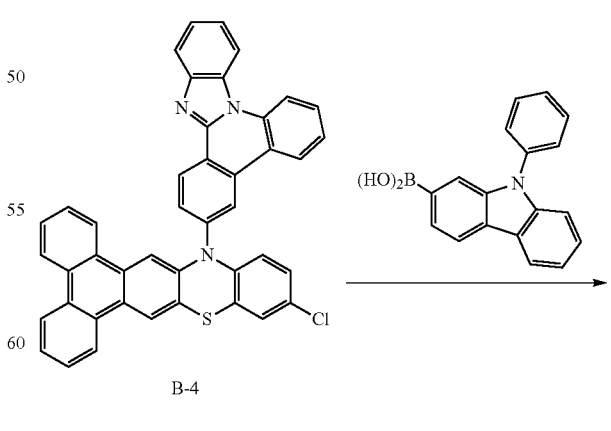

B-4

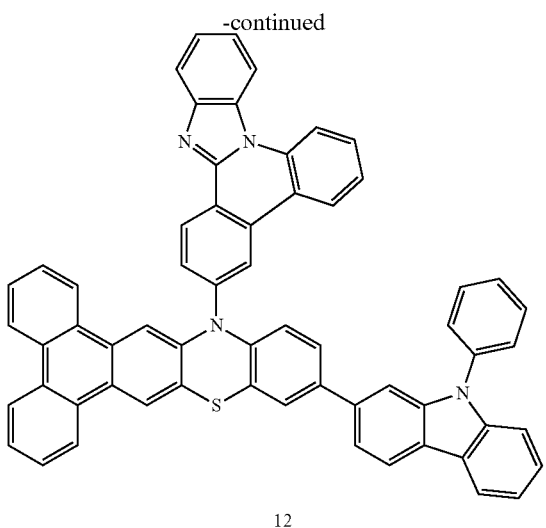

12

By the same method as the synthetic method of Compound 10 except for utilizing (9-phenyl-9H-carbazol-2-yl)boronic acid instead of dibenzo[b,d]furan-3-ylboronic acid (1.2 eq), Compound 12 was obtained (yield 83.8%).

HRMS for $C_{61}H_{36}N_4S$ [M]+: calcd: 857.05 found: 856

Elemental Analysis for calcd: C, 85.49; H, 4.23; N, 6.54; S, 3.74

(11) Synthesis of Compound 13

Fused Polycyclic Compound 13 according to an embodiment may be synthesized, for example, by the reaction.

Synthesis of Intermediate Compound C

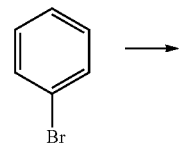

C

To a flask including 2,3-dibromotriphenylene (1 eq) and 4-chlorobenzene-1,2-diamine (1.2 eq), Pd(dba)$_3$ (0.06 eq), (t-Bu)$_3$P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. The resultant solution was dried with MgSO$_4$ and distilled under a reduced pressure, and the crude product thus obtained was separated by a column to obtain Intermediate Compound C (yield 34.7%).

HRMS for $C_{24}H_{15}ClN_2$[M]+: calcd: 366.85, found: 365

Elemental Analysis for calcd: C, 78.58; H, 4.12; Cl, 9.66; N, 7.64

Synthesis of Intermediate Compound C-1

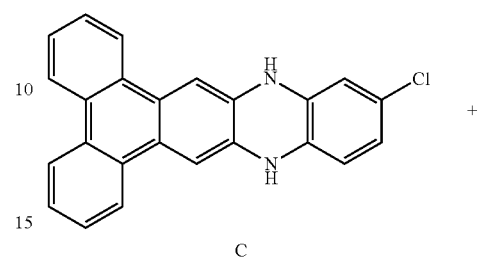

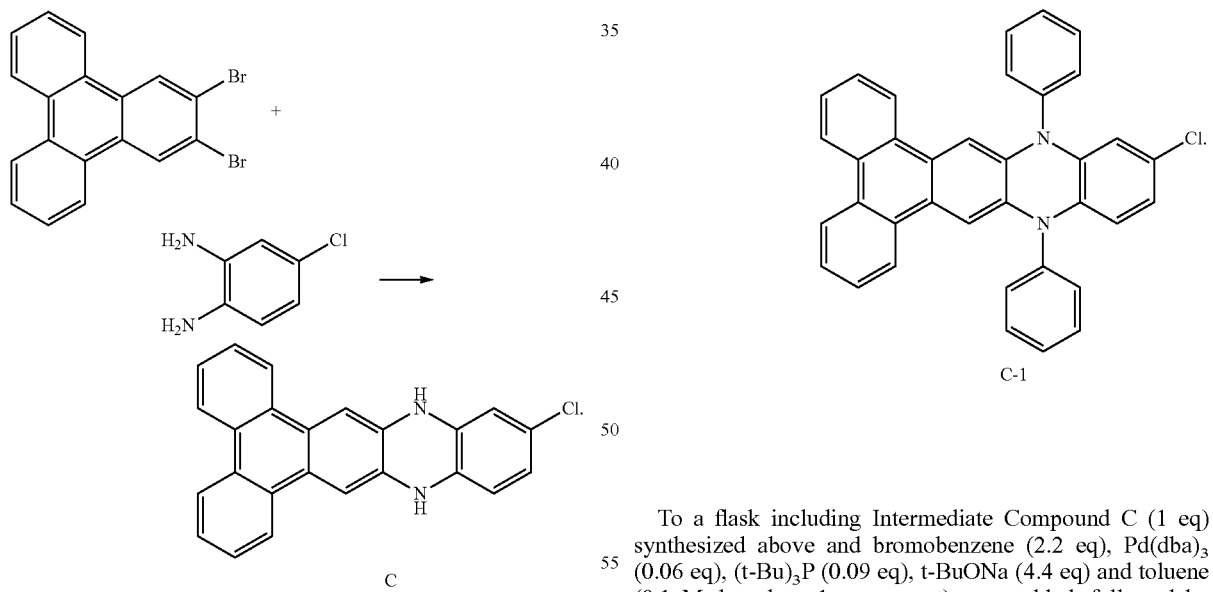

C-1

To a flask including Intermediate Compound C (1 eq) synthesized above and bromobenzene (2.2 eq), Pd(dba)$_3$ (0.06 eq), (t-Bu)$_3$P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. The resultant solution was dried with MgSO$_4$ and distilled under a reduced pressure, and the crude product thus obtained was separated by a column to obtain Intermediate Compound C-1 (yield 71.3%).

HRMS for $C_{36}H_{23}ClN_2$[M]+: calcd: 519.04, found: 518

Elemental Analysis for calcd: C, 83.31; H, 4.47; Cl, 6.83; N, 5.40

Synthesis of Compound 13

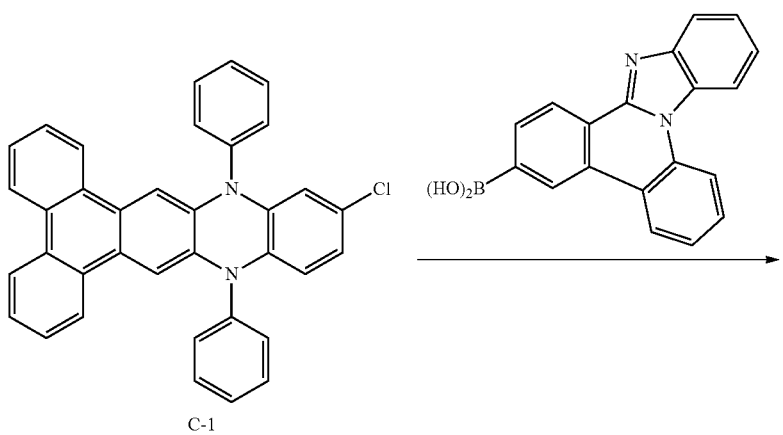

C-1

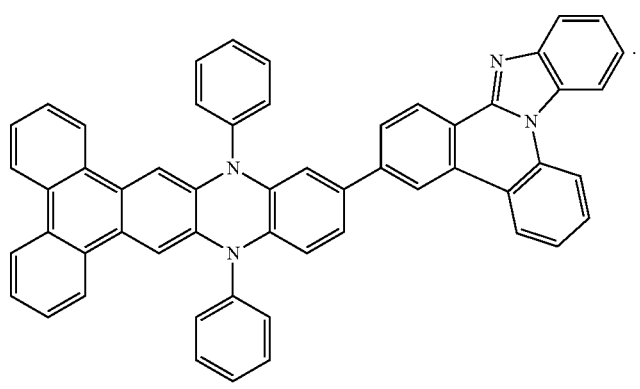

13

To a flask including Intermediate Compound C-1 (1 eq), benzo[4,5]imidazo[1,2-f]phenanthridin-6-ylboronic acid (1.2 eq) and Pd(PPh$_3$)$_4$ (0.9 g, 0.03 eq) were added and dissolved in 120 mL of toluene under nitrogen charge. Then, 40 mL of an aqueous solution in which 10 g of sodium carbonate was dissolved was added thereto, followed by refluxing and stirring for about 12 hours. After finishing the reaction, the reaction solution was extracted with dichloromethane, and column chromatography was conducted utilizing hexane:MC=4:1 (v:v) to obtain Compound 13 (yield 77.8%).

HRMS for C$_{55}$H$_{34}$N$_4$[M]+: calcd: 750.91 found: 749
Elemental Analysis for calcd: C, 87.97; H, 4.56; N, 7.46
(12) Synthesis of Compound 37
Synthesis of Intermediate Compound B-1-1

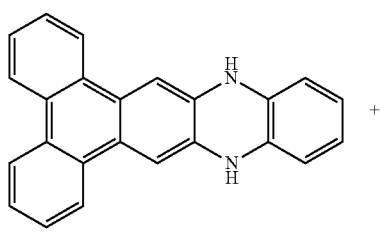

A

-continued

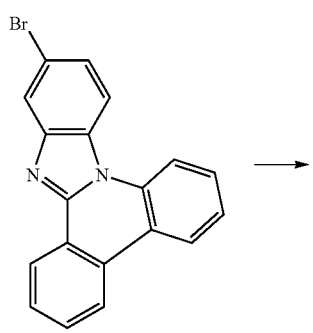

-continued

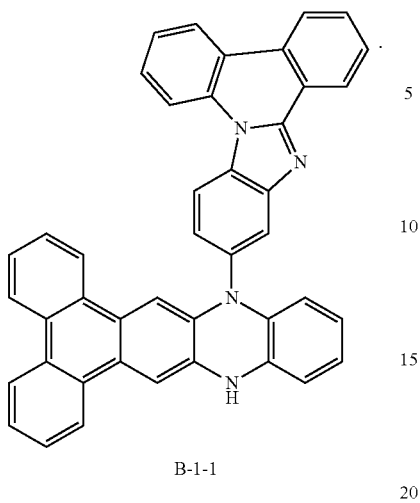

B-1-1

To a flask including Intermediate Compound A (1 eq) synthesized above and 11-bromobenzo[4,5]imidazo[1,2-f]phenanthridine (0.8 eq), Pd(dba)₃ (0.06 eq), (t-Bu)₃P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. The resultant solution was dried with MgSO₄ and distilled under a reduced pressure, and the crude product thus obtained was separated by a column to obtain Intermediate Compound B-1-1 (yield 81.7%).

HRMS for $C_{43}H_{26}N_4$[M]+: calcd: 598.71, found: 597

Elemental Analysis for calcd: C, 86.26; H, 4.38; N, 9.36

Synthesis of Compound 37

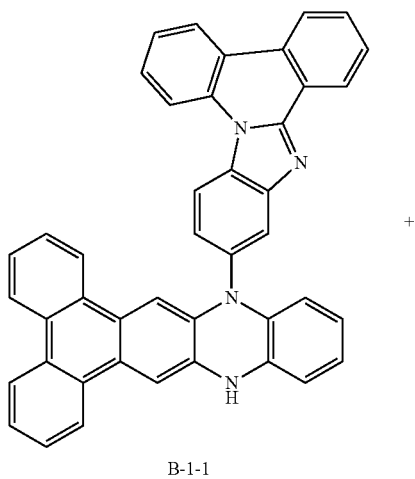

B-1-1

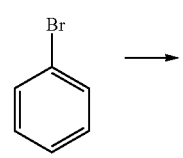

-continued

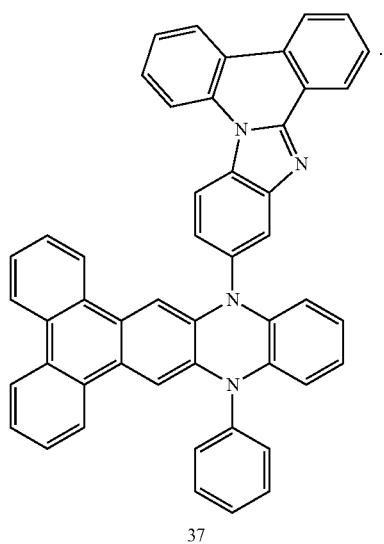

37

To a flask including Intermediate Compound B-1-1 (1 eq) and bromobenzene (1.2 eq), Pd(dba)₃ (0.06 eq), (t-Bu)₃P (0.09 eq), t-BuONa (4.4 eq) and toluene (0.1 M, based on 1 eq reagent) were added, followed by refluxing and stirring for about 24 hours. The reaction solution was cooled to room temperature, extracted with MC and washed with distilled water. The resultant solution was dried with MgSO₄ and distilled under a reduced pressure, and the crude product thus obtained was separated by a column to obtain Compound 37 (yield 88.4%).

HRMS for $C_{49}H_{30}N_4$[M]+: calcd: 674.81 found: 673

Elemental Analysis for calcd: C, 87.22; H, 4.48; N, 8.30

(13) Synthesis of Compound 40

Synthesis of Intermediate Compound A-3-1

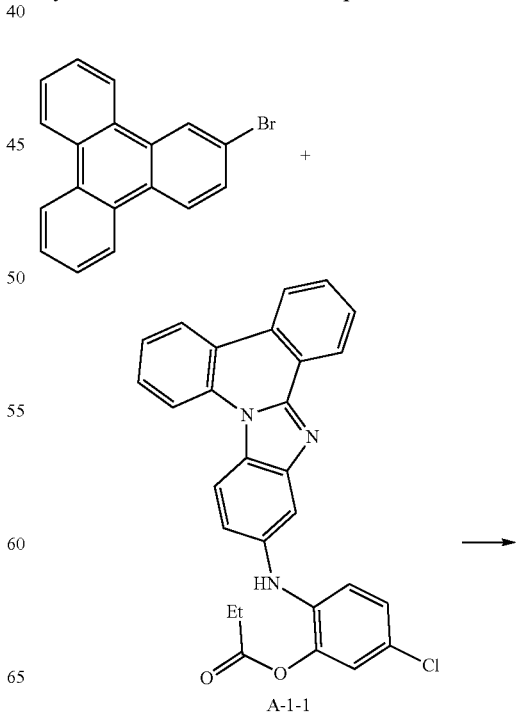

A-1-1

-continued

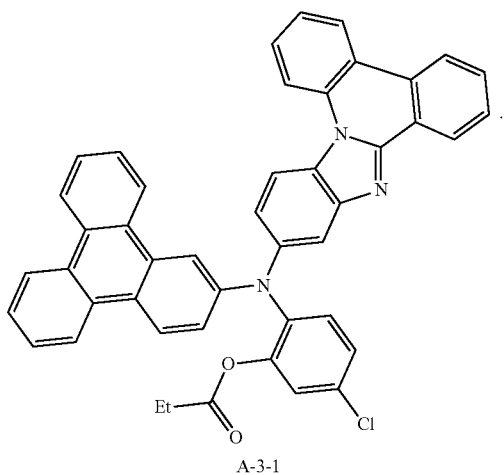

A-3-1

-continued

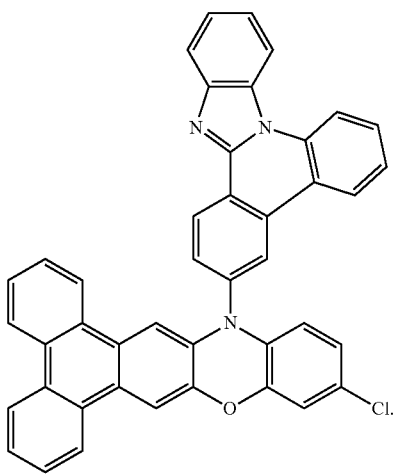

A-4-1

To a flask including 2-bromotriphenylene (1 eq) and Intermediate Compound A-1-1 (2-(benzo[4,5]imidazo[1,2-f]phenanthridin-11-ylamino)-5-chlorophenyl propionate)) (1.2 eq), Pd(dba)$_3$ (0.06 eq), (t-Bu)$_3$P (0.09 eq), t-BuONa (4.4 eq) and toluene (0.1 M, based on 1 eq reagent) were added, followed by refluxing and stirring for about 12 hours. The reaction solution was cooled to room temperature, extracted with MC and washed with distilled water. The resultant solution was dried with MgSO$_4$ and distilled under a reduced pressure, and the crude product thus obtained was separated by a column to obtain Intermediate Compound A-3-1 (yield 74.8%).

HRMS for C$_{46}$H$_{31}$N$_3$O$_2$[M]+: calcd: 657.77 found: 656

Elemental Analysis for calcd: C, 84.00; H, 4.75; N, 6.39; 0, 4.86

Synthesis of Intermediate Compound A-4-1

To a flask including Intermediate Compound A-3-1 (1 eq), trifluoromethanesulfonic acid (CF$_3$SO$_3$H) was added and stirred at room temperature for about 24 hours. Then, 30 mL of water and pyridine (8:1) was added thereto, followed by refluxing and stirring for about 30 minutes. The reaction solution was cooled to room temperature and extracted with MC, and the reaction produce was dried with MgSO$_4$ and distilled under a reduced pressure. The crude product thus obtained was separated by a column to obtain Intermediate Compound A-4-1 (yield 32%).

HRMS for C$_{43}$H$_{24}$ClN$_3$O[M]+: calcd: 634.14 found: 633

Elemental Analysis for calcd: C, 81.45; H, 3.81; Cl, 5.59; N, 6.63; 0, 2.52

Synthesis of Compound 40

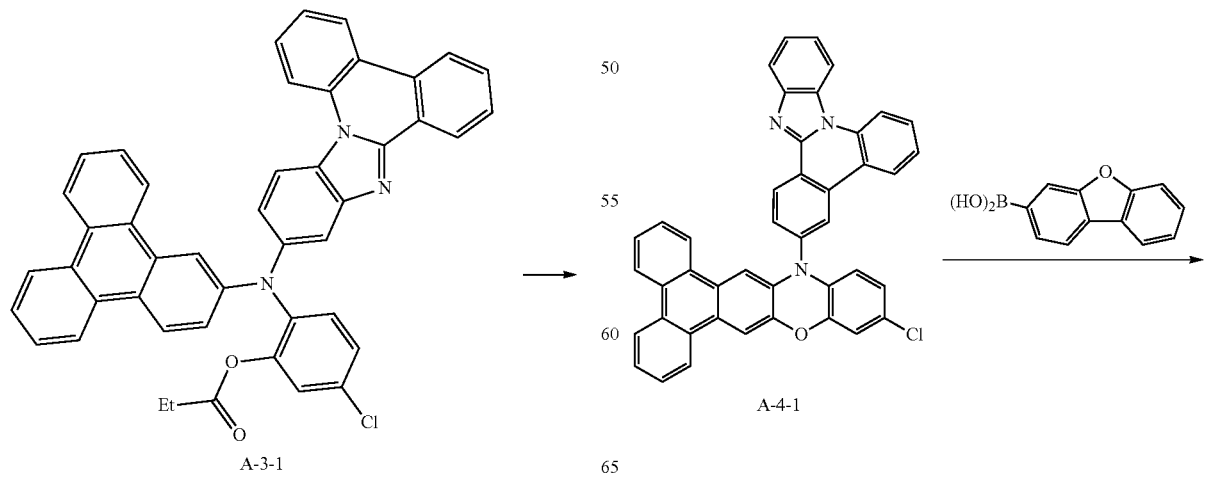

-continued

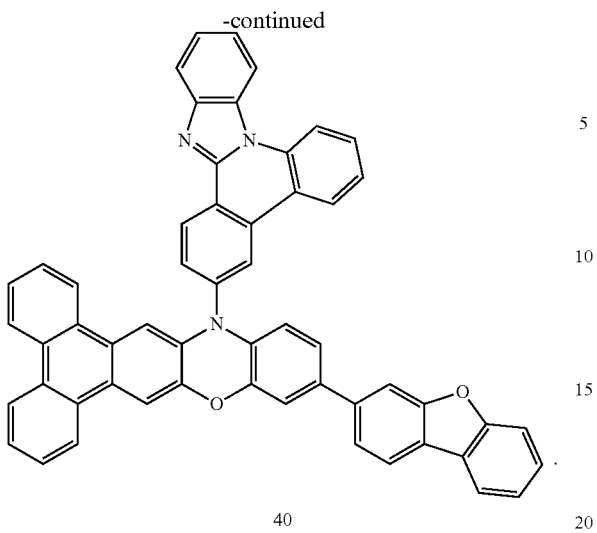

40

To a flask including Intermediate Compound A-4-1 (1 eq), dibenzo[b,d]furan-3-ylboronic acid (1.2 eq) and Pd(PPh$_3$)$_4$ (0.9 g, 0.03 eg) were added and dissolved in 120 mL of toluene under nitrogen charge. 40 mL of an aqueous solution in which 10 g of sodium carbonate was dissolved was added thereto, followed by refluxing and stirring for about 12 hours. After finishing the reaction, the reaction solution was extracted with dichloromethane, and column chromatography was performed utilizing hexane:MC=4:1 (v/v) to obtain Compound 40 (yield 87.3%).

HRMS for C$_{55}$H$_{31}$N$_3$O$_2$[M]+: calcd: 765.87 found: 764

Elemental Analysis for calcd: C, 86.26; H, 4.08; N, 5.49; O, 4.18

2. Manufacture and Evaluation of Light Emitting Device Including Fused Polycyclic Compound Manufacture of Light Emitting Device Light emitting devices of Examples 1 to 13 were manufactured utilizing Compounds 1, 2, 3, 5, 6, 7, 9, 10, 11, 12, 13, 37 and 40 as dopant materials of an emission layer.

Example Compounds

1

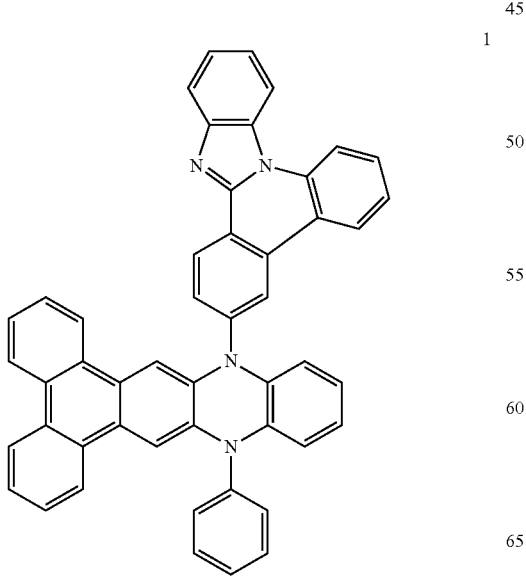

2

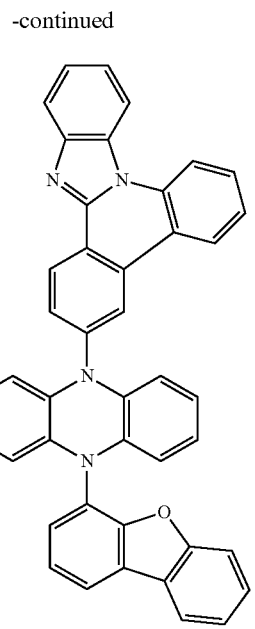

3

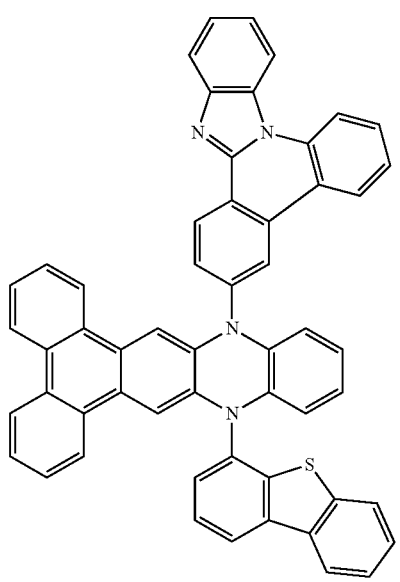

5

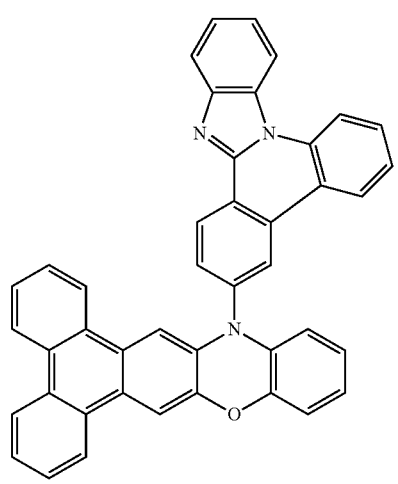

147
-continued
6
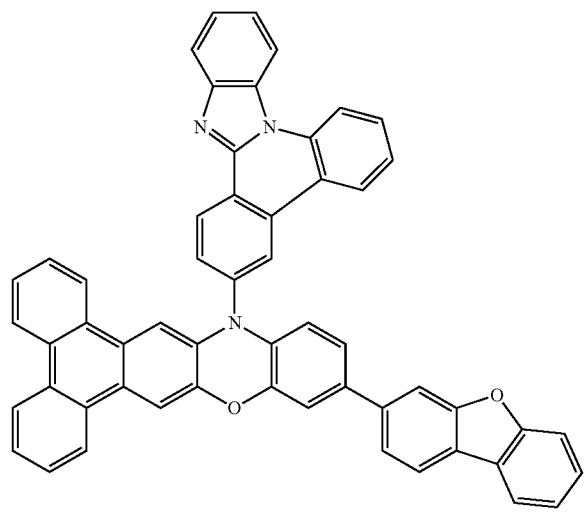
7
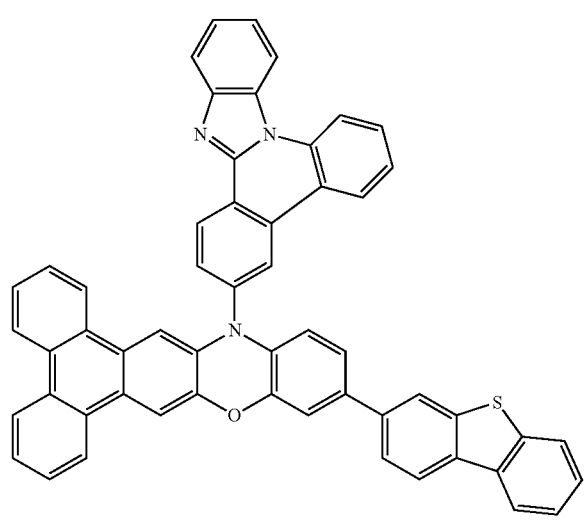
9
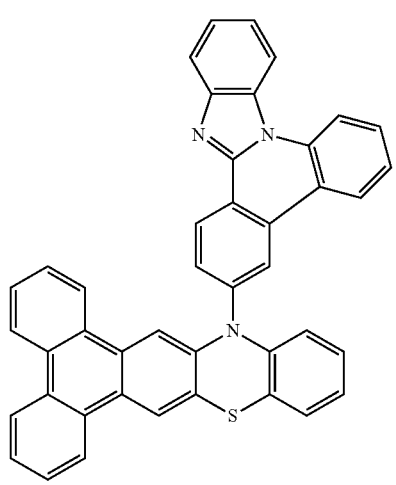
148
-continued
10
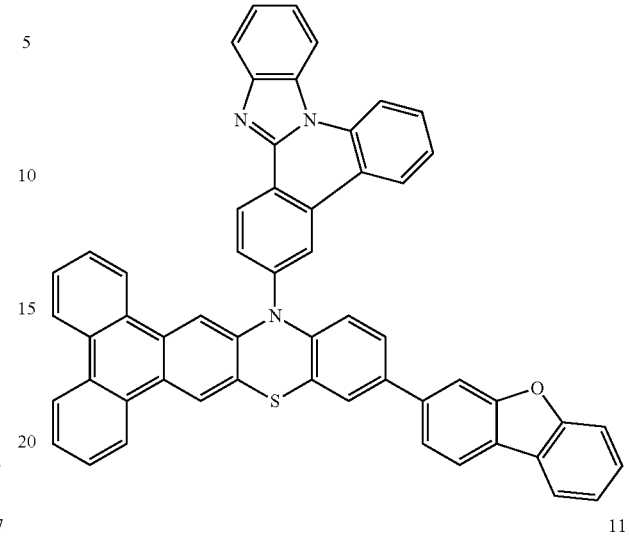
11
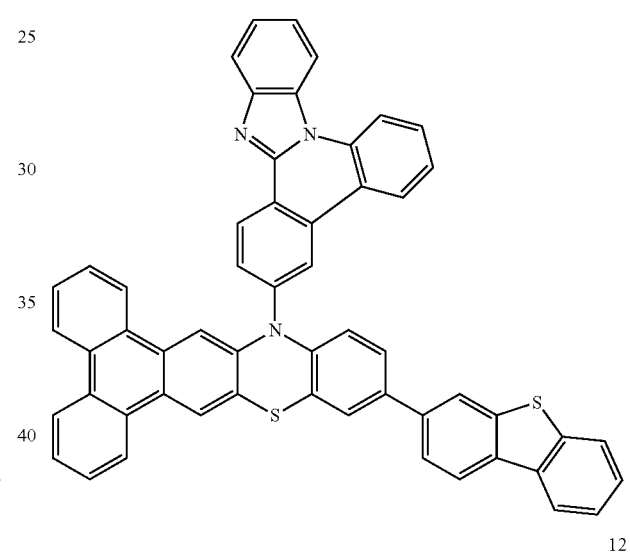
12
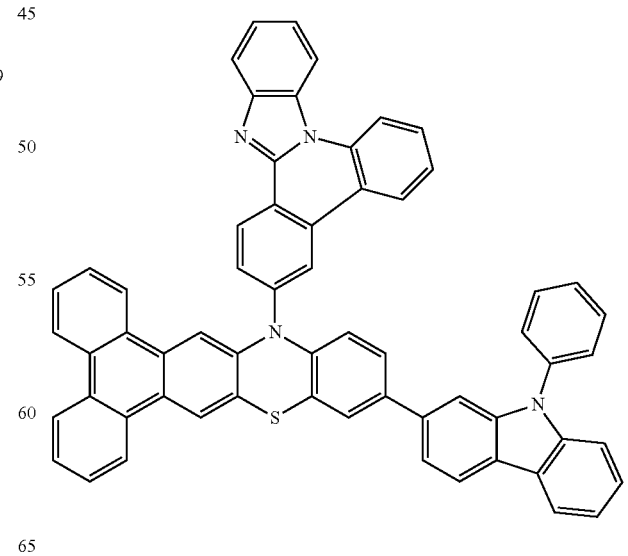

-continued
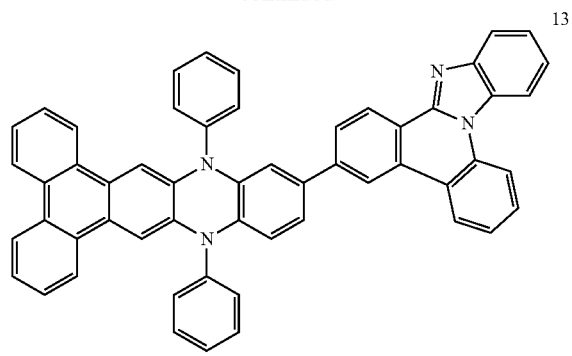
37
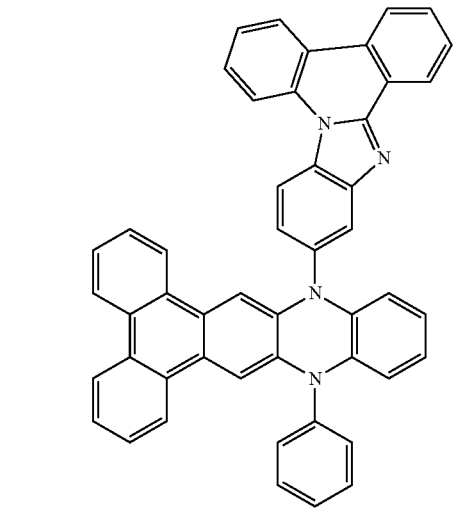
40
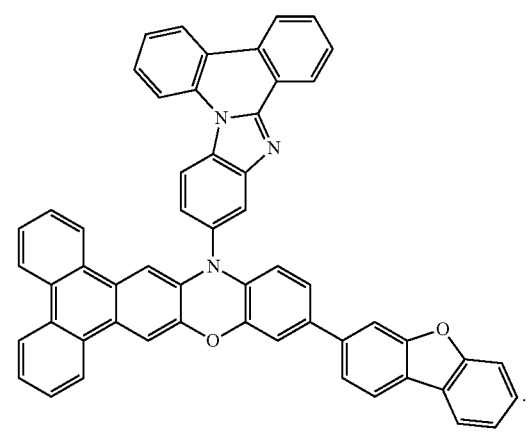
Comparative Compounds
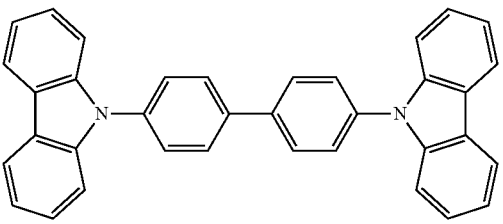
X1
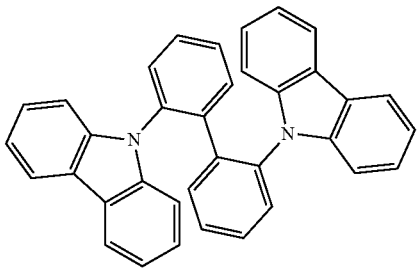
X2
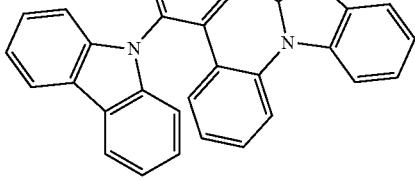
X3
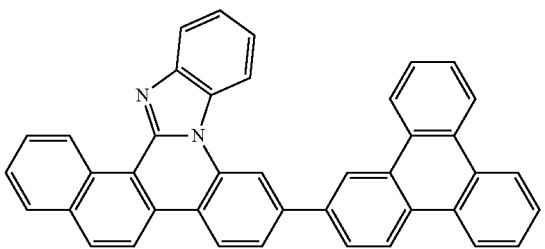
X4
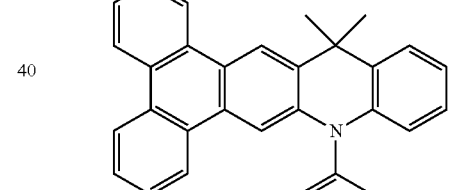
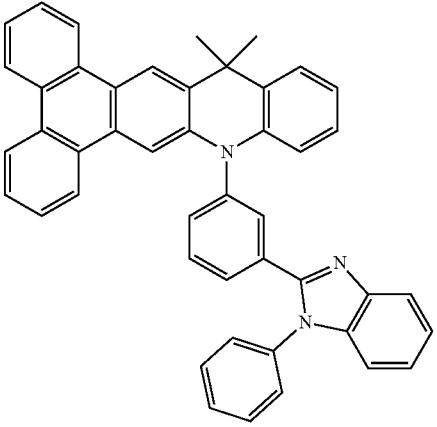
X5
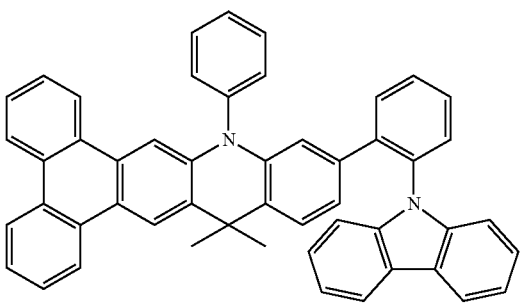
Comparative Compounds X1 to X8 were utilized for the manufacture of the devices of the Comparative Examples.

-continued

X6
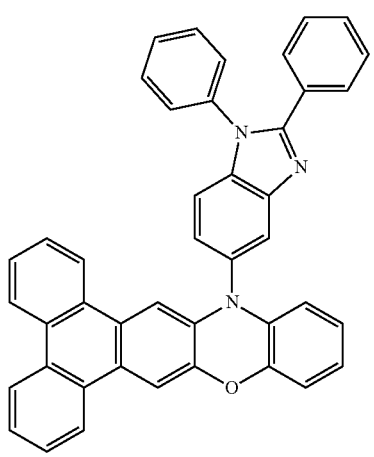

X7
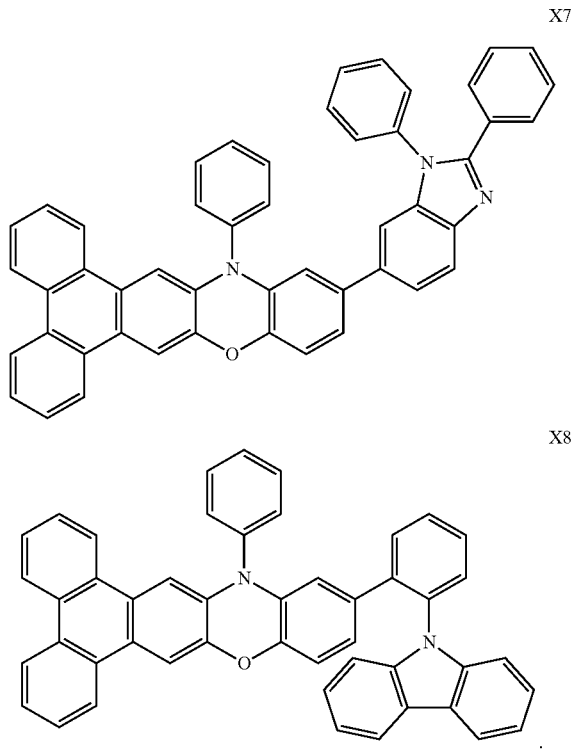

X8

Light emitting devices of embodiments, each including the fused polycyclic compound of an embodiment in an emission layer, were manufactured by the method below. Example 1 to Example 13 correspond to light emitting devices manufactured by respectively utilizing Compounds 1, 2, 3, 5, 6, 7, 9, 10, 11, 12, 13, 37 and 40, which are the aforementioned Example Compounds, as light emitting materials. Comparative Example 1 to Comparative Example 8 correspond to light emitting devices manufactured by respectively utilizing Comparative Compound X1 to Comparative Compound X8 as light emitting materials.

An ITO glass substrate was cut into a size of 50 mm×50 mm×0.5 mm, cleaned with ultrasonic waves utilizing isopropyl alcohol and pure water for about 10 minutes each, and then cleaned by irradiating with ultraviolet rays (UV) and exposing to ozone for about 10 minutes. This glass substrate was installed in a vacuum deposition apparatus. On the substrate, a hole injection layer with a thickness of about 4 nm was formed utilizing 4,4',4''-[tris(3-methylphenyl) phenylamino] triphenylamine (m-MTDATA), a hole transport layer with a thickness of about 5 nm was formed utilizing N,N'-di(naphthalen-1-yl)-N,N'-diphenyl-benzidine (NPB), an emission layer with a thickness of about 30 nm was formed utilizing the Example Compound or Comparative Compound doped with 1% of Compound D-1, an electron transport layer with a thickness of about 30 nm was formed utilizing Compound ET1, and a second electrode with a thickness of about 120 nm was formed utilizing Al. All layers were formed by a deposition method under a vacuum atmosphere.

The compounds utilized for the manufacture of the light emitting devices of the Examples and the Comparative Example are shown below. The commercial materials were purified by sublimation and then utilized for the manufacture of the devices.

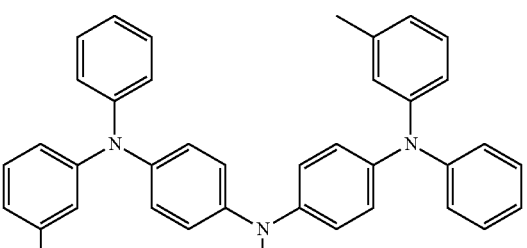

m-MTDATA

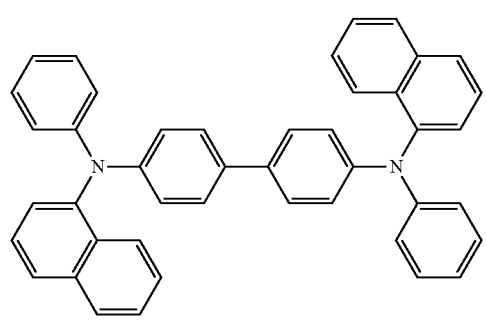

NPB

D-1
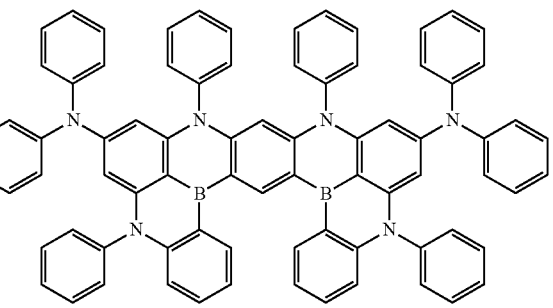

-continued

ET1

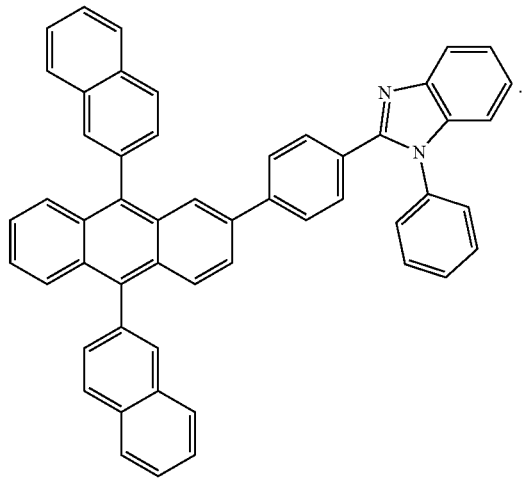

Experimental Examples

The device efficiencies of the light emitting devices manufactured utilizing Example Compounds 1, 2, 3, 5, 6, 7, 9, 10, 11, 12, 13, 37 and 40, and Comparative Compound X1 to Comparative Compound X8 were evaluated. Evaluation results are shown in Table 1. In the device evaluation, the device efficiency and device life were measured at a current density of about 10 mA/cm$^2$.

TABLE 1

| Device manufacturing example | Dopant compound | Emission efficiency (cd/A) | Device life (T$_{90}$, h) |
| --- | --- | --- | --- |
| Example 1 | Compound 1 | 22.9 | 15 |
| Example 2 | Compound 2 | 23.8 | 17 |
| Example 3 | Compound 3 | 23.6 | 15.5 |
| Example 4 | Compound 5 | 24.6 | 16.7 |
| Example 5 | Compound 6 | 25.2 | 15.4 |
| Example 6 | Compound 7 | 24 | 14.6 |
| Example 7 | Compound 9 | 25.4 | 16.4 |
| Example 8 | Compound 10 | 23.5 | 17.2 |
| Example 9 | Compound 11 | 25.6 | 17.6 |
| Example 10 | Compound 12 | 22.2 | 14.2 |
| Example 11 | Compound 13 | 24.7 | 15.9 |
| Example 12 | Compound 37 | 23.2 | 15.5 |
| Example 13 | Compound 40 | 23.6 | 17 |
| Comparative Example 1 | Comparative Compound X1 | 16 | 8 |
| Comparative Example 2 | Comparative Compound X2 | 20 | 11 |
| Comparative Example 3 | Comparative Compound X3 | 19.8 | 11.1 |
| Comparative Example 4 | Comparative Compound X4 | 17.4 | 10.8 |
| Comparative Example 5 | Comparative Compound X5 | 18.2 | 12.5 |
| Comparative Example 6 | Comparative Compound X6 | 17.7 | 11.6 |
| Comparative Example 7 | Comparative Compound X7 | 16.4 | 9.4 |
| Comparative Example 8 | Comparative Compound X8 | 17.1 | 10.9 |

Referring to the results of Table 1, it could be confirmed that the Examples of the light emitting devices utilizing the fused polycyclic compounds according to embodiments of the present disclosure as light emitting materials each showed improved emission efficiency and device life when compared with the Comparative Examples.

The Example Compounds each have a skeleton structure in which a triphenylene moiety is fused to an additional structure (e.g., additional ring) through an additional connecting group including an amine group, an oxy group, a thio group, and/or a carbonyl group, and further includes a fused ring substituent including an imidazole moiety. Accordingly, when the Example Compounds are included in an emission layer, the electron concentration of an emission layer may be controlled or selected, formation of excitons in the emission layer may be improved, and the efficiency and/or life span of the light emitting device including the compound may be improved. For example, by including the fused polycyclic compound of an embodiment as a host material of a light emitting device, the efficiency and/or life span of the light emitting device may be improved.

Comparative Compound X1 and Comparative Compound X2 respectively included in Comparative Example 1 and Comparative Example 2 do not include a skeleton structure having a triphenylene moiety and a fused ring substituent including an imidazole moiety, and the devices of Comparative Example 1 and Comparative Example 2 showed degraded emission efficiency and device life span when compared with the Examples. Comparative Compound X3 included in Comparative Example 3 includes a triphenylene moiety and a fused ring substituent including an imidazole moiety, but an additional fused structure is not formed at the triphenylene moiety via an additional connecting group. Accordingly, it could be confirmed that Comparative Example 3 showed degraded emission efficiency and device life span when compared with the Examples. Comparative Compounds X4, X6 and X7 respectively included in Comparative Examples 4, 6 and 7 include a skeleton structure in which an additional fused structure is formed at a triphenylene moiety via an additional connecting group and a substituent including an imidazole moiety is present, but the structures in which an imidazole moiety substituent is fused are different from that of the fused polycyclic compound of an embodiment. Accordingly, it could be confirmed that Comparative Examples 4, 6 and 7 showed degraded emission efficiency and device life span when compared with the Examples. Comparative Compounds X5 and X8 respectively included in Comparative Examples 5 and 8 have a skeleton structure in which an additional fused ring is formed at a triphenylene moiety via an additional connecting group, but do not include a substituent having an imidazole moiety. Accordingly, it could be confirmed that Comparative Examples 5 and 8 showed degraded emission efficiency and device life span when compared with the Examples.

The light emitting device of an embodiment may show improved device properties of high efficiency and/or long life span.

The fused polycyclic compound of an embodiment may be included in an emission layer of a light emitting device and may contribute to the increase of the efficiency and life of an organic electroluminescence device.

As used herein, the terms "substantially," "about," and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although embodiments of the present disclosure have been described, it is understood that the present disclosure should not be limited to these embodiments, but various suitable changes and modifications can be made by one ordinary skilled in the art within the spirit and scope of the present disclosure as set forth in the following claims and their equivalents.

What is claimed is:

1. A light emitting device, comprising:
a first electrode;
a second electrode opposite the first electrode; and
multiple organic layers between the first electrode and the second electrode,
wherein at least one organic layer among the organic layers comprises a fused polycyclic compound, and
the fused polycyclic compound is represented by Formula 1:

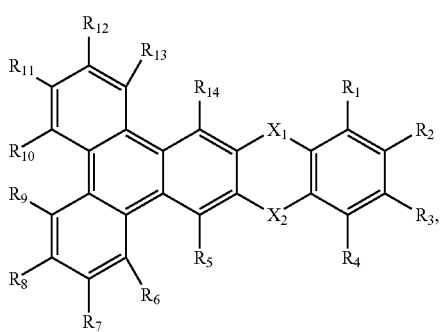

Formula 1 wherein in Formula 1,
$X_1$ and $X_2$ are each independently $NR_{15}$, O or S, at least one among $X_1$ and $X_2$ is $NR_{15}$,
$R_1$ to $R_{15}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and/or combined with an adjacent group to form a ring, and at least one among $R_1$ to $R_{15}$ is a substituent represented by Formula 2:

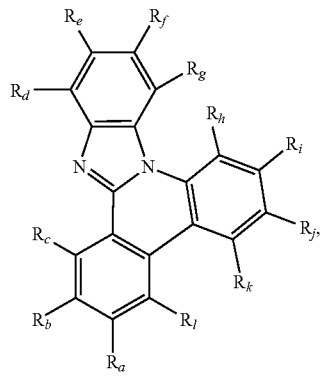

Formula 2 and
wherein in Formula 2,
$R_a$ to $R_l$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and/or combined with an adjacent group to form a ring, and any one among $R_a$ to $R_l$ is a position connected with Formula 1.

2. The light emitting device of claim 1, wherein the organic layers comprise:
a hole transport region on the first electrode;
an emission layer on the hole transport region; and
an electron transport region on the emission layer, and
wherein the emission layer comprises the fused polycyclic compound.

3. The light emitting device of claim 2, wherein the emission layer is to emit delayed fluorescence.

4. The light emitting device of claim 2, wherein the emission layer is a delayed fluorescence emission layer comprising a host and a dopant, and
the host comprises the fused polycyclic compound.

5. The light emitting device of claim 2, wherein the emission layer is to emit light with a central wavelength of about 430 nm to about 490 nm.

6. The light emitting device of claim 1, wherein the fused polycyclic compound represented by Formula 1 is represented by Formula 1-1 or Formula 1-2:

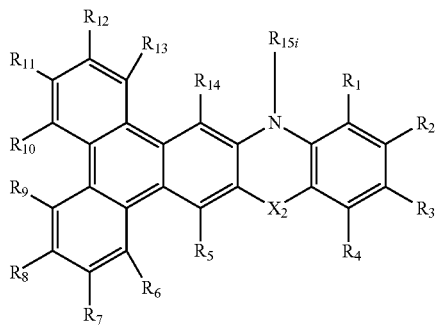

Formula 1-1

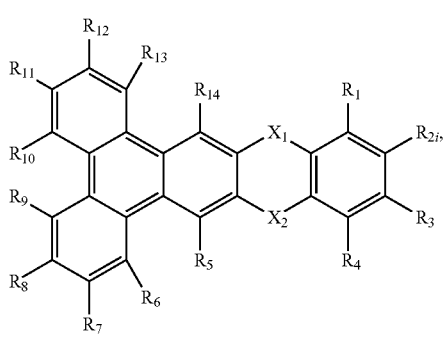

Formula 1-2 and wherein in Formula 1-1 and Formula 1-2, $R_{2i}$ and $R_{15i}$ are each independently the substituent represented by Formula 2, and $X_1$, $X_2$, and $R_1$ to $R_{15}$ are each independently the same as defined in Formula 1.

7. The light emitting device of claim 1, wherein the substituent represented by Formula 2 is represented by any one among Formula 2-1 to Formula 2-4:

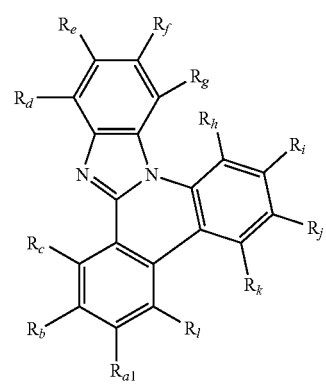

Formula 2-1

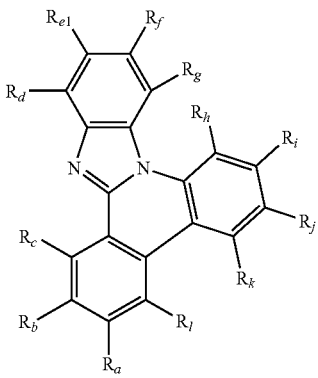

Formula 2-2

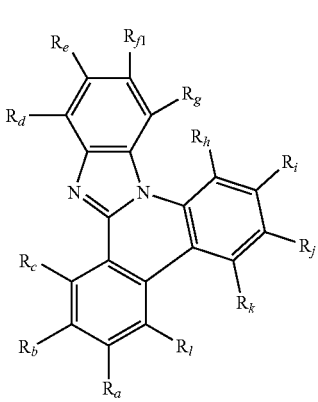

Formula 2-3

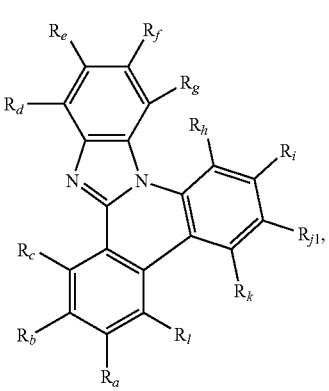

Formula 2-4 and wherein in Formula 2-1 to Formula 2-4, $R_{a1}$, $R_{e1}$, $R_{f1}$, and $R_{j1}$ are each independently a position connected with Formula 1, and $R_a$ to $R_l$ are each independently the same as defined in Formula 2.

8. The light emitting device of claim 1, wherein the fused polycyclic compound represented by Formula 1 is represented by any one among Formula 3-1 to Formula 3-9:

Formula 3-1
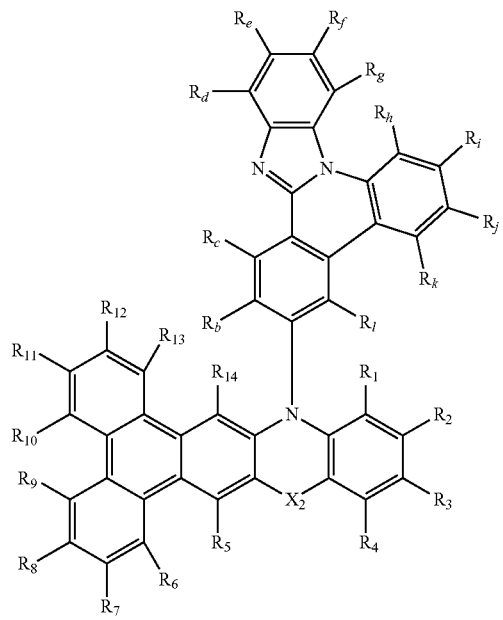
Formula 3-2
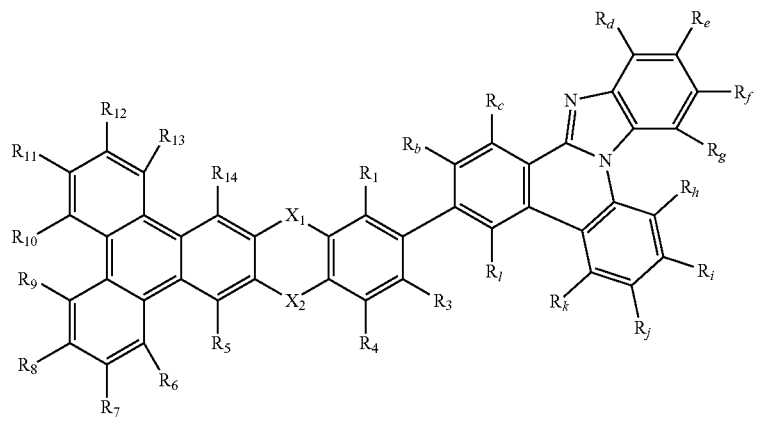
Formula 3-3
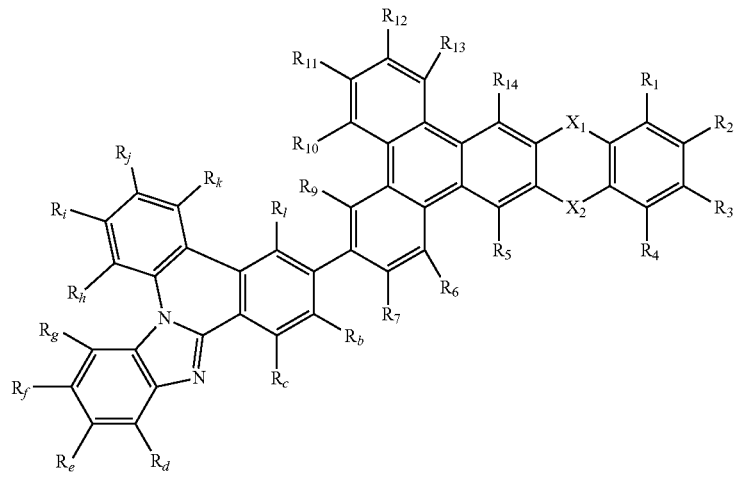

Formula 3-4
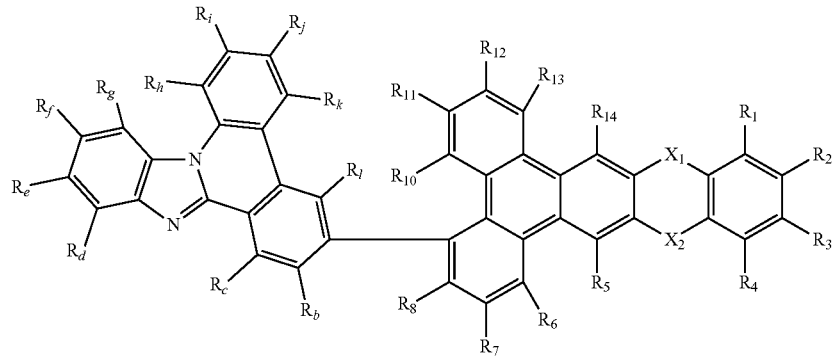
Formula 3-5
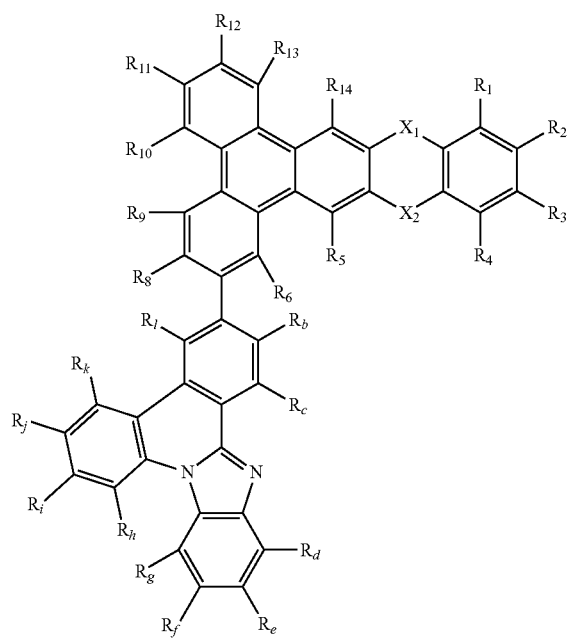
Formula 3-6
Formula 3-7
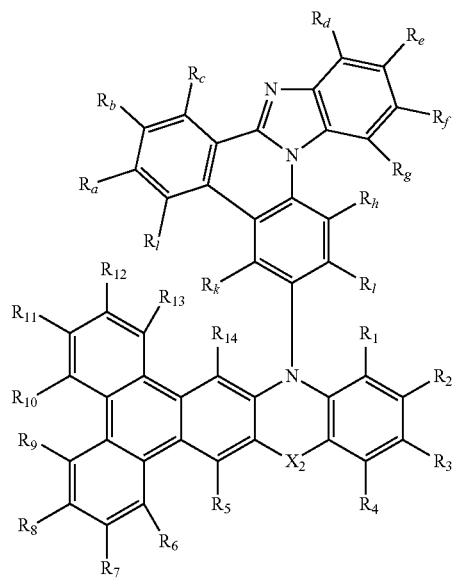
Formula 3-8
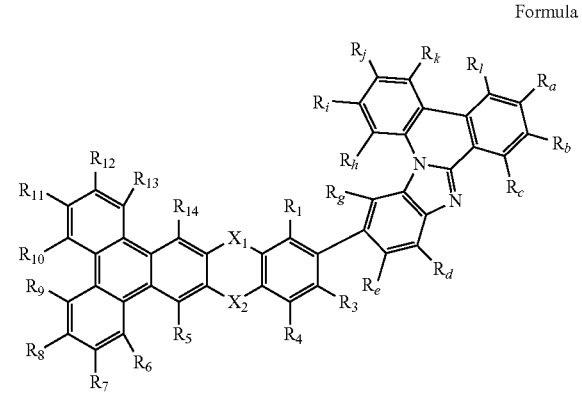

Formula 3-9

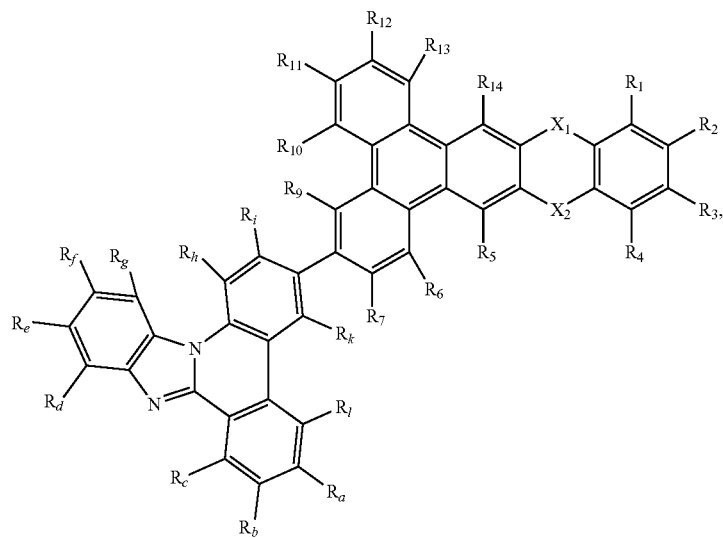

and wherein in Formula 3-1 to Formula 3-9, $X_1$, $X_2$, $R_1$ to $R_{15}$, and $R_a$ to $R_l$ are each independently the same as defined in Formula 1 and Formula 2.

9. The light emitting device of claim 1, wherein the fused polycyclic compound represented by Formula 1 is represented by any one among Formula 4-1 to Formula 4-3:

Formula 4-1

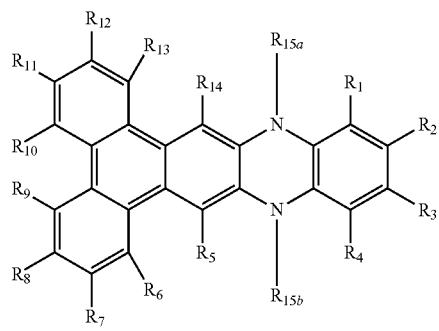

Formula 4-2

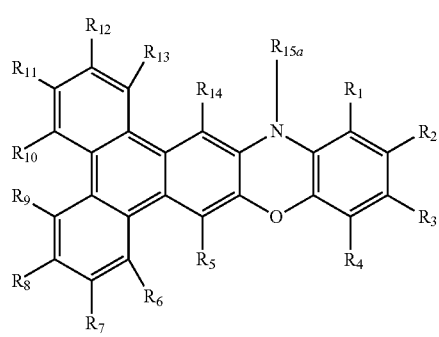

Formula 4-3

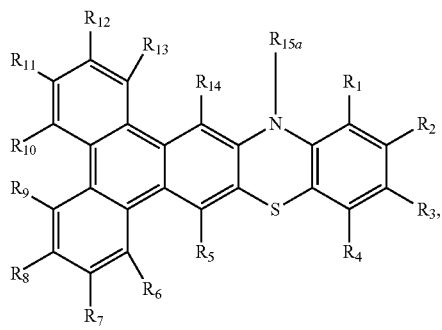

and wherein in Formula 4-1 to Formula 4-3, $R_{15a}$ and $R_{15b}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, a substituted or unsubstituted heteroaryl group of 2 to 60 ring-forming carbon atoms, or the substituent represented by Formula 2, and $R_1$ to $R_{14}$ are each independently the same as defined in Formula 1.

10. The light emitting device of claim 1, wherein, in Formula 1, $R_1$ to $R_{15}$ are each independently a hydrogen atom, a deuterium atom, a halogen atom, a substituted or unsubstituted silyl group, a substituted or unsubstituted phenyl group, a substituted or unsubstituted carbazole group, a substituted or unsubstituted dibenzofuran group, a substituted or unsubstituted dibenzothiophene group, or the substituent represented by Formula 2.

11. The light emitting device of claim 1, wherein, in Formula 2,
R$_a$ to R$_l$ are each independently a hydrogen atom, a deuterium atom, or a position connected with Formula 1.

12. The light emitting device of claim 1, further comprising a capping layer on the second electrode, and
the capping layer has a refractive index of 1.6 or more.

13. The light emitting device of claim 1, wherein the fused polycyclic compound comprises at least one among compounds in Compound Group 1:

Compound Group 1

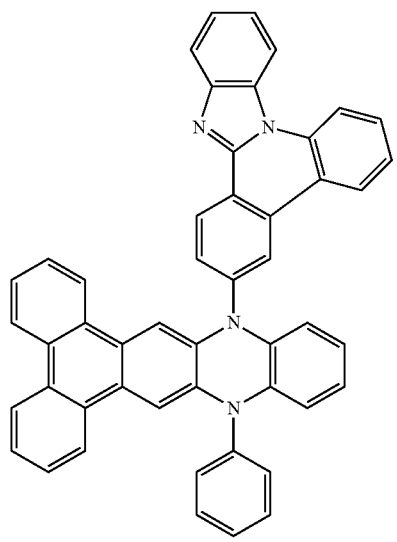

1

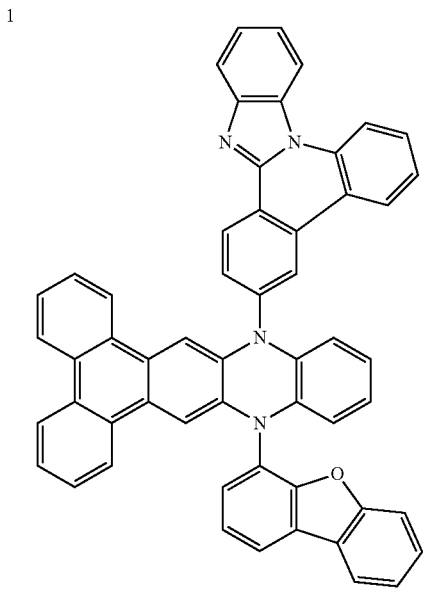

2

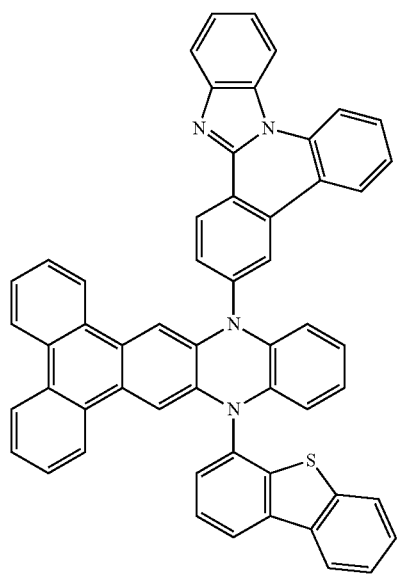

3

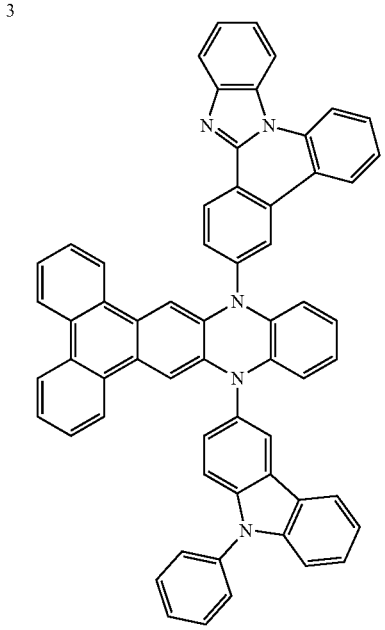

4

-continued
5
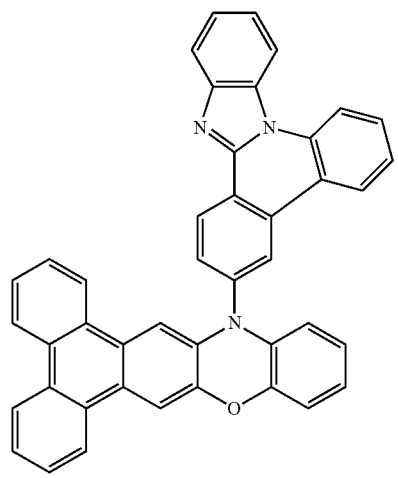
6
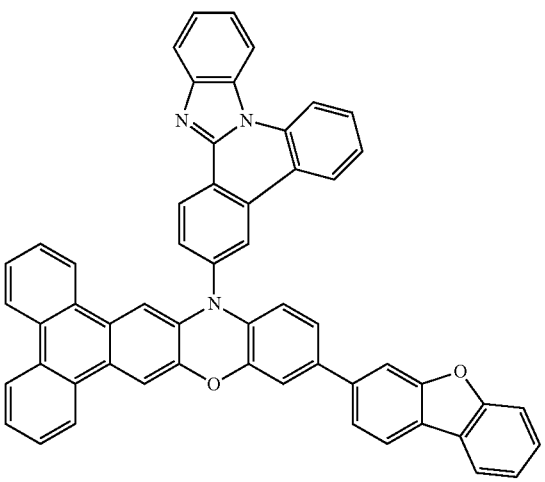
7
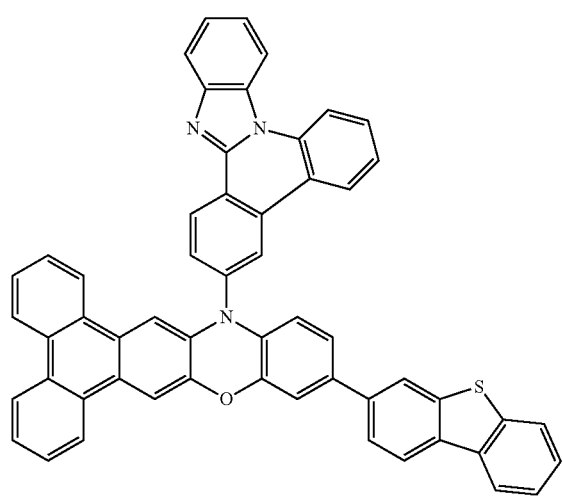
8
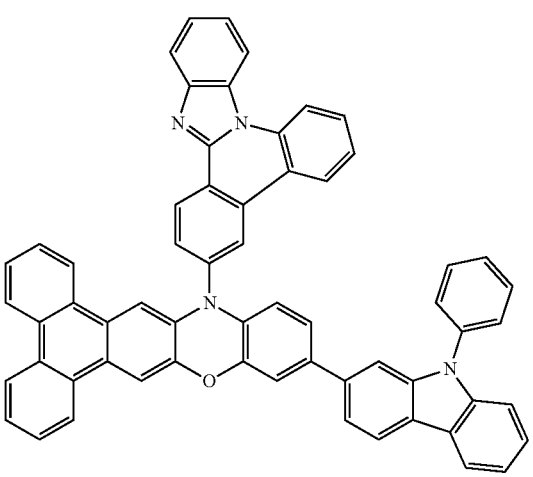
9
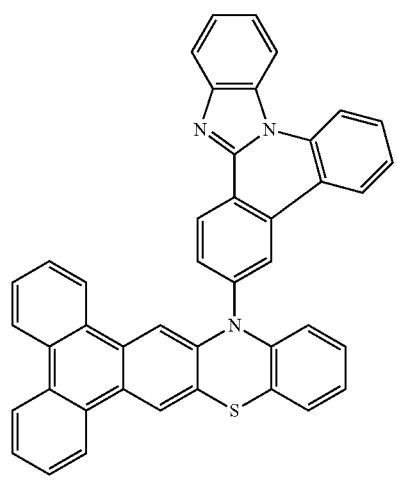
10
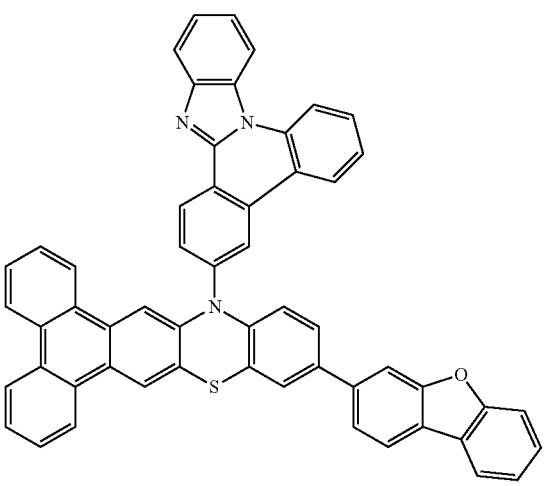

-continued
11
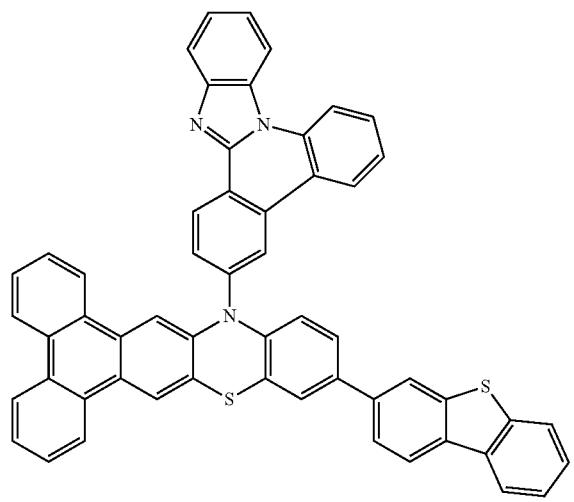
12
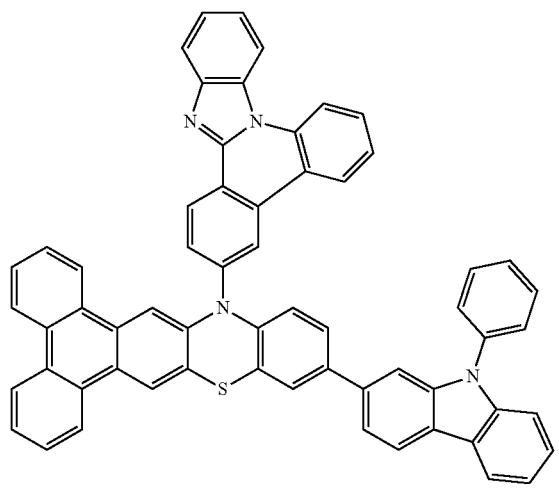
13
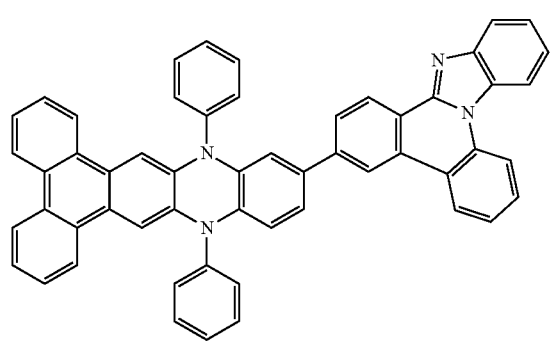
14
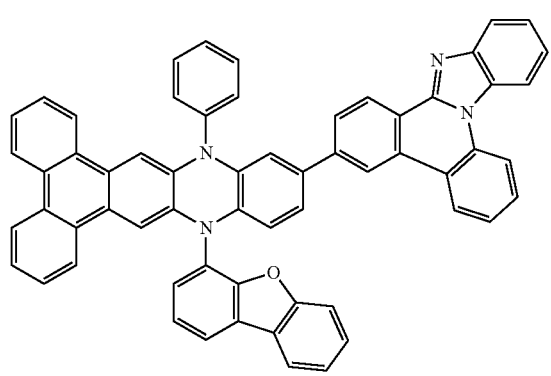
15
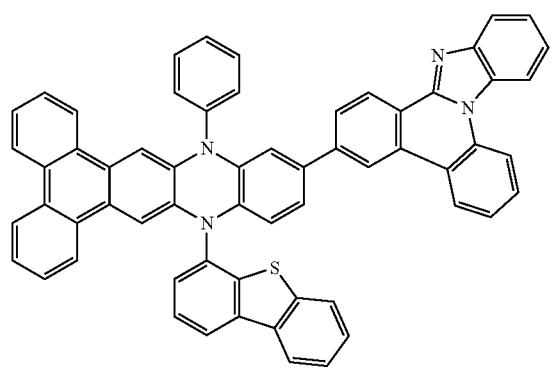
16
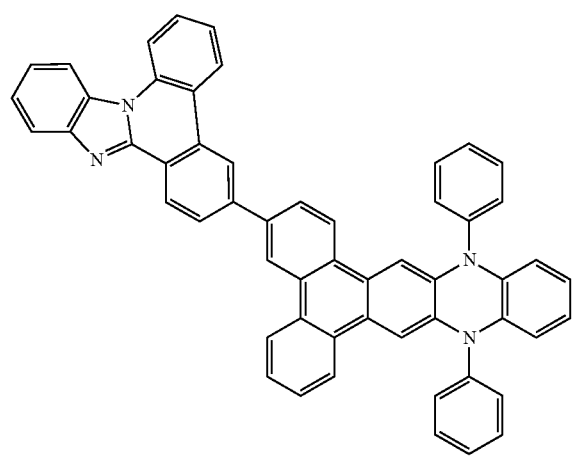

-continued
17
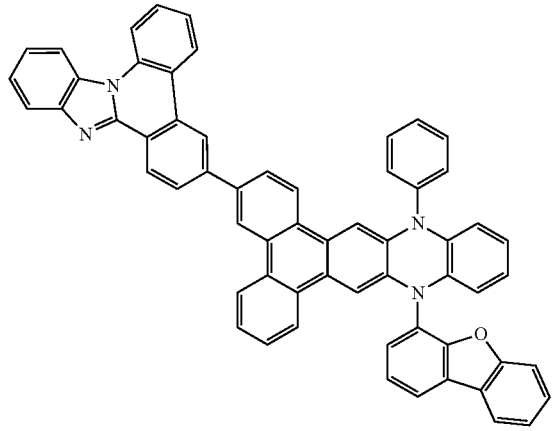
18
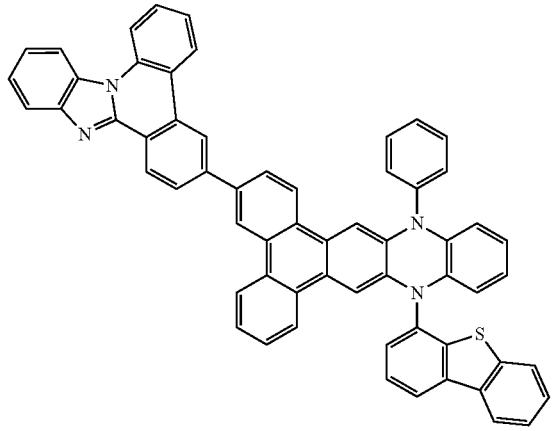
19
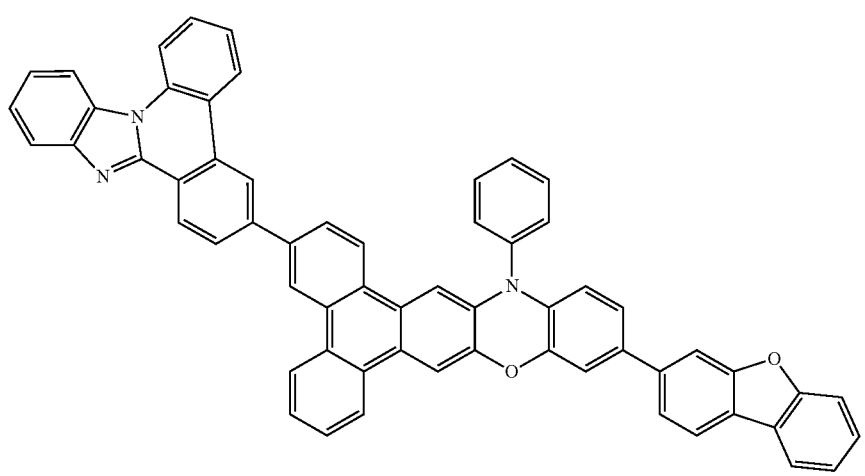
20
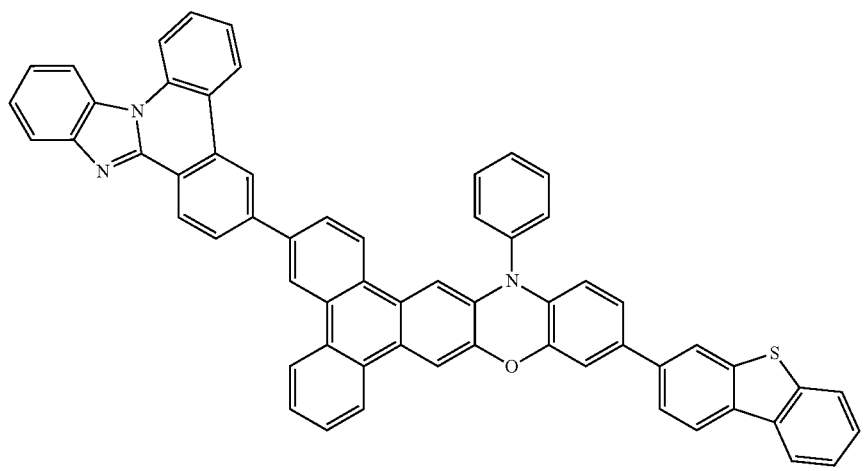

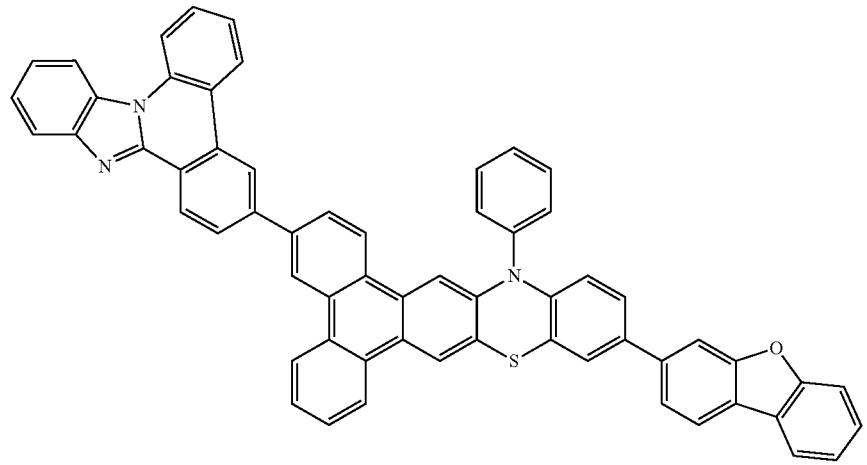
21
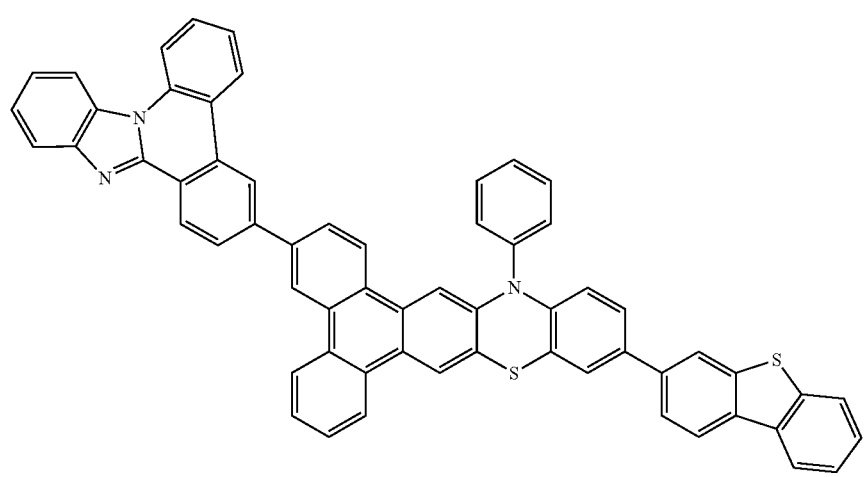
22
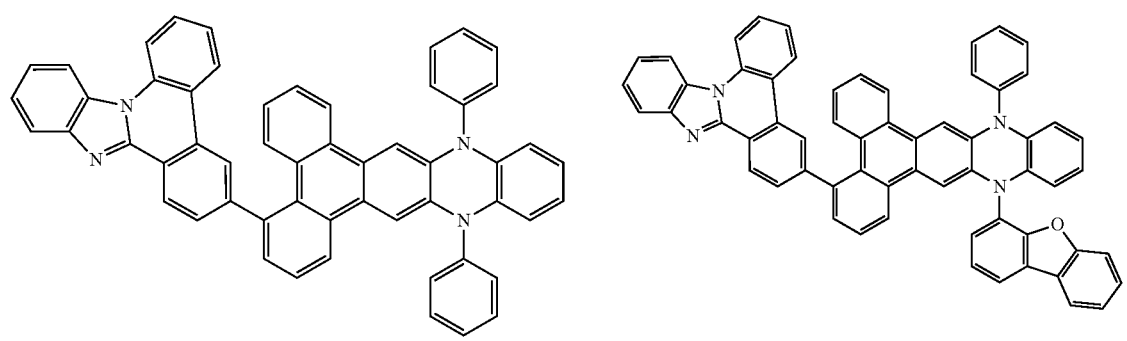
23 24

-continued
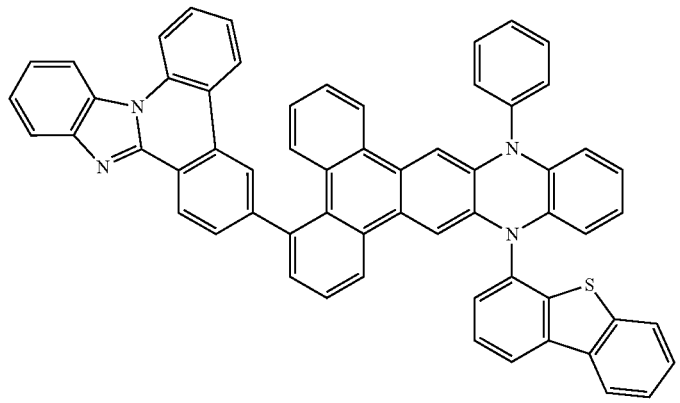
25
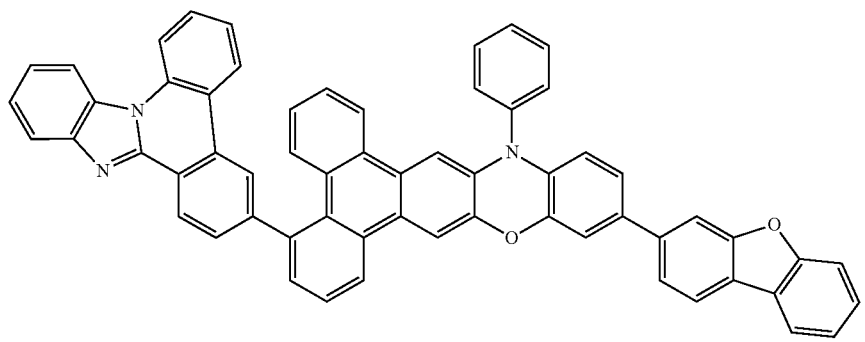
26
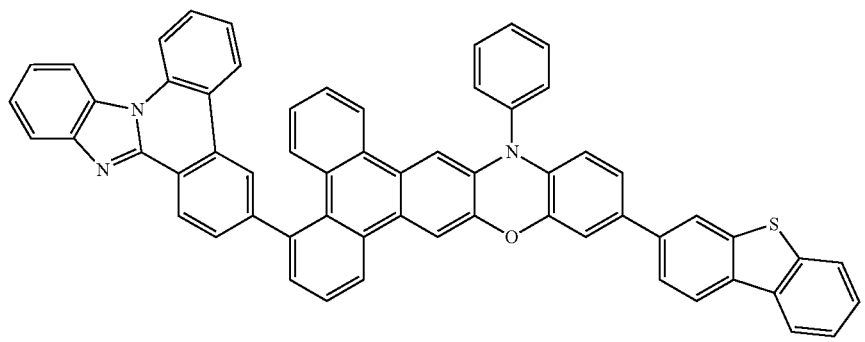
27
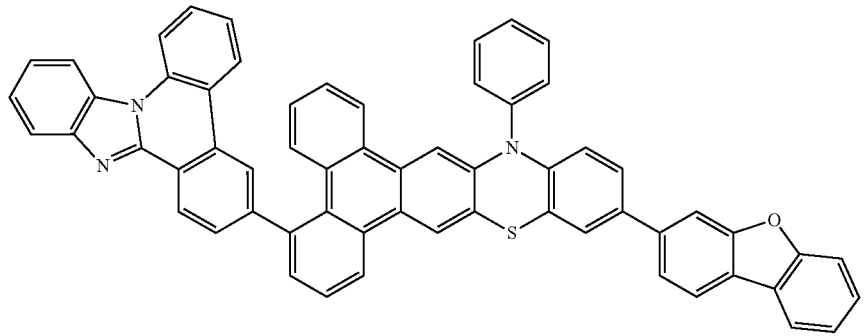
28

29
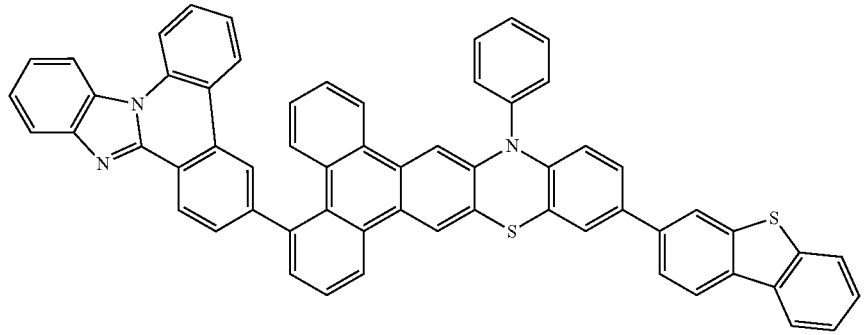
30
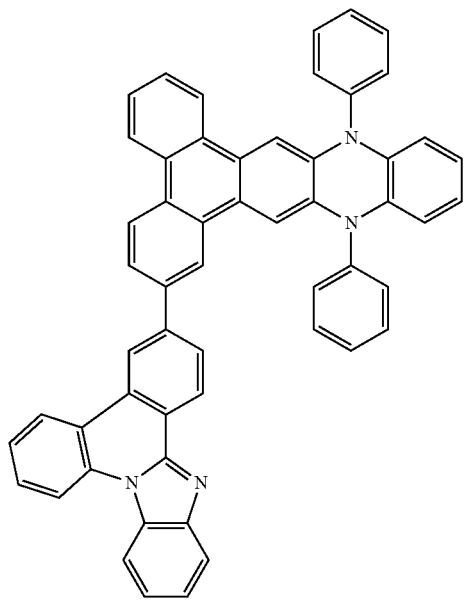
31
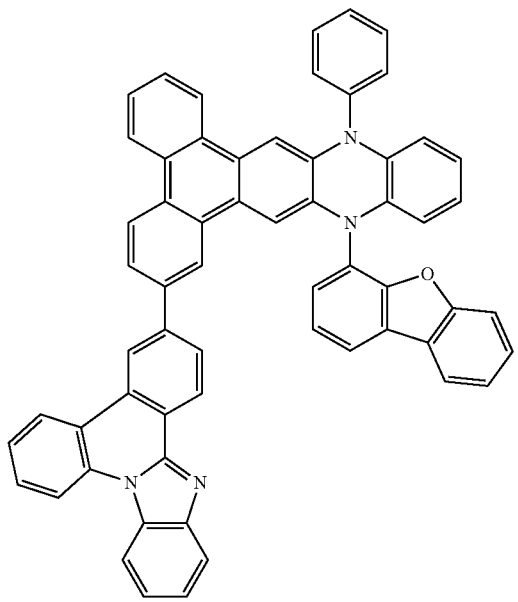
32
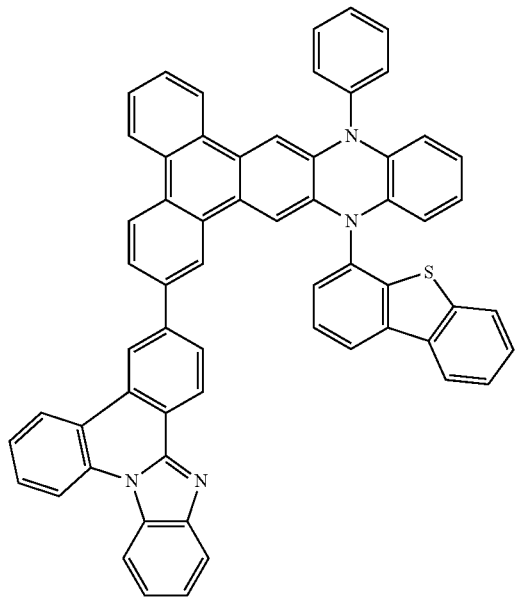
33
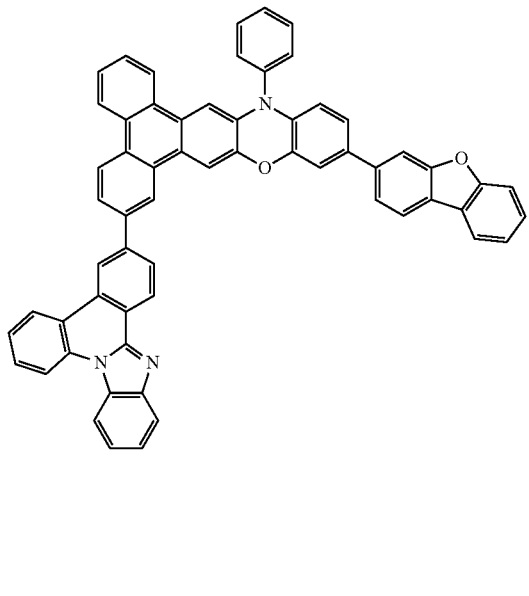

-continued
34
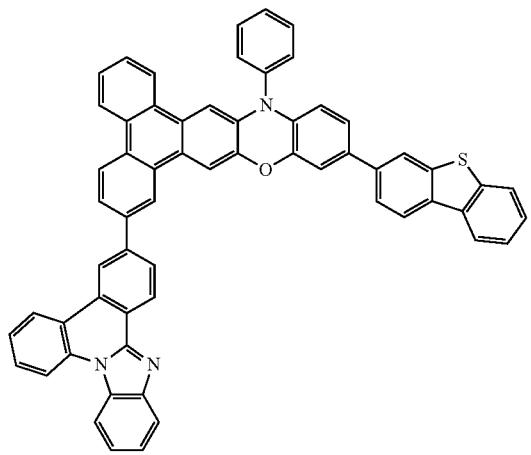
35
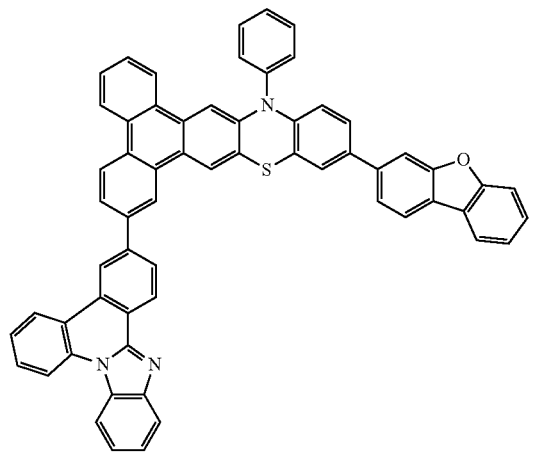
36
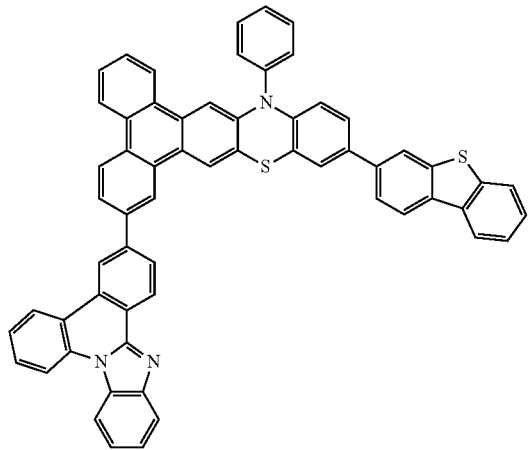
37
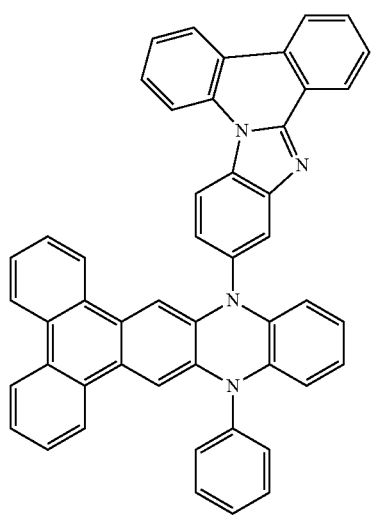
38
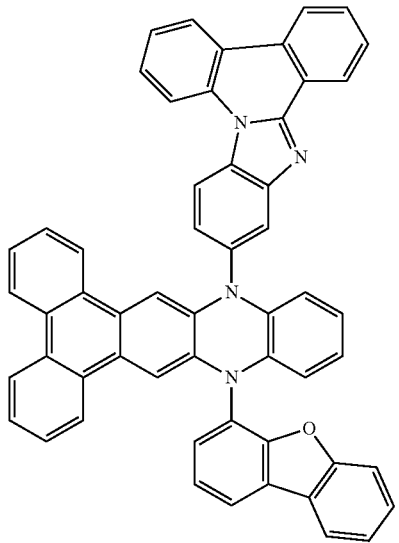
39
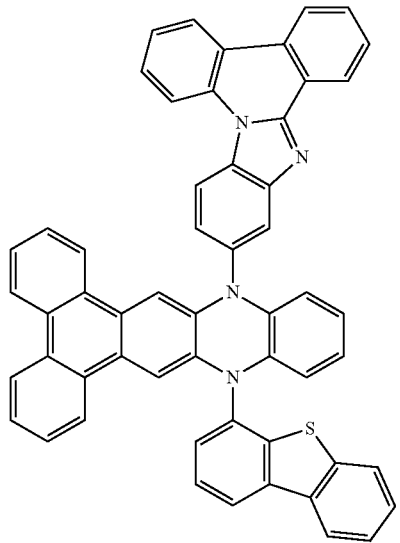

-continued
40
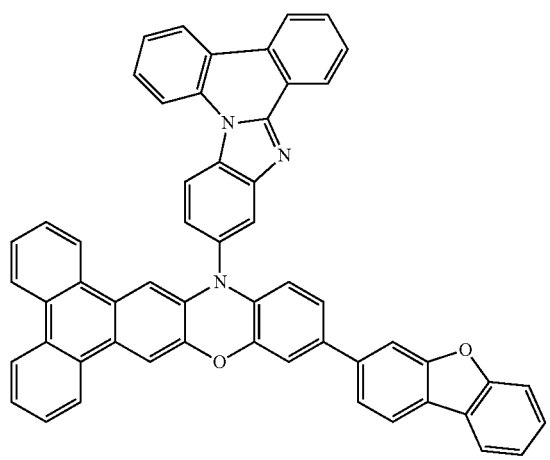
41
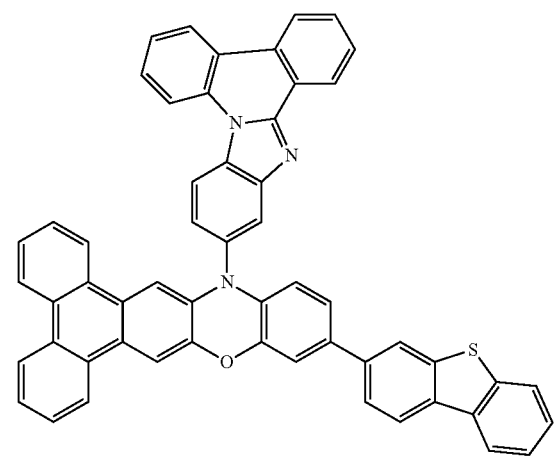
42
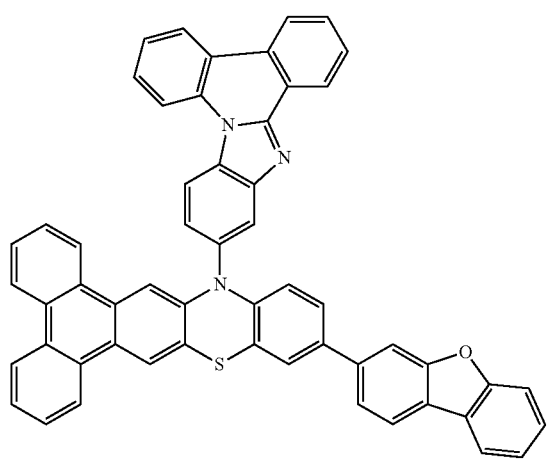
43
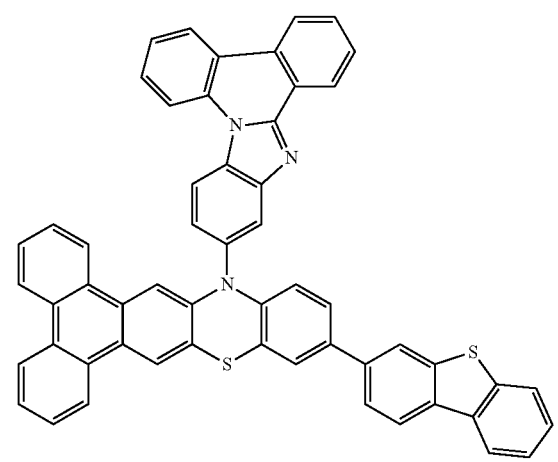
44
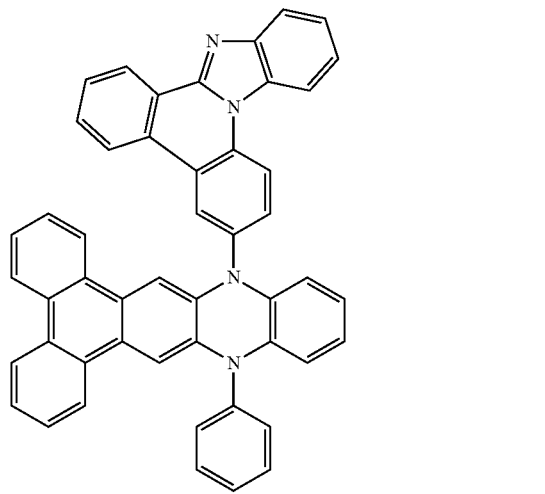
45
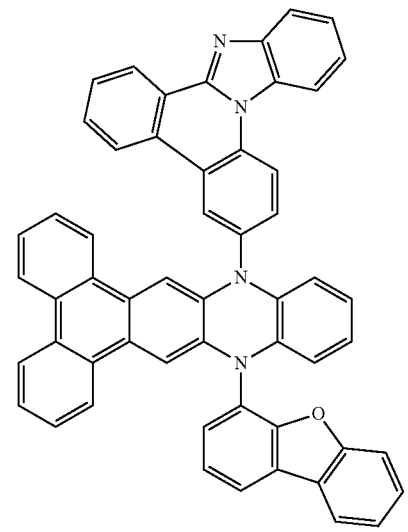

-continued
46
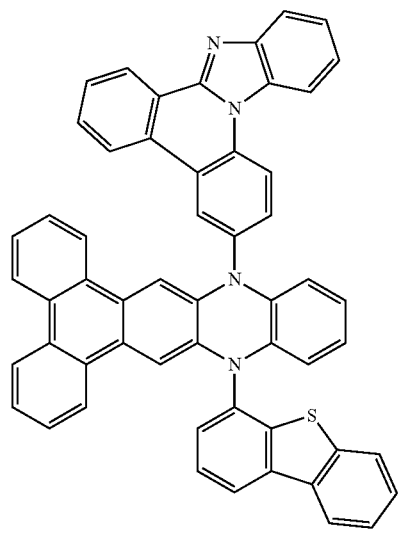
47
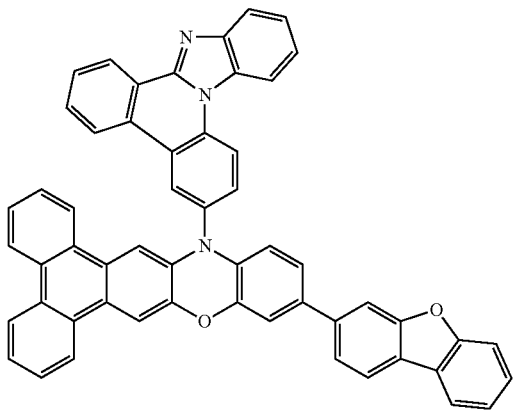
48
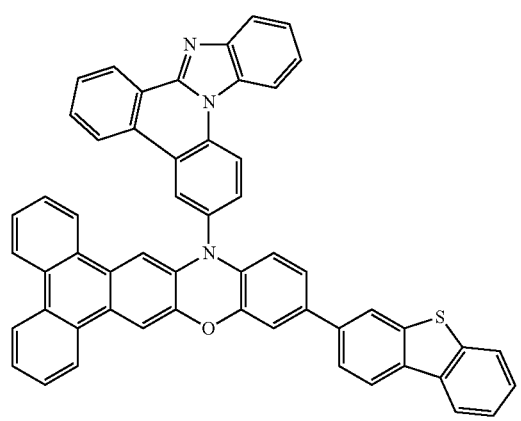
49
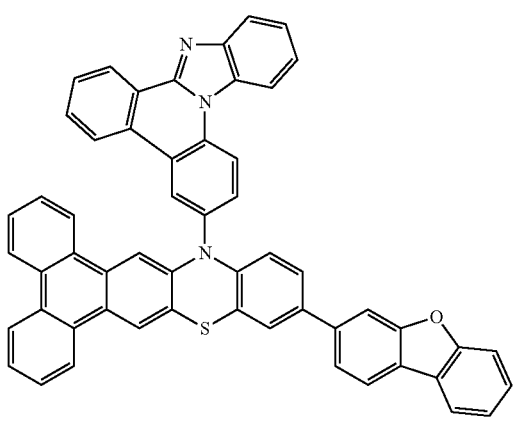
50
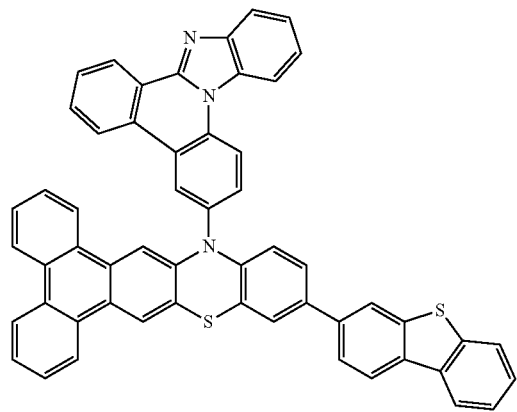
51
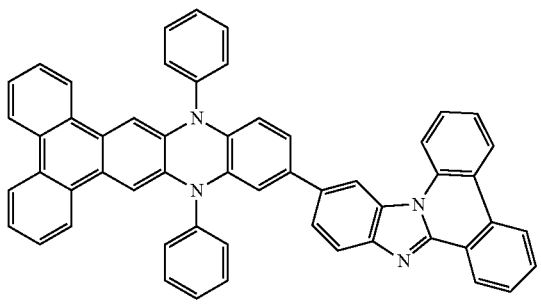

-continued
52
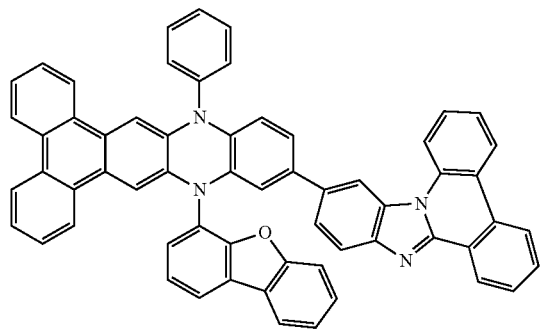
53
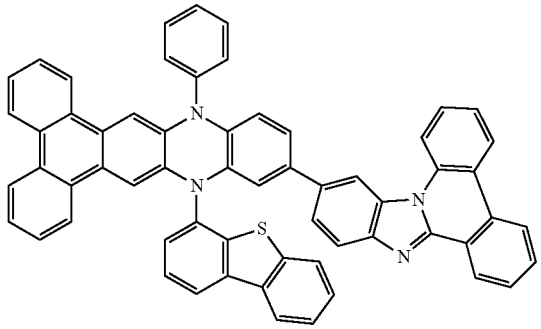
54
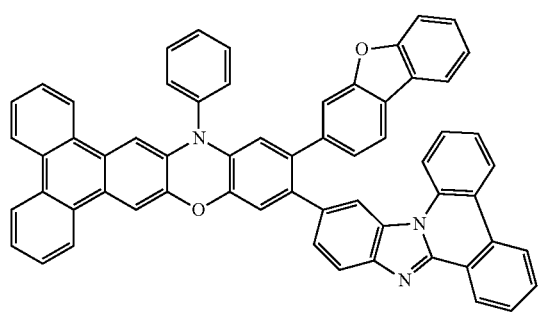
55
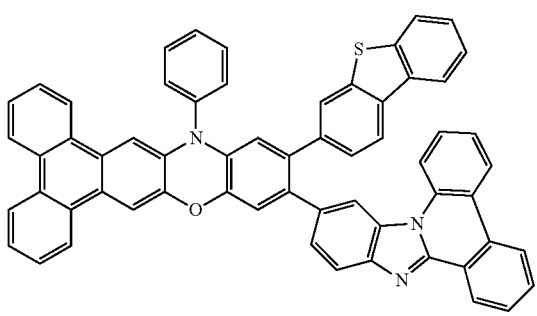
56
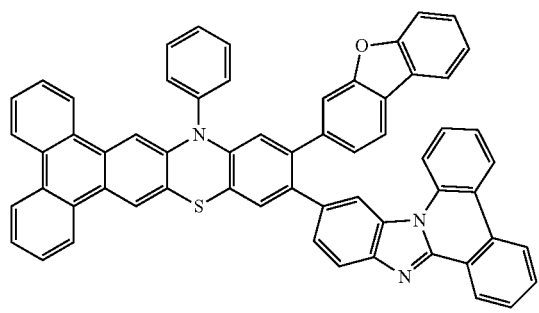
57
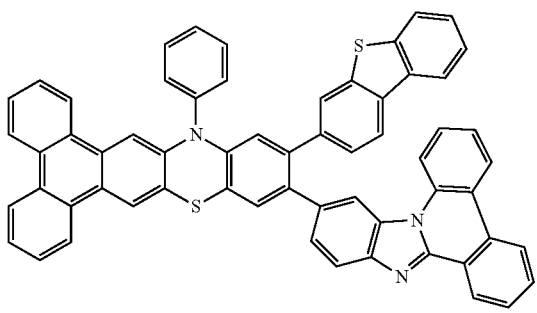
58
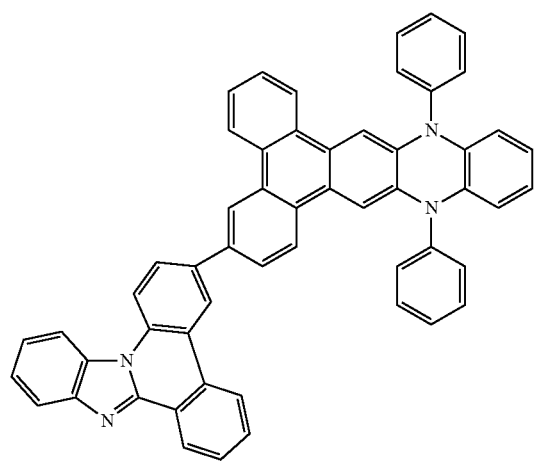
59
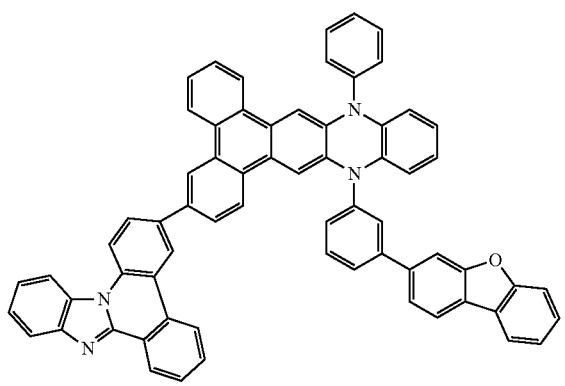

-continued
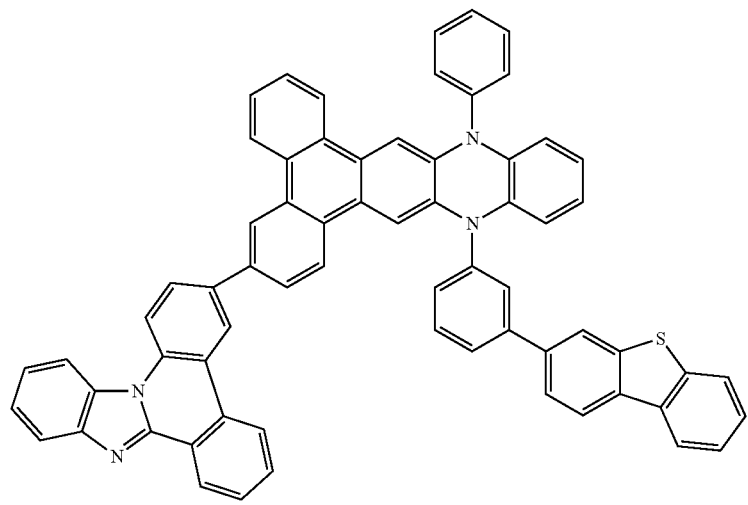
60
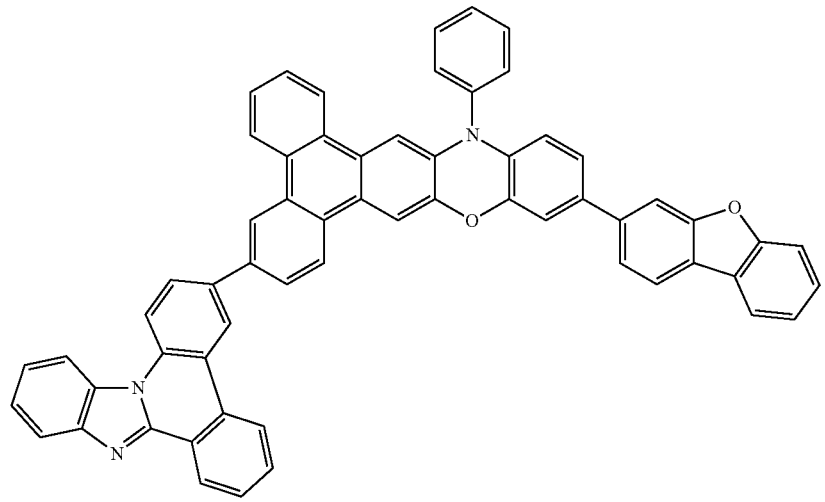
61
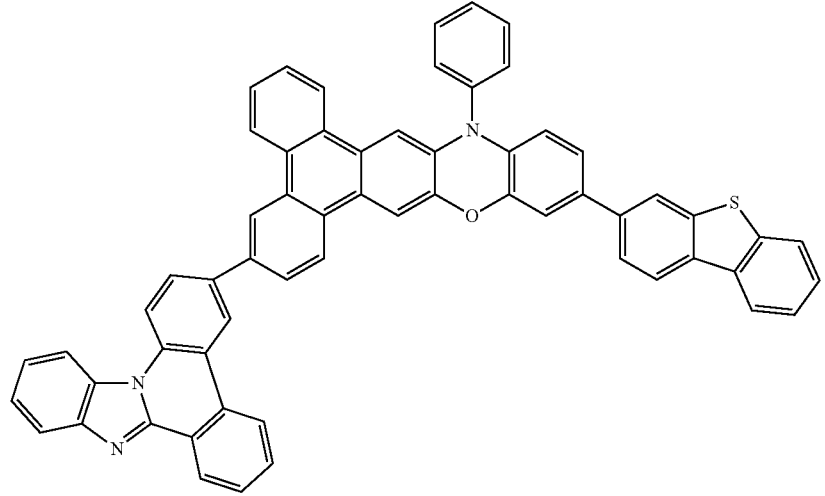
62

63
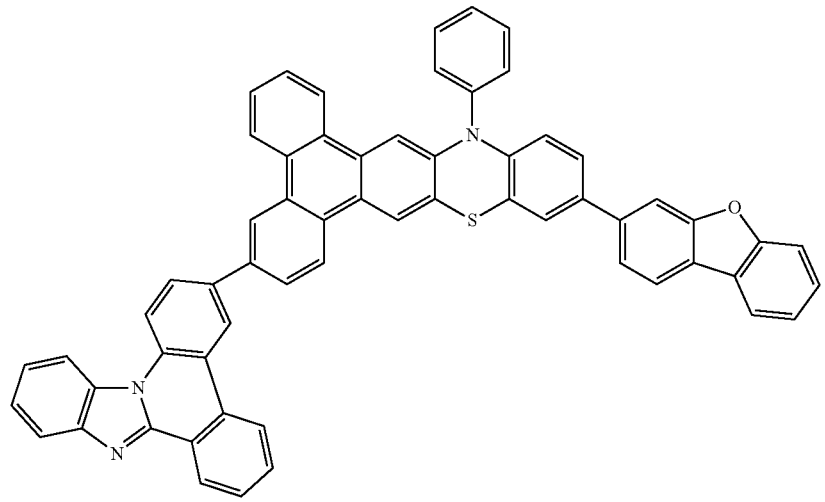
64
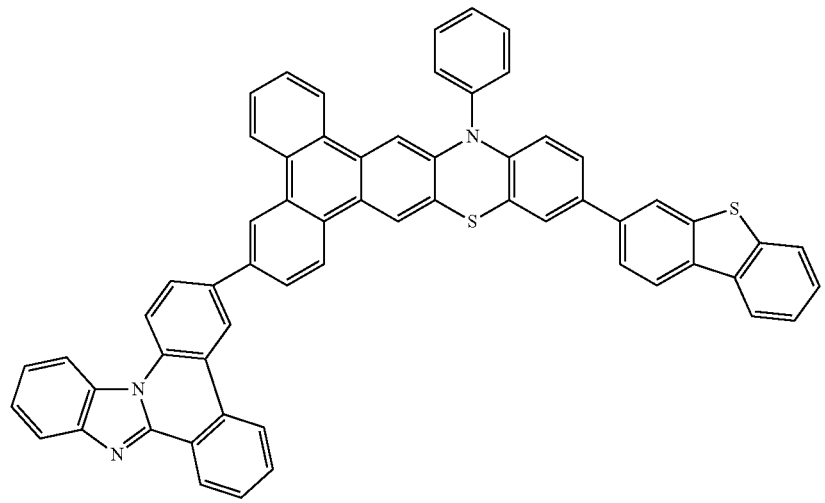
65
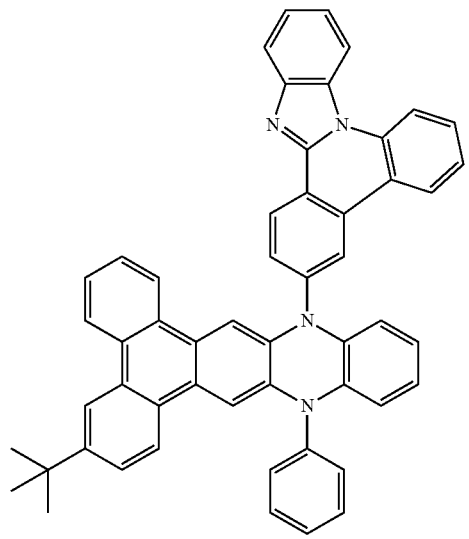
66
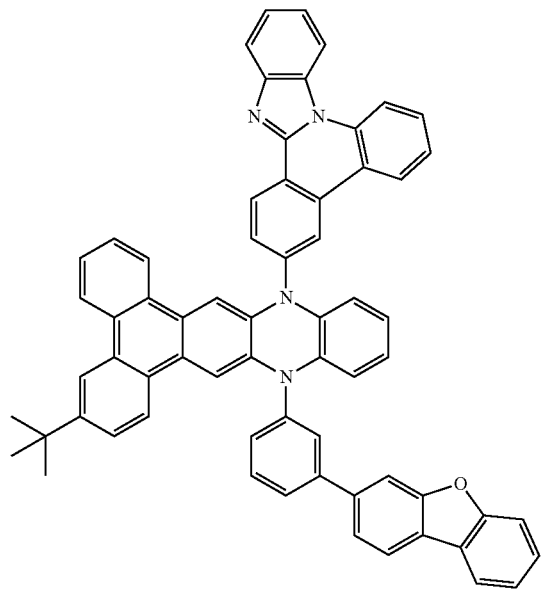

67
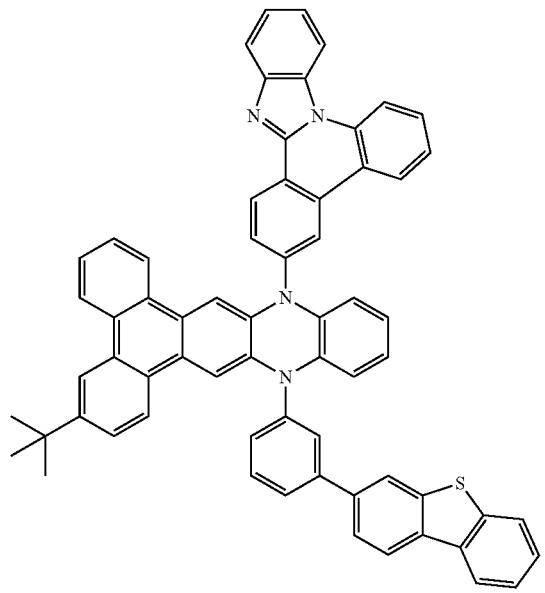
68
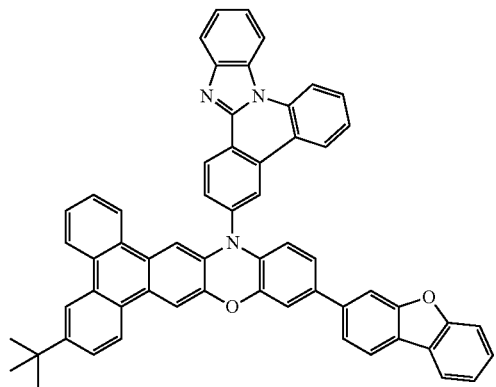
69
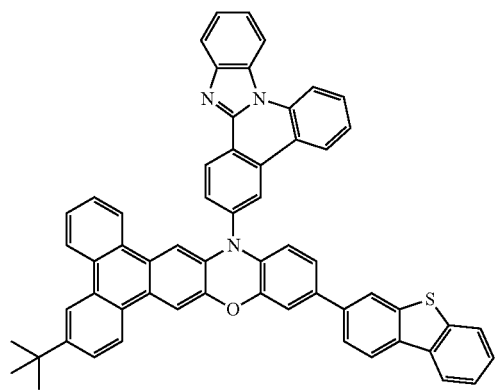
70
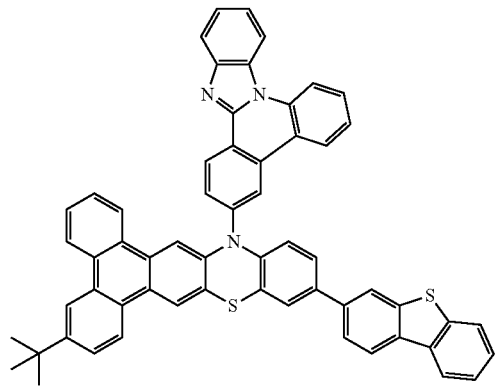
71
72
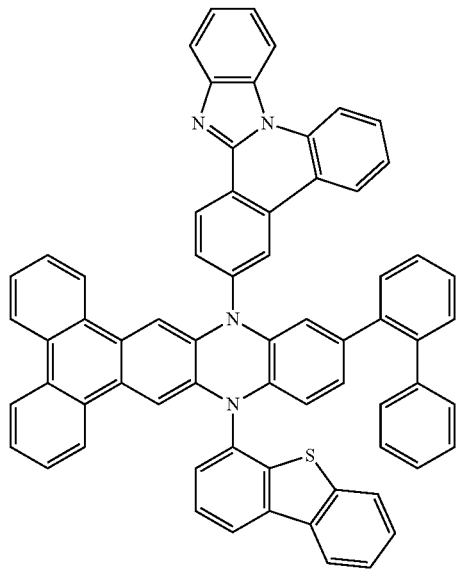

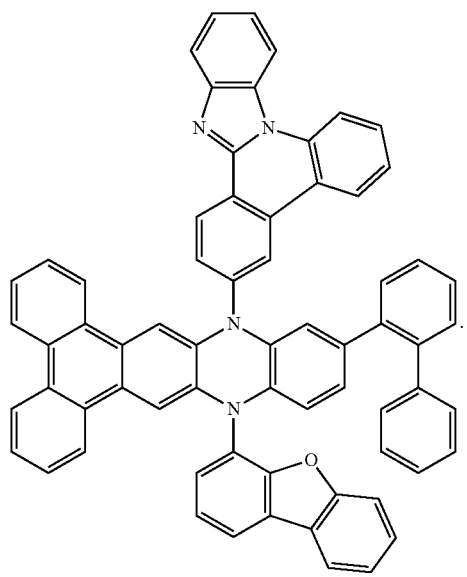

14. A light emitting device, comprising:
a first electrode;
a second electrode opposite to the first electrode; and
an emission layer between the first electrode and the second electrode,
wherein the emission layer comprises a host and a dopant, and
the host comprises a fused polycyclic compound represented by Formula 1:

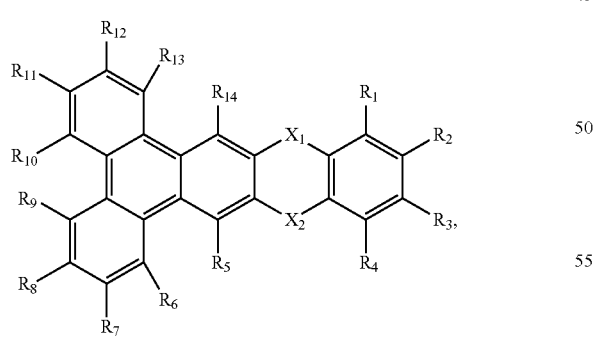

Formula 1 wherein in Formula 1,
$X_1$ and $X_2$ are each independently $NR_{15}$, O or S,
$R_1$ to $R_{15}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and/or combined with an adjacent group to form a ring, and
at least one among $R_1$ to $R_{15}$ is a substituent represented by Formula 2:

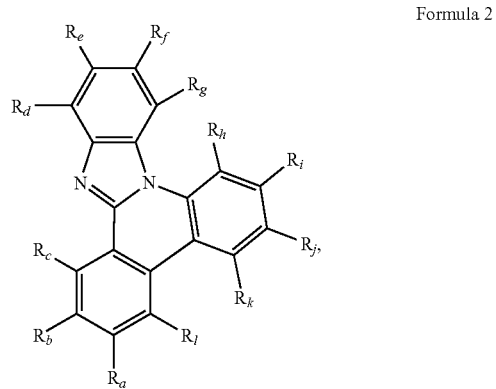

Formula 2 and
wherein in Formula 2,
$R_a$ to $R_l$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, or combined with an adjacent group from each other to form a ring, and at least one among $R_a$ to $R_l$ is a position connected with Formula 1.

15. The light emitting device of claim 14, wherein the dopant comprises a compound represented by Formula D:

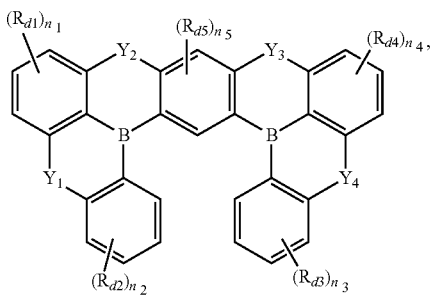

Formula D and wherein in Formula D, $Y_1$ to $Y_4$ are each independently $NR_{d6}$, O or S, $R_{d1}$ to $R_{d6}$ are each independently a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group from each other to form a ring, "$n_1$" and "$n_4$" are each independently an integer of 0 to 3, "$n_2$" and "$n_3$" are each independently an integer of 0 to 4, and "$n_5$" is an integer of 0 to 2.

16. The light emitting device of claim 14, wherein the fused polycyclic compound represented by Formula 1 is represented by any one among Formula 1-1 to Formula 1-5:

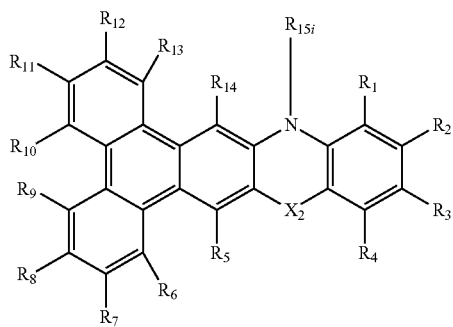

Formula 1-1

-continued

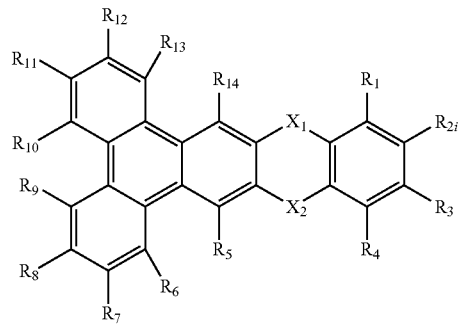

Formula 1-2

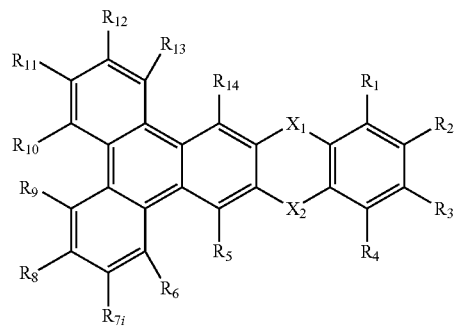

Formula 1-3

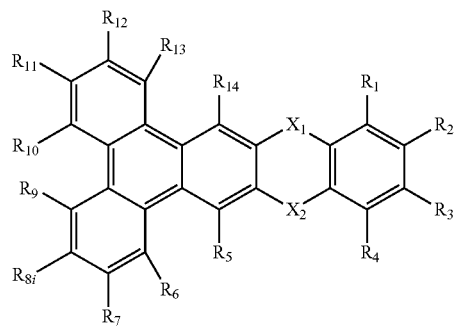

Formula 1-4

-continued

Formula 1-5

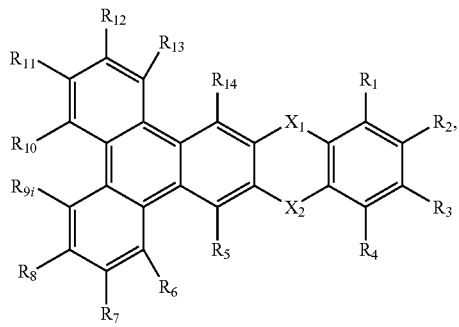

and
wherein in Formula 1-1 to Formula 1-5,
$R_{2i}$, $R_{7i}$, $R_{8i}$, $R_{9i}$, and $R_{15i}$ are each independently the substituent represented by Formula 2, and
$X_1$, $X_2$, and $R_1$ to $R_{15}$ are each independently the same as defined in Formula 1.

17. The light emitting device of claim 14, wherein the substituent represented by Formula 2 is represented by any one among Formula 2-1 to Formula 2-4:

Formula 2-1

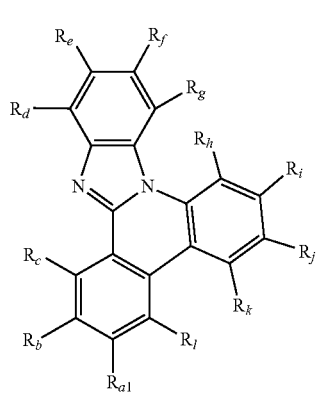

Formula 2-2

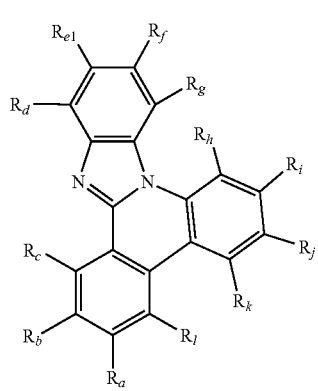

Formula 2-3

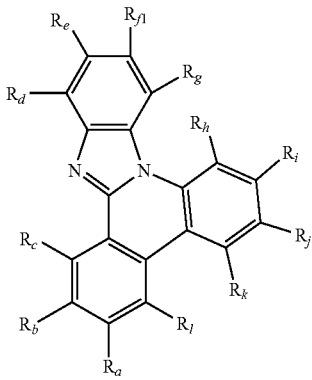

Formula 2-4

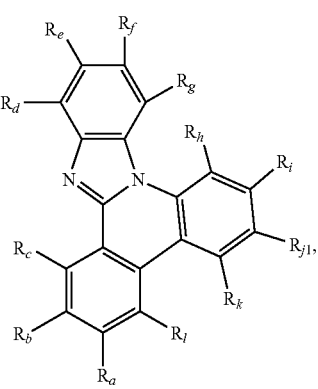

and
wherein in Formula 2-1 to Formula 2-4, $R_{a1}$, $R_{e1}$, $R_{f1}$, and $R_{j1}$ are each independently a position connected with Formula 1, and $R_a$ to $R_l$ are each independently the same as defined in Formula 2.

18. The light emitting device of claim 14, wherein the fused polycyclic compound represented by Formula 1 is represented by any one among Formula 3-1 to Formula 3-9:

Formula 3-1
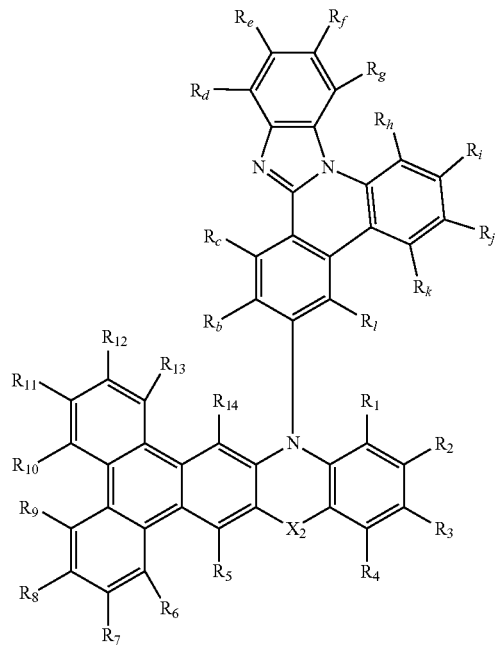
Formula 3-2
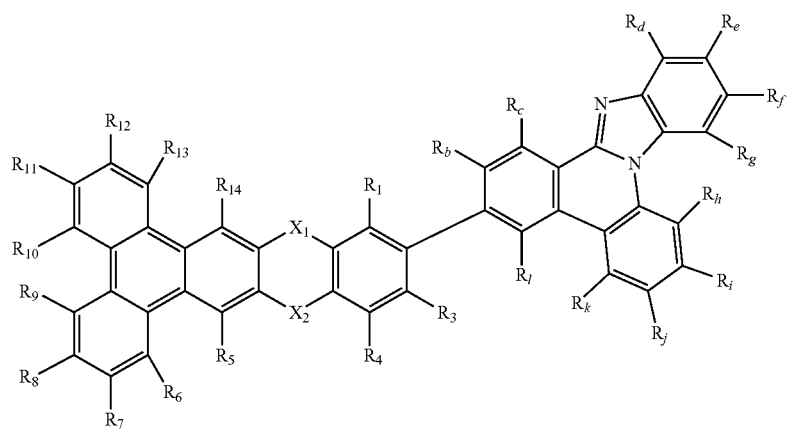
Formula 3-3
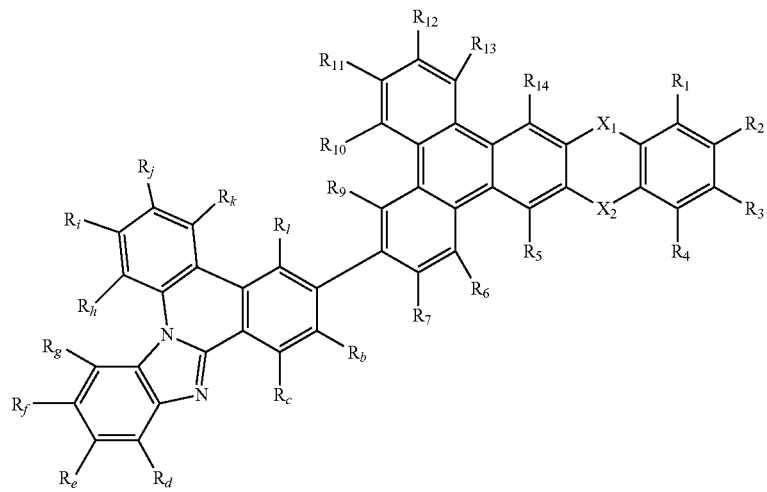

Formula 3-4
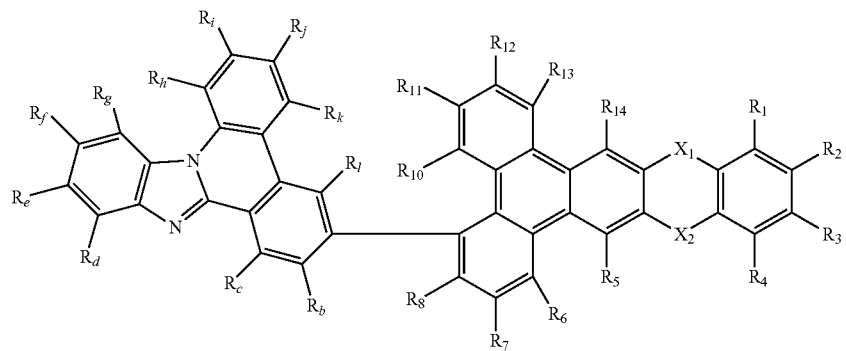
Formula 3-5
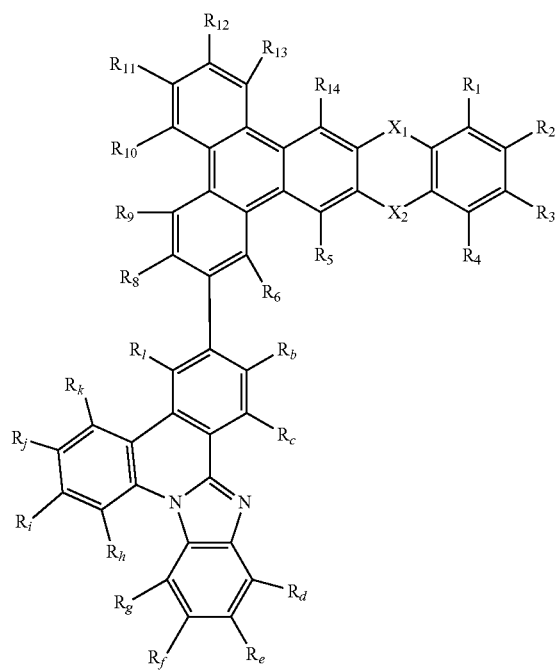
Formula 3-6
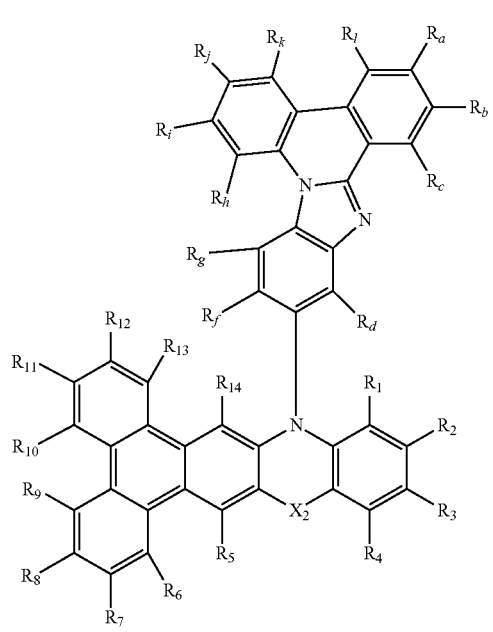

-continued
Formula 3-7
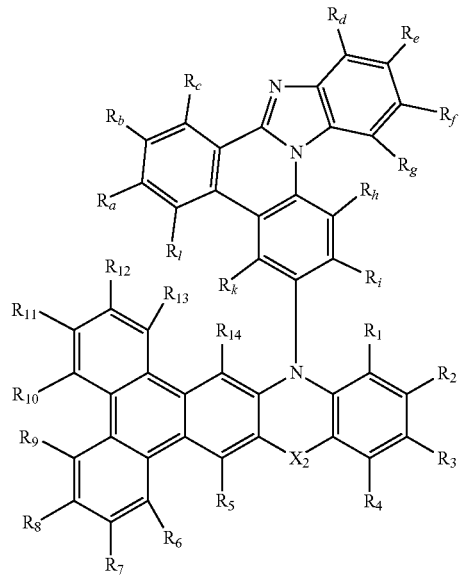
Formula 3-8
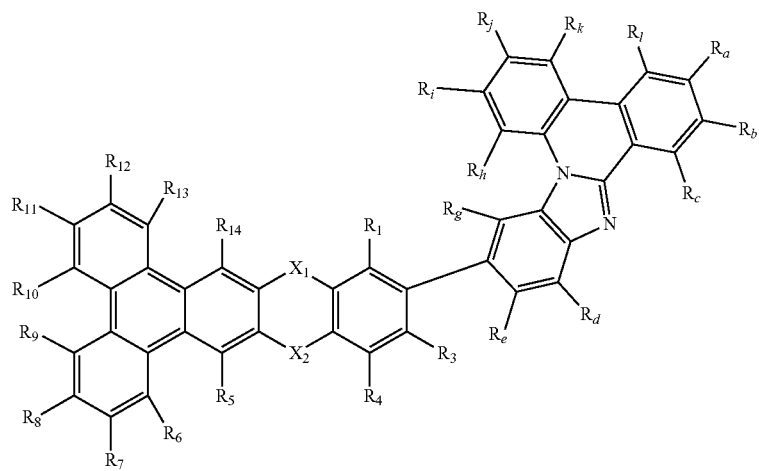
Formula 3-9
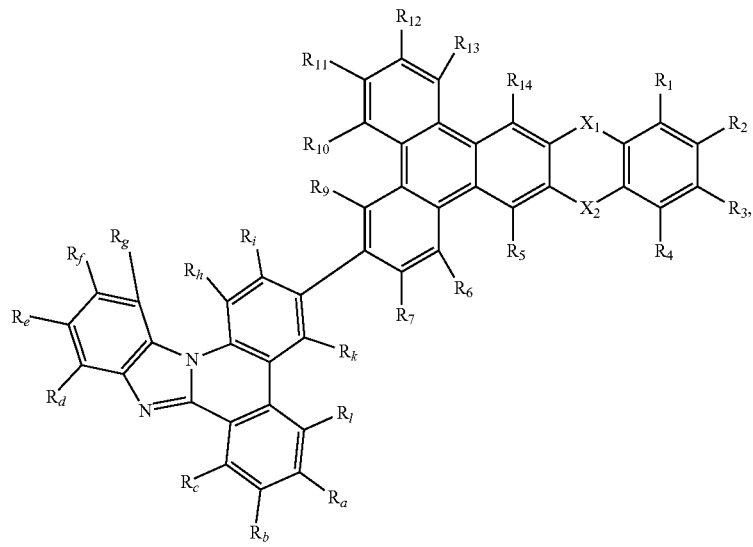

and
wherein in Formula 3-1 to Formula 3-9,
$X_1$, $X_2$, $R_1$ to $R_{15}$, and $R_a$ to $R_l$ are each independently the same as defined in Formula 1 and Formula 2.

19. The light emitting device of claim 14, wherein the fused polycyclic compound represented by Formula 1 is represented by any one among Formula 4-1 to Formula 4-3:

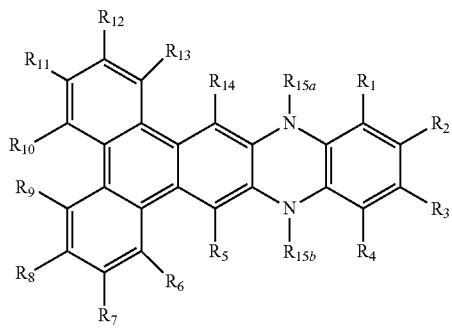

Formula 4-1

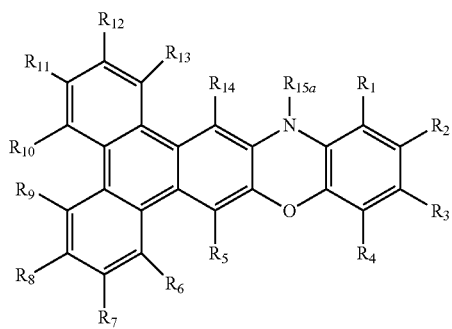

Formula 4-2

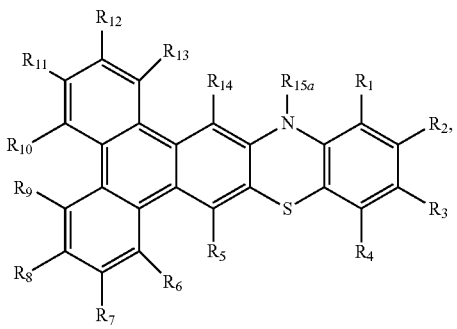

Formula 4-3 and
wherein in Formula 4-1 to Formula 4-3,
$R_{15a}$ and $R_{15b}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted thio group, a substituted or unsubstituted carbonyl group, a substituted or unsubstituted alkyl group of 2 to 30 carbon atoms, a substituted or unsubstituted aryl group of 6 to 60 ring-forming carbon atoms, a substituted or unsubstituted heteroaryl group of 2 to 60 ring-forming carbon atoms, or a substituent represented by Formula 2, and
$R_1$ to $R_{14}$ are each independently the same as defined in Formula 1.

20. The light emitting device of claim 14, wherein the fused polycyclic compound comprises at least one among compounds in Compound Group 1:

Compound group 1

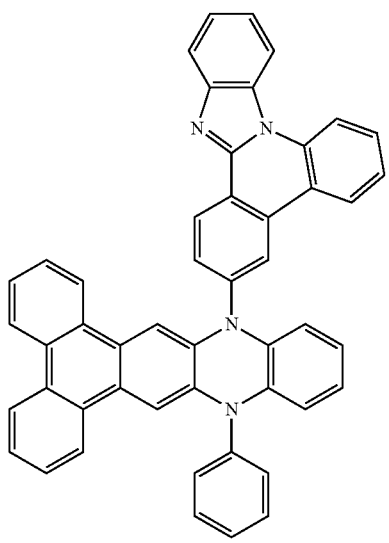

1

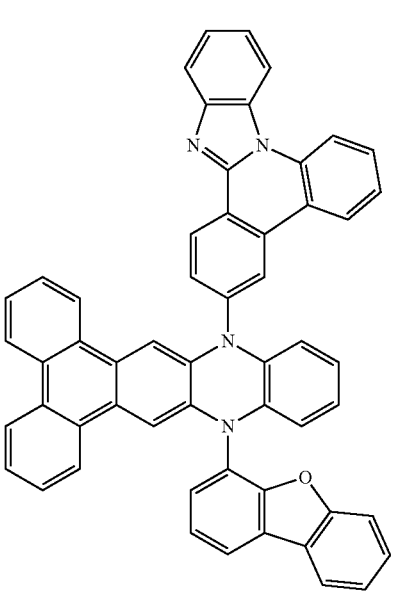

2

-continued
207
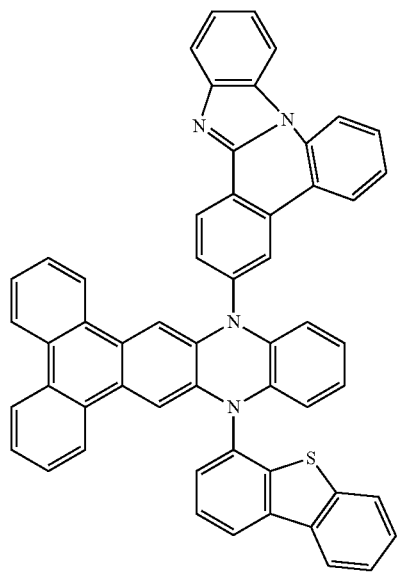
3
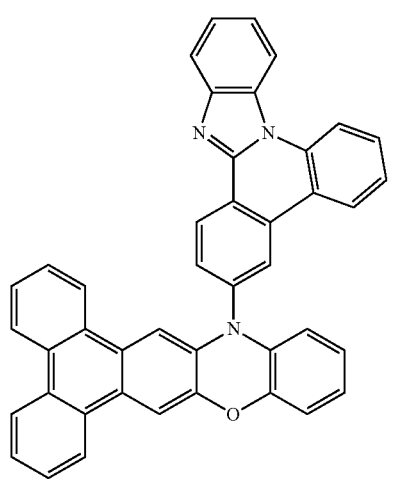
5
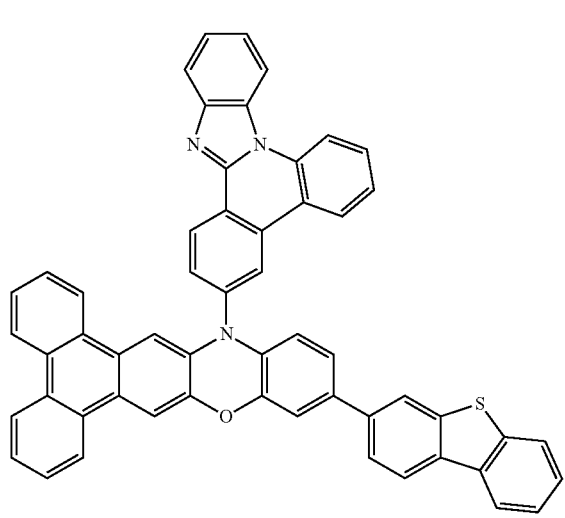
7
208
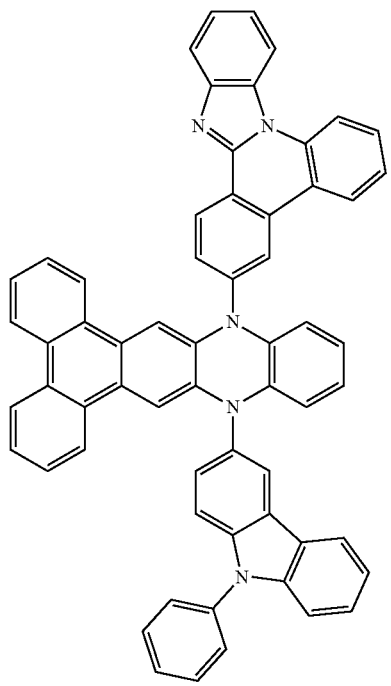
4
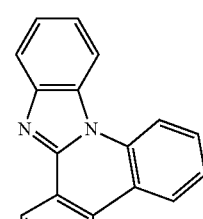
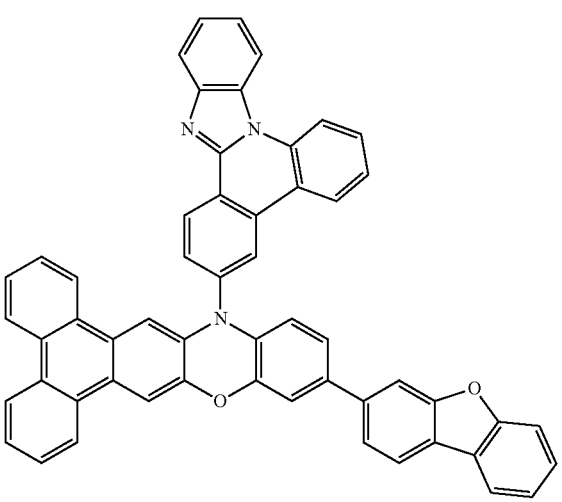
6
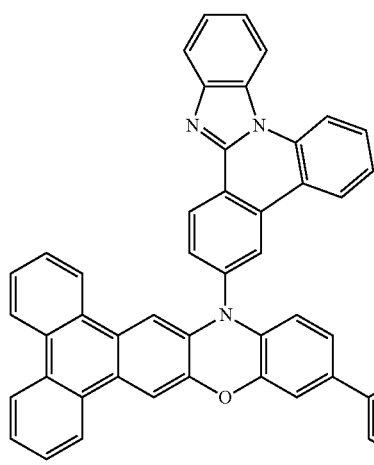
8

9
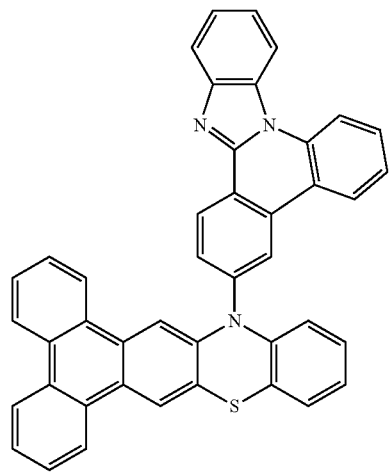
10
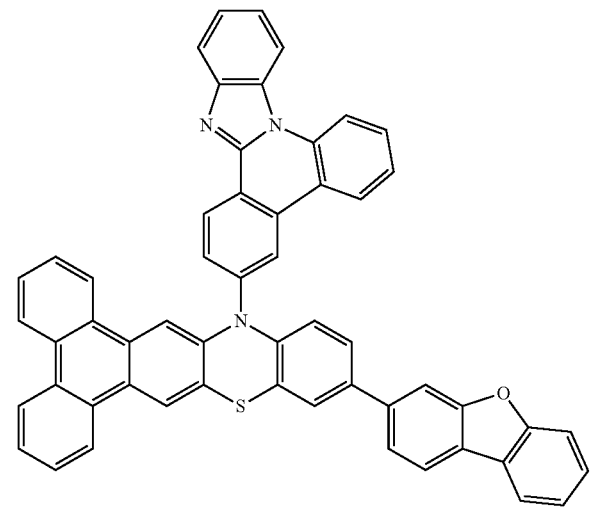
11
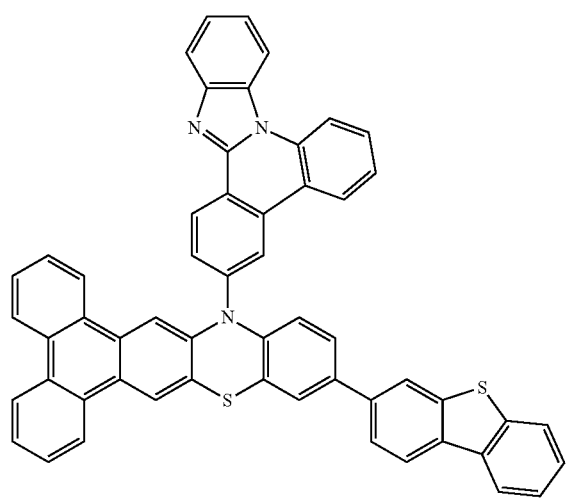
12
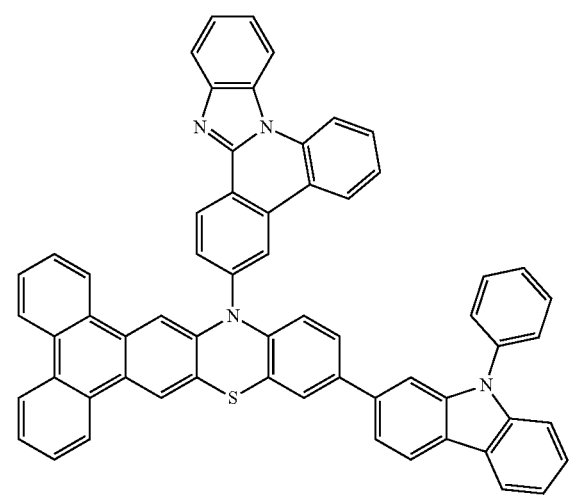
13
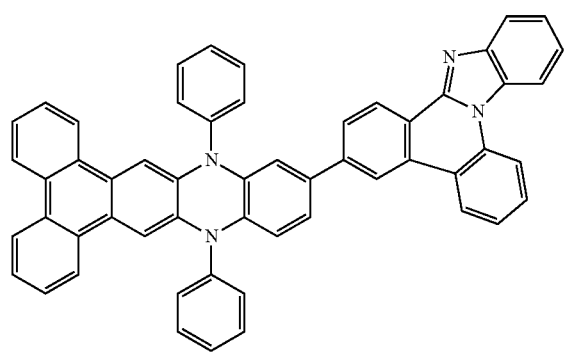
14
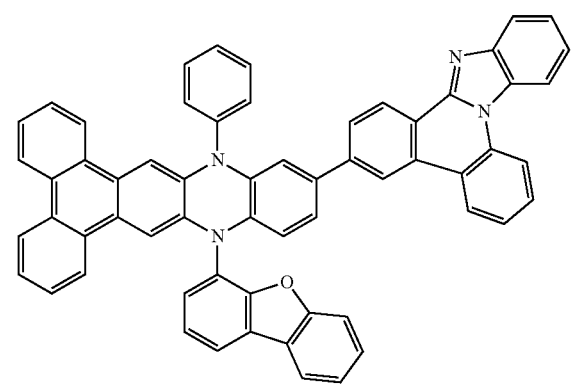

15
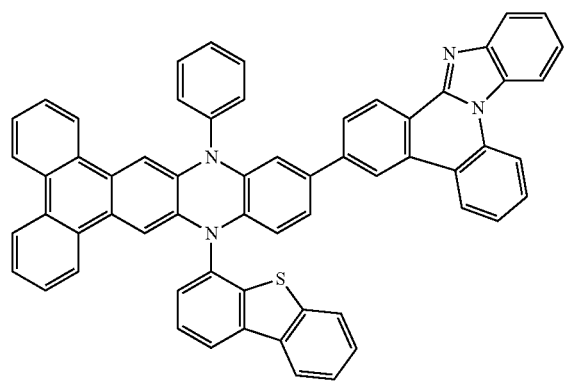
16
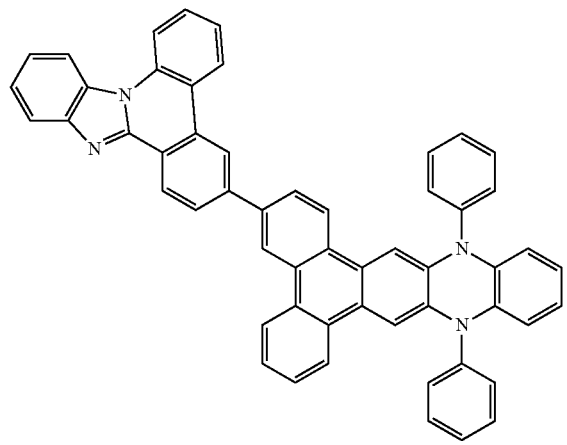
17
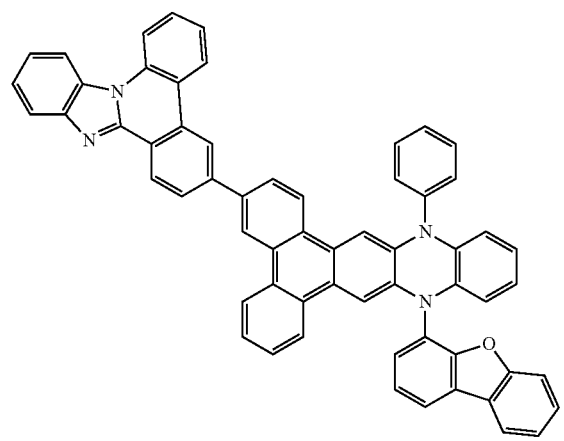
18
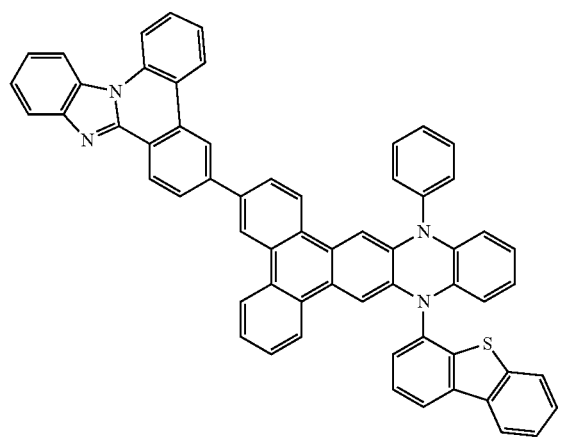
19
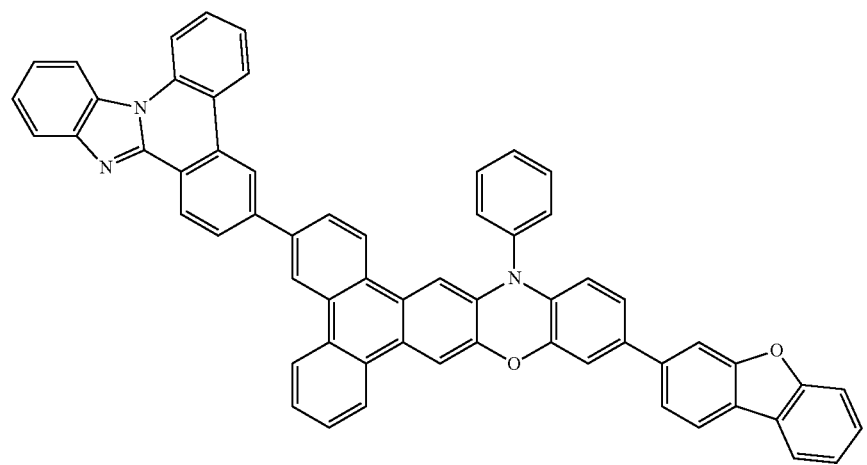

20
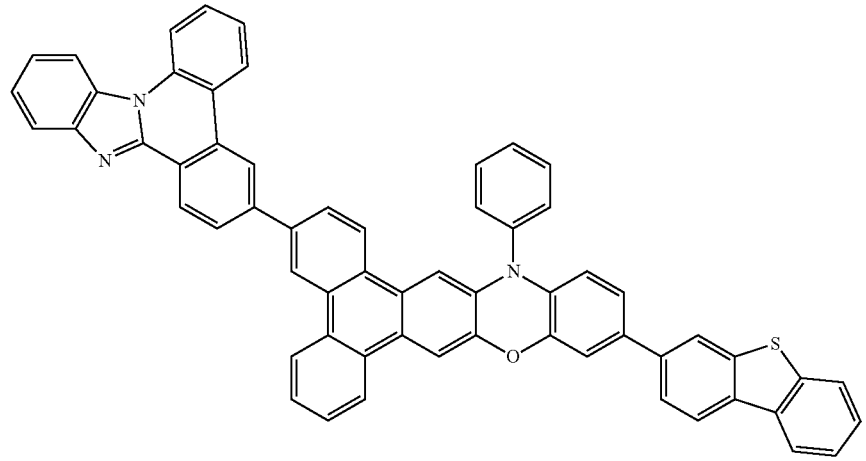
21
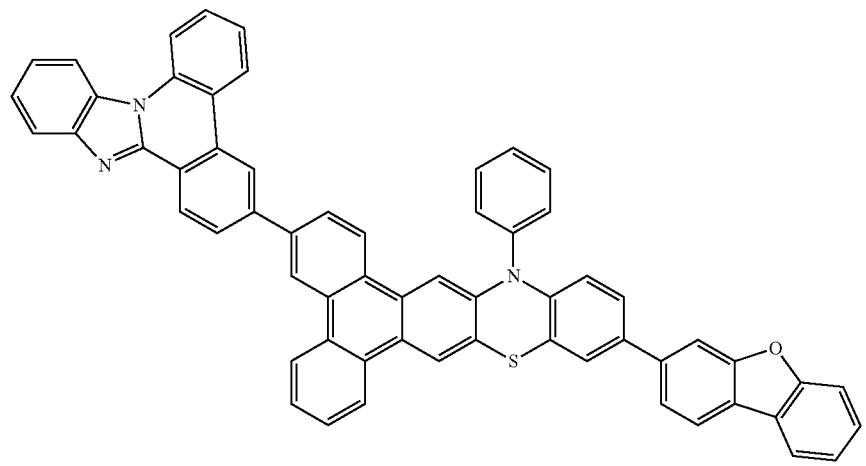
22
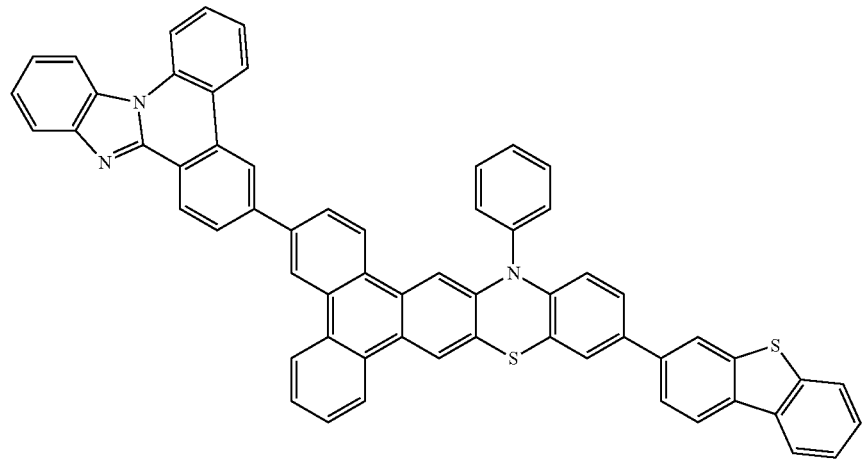

23
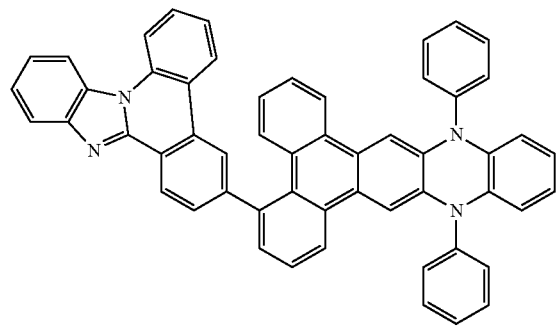
24
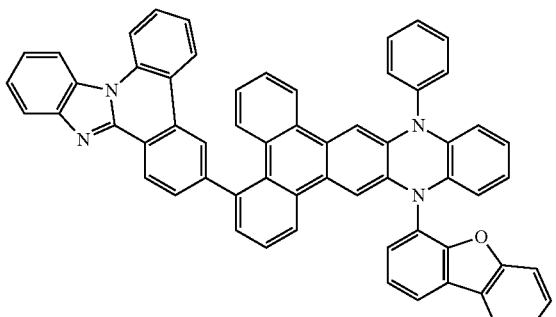
25
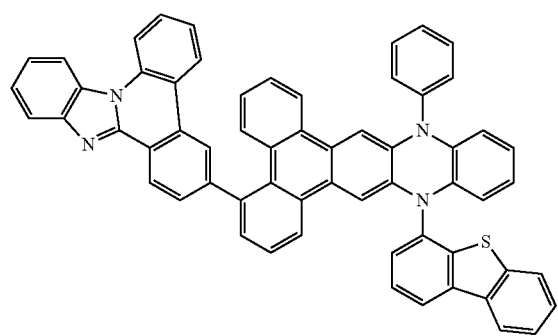
26
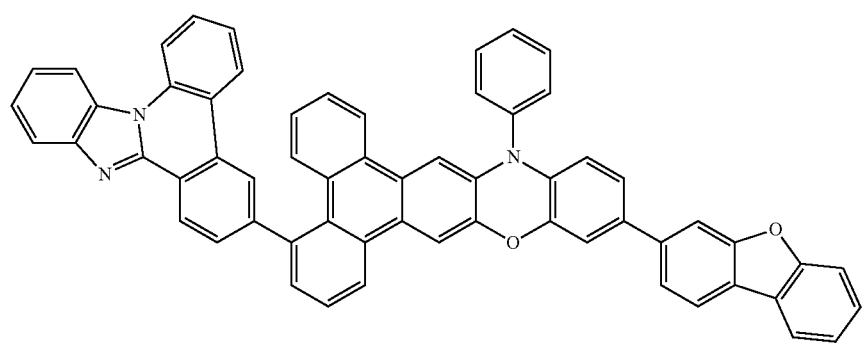
27
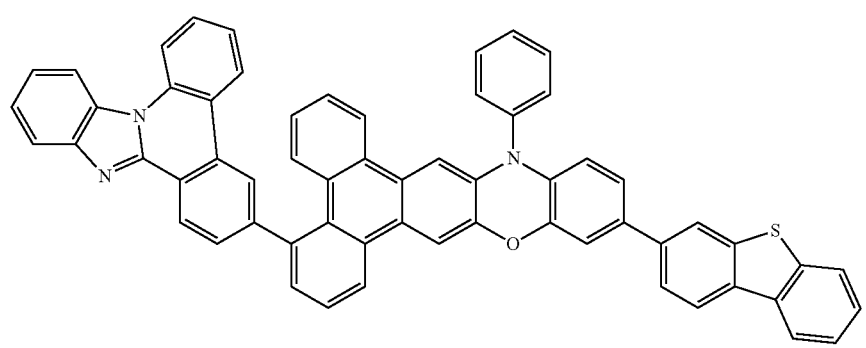

28
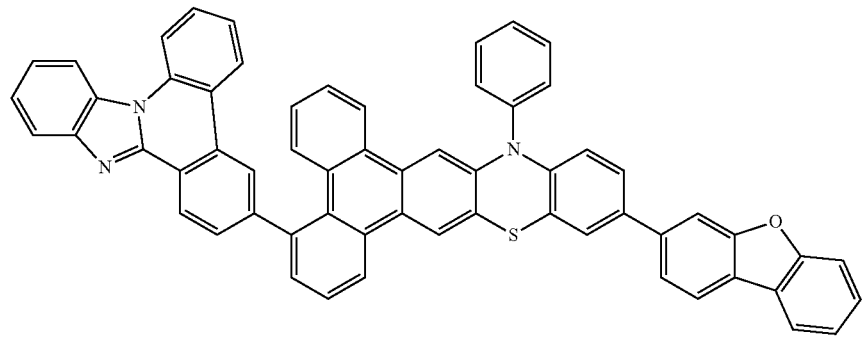
29
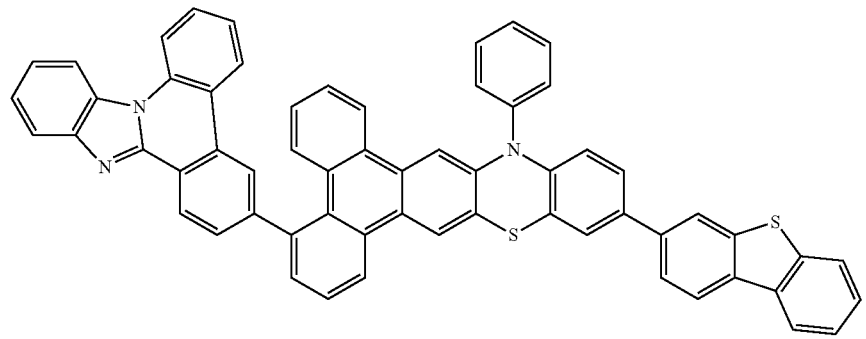
30
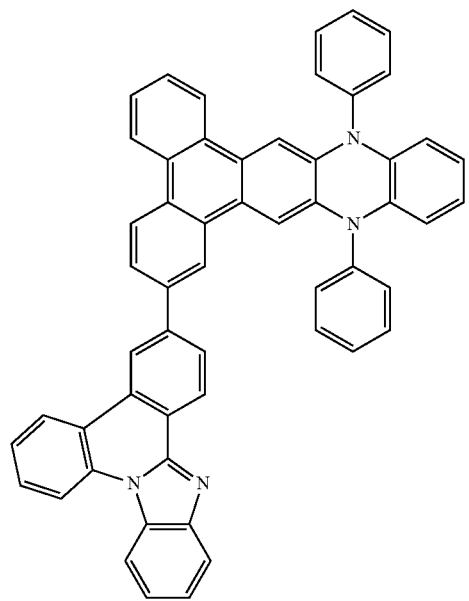
31
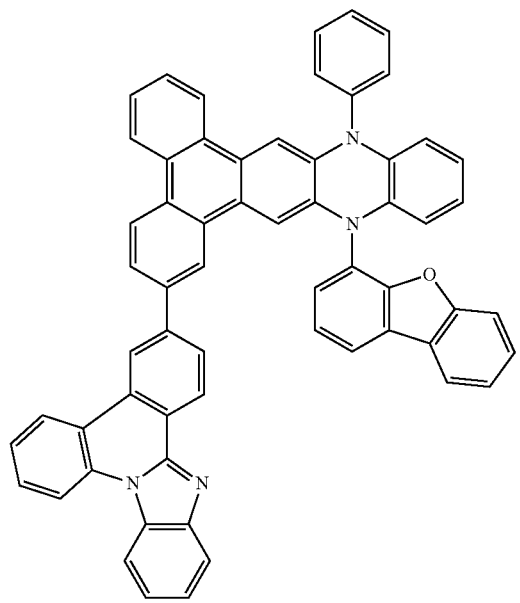

-continued
32
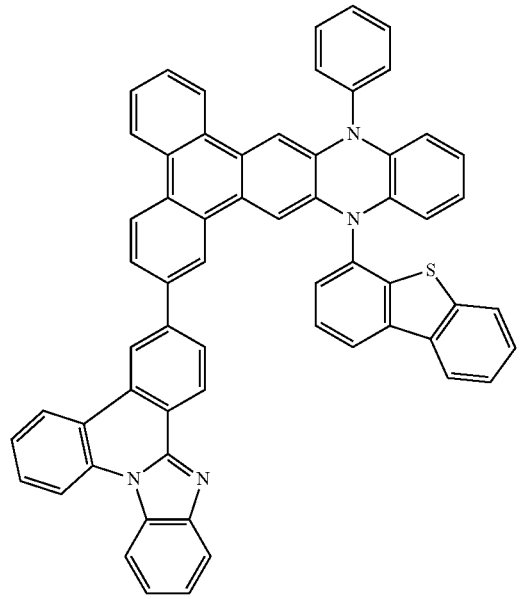
33
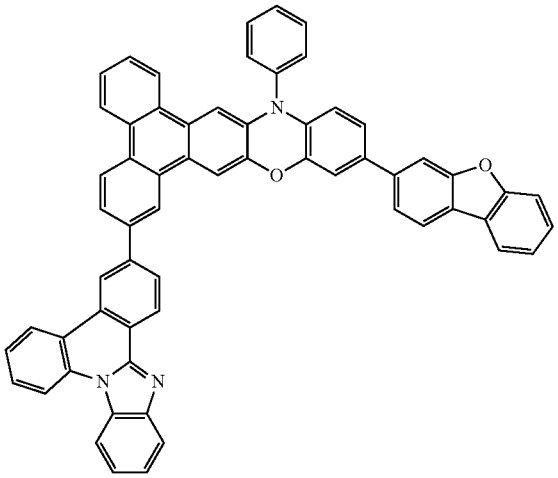
34
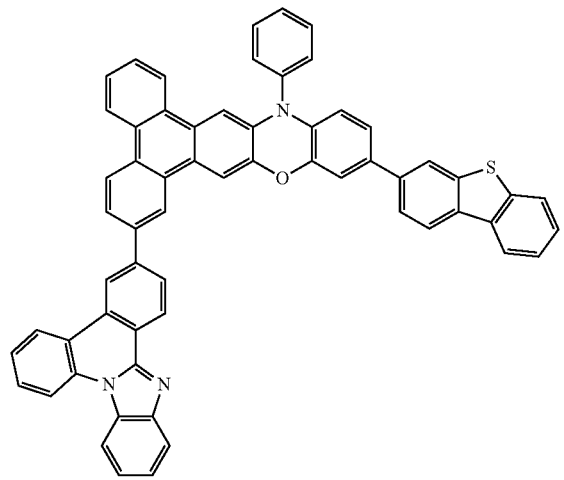
35
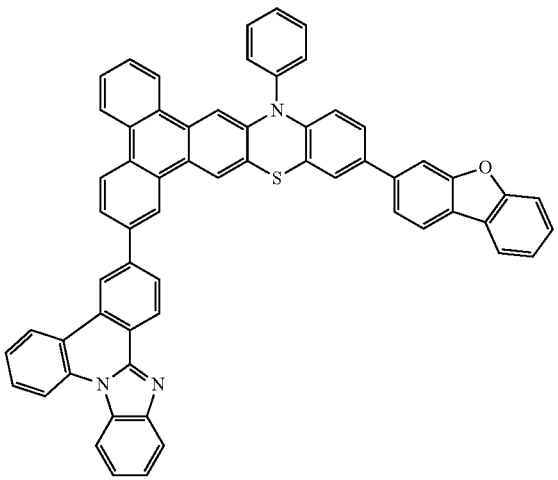
36
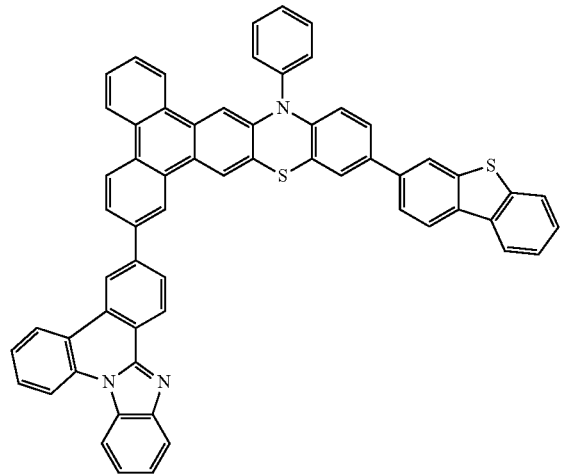
37
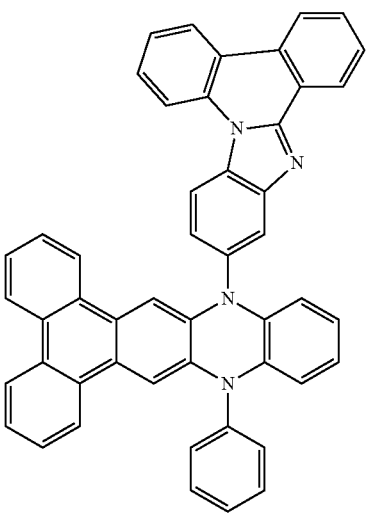

38
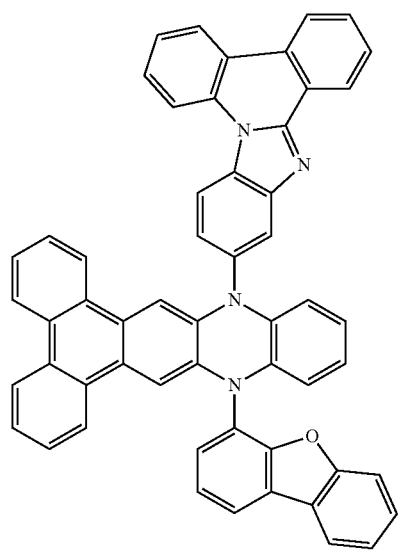
39
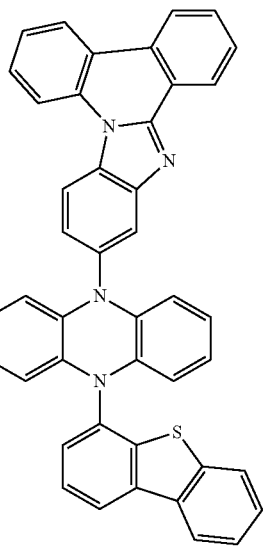
40
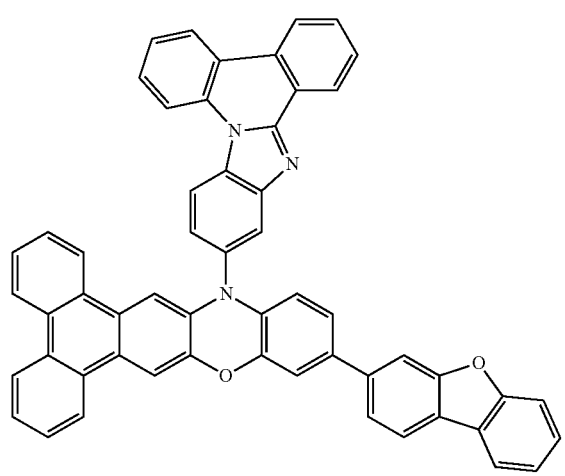
41
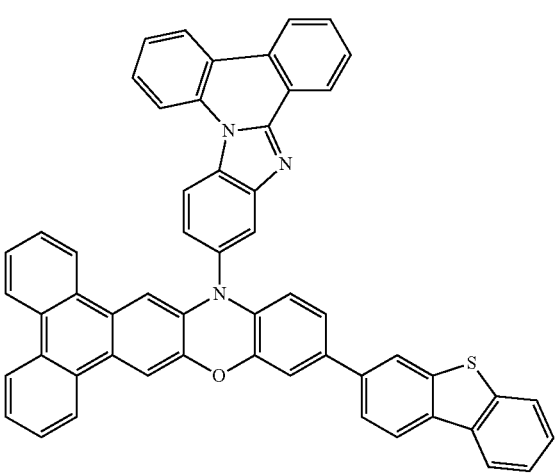
42
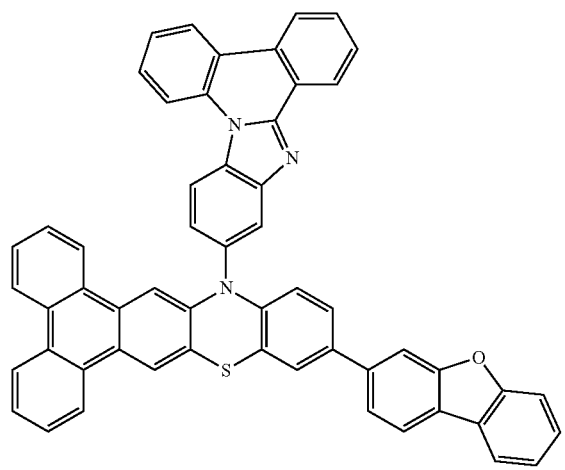
43
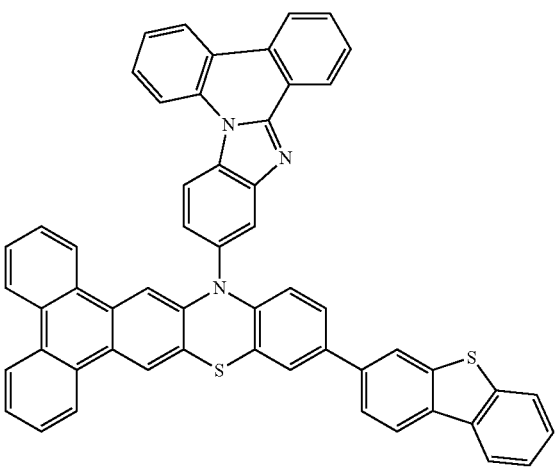

-continued
44
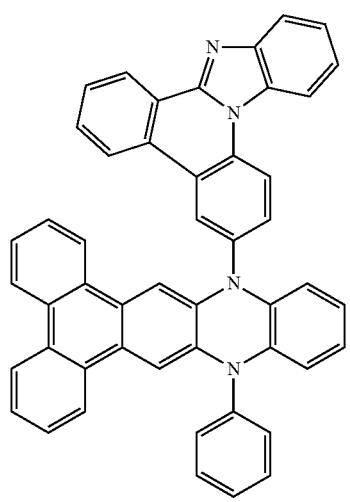
45
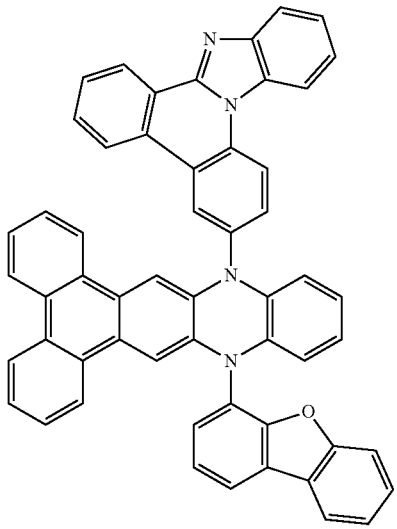
46
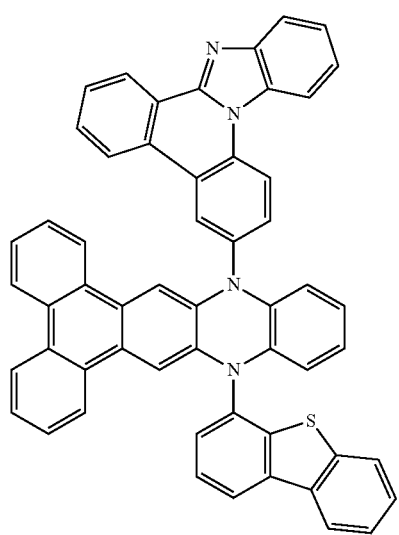
47
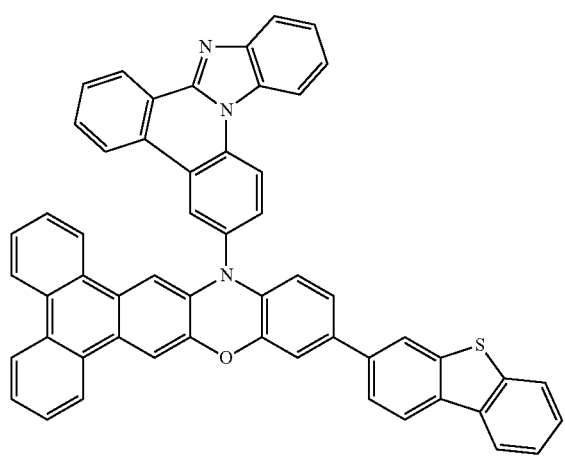
48
49
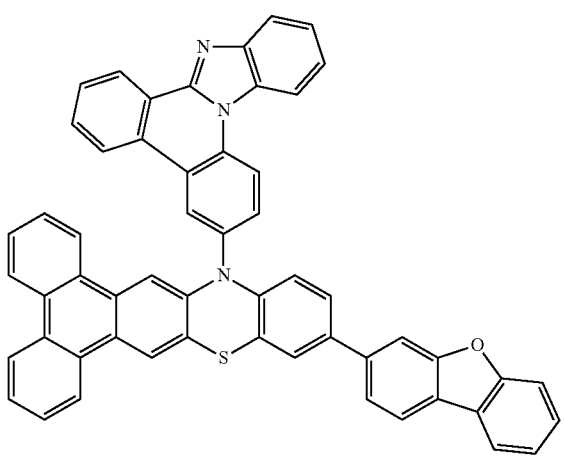

-continued
50
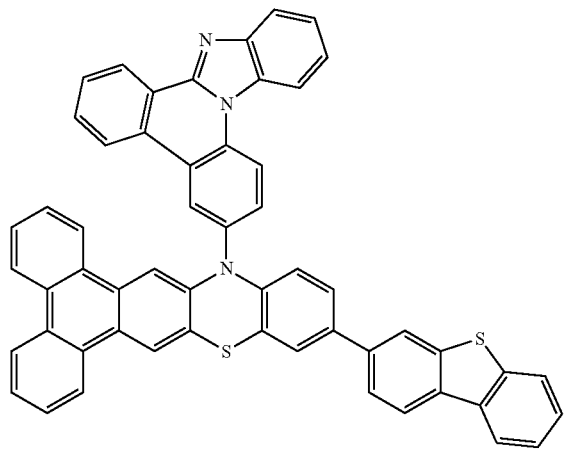
51
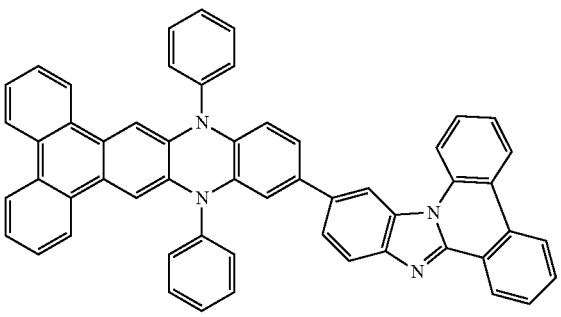
52
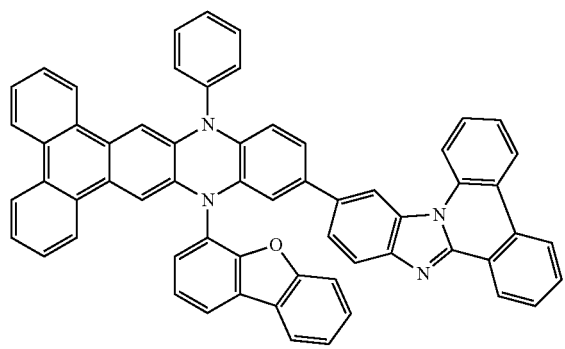
53
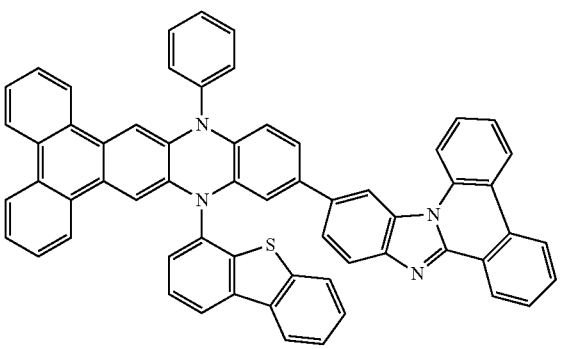
54
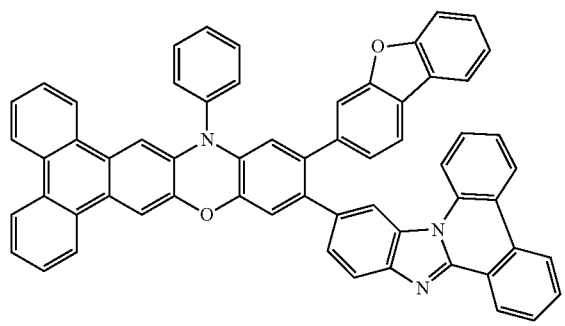
55
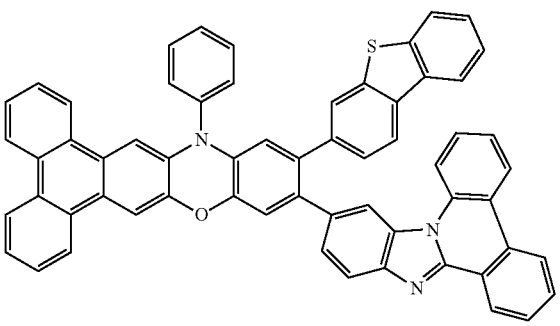
56
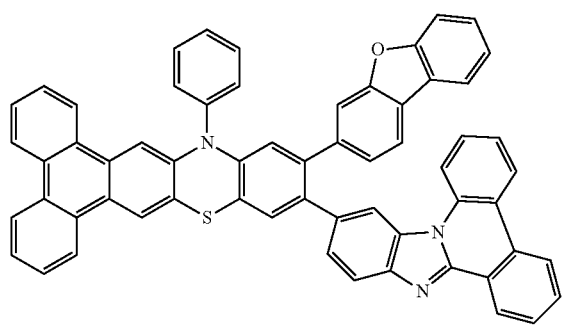
57
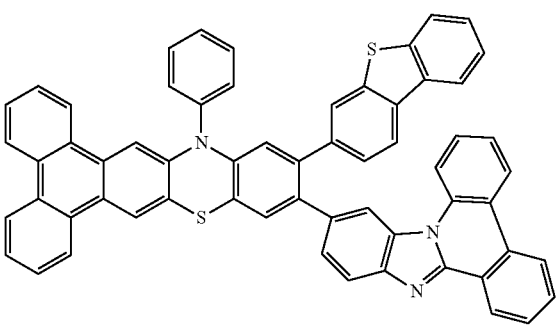

-continued
58
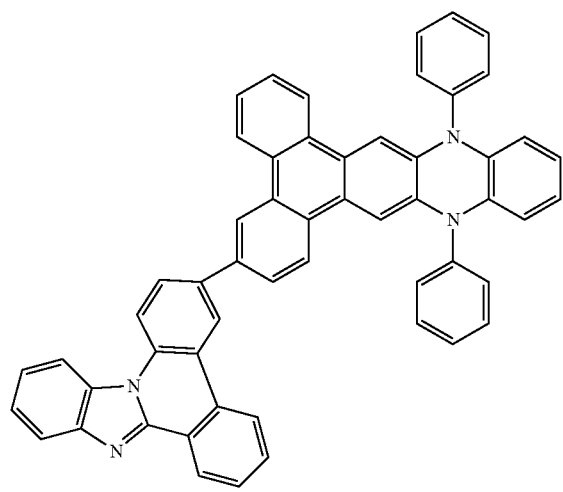
59
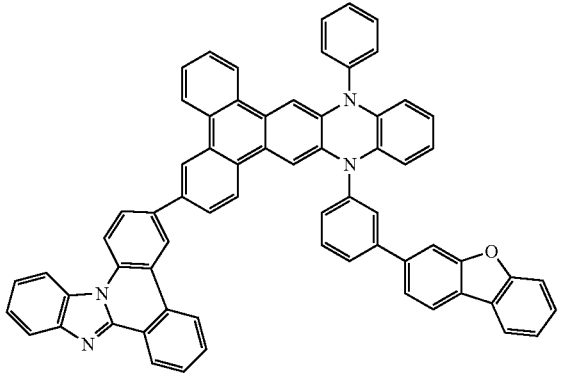
60
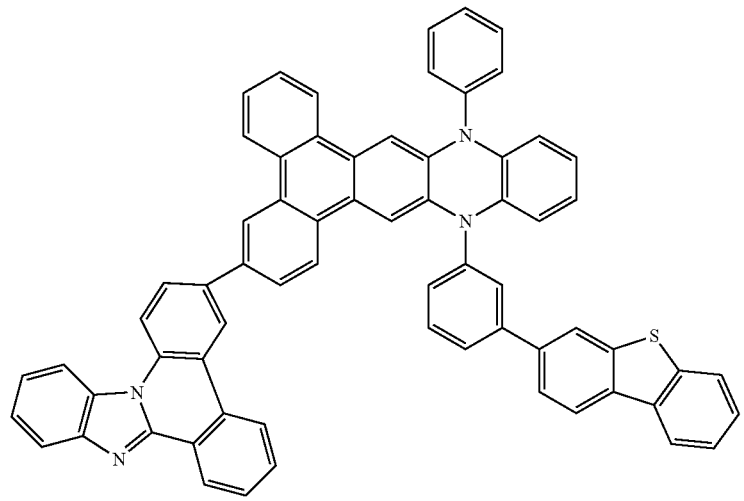
61
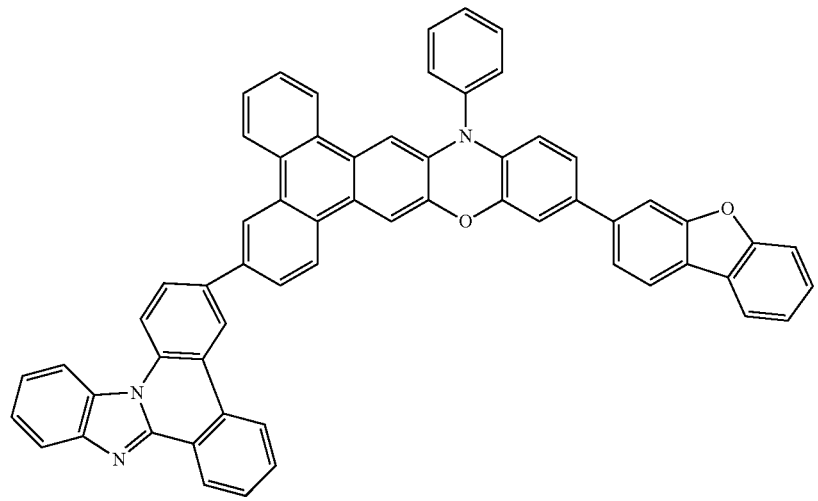

62
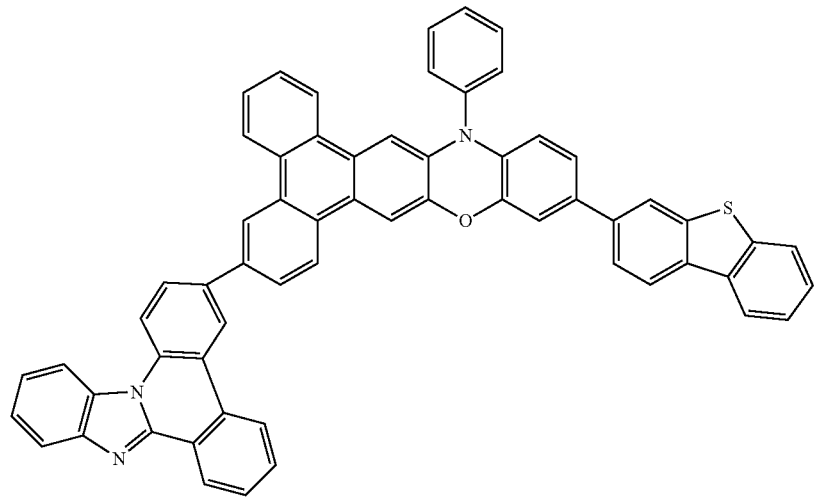
63
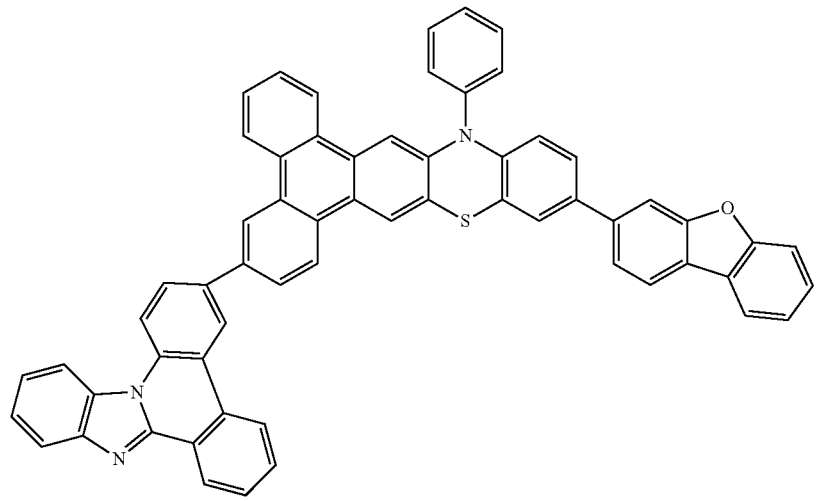
64
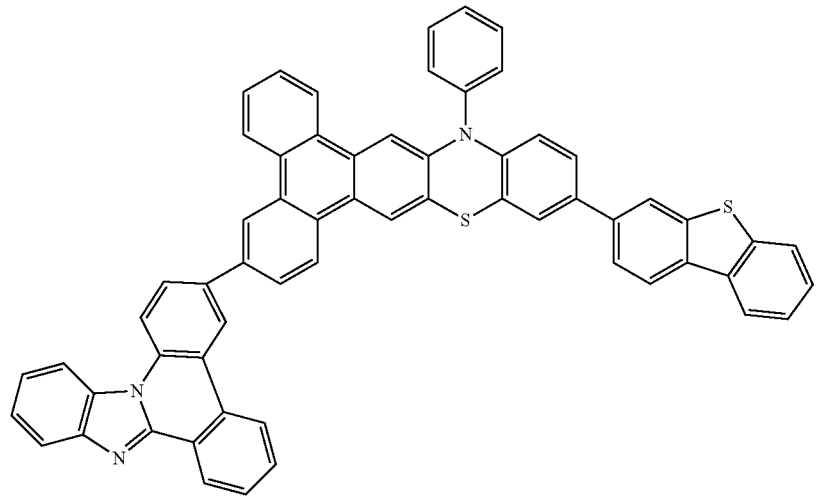

231
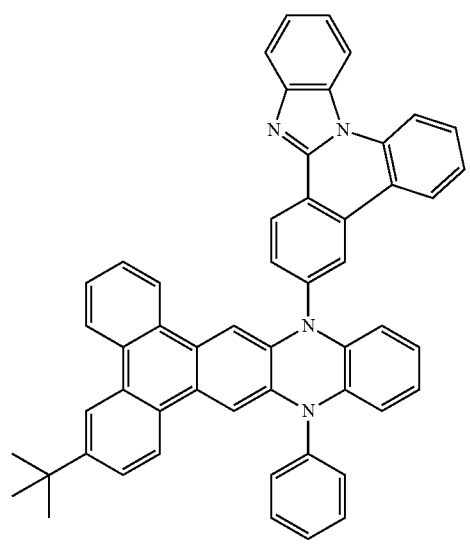
232
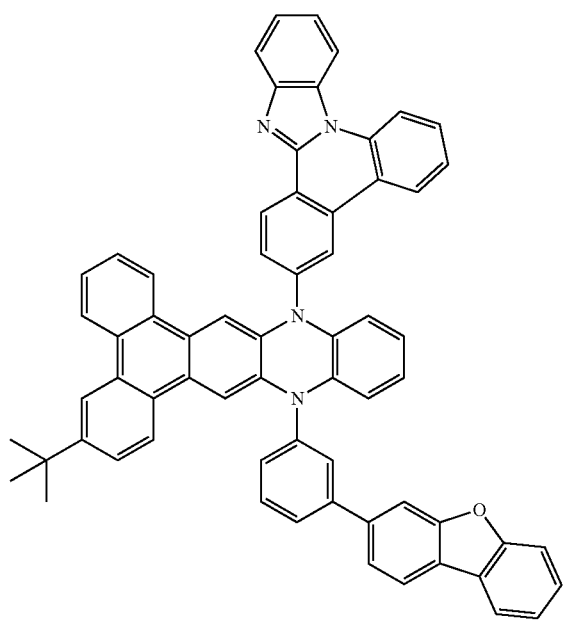
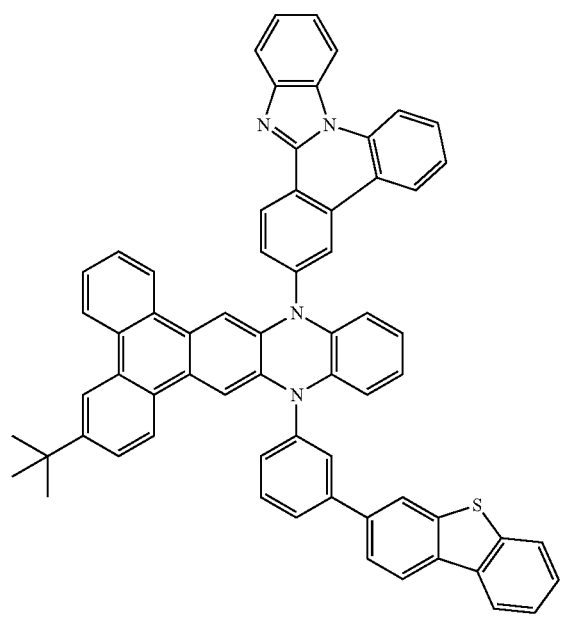
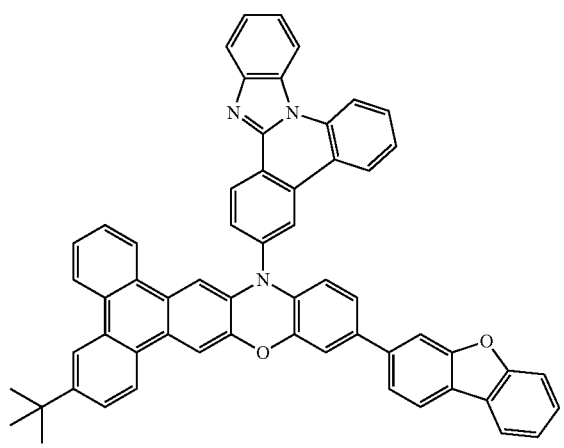

-continued
233
69
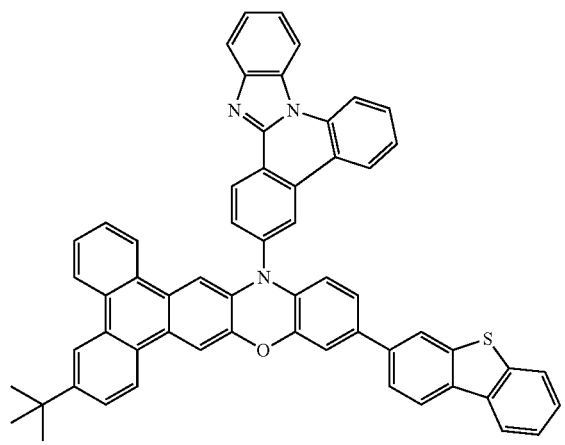
70
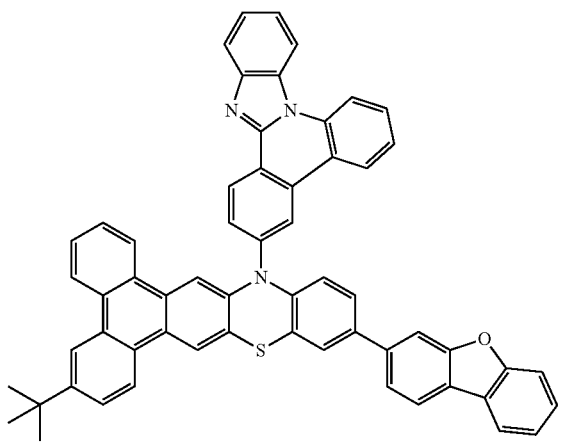
234
71
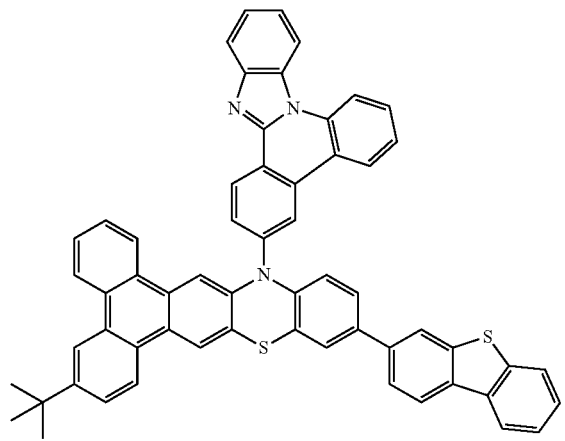
72
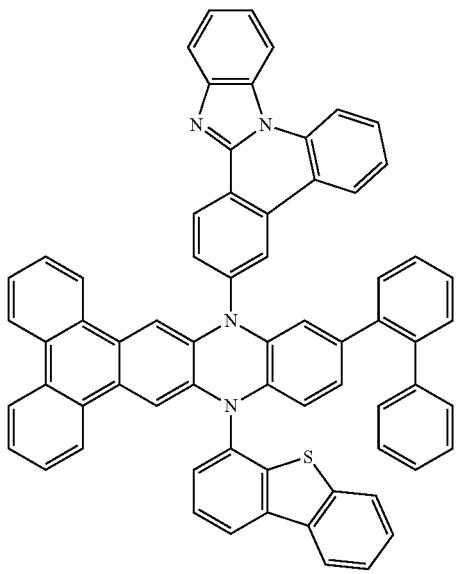
73
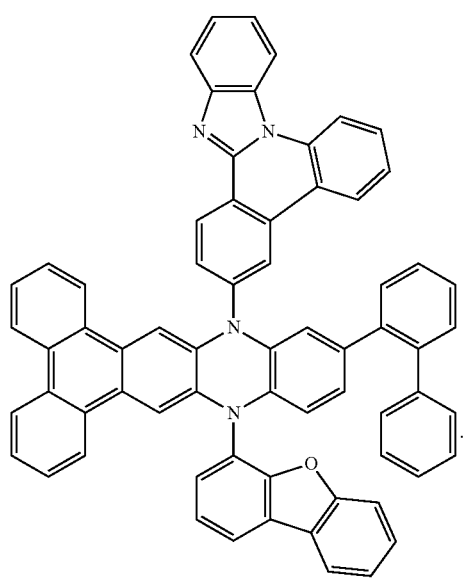
* * * * *